(12) United States Patent
Kawabata et al.

(10) Patent No.: US 7,910,380 B2
(45) Date of Patent: Mar. 22, 2011

(54) STRUCTURE FOR INTRODUCING A PLURALITY OF SOLUTIONS, MICRO FLUIDIC DEVICE HAVING SAID STRUCTURE AND METHOD FOR INTRODUCING SOLUTION

(75) Inventors: Tomohisa Kawabata, Hyogo (JP); Shinji Satomura, Hyogo (JP); Henry Garrett Wada, Atherton, CA (US)

(73) Assignee: Wako Pure Chemical Industries, Ltd., Osaka (JP)

( * ) Notice: Subject to any disclaimer, the term of this patent is extended or adjusted under 35 U.S.C. 154(b) by 0 days.

(21) Appl. No.: 12/899,838

(22) Filed: Oct. 7, 2010

(65) Prior Publication Data
US 2011/0027902 A1     Feb. 3, 2011

Related U.S. Application Data

(62) Division of application No. 12/226,017, filed as application No. PCT/US2007/066461 on Apr. 11, 2007, now Pat. No. 7,833,804.

(60) Provisional application No. 60/792,172, filed on Apr. 14, 2006.

(51) Int. Cl.
*G01N 1/18* (2006.01)
*G01N 1/10* (2006.01)
*G01N 35/00* (2006.01)
*B01L 3/02* (2006.01)

(52) U.S. Cl. .............. 436/180; 436/43; 436/63; 436/86; 436/174; 436/178; 436/179; 422/50; 422/58; 422/68.1; 422/81; 422/82; 422/100; 422/102

(58) Field of Classification Search .................. 422/68.1, 422/50, 81, 100; 436/43, 177, 178, 179, 436/180
See application file for complete search history.

(56) References Cited

U.S. PATENT DOCUMENTS

| | | | |
|---|---|---|---|
| 5,869,004 A | 2/1999 | Parce et al. | |
| 6,403,338 B1 | 6/2002 | Knapp et al. | |
| 7,378,280 B2 * | 5/2008 | Quake et al. | 436/63 |
| 2002/0076806 A1 | 6/2002 | Van Gelder | |
| 2006/0191792 A1 * | 8/2006 | Herr et al. | 204/455 |
| 2008/0254997 A1 * | 10/2008 | Oku et al. | 506/9 |

FOREIGN PATENT DOCUMENTS

WO  WO 01/59440 A2  8/2001

OTHER PUBLICATIONS

Effenhauser et al., "Glass Chips for High-Speed Capillary Electrpphoresis Separations with Submicrometer Plate Heights," Analytical Chemistry, Oct. 1, 1993, 65(19):2637-2642.

* cited by examiner

*Primary Examiner* — Brian J Sines
(74) *Attorney, Agent, or Firm* — Foley & Lardner LLP

(57) ABSTRACT

The present invention relates to a structure (a solution introducing structure) for introducing a plurality of solutions (a sample and/or a reagent solution) in highly accurate volume, in high amount and simply, into a channel, in particular a channel of a micro fluidic device, a micro fluidic device having said structure, a method for introducing a solution using said device, a method for separation of a substance, and a method for separating a complex between an analyte or analogue thereof, and a substance binding to said analyte or analogue thereof (hereinafter may be abbreviated as a complex forming substance or CFS) which is obtained by reacting a plurality of solutions introduced by these, and said CFS or analogue not involved in formation of said complex, rapidly, simply and in high accuracy, along with a method for measuring an analyte or an analogue thereof in a sample in high sensitivity.

2 Claims, 22 Drawing Sheets

[Figure 1]
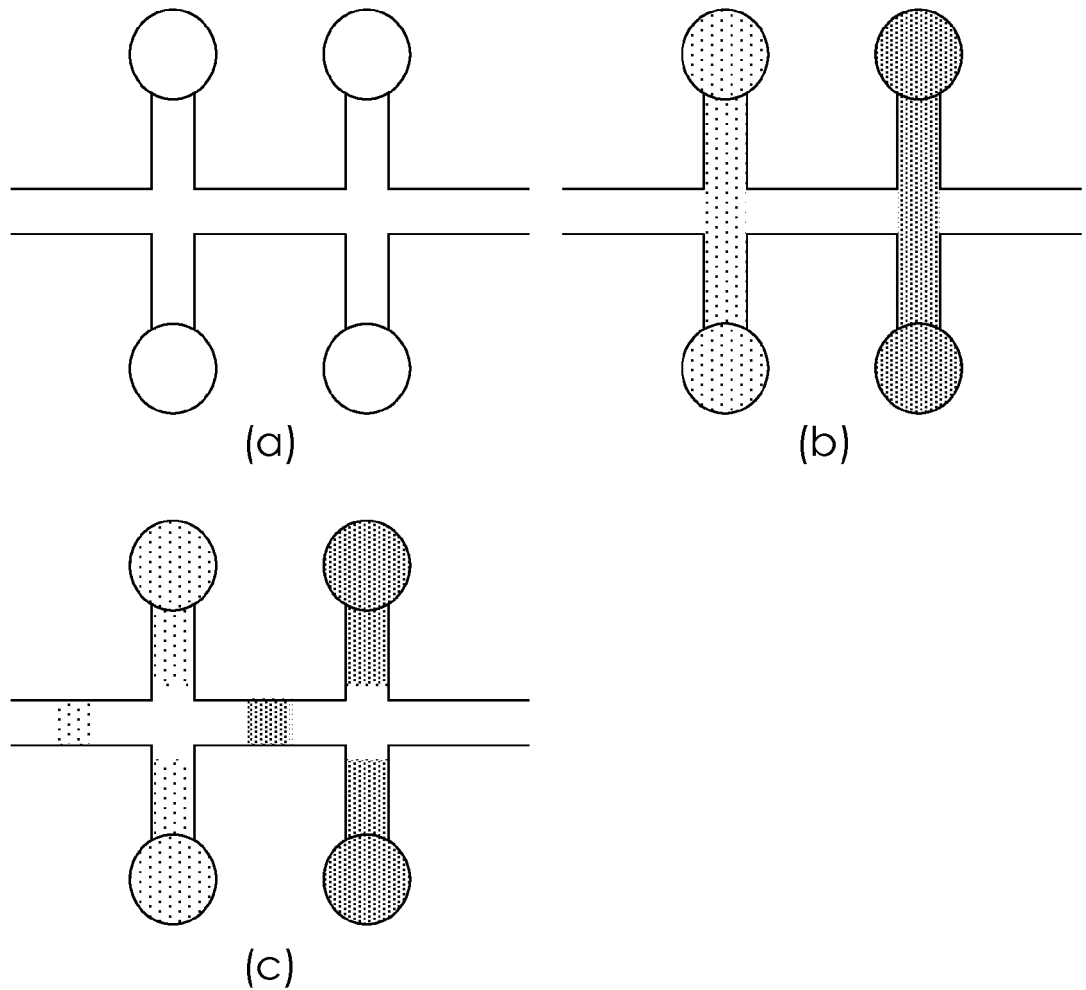
[Figure 2]
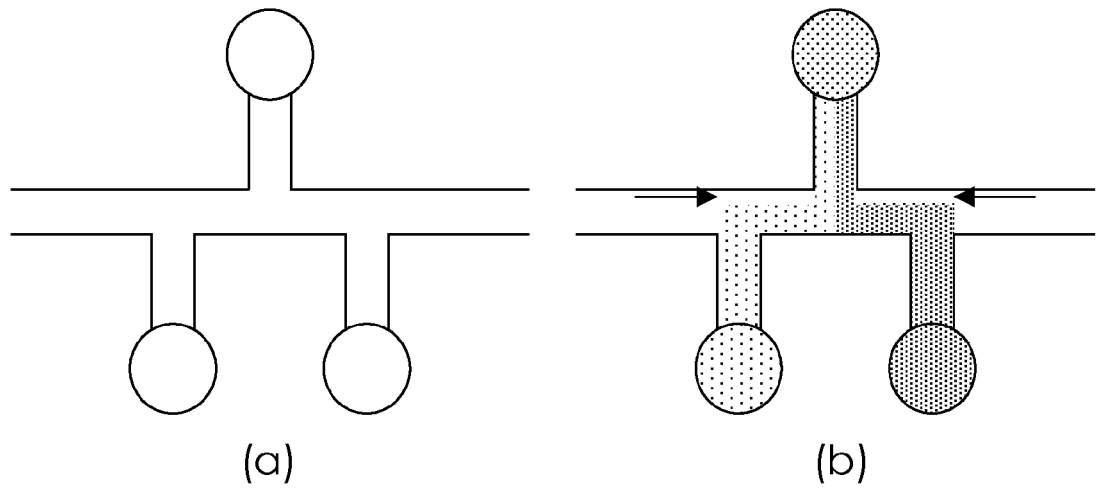

[Figure 3]
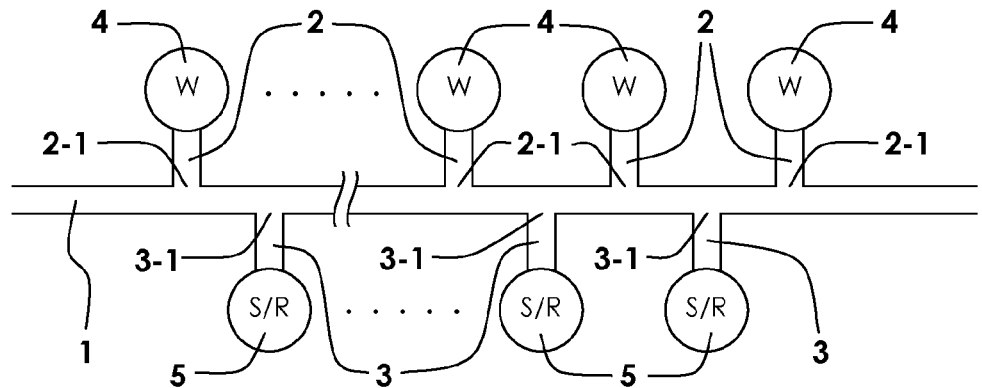
[Figure 4]
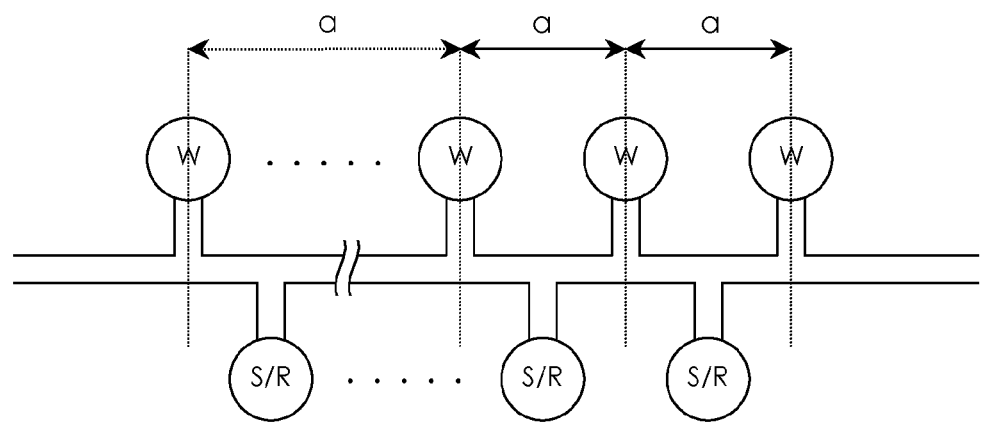
[Figure 5]
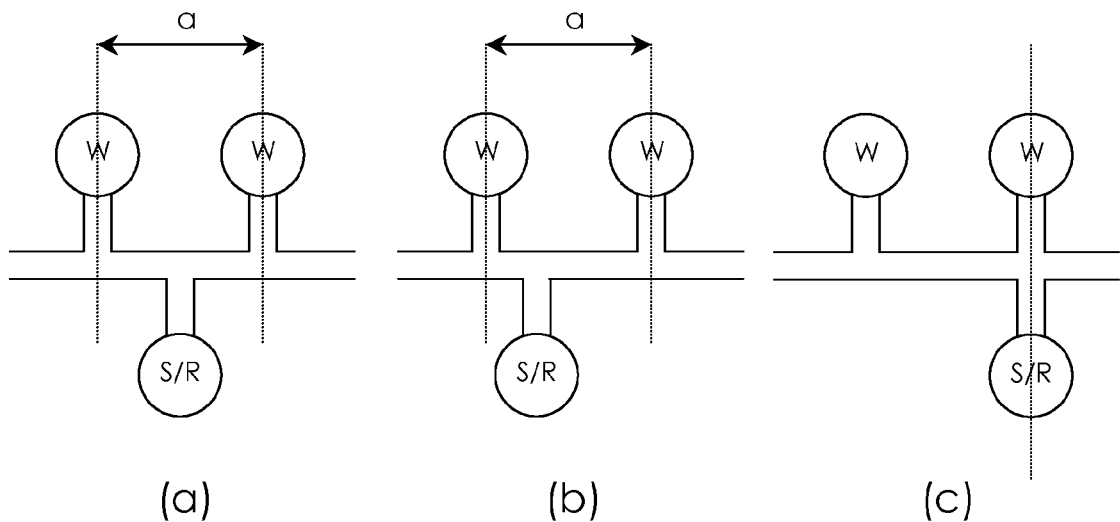
(a)　　　　　　　　(b)　　　　　　　　(c)

[Figure 6]
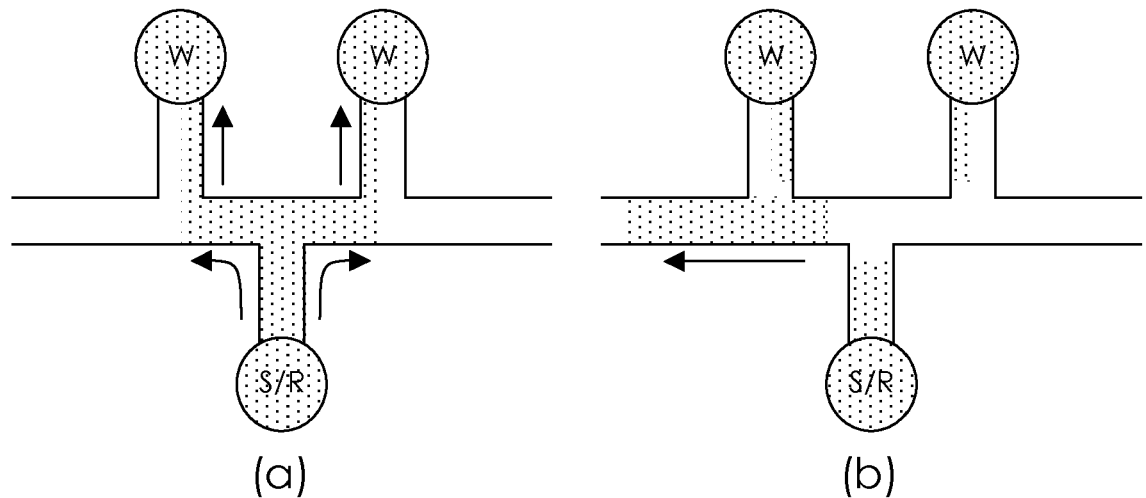
(a)  (b)
[Figure 7]
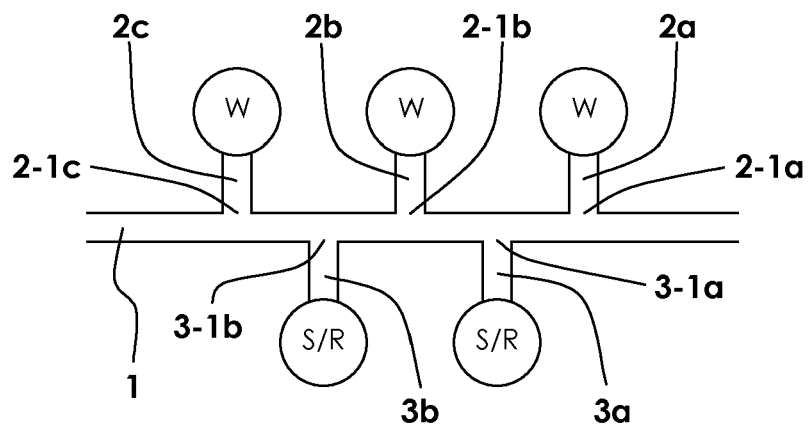

[Figure 8]
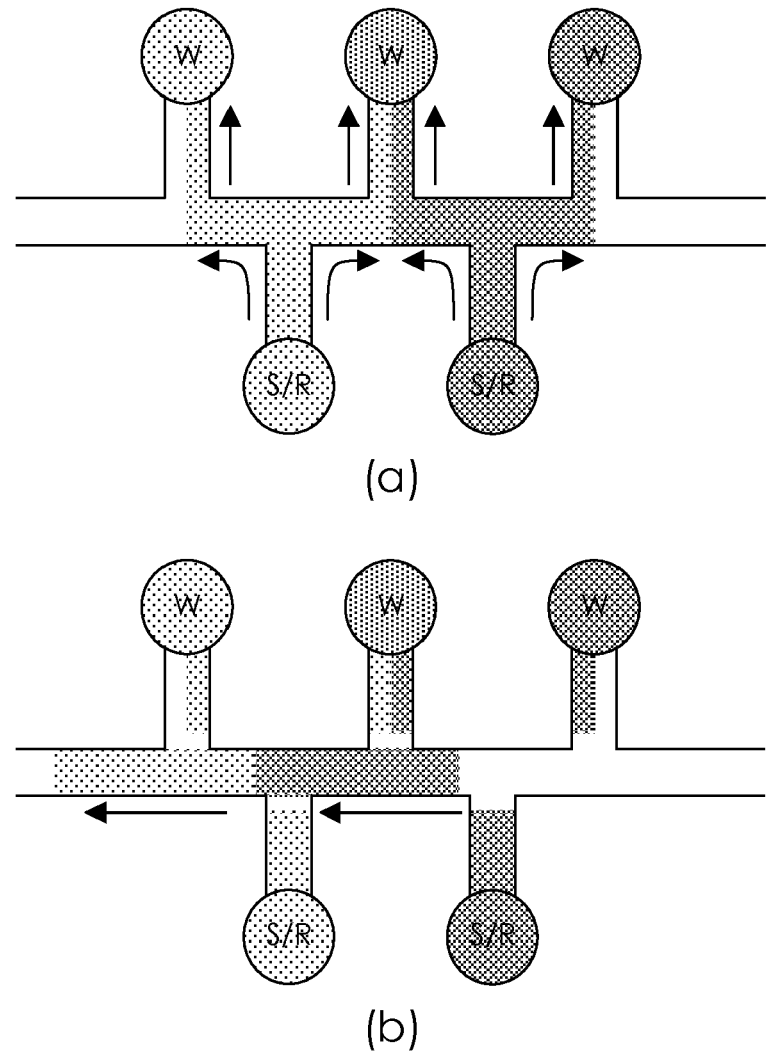
(a)
(b)
[Figure 9]
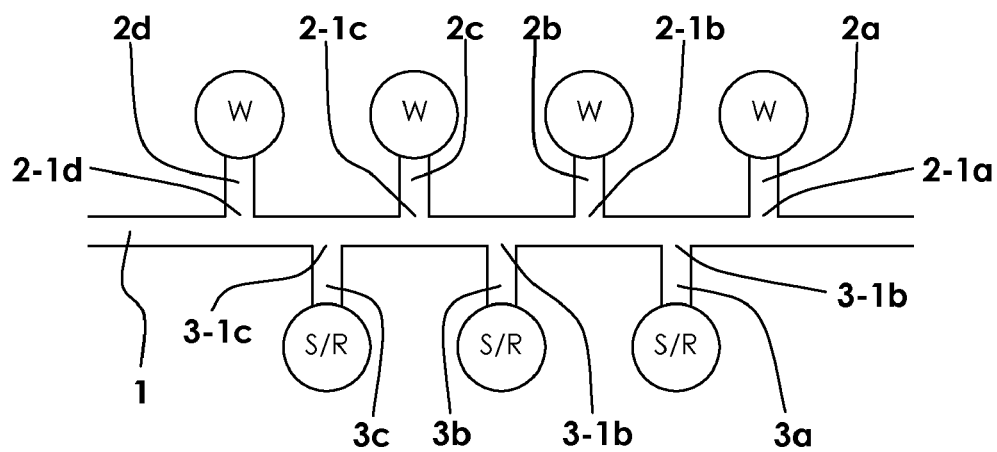

[Figure 10]
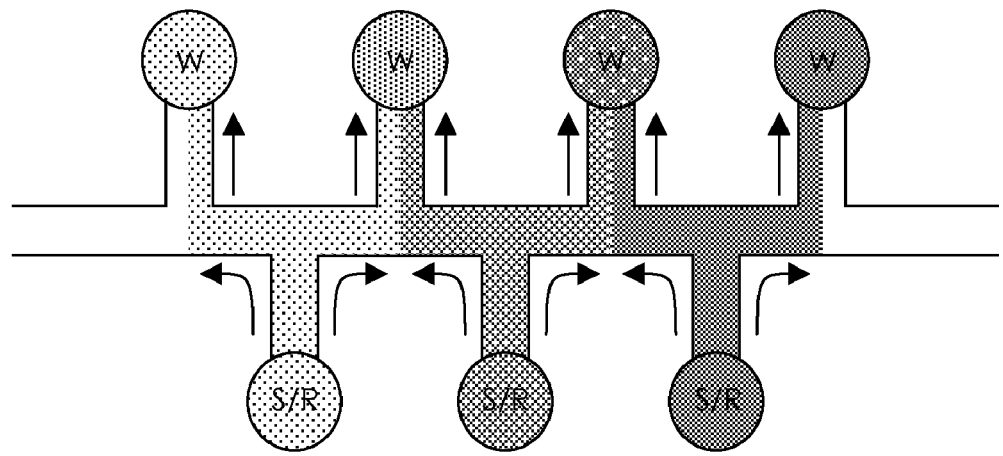
(a)
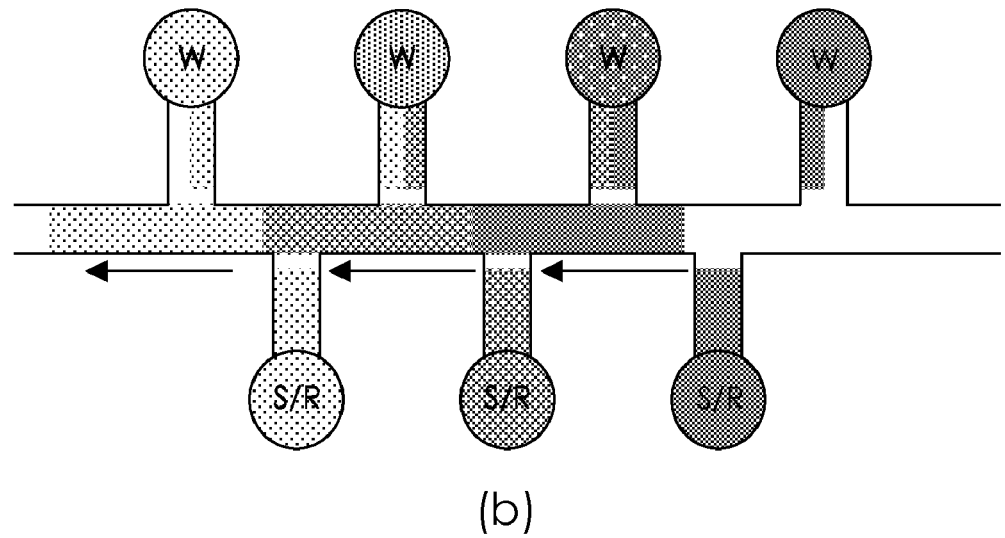
(b)

[Figure 11]
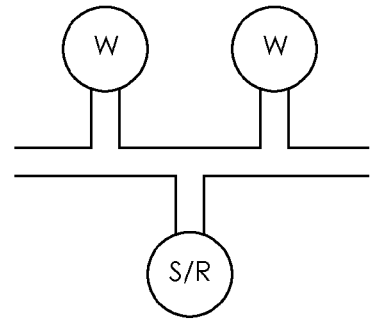
(a)
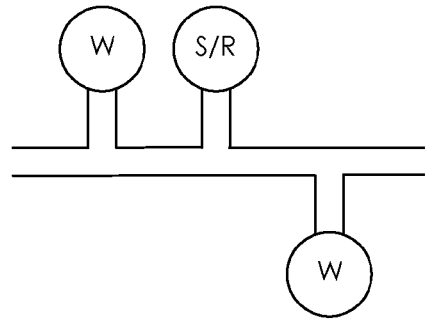
(b)
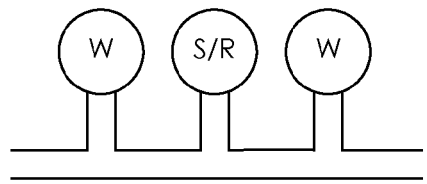
(c)
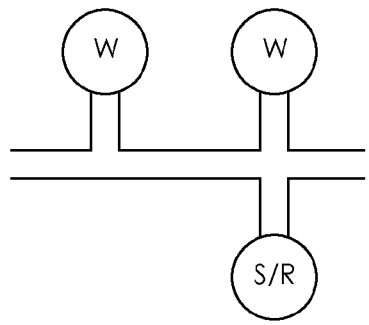
(d)
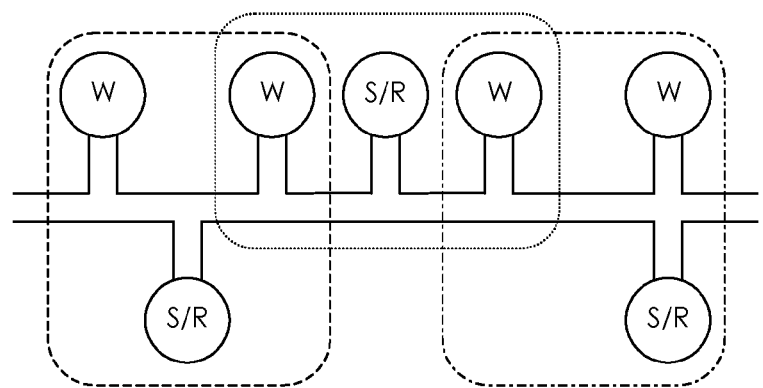
(e)

[Figure 12]
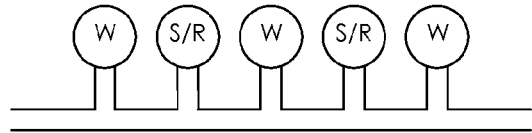
(a)
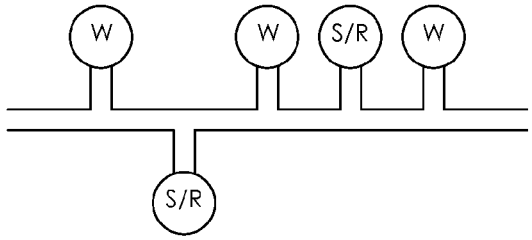
(b)
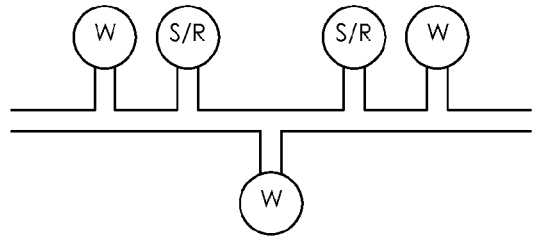
(c)
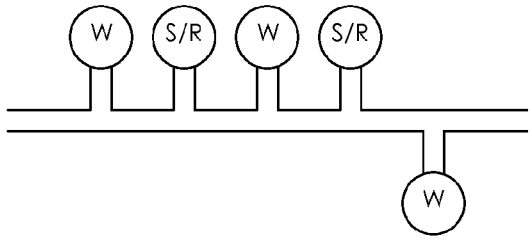
(d)
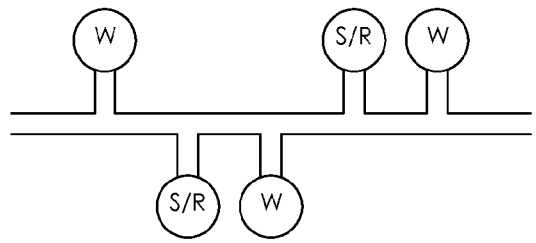
(e)
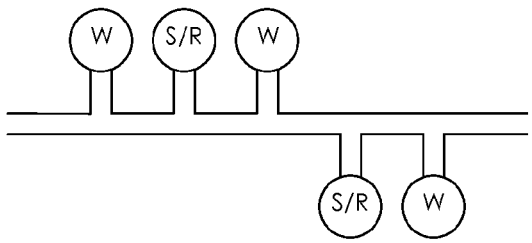
(f)
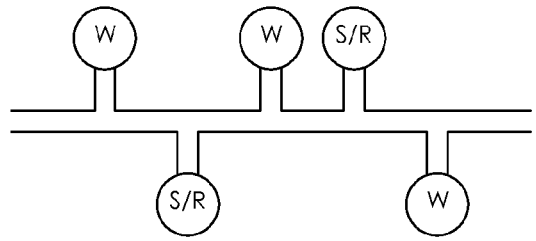
(g)
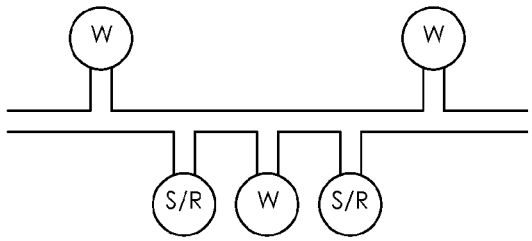
(h)

[Figure 12 (Cont.)]
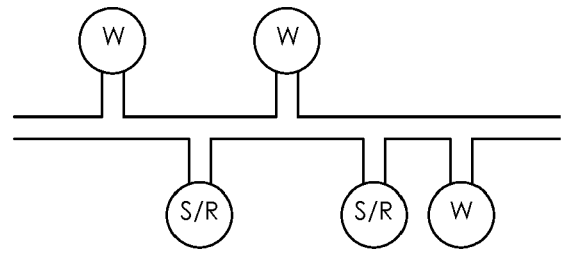
(i)
[Figure 13]
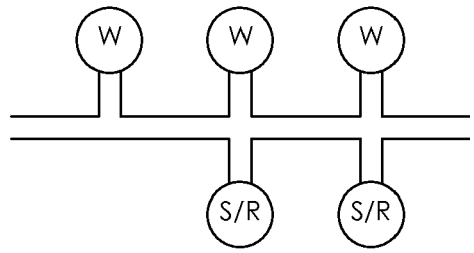
(a)
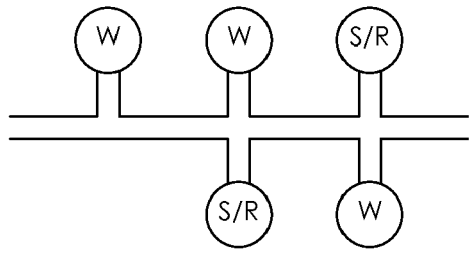
(b)
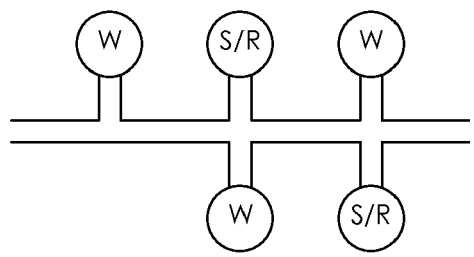
(c)
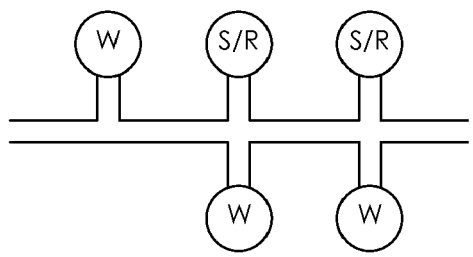
(d)

[Figure 14]
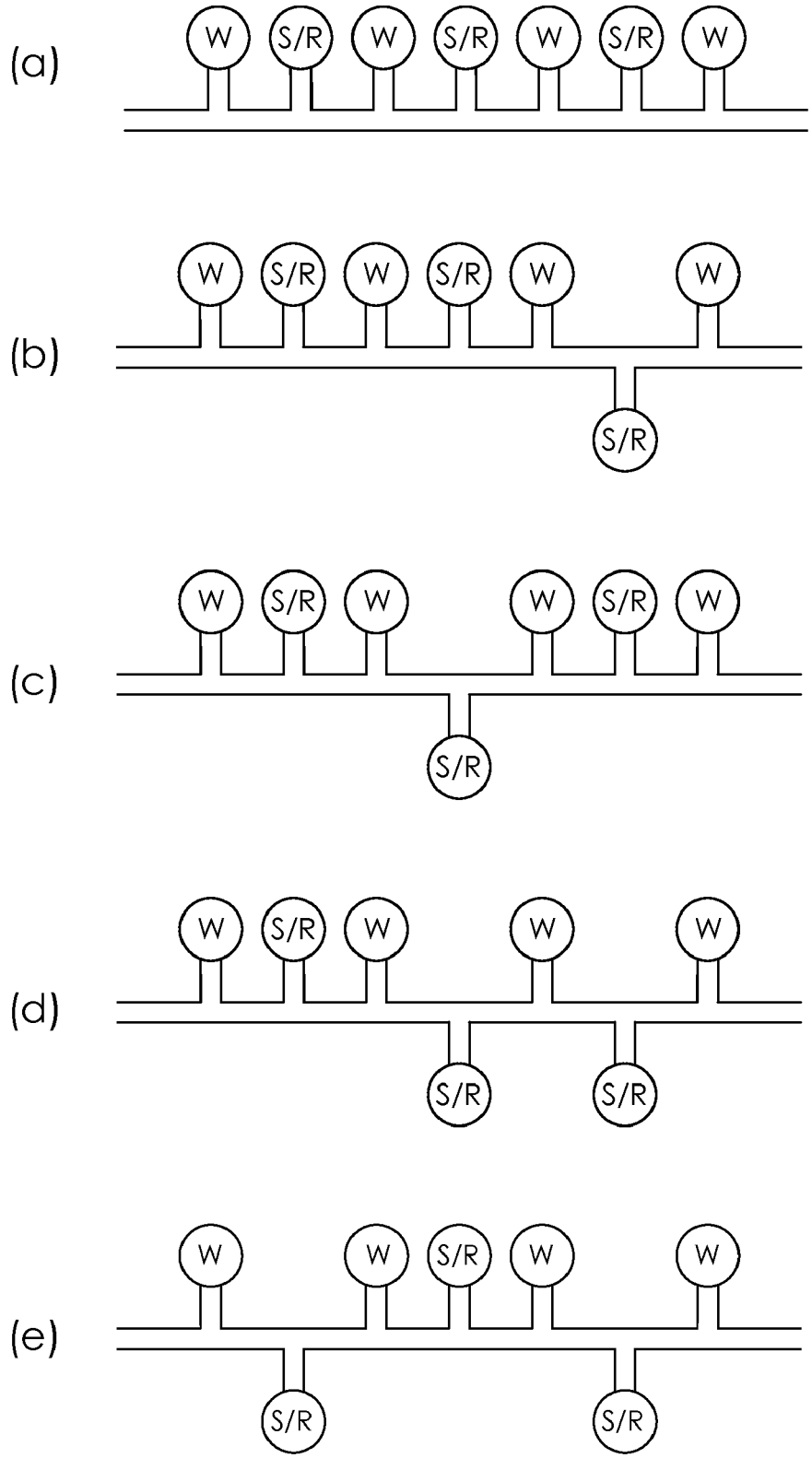

[Figure 14 (Cont.)]
(f) 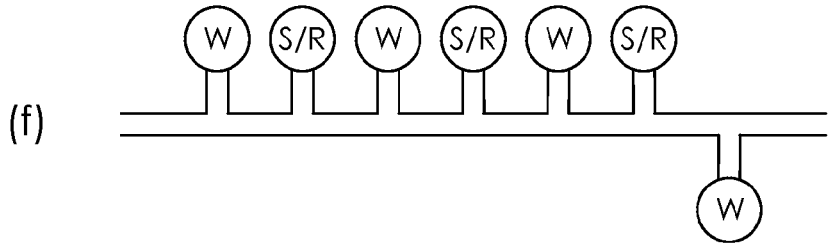
(g) 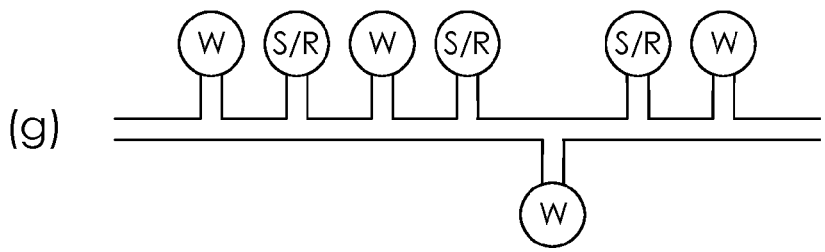
(h) 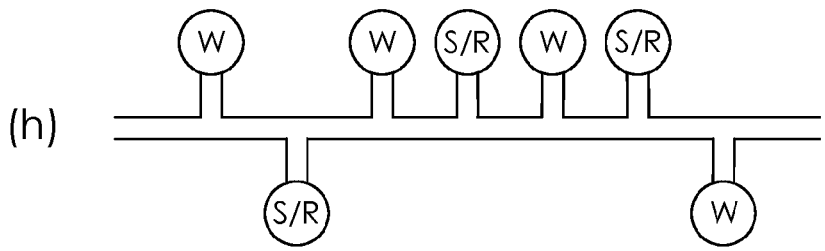
(i) 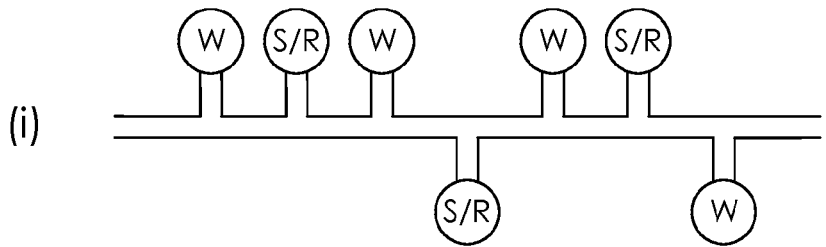
(j) 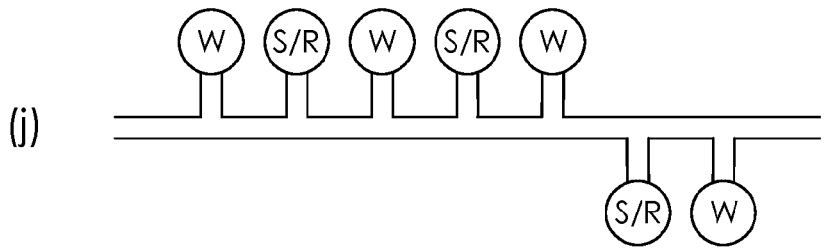

[Figure 14 (Cont.)]
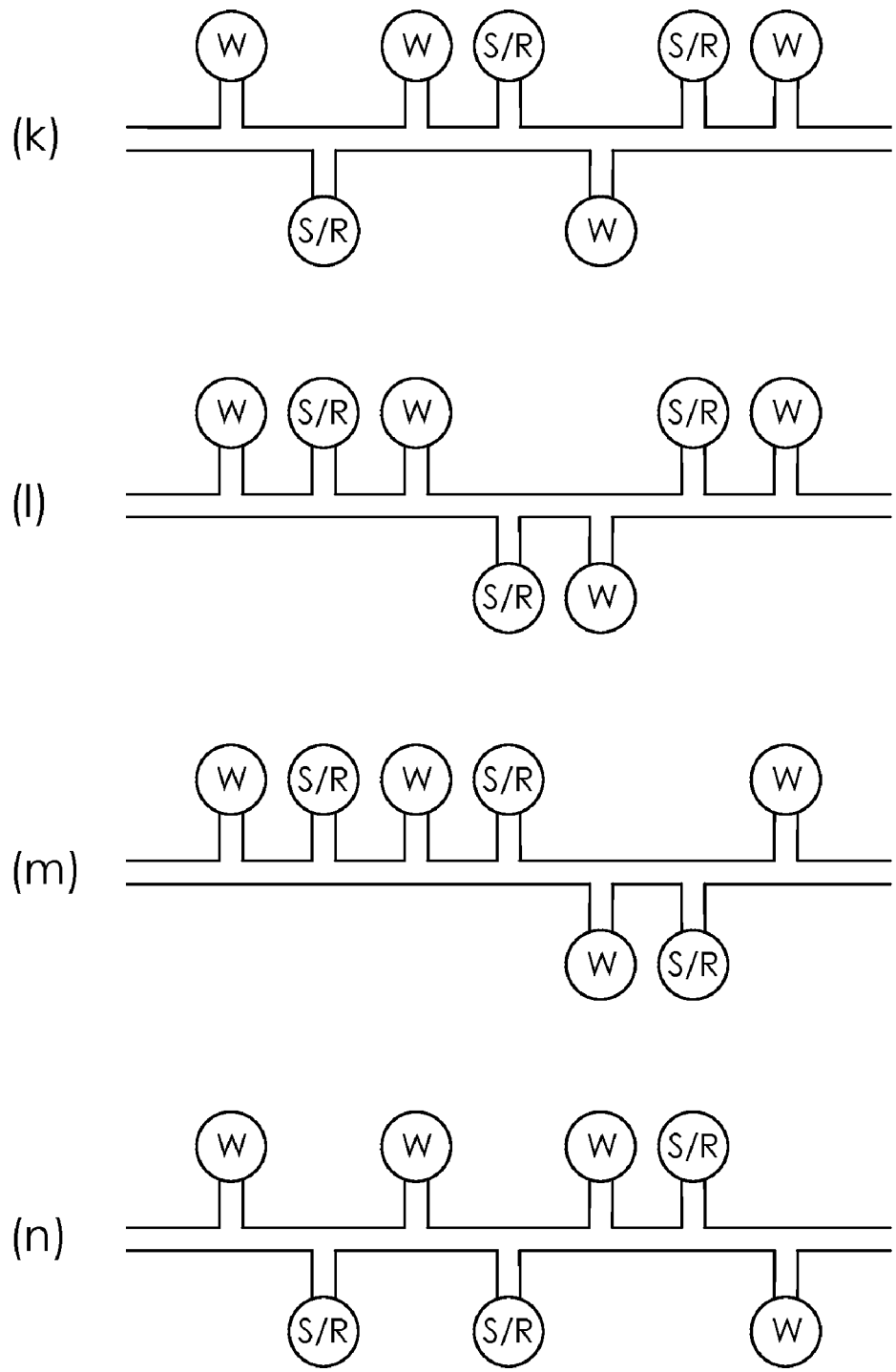

[Figure 14 (Cont.)]
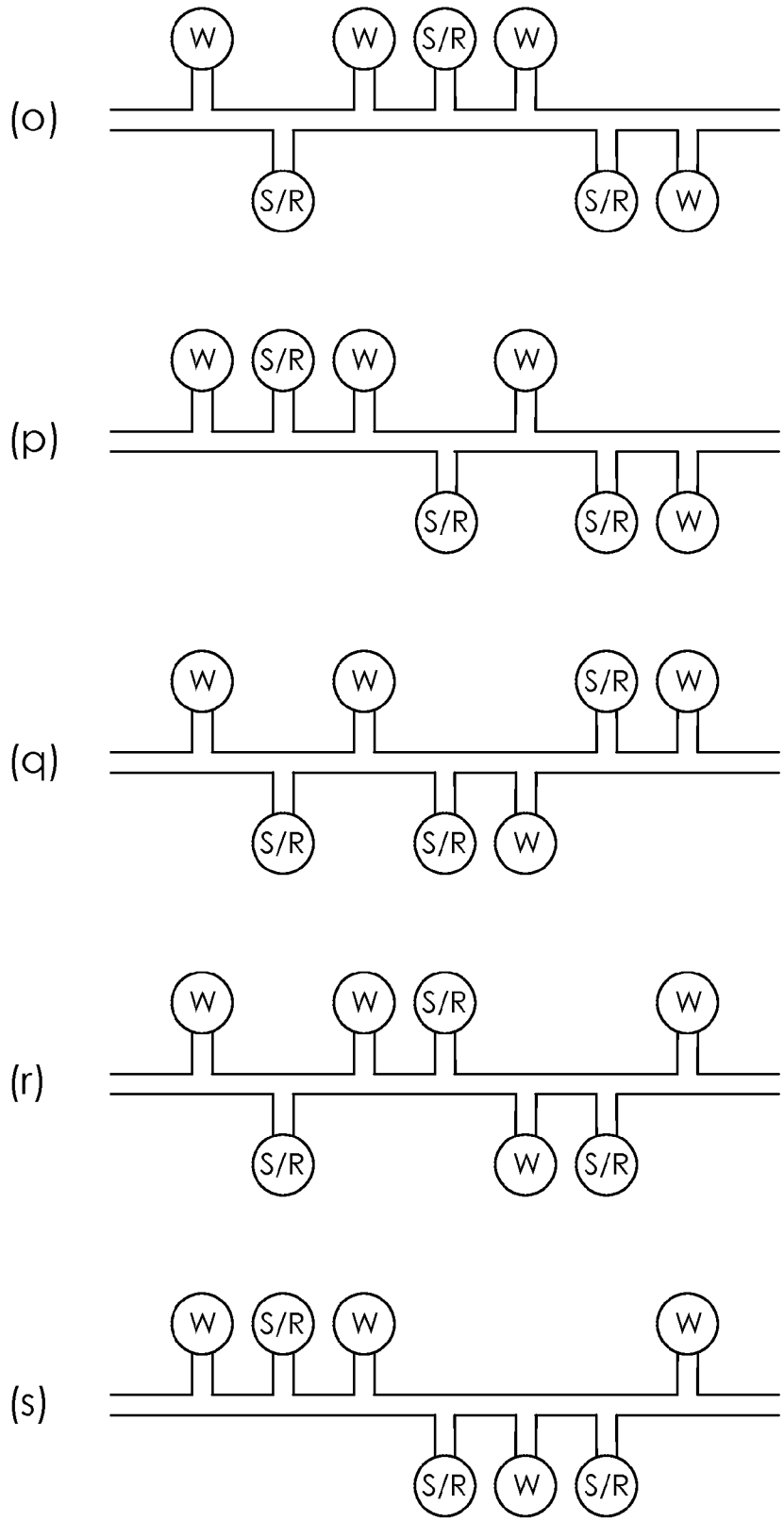

[Figure 14 (Cont.)]
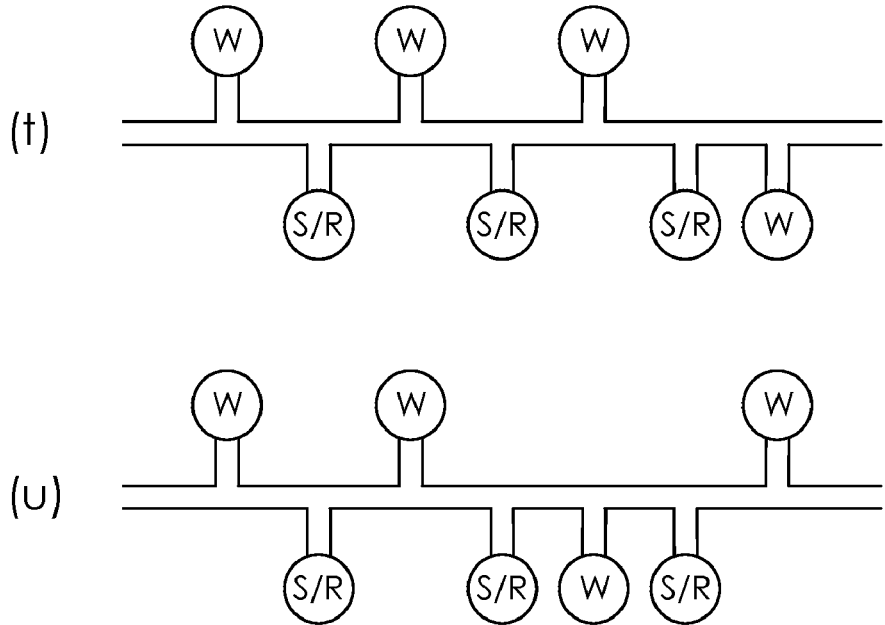
[Figure 15]
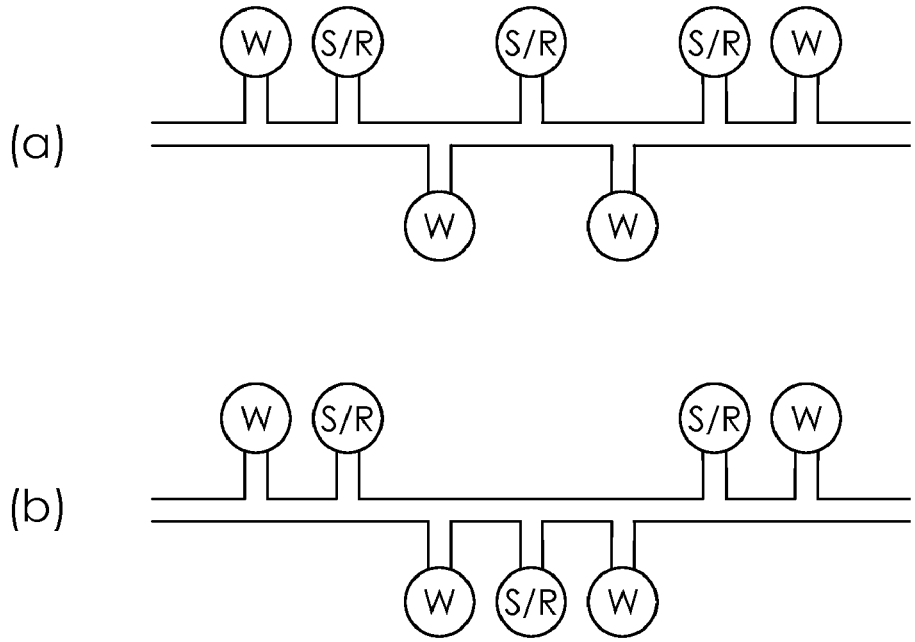

[Figure 15 (Cont.)]
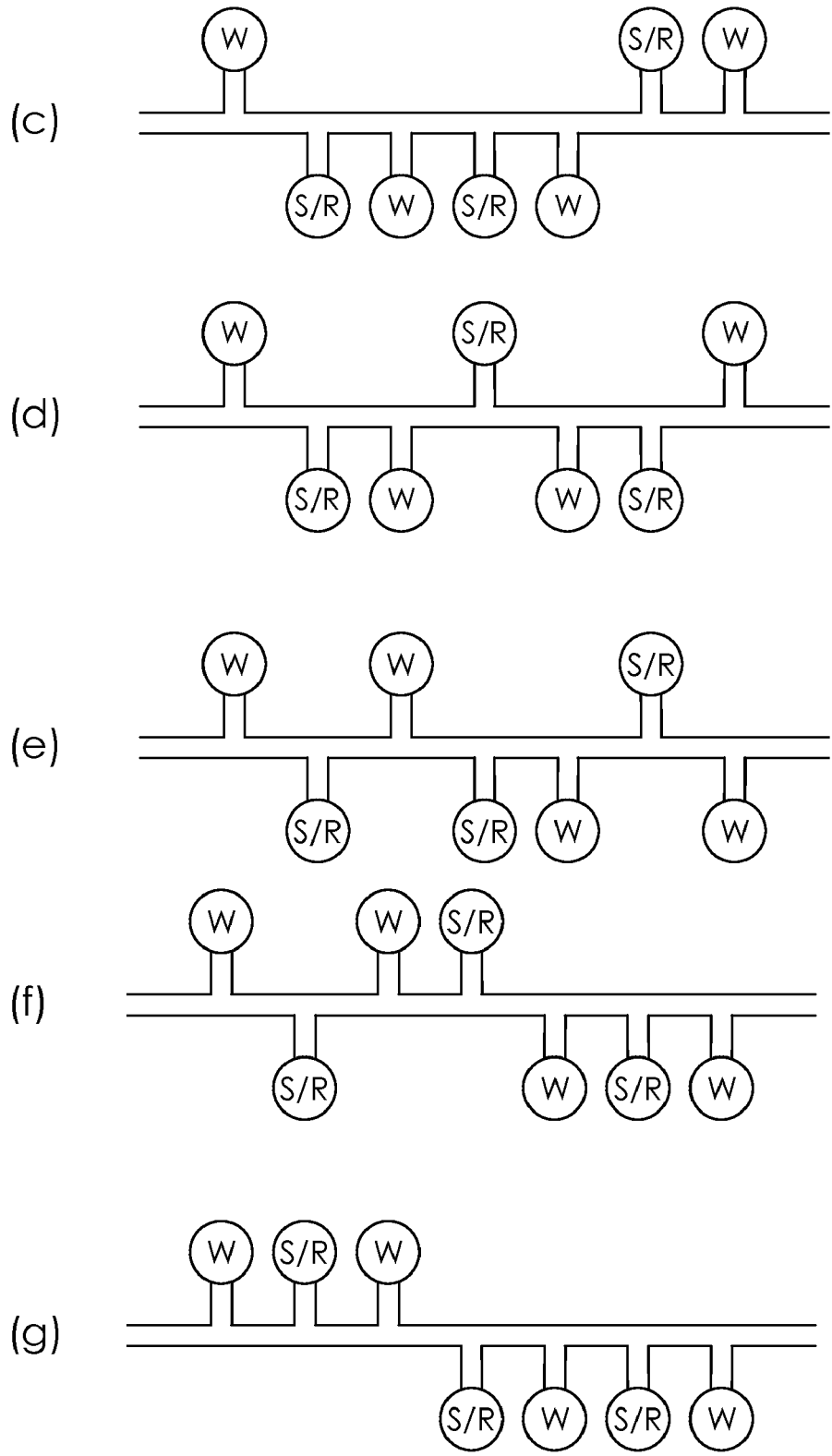

[Figure 15 (Cont.)]
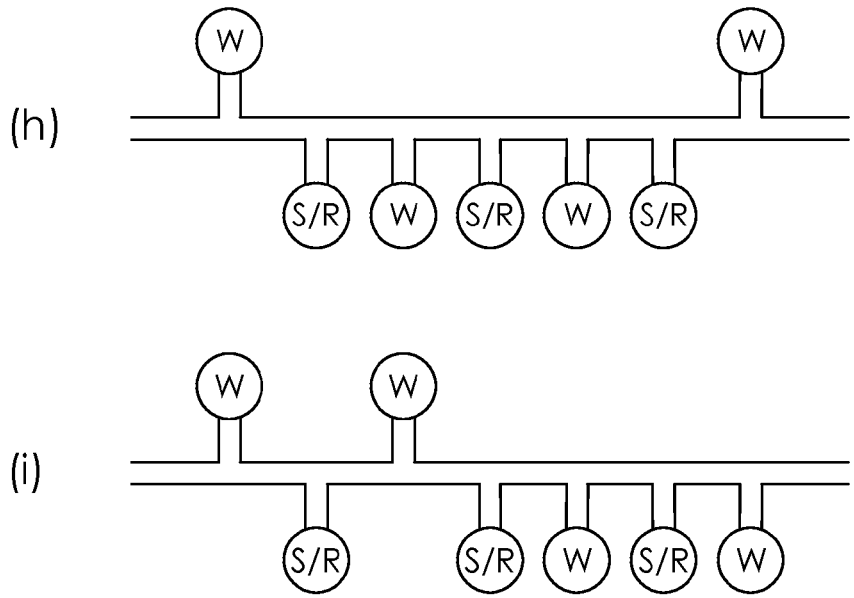
[Figure 16]
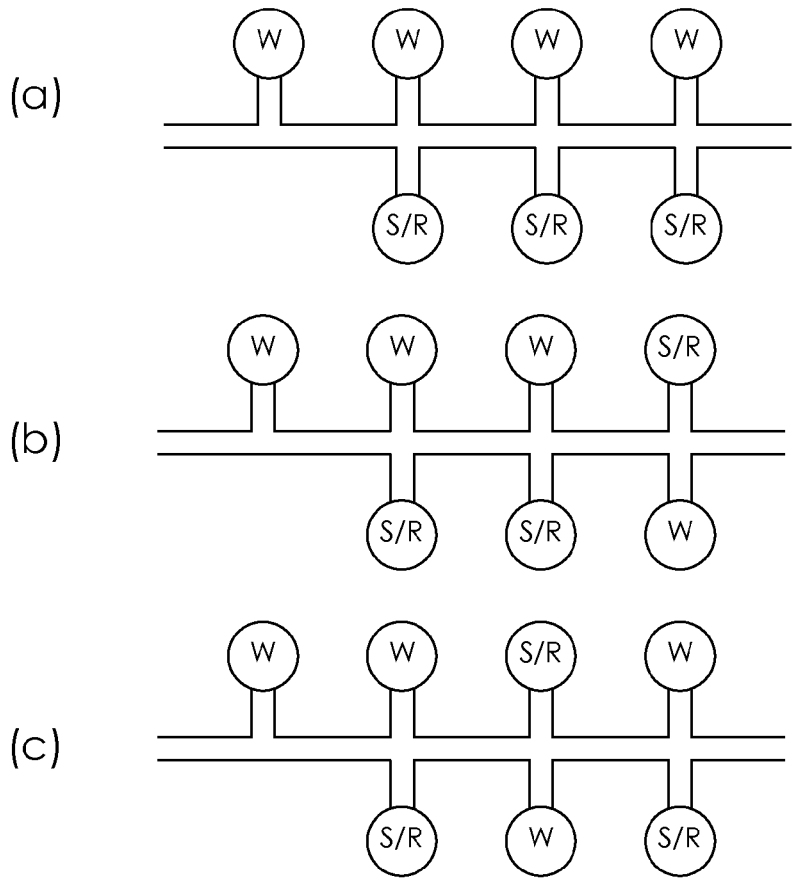

[Figure 16 (Cont.)]
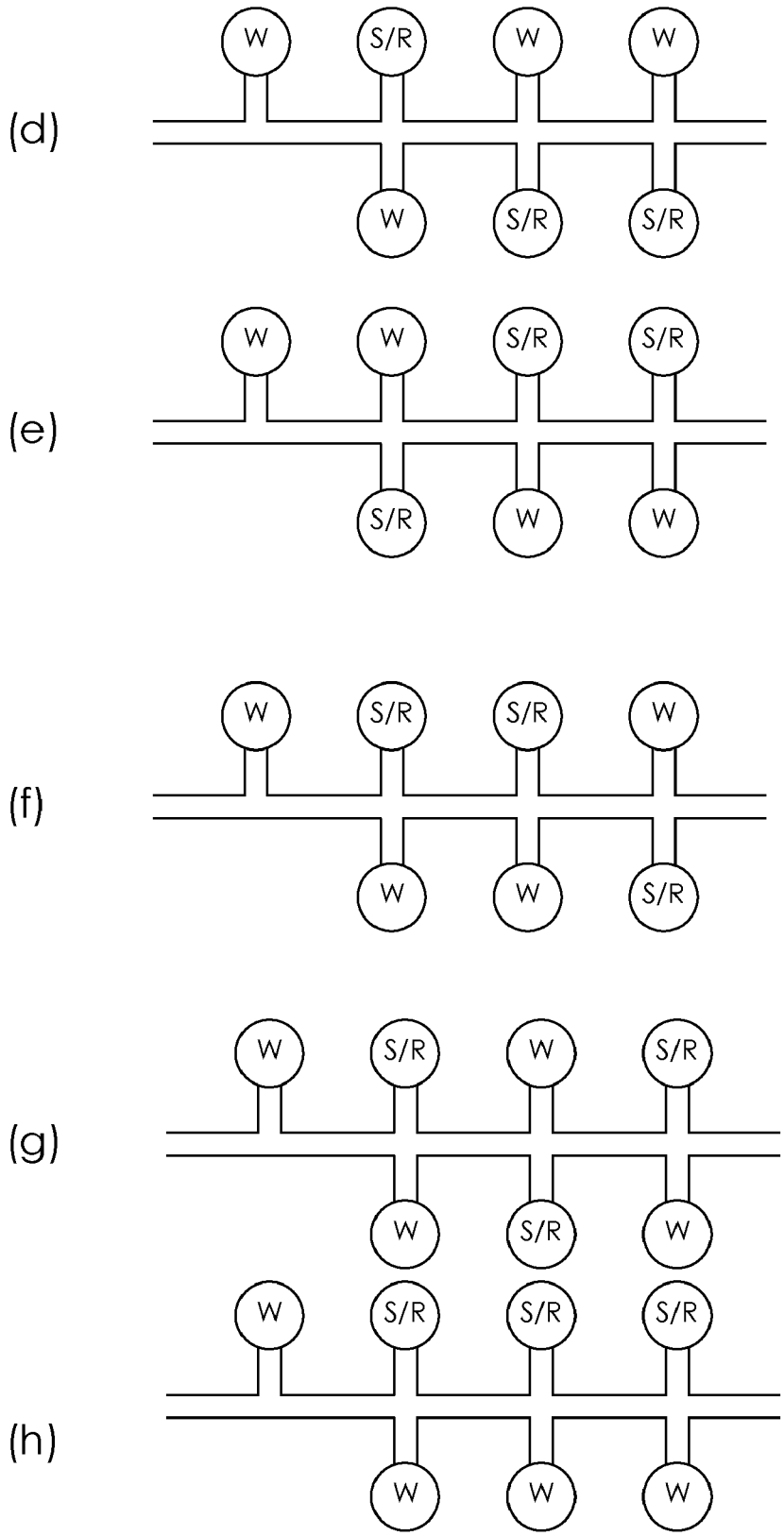

[Figure 17]
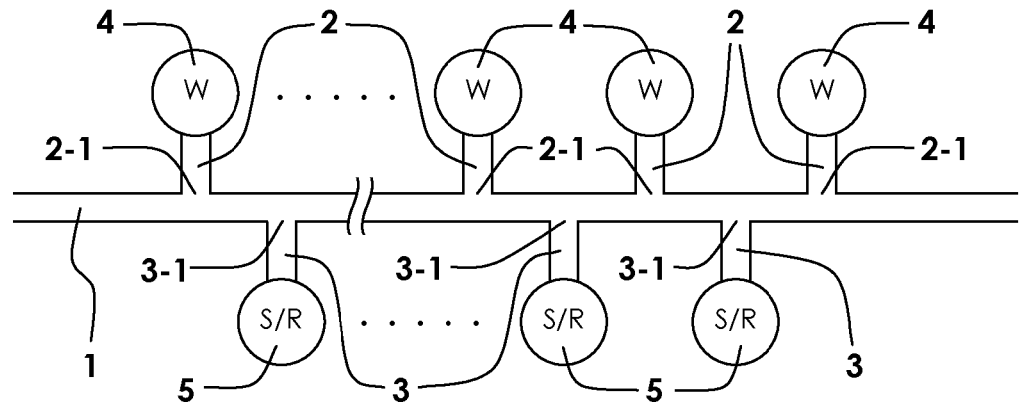
[Figure 18]
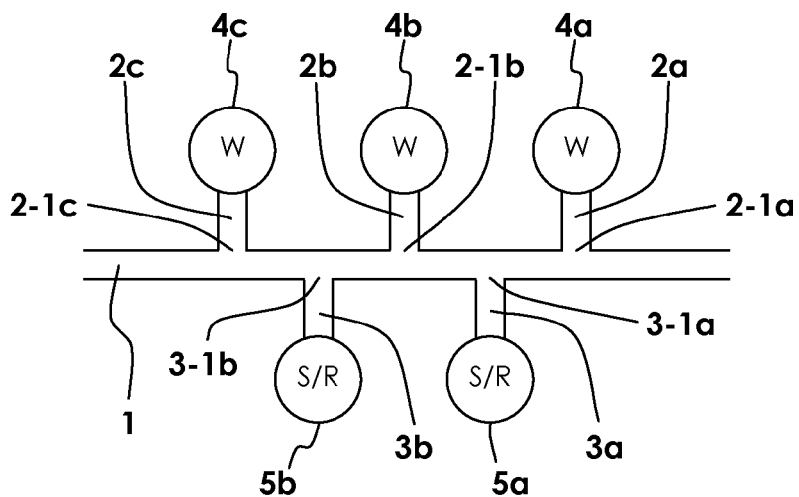
[Figure 19]
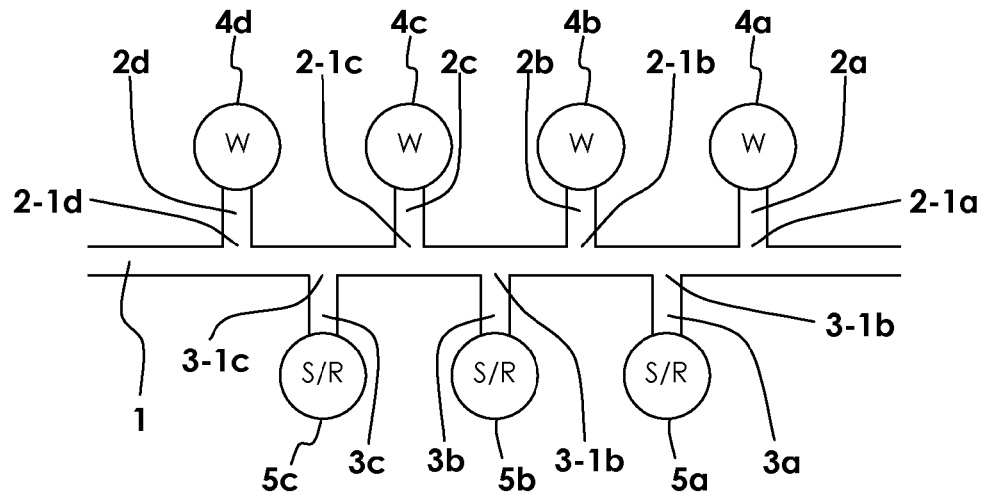

[Figure 20]
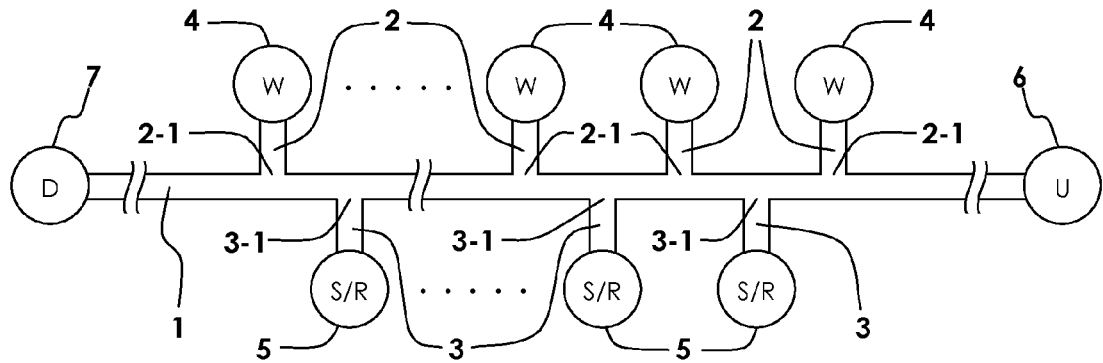
[Figure 21]
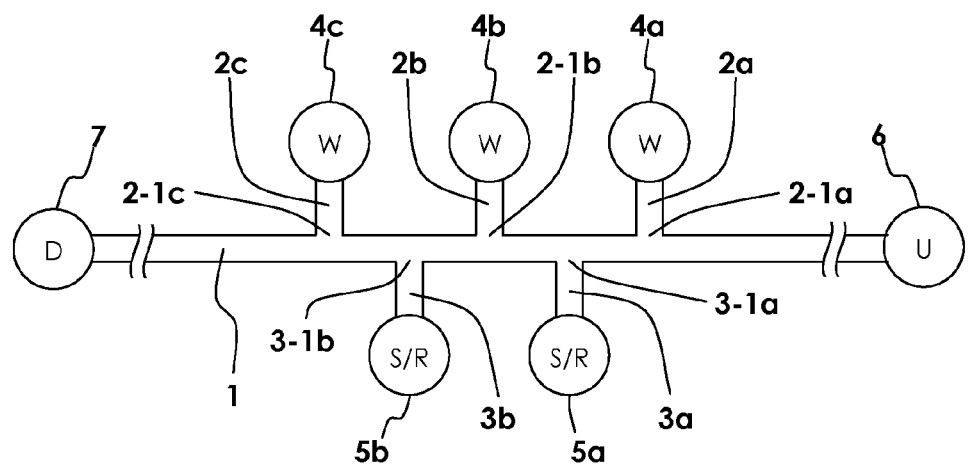
[Figure 22]
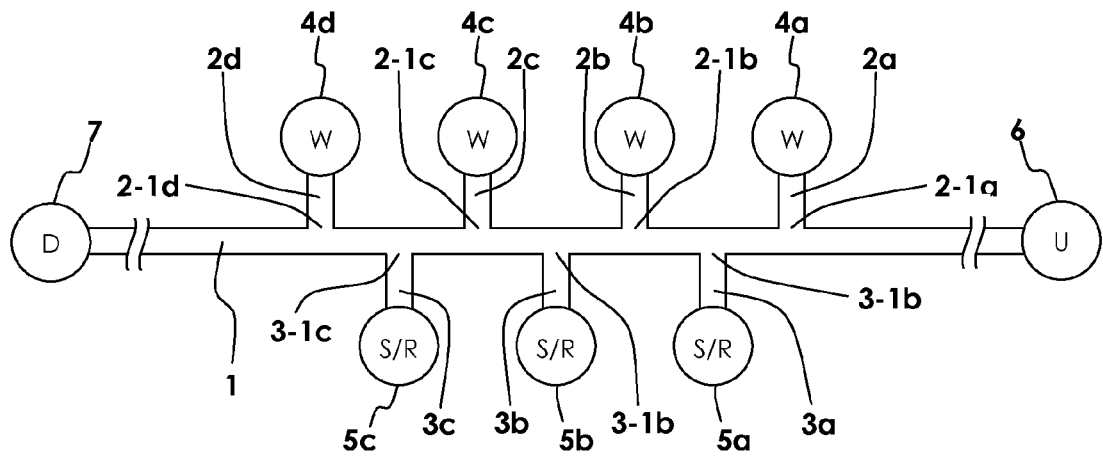

[Figure 23]
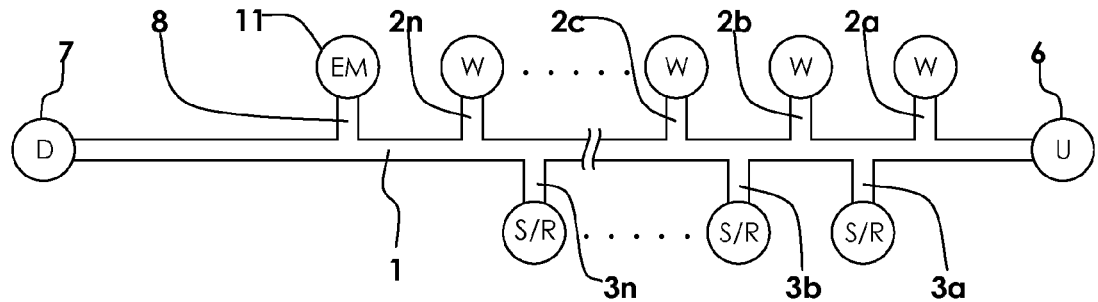
[Figure 24]
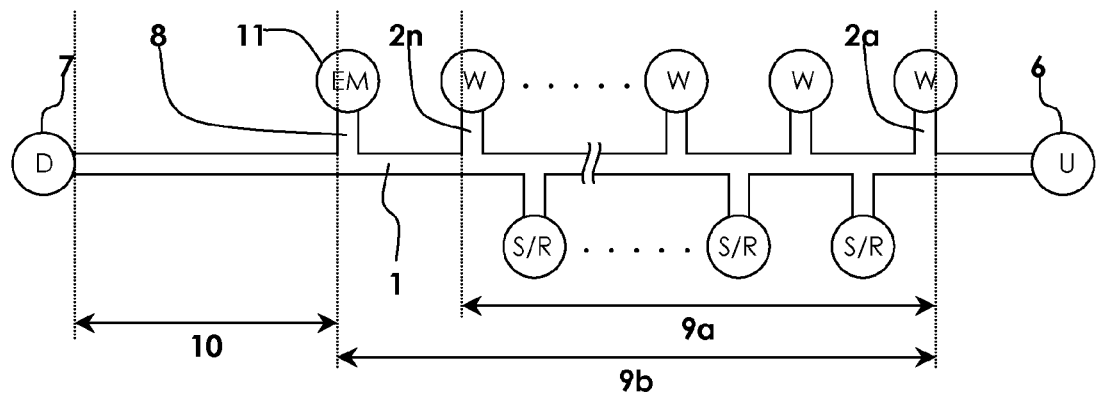
[Figure 25]
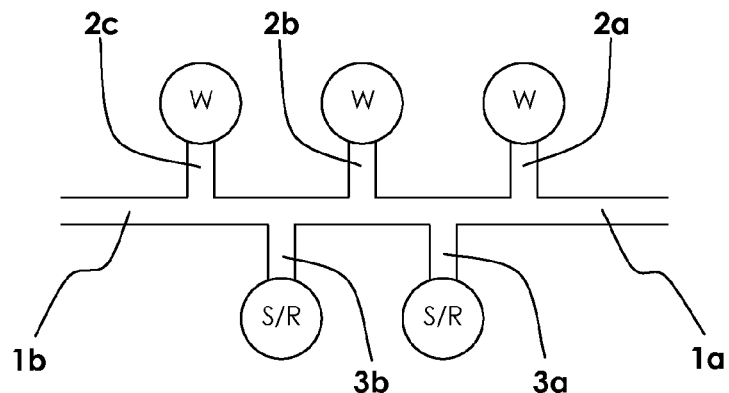

[Figure 26]
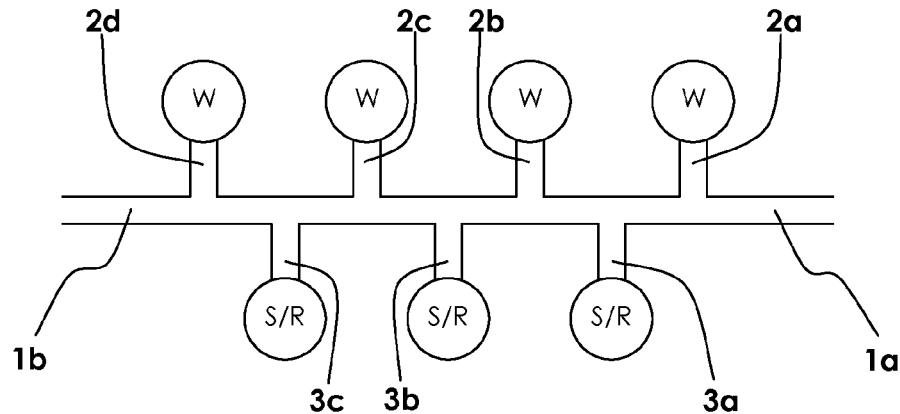
[Figure 27]
Purified terminal aminated DNA
←Sulfo-SMPB linker reaction
←Removal of un-reacted Linker by gel filtration
←Reaction with an anti-AFP antibody Fab' fragment
←Purification of DNA-antibody by a DEAE column
DNA-antibody
[Figure 28]
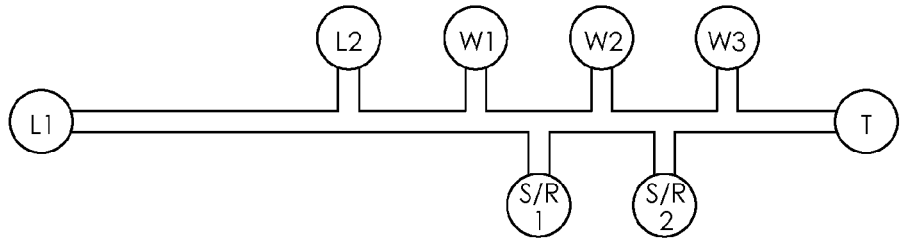
[Figure 29]
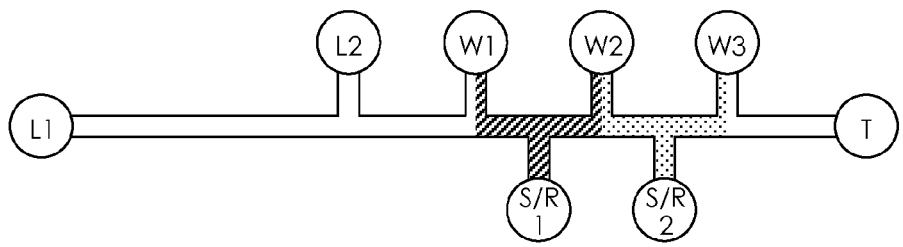

[Figure 30]
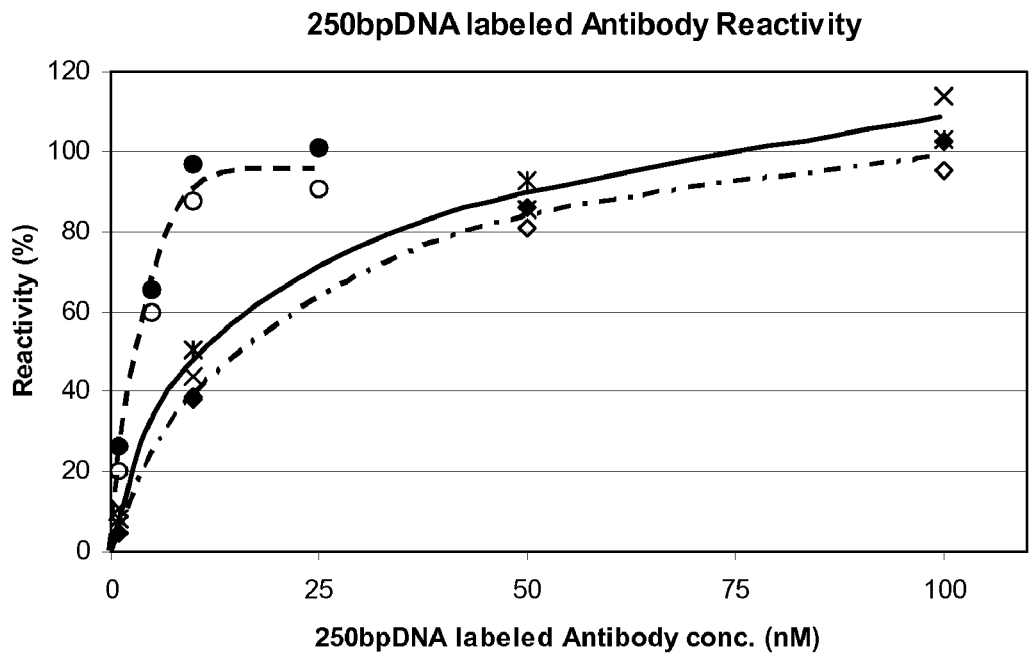
[Figure 31]
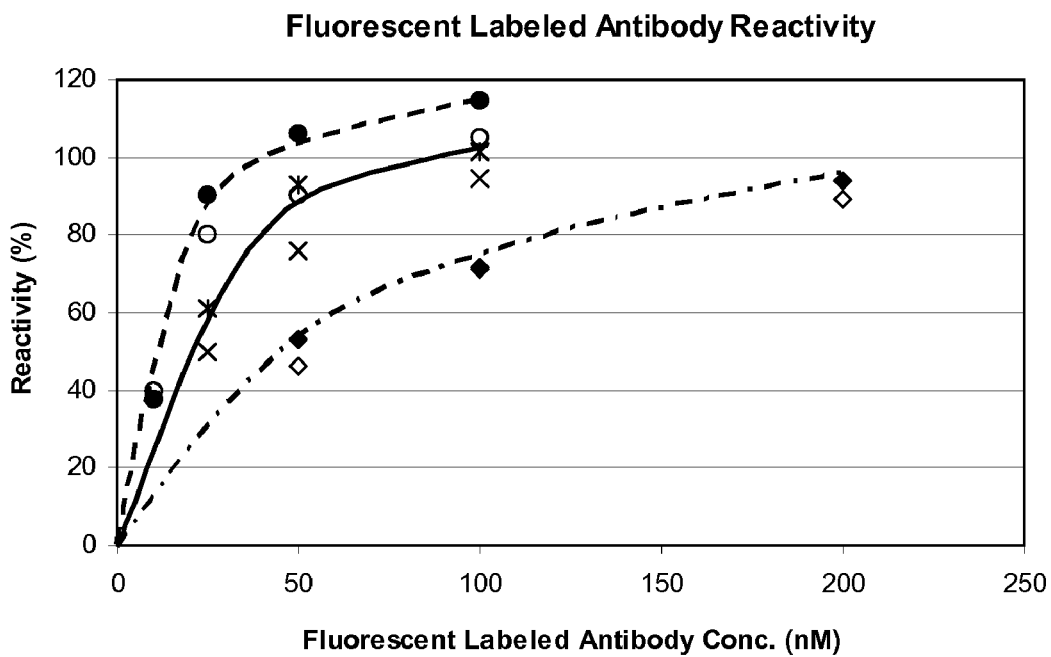

[Figure 32]
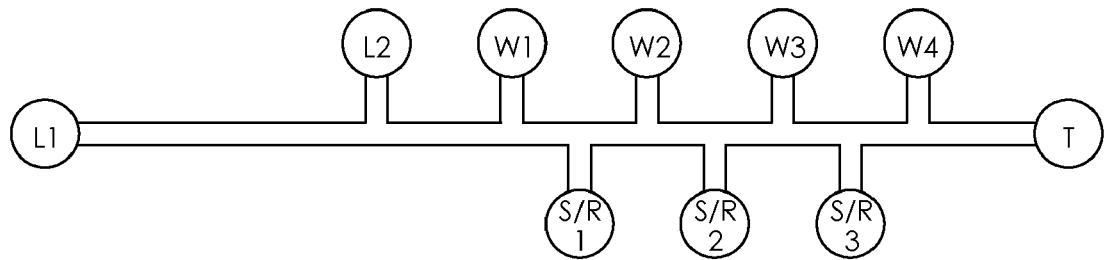
[Figure 33]
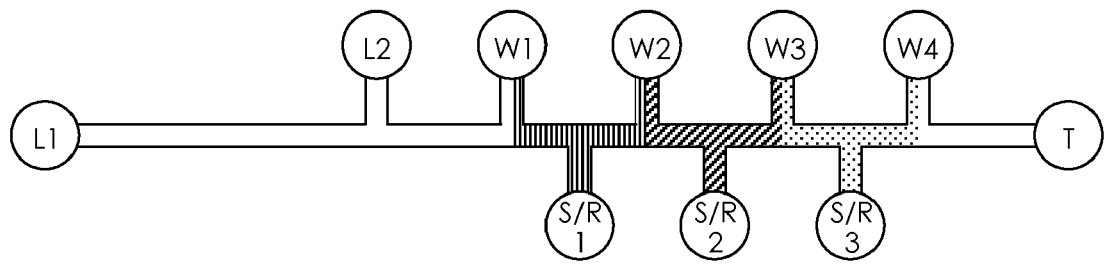

STRUCTURE FOR INTRODUCING A PLURALITY OF SOLUTIONS, MICRO FLUIDIC DEVICE HAVING SAID STRUCTURE AND METHOD FOR INTRODUCING SOLUTION

CROSS REFERENCE TO RELATED APPLICATIONS

This application is a Divisional of U.S. application Ser. No. 12/226,017, which is the US National Stage application of PCT/US2007/066461, filed Apr. 11, 2007, which claims priority to U.S. Provisional Application No. 60/792,172, filed Apr. 14, 2006, the disclosure of which is incorporated herein by reference.

BACKGROUND OF THE INVENTION

1. Technical Field

The present invention relates to a structure for introducing a plurality of solutions (a sample and/or a reagent solution) into a channel, in particular a channel of micro fluidic device, a micro fluidic device having said structure, a method for introducing a solution using said device, a method for separation of a substance and a method for measurement of a substance.

2. Background Art

Analysis of an analyte in a sample usually requires mixing a plurality of solutions such as a sample and various reagent solutions (for example, a reagent solution including an antibody to an analyte, a reagent solution containing a labeling substance, and the like) etc., and subjecting an analyte in a sample and a reactant in a reagent solution (an antibody to an analyte or a labeling substance, and the like) to a reaction.

In "Micro Total Analysis System (μ-TAS)" using micro fluidics device, technology thereof has recently been developing and various researches thereon have been made, and as a method for introducing a plurality of solutions such as including an antibody for an analyte or a reagent solution containing a labeling substance, and the like) into a channel, for example, the following method for using micro fluidics device having various structures has been known.

For example, there is a method for making a plurality of solutions presence in a main channel, by using a micro fluidic device (FIG. 1(a)) with a structure (a cross type structure) having a plurality of a side channel crossed a main channel for electrophoresis, wherein one end of said side channel is connected with a solution reservoir and the other end is connected with a waste reservoir, and by making a solution presence in a main channel by transferring the solution fed to a single solution reservoir into a single waste reservoir, and by carrying out this operation on a plurality of different combination of a solution reservoir (FIG. 1(b)) and a waste reservoir for a plurality of different solutions (FIG. 1(c)).

In addition, there is a method for making 2 solutions present in a main channel, by using a micro fluidic device (FIG. 2(a)) with a structure (a double T-form structure) having 2 side channels for introducing a solution communicated to a main channel for electrophoresis and one side channel for drain communicated to a main channel between said 2 side channels, wherein the end of said side channel for introducing a solution is connected with a solution reservoir and the end of said channel for drain is connected with a waste reservoir, as is shown in JP-A-2003-534532 (Patent Literature 1), and by transferring each different solutions fed to 2 solution reservoirs into one waste reservoir (FIG. 2(b)).

However, in the former method, because the volume of a solution introduced in a main channel is limited to the volume of a crossed part between a main channel and a side channel (FIG. 1(c)), much amount of a solution cannot be introduced in a main channel. In the latter method, although much amount of a solution can be introduced in a main channel, introducing only an objective solution into a main channel is difficult in the case when using pressure difference in (pressure control for) introducing a solution into a main channel because a solution (for example, a buffer for electrophoresis, and the like) other than an objective solution flows into the objective solution from the main channel (a white part shown by arrow mark in FIG. 2(b)). As a result, there is a problem that it is difficult to introduce an objective solution into a main channel by highly accurate volume. In addition, when a solution is introduced into a main channel electrically by applying electric field from a solution reservoir to a waste reservoir, only a substance (solution) having a charge can be introduced into a main channel. Furthermore, there is a problem that the introduction time must be severely set to a certain degree depending on kind (difference in mobility) of a charged substance (solution) because introduction time varies depending on difference in mobility of a charged substance (solution), or a problem that electrophoresis mobility is varied as a result of variation of electrophoresis mobility condition such as buffer property (pH) because of electrolysis generating in a solution by application of electric field.

Patent Literature 1: JP-A-2003-534532

BRIEF DESCRIPTION OF THE DRAWINGS

FIG. 1 is a conceptual diagram of a solution introducing structure in the conventional micro fluidic device.

FIG. 2 is a conceptual diagram of other solution introducing structure in the conventional micro fluidic device.

FIG. 3 is a conceptual diagram of a solution introducing structure of the present invention.

FIG. 4 is a conceptual diagram showing relative position between not less than 2 side channels for introducing a sample or a reagent solution and not less than 3 side channels for drain in a solution introducing structure of the present invention.

FIG. 5 is a conceptual diagram showing combination examples of 2 (a pair of) side channels for drain and one side channel for introducing a sample or a reagent solution in a solution introducing structure of the present invention.

FIG. 6 is a conceptual diagram showing an introducing state of a sample or a reagent solution from a side channel for introducing a sample or a reagent solution to a first channel in the present invention.

FIG. 7 is a conceptual diagram of a solution introducing structure in the case of introducing 2 kinds of solutions in the present invention.

FIG. 8 is a conceptual diagram showing an introducing state of a sample or a reagent solution from a side channel for introducing a sample or a reagent solution to a first channel in a solution introducing structure of the present invention for introducing 2 kinds of solutions.

FIG. 9 is a conceptual diagram of a solution introducing structure in the case of introducing 3 kinds of solutions in the present invention.

FIG. 10 is a conceptual diagram showing an introducing state of a sample or a reagent solution from a side channel for introducing a sample or a reagent solution to a first channel in a solution introducing structure of the present invention for introducing 3 kinds of solutions.

FIG. 11 is a conceptual diagram of a structure unit in a solution introducing structure of the present invention and a way to combine said structure unit.

FIG. 12 is a conceptual diagram of other solution introducing structure in the case of introducing 2 kinds of solutions in the present invention.

FIG. 13 is a conceptual diagram of different solution introducing structure in the case of introducing 2 kinds of solutions in the present invention.

FIG. 14 is a conceptual diagram of other solution introducing structure in the case of introducing 3 kinds of solutions in the present invention.

FIG. 15 is a conceptual diagram of different solution introducing structure in the case of introducing 3 kinds of solutions in the present invention.

FIG. 16 is a conceptual diagram of further different solution introducing structure in the case of introducing 3 kinds of solutions in the present invention.

FIG. 17 is a conceptual diagram of a solution introducing structure of the present invention having a reservoir connecting to a side channel.

FIG. 18 is a conceptual diagram of a solution introducing structure of the present invention having a reservoir connecting to a side channel used in the case of introducing 2 kinds of solutions.

FIG. 19 is a conceptual diagram of a solution introducing structure of the present invention having a reservoir connecting to a side channel used in the case of introducing 3 kinds of solutions.

FIG. 20 is a conceptual diagram of a solution introducing structure of the present invention having a reservoir connecting to a side, and a downstream reservoir and an upstream reservoir connecting to a first channel.

FIG. 21 is a conceptual diagram of a solution introducing structure of the present invention having a reservoir connecting to a side channel, and a downstream reservoir and an upstream reservoir connecting to a first channel used in the case of introducing 2 kinds of solutions.

FIG. 22 is a conceptual diagram of a solution introducing structure of the present invention having a reservoir connecting to a side channel, and a downstream reservoir and an upstream reservoir connecting to a first channel used in the case of introducing 3 kinds of solutions.

FIG. 23 is a conceptual diagram of a solution introducing structure and micro fluidic device of the present invention, having a side channel for introducing a electrophoresis medium.

FIG. 24 is a conceptual diagram showing a region for reacting or a region for concentrating and reacting of a first channel and a region for separating of a first channel in a solution introducing structure and micro fluidic device of the present invention, having a side channel for introducing a electrophoresis medium.

FIG. 25 is a conceptual diagram of a solution introducing structure and micro fluidic device of the present invention, used for explanation of a method for introducing 2 kinds of solutions into a first channel by increasing and/or decreasing pressure in the channel.

FIG. 26 is a conceptual diagram of a solution introducing structure and micro fluidic device of the present invention, used for explanation of a method for introducing 3 kinds of solutions into a first channel by increasing and/or decreasing pressure in the channel.

FIG. 27 shows a preparation scheme of a DNA labeled antibody [an anti-AFP antibody WA1 Fab' fragment bound with a 250 bp DNA fragment (a reaction improvement CFS)], prepared in Example 1.

FIG. 28 shows a layout of a capillary chip prepared in Example 1.

FIG. 29 shows an arrangement relation of an electrophoresis sample and a reagent solution introduced in a capillary in Example 1.

FIG. 30 shows relation between concentration of a 250 bp DNA labeled antibody and reaction efficiency in the case of formation of an immune complex of [a fluorescent labeled antibody-AFP-a 250 bp DNA labeled antibody] by introducing an electrophoresis sample 1 (a solution containing a [fluorescence labeled antibody-AFP] immune complex) from an S/R1 well and a reagent solution 1 (a solution containing a DNA labeled antibody) from an S/R2 well, and then subjecting these to a reaction, obtained in Example 1.

FIG. 31 shows relation between concentration of a fluorescence labeled antibody and reaction efficiency in the case of formation of an immune complex of [a fluorescent labeled antibody-AFP-a 250 bp DNA labeled antibody] by introducing a reagent solution 2 (a solution containing a fluorescence labeled antibody) from an S/R1 well and an electrophoresis sample 2 (a solution containing a [DNA labeled antibody-AFP] immune complex) from an S/R2 well, and then subjecting these to a reaction, obtained in Example 1.

FIG. 32 shows a layout of a capillary chip prepared in Example 2.

FIG. 33 shows an arrangement relation of an electrophoresis sample, a $1^{st}$ reagent solution and a $2^{nd}$ reagent solution introduced in a capillary in Example 2.

DISCLOSURE OF THE INVENTION

Problems to be Solved by the Invention

The present invention relates to a structure (a solution introducing structure) for introducing a plurality of solutions (a sample and/or a reagent solution) in highly accurate volume, in high amount and simply, into a channel, in particular a channel of a micro fluidic device, a micro fluidic device having said structure, a method for introducing a solution using said device, a method for separation of a substance, and a method for separating a complex between an analyte or analogue thereof, and a substance binding to said analyte or analogue thereof (hereinafter may be abbreviated as a complex forming substance or CFS) which is obtained by reacting a plurality of solutions introduced by these, and said CFS or analogue not involved in formation of said complex, rapidly, simply and in high accuracy, along with a method for measuring an analyte or an analogue thereof in a sample in high sensitivity.

Means for Solving Problems

The present invention is composed of the following framework:

1. A structure for introducing a sample or a reagent solution to a first channel (1), which comprises:
   (i) the first channel (1);
   (ii) not less than 3 side channels (2) for drain, each said side channel (2) for drain having a opening (2-1) opened on a wall of said first channel (1), and said openings (2-1) arranged in spaced relation to one another; and
   (iii) not less than 2 side channels (3) for introducing a sample or a reagent solution, each said side channel (3) for introducing a sample or a reagent solution having a opening (3-1) opened on the wall of said first channel (1) at the different position (part) from said openings (2-1) of said side channels (2) for drain, and each said opening (3-1) arranged between adjacent 2 openings (2-1) of side channels (2) for drain, wherein each said opening (3-1) of these not less than 2 side channels (3) for introducing a sample or a reagent solution are each arranged at the different portion between adjacent 2 openings (2-1) of side channels (2) for drain.

2. A micro fluidic device comprising at least one structure according to the above 1 in a substrate.

3. A method for introducing not less than 2 kinds of samples and/or reagent solutions to a channel of a micro fluidic device comprising using the micro fluidic device according to the above 2.

4. A method for separating a complex between an analyte or an analogue thereof in a sample, and a substance (CFS) binding to said analyte or analogue thereof comprising using the micro fluidic device according to the above 2.

5. A method for measuring an analyte or an analogue thereof in a sample comprising using the micro fluidic device according to the above 2

6. A kit for measuring an analyte or an analogue thereof in a sample comprising: (i) the micro fluidic device according to the above 2; and (ii) a reagent solutions containing a substance (CFS) binding to an analyte or an analogue thereof in a sample.

Namely, the present inventors have found that a plurality of solutions (a sample and/or a reagent solution) can be introduced into a channel, in particular a channel of a micro fluidic device, in highly accurate volume, in high amount and simply using a solution introducing structure as that of the present invention, and thus completed the present invention.

Effect of the Invention

In accordance with a method of the present invention, a plurality of solutions (a sample and/or a reagent solution) for example, those having different viscosity each other, can be introduced into a channel, in particular a channel of a micro fluidic device, in highly accurate volume, in high amount and simply. In addition, by quantitatively forming a zone composed of a plurality of solutions in a channel and subjecting a electrophoretically concentration, a reaction between an analyte or an analogue thereof in a sample, and a substance binding to said analyte or analogue thereof (a CFS) can be carried out in a short time and in high reaction efficiency, and a complex between said analyte or analogue thereof, and CFS can be separated from a CFS not involved in formation of said complex or analogue not involved in formation of said complex rapidly, simply and in high accuracy, and furthermore high sensitivity measurement of an analyte or an analogue thereof in a sample becomes possible, based on the amount of a separated complex or the amount of a separated CFS not involved in formation of said complex or the amount of a separated analogue not involved in formation of said complex.

BEST MODES FOR CARRYING OUT THE INVENTION

1. A Solution Introducing Structure of the Present Invention

Embodiments of a solution introducing structure of the present invention are explained based on drawings.

FIG. 3 is a conceptual diagram of a solution introducing structure of the present invention. Each 3 or more side channels (2) for drain has an opening (2-1) opened on a wall of the first channel (1) so as to be communicatable and said openings (2-1) are arranged in spaced relation to one another (with space) in an axis direction (from right to left in FIG. 3) of the first channel (1). In addition, each not less than 2 side channels (3) for introducing a sample or a reagent solution has an opening (3-1) opened on the wall of the above-described first channel (1) at the different position (part) from the opening (2-1) of the side channels (2) for drain, and each said openings (3-1) is arranged between adjacent 2 openings (2-1) of side channels (2) for drain (provided that each openings (3-1) of these not less than 2 side channels (3) for introducing a sample or a reagent solution are each arranged at the different portion between different adjacent openings (2-1) of side channels (2) for drain.

Hereinafter, the side channel for drain may be abbreviated as a "D side channel", and the side channel for introducing a sample or a reagent solution may be abbreviated as a "S/R side channel".

In the above description, "opening (3-1) opened on the wall of the first channel (1) at the different position (part) from the opening (2-1) of the side channels (2) for drain" means "opening (2-1) of the side channel (2) for drain and opening (3-1) of the side channel (3) for introducing a sample or a reagent solution are not the same, namely, one opening does not double as the opening of the side channel for drain and the opening of the side channel for introducing a sample and a reagent solution".

In addition, "each said openings (3-1) of not less than 2 side channels (3) for introducing a sample or a reagent solution is arranged between adjacent 2 openings (2-1) of side channels (2) for drain" means, as shown in FIG. 4, "only one opening (3-1) of one S/R side channel (3) among not less than 2 S/R side channels (3) is opened so as to be communicated on a wall of the part (a in FIG. 4) of the first channel (1) formed (sandwiched) by 2 (a pair of) openings (2-1) of D side channels (2)". Namely, the openings (3-1) of these 2 or more S/R side channels (3) are each arranged a different part (a) of the first channel (1) formed (sandwiched) by a different pair of the adjacent 2 openings (2-1) of D side channels (2), and the openings (3-1) of these 2 or more S/R side channels (3) are not arranged at the same part (a) of the first channel (1) formed (sandwiched) by the same pair of the adjacent 2 openings (2-1) of D side channels (2). The openings (3-1) of the S/R side channels (3), as shown in FIG. 5(*a*) or FIG. 5(*b*), may be arranged (opened) at inward part (a) of the first channel (1) in an axis direction of 2 (a pair of) openings (2-1) of D side channels (2). In addition, the openings (3-1) of the S/R side channels (3) may be arranged (opened), as shown in FIG. 5(*c*), just on the axis direction of any one opening (2-1) of the 2 (the pair of) openings (2-1) of D side channels (2), in other words, it may be opened on the first channel (1) part (a) at a coaxial part of either of the openings (2-1). Among others, the openings (3-1) of the S/R side channels (3) preferably be arranged at inward part (a) of the first channel (1) in an axis direction of 2 (a pair of) the openings (2-1) of the D side channels (2). As the case that the openings (3-1) of the S/R side channels (3) are arranged (opened) at inward part (a) of the first channel (1) in an axis direction of the 2 (the pair of) openings (2-1) of the D side channels (2), any of the following cases may be allowed: As shown in FIG. 5(*a*), the openings (3-1) of the S/R side channels (3) are arranged at nearly the center of the part (a) of the first channel (1) in an axis direction of the 2 (a pair of) openings (2-1) of the D side channels (2); or as shown in FIG. 5(*b*), at the part (a) nearer to either of the 2 (a pair of) openings (2-1) of the D side channels (2).

In this connection, in the present invention, "in an axis direction of the first channel" and "an axis direction" means "in a longer side direction of the first channel, in other words, in an electrophoresis direction (from upstream to downstream, or from downstream to upstream)", which means a right-left or left-right direction in drawing of the present invention.

(1) The First Channel

In the present invention, "the first channel" means "a channel (capillary) used in the field of micro fluidics", and preferably a channel (capillary) used in so-called "an electrokinetic material transport systems", wherein a substance is transported (guided) to cause the migration (movement) of a substance by application of the electric field onto a substance, in particular a channel (capillary) used in "an electrophoretic material transport system" using electrophoresis. Specifically, for example, a channel (capillary) is any one used in electrophoresis such as a capillary electrophoresis method, a capillary chip electrophoresis method, and the like. The first channel may be any one as long as it can be used in such objective. Usually, it is a main channel for carrying out electrophoresis analysis. Because various solutions such as a sample and a reagent solution are introduced into said first channel and analyzed through said first channel, the first channel preferably be one comprising at least a region where a sample react with a reagent solution, and more preferably be one comprising at least a region where at least one kind of a CFS react with an analyte or an analogue thereof in a sample while concentrating said analyte or said analogue thereof in the sample and/or at least one kind of the CFS in the reagent solution. In addition, it may further comprising a region where a complex between said analyte or said analogue thereof, and a CFS is separated from said CFS not involved in the formation of said complex, or said analogue not involved in the formation of said complex.

In the present invention, a direction toward which a complex between an analyte or an analogue thereof, and not less than one kind of CFSs, finally formed and measured, or a free analogue finally measured, when voltage is applied, moves is defined as "downstream" side, and the opposite direction is defined as "upstream" side (the same hereinafter).

(2) A Side Channel for Drain and a Side Channel for Introducing a Sample or a Reagent Solution A side channel for drain (D side channel) is a side channel for receiving a sample or a reagent solution, and a side channel for introducing a sample or a reagent solution (S/R side channel) is also a side channel for supplying (transferring) a sample and/or a reagent solution. As shown in FIG. 6(a), a sample or a reagent solution supplied into a S/R side channel passes through a crossing part between the S/R side channel and the first channel, and further passes through each 2 crossing parts between the first channel and 2 D side channels, and is transported to 2 D side channels, and is transported to the 2 D side channels. Then, as shown in FIG. 6(b), a sample or a reagent solution arranged at a part of the first channel formed (sandwiched) by 2 (a pair of) openings of D side channels, is transported to downstream along the first channel. As described above, an amount (a volume) of a sample or a reagent solution introduced into the first channel relates to a volume of the part of the first channel formed (sandwiched) by 2 (a pair of) openings of D side channels, and the amount (volume) is determined by length (and inner diameter) of the part of the first channel formed (sandwiched) by 2 (a pair of) openings of D side channels. Therefore the amount (volume) of a sample or a reagent solution introduced into the first channel can be adjusted (measured) by length (and inner diameter) of this part of the first channel. As a result, much amount (volume) of a sample or a reagent solution can be arranged and introduced into the first channel (a channel for analysis) compared with a conventional cross type structure.

In this connection, into a D side channel positioned at the most upstream side, among 3 or more D side channels, not only a sample or a reagent solution but also an electrophoresis medium present in the first channel region further upstream than the first channel part where said opening of the D side channel positioned at the most upstream opens may be received (flowed in). In addition, into a D side channel positioned at the most downstream side, not only a sample or a reagent solution but also an electrophoresis medium present in the first channel region further downstream than the first channel part where said opening of the D side channel positioned at the most downstream opens may be received (flowed in).

In this connection, these side channels are, similarly as in the first channel, channels usually used in this field such as a capillary electrophoresis method, a capillary chip electrophoresis method, and the like.

(3) Material and Shape of a Channel

A first channel, a D side channel and a S/R side channel used in the present invention are any one usually used in this field such as a capillary electrophoresis method, a capillary chip electrophoresis method, and the like, and not especially limited.

Material of the channel used in the present invention is any one usually used in this field. Examples of a material of the channel are, for example, silica-based compounds such as glass, quartz and silicon; synthetic polymers such as cyclic olefin copolymer (COC), cyclic olefin polymer (COP), polymethyl methacrylate, polymethylsiloxane, polyvinyl chloride, polyurethane, polystyrene, polysulfone, polycarbonate, polytetrafluoroethylene, and the like. In addition, inner diameter and length of the channel are not especially limited. For example, inner diameter is usually 1 to 1000 μm, preferably 1 to 200 μm and more preferably 1 to 100 μm, and length is usually 0.1 mm to 1000 cm, preferably 0.1 mm to 20 cm and more preferably 0.1 mm to 10 cm. The inner diameter, the length and the shape of these channels (the first channel, the D side channel and a S/R side channel) may be the same as or different from each other. Length of the part of the first channel formed (sandwiched) by 2 (a pair of) openings of D side channels, namely distance (length) of the 2 (the pair of) openings of D side channels is usually 10 μm to 100 cm, preferably 100 μm to 10 cm and more preferably 500 μm to 5 cm.

Shape at cross section of the channel may be any one for example, polygon such as triangle, square, rectangle, and trapezoid; circle; eclipse; fan-like; and the like.

(4) Specific Structure

FIG. 7 is a conceptual diagram of a solution introducing structure of the present invention in the case of introducing 2 kinds of solutions (for example, a sample and a reagent solution). Each 3 D side channels of the first D side channel (2a), the second D side channel (2b) and the third D side channel (2c) has an opening (2-1a, 2-1b and 2-1c) opened on a wall of the first channel (1) so as to be communicatable and said openings (2-1a, 2-1b and 2-1c) are arranged in spaced relation to one another (with space) in an axis direction (from right to left in FIG. 7) of the first channel (1). In addition, each 2 S/R side channels of the first S/R side channel (3a) and the second S/R side channel (3b) has an opening (3-1a and 3-1b) opened on the wall of the above-described first channel (1) at the different position (part) from the openings (2-1a, 2-1b and 2-1c) of the 3 D side channels (2a 2b and 2c). Further, the opening (3-1a) of the first S/R side channel (3a) is arranged between the opening (2-1a) of the first D side channel (2a) and the opening (2-1b) of the second D side channel (2b) in an axis direction, namely the opening (3-1a) of the first S/R side channel (3a) is arranged at a part of the first channel (1) formed (sandwiched) by 2 (a pair of) the opening (2-1a) of the first D side channel (2a) and the opening (2-1b) of the second D side channel (2b); and the opening (3-1b) of the second S/R side channel (3b) is arranged between the opening (2-1b) of the second D side channel (2b) and the opening (2-1c) of the third D side channel (2c) in an axis direction, namely the opening (3-1b) of the second S/R side channel (3b) is arranged at a part of the first channel (1) formed (sandwiched) by 2 (a pair of) the opening (2-1b) of the second D side channel (2b) and the opening (2-1c) of the third D side channel (2c).

In the above description, the first D side channel (2a) is a side channel for receiving a first sample or reagent solution, the second D side channel (2b) is a side channel for receiving a first sample or reagent solution and a second sample or reagent, and the third D side channel (2c) is a side channel for receiving a second sample or reagent solution. The first S/R side channel (3a) is a side channel for supplying (transferring) a first sample or reagent solution, and the second S/R side channel (3b) is a side channel for supplying (transferring) a second sample or reagent solution. As shown in FIG. 8(a), the first sample or reagent solution supplied into the first S/R side channel (3a) passes through a crossing part between the first S/R side channel (3a) and the first channel (1), and further passes through each 2 crossing parts of a crossing part between the first channel (1) and the first D side channel (2a) and a crossing part between the first channel and the second D side channel (2b), and is transported to the first D side channel (2a) and the second D side channel (2b). The second sample or reagent solution supplied into the second S/R side channel (3b) passes through a crossing part between the second S/R side channel (3b) and the first channel (1), and further passes through each 2 crossing parts of a crossing part between the first channel (1) and the second D side channel (2b) and a crossing part between the first channel (1) and the third D side channel (2c), and is transported to the second D side channel (2b) and the third D side channel (2c). Then, as shown in FIG. 8(b), the first sample or reagent solution arranged at a part of the first channel (1) formed (sandwiched) by the opening (2-1a) of the first D side channel (2a) and the opening (2-1b) of the second D side channel (2b), and the second sample or reagent solution arranged at a part of the first channel (1) formed (sandwiched) by the opening (2-1b) of the second D side channel (2b) and the opening (2-1c) of the third D side channel (2c) are each transported to downstream side along the first channel. In this connection, into a first D side channel (2a) positioned at the most upstream side, not only the first sample or reagent solution but also an electrophoresis medium present in the first channel region further upstream than the first channel part wherein said opening (2-1a) of the first D side channel (2a) positioned at the most upstream opens may be received (flowed in). In addition, into a third D side channel (2c) positioned at the most downstream side, not only the second sample or reagent solution but also an electrophoresis medium present in the first channel region further downstream than the first channel part wherein said opening (2-1c) of the third D side channel (2c) positioned at the most downstream opens may be received (flowed in).

In this connection, the terminologies used in the above description and the meanings thereof are the same as described above, and the names of specified side channels such as "the first" D side channel, "the second" D side channel, "the third" D side channel, "the first" S/R side channel and "the second" S/R side channel are for convenience purpose as explanation in the above case.

FIG. 9 is a conceptual diagram of a solution introducing structure of the present invention in the case of introducing 3 kinds of solutions (for example, a sample and 2 kinds of reagent solutions). Each 4 D side channels of the first D side channel (2a), the second D side channel (2b), the third D side channel (2c) and the fourth D side channel (2d) has an opening (2-1a, 2-1b, 2-1c and 2-1d) opened on a wall of the first channel (1) so as to be communicatable and said openings (2-1a, 2-1b, 2-1c and 2-1d) are arranged in spaced relation to one another (with space) in an axis direction (from right to left in FIG. 9) of the first channel (1). In addition, each 3 S/R side channels of the first S/R side channel (3a), the second S/R side channel (3b) and the third S/R side channel (3c) has an opening (3-1a, 3-1b and 3-1c) opened on the wall of the above-described first channel (1) at the different position (part) from the openings (2-1a, 2-1b, 2-1c and 2-1d) of the above-described 4 D side channels (2a 2b, 2c and 2d). Further, the opening (3-1a) of the first S/R side channel (3a) is arranged between the opening (2-1a) of the first D side channel (2a) and the opening (2-1b) of the second D side channel (2b) in an axis direction, namely the opening (3-1a) of the first S/R side channel (3a) is arranged at a part of the first channel (1) formed (sandwiched) by 2 (a pair of) the opening (2-1a) of the first D side channel (2a) and the opening (2-1b) of the second D side channel; the opening (3-1b) of the second S/R side channel (3b) is arranged between the opening (2-1b) of the second D side channel (2b) and the opening (2-1c) of the third D side channel (2c) in an axis direction, namely the opening (3-1b) of the second side channel (3b) is arranged at a part of the first channel (1) formed (sandwiched) by 2 (a pair of) the opening (2-1b) of the second D side channel (2b) and the opening (2-1c) of the third D side channel (2c); and the opening (3-1c) of the third S/R side channel (3c) is arranged between the opening (2-1c) of the third D side channel (2c) and the opening (2-1d) of the fourth D side channel (2d) in an axis direction, namely the opening (3-1c) of the third S/R side channel (3c) is arranged at a part of the first channel (1) formed (sandwiched) by 2 (a pair of) the opening (2-1c) of the third D side channel (2c) and the opening (2-1d) of the fourth D side channel (2d).

In the above description, the first D side channel (2a) is a side channel for receiving a first sample or reagent solution, the second D side channel (2b) is a side channel for receiving a first sample or reagent solution and a second sample or reagent solution, the third D side channel (2c) is a side channel for receiving a second sample or reagent solution and a third sample or reagent solution, and the fourth D side channel (2d) is a side channel for receiving a third sample or reagent solution. The first S/R side channel (3a) is a side channel for supplying (transferring) a first sample or reagent solution, the second S/R side channel (3b) is a side channel for supplying (transferring) a second sample or reagent solution, and the third S/R side channel (3c) is a side channel for supplying (transferring) a third sample or reagent solution. As shown in FIG. 10(a), the first sample or reagent solution supplied into the first S/R side channel (3a) passes through a crossing part between the first S/R side channel (3a) and the first channel (1), and further passes through each 2 crossing parts of a crossing part between the first channel (1) and the first D side channel (2a) and a crossing part between the first channel and the second D side channel (2b), and is transported to the first D side channel (2a) and the second D side channel (2b). The second sample or reagent solution supplied into the second S/R side channel (3b) passes through a crossing part between the second S/R side channel (3b) and the first channel (1), and further passes through each 2 crossing parts of a crossing part between the first channel (1) and the second D side channel (2b) and a crossing part between the first channel (1) and the third D side channel (2c), and is transported to the second D side channel (2b) and the third D side channel (2c). In addition, the third sample or reagent solution supplied into the third S/R side channel (3c) passes through a crossing part between the third S/R side channel (3c) and the first channel (1), and further passes through each 2 crossing parts of a crossing part between the first channel (1) and the third D side channel (2c) and a crossing part between the first channel (1) and the fourth D side channel (2d), and is transported to the third D side channel (2c) and the fourth D side channel (2d). Then, as shown in FIG. 10(b), the first sample or reagent solution arranged at a part of the first channel (1) formed (sandwiched) by the opening (2-1a) of the first D side channel (2a) and the opening (2-1b) of the second D side channel (2b), the second sample or reagent solution arranged at a part of the first channel (1) formed (sandwiched) by the opening (2-1b) of the second D side channel (2b) and the opening (2-1c) of the third D side channel (2c), and the third sample or reagent solution arranged at a part of the first channel (1) formed (sandwiched) by the opening (2-1c) of the third D side channel (2c) and the opening (2-1d) of the fourth D side channel (2d) are each transported to downstream side along the first channel. In this connection, into a first D side channel (2a) positioned at the most upstream side, not only the first sample or reagent solution but also an electrophoresis medium present in the first channel region further upstream than the first channel part wherein said opening (2-1a) of the first D side channel (2a) positioned at the most upstream opens may be received (flowed in). In addition, into a fourth D side channel (2d) positioned at the most downstream side, not only the third sample or reagent solution but also an electrophoresis medium present in the first channel region further downstream than the first channel part wherein said opening (2-1d) of the fourth D side channel (2d) positioned at the most downstream opens may be received (flowed in).

In this connection, the terminologies used in the above description and the meanings thereof are the same as described above, and the names of specified side channels such as "the first" D side channel, "the second" D side channel, "the third" D side channel, "the fourth" D side channel, "the first" S/R side channel, "the second" S/R side channel and "the third" S/R side channel are for convenience purpose as explanation in the above case.

As described above, a solution introducing structure of the present invention features in having 2 or more (n pieces) of S/R side channels and 3 or more (n+1 pieces) of D side channels (n is an integer of 2 or more), and being constructed of so that a sample or reagent solution is present (introduced) inside the first channel (for example, a channel for analysis) by receiving one sample or reagent solution which is supplied into one S/R side channel, from said one S/R side channel to 2 (a pair of) D side channels, and being constructed of so that each 2 D side channels positioned at the most downstream and most upstream sides of the first channel can receive one sample or reagent solution supplied into one adjacent (positioned at the nearest) S/R side channel; and each of other D side channel can commonly receive 2 kinds of sample or reagent solution supplied into 2 adjacent (positioned at the nearest) S/R side channels.

In other words, a solution introducing structure of the present invention is one wherein 2 or more structure units selected from structure units shown in FIGS. 11(a) to 11(d), are combined so that one D channel among said structure unit are duplicated (commonly used) between structure units [one wherein 2 or more structure units are combined in parallel (series). (FIG. 11(e))]. In this connection, these structure units include, one wherein structure units shown by FIGS. 11(a) to 11(d) are reversed left and right, up and down or in 180 degree. Among them, it is preferable that 2 or more structure units selected from structure units shown by FIGS. 11(a) to 11(c) are combined.

In this connection, into a D side channel positioned at the most upstream side, among 3 or more D side channels, not only a sample or a reagent solution but also an electrophoresis medium present in the first channel region further upstream than the first channel part where said opening of the D side channel positioned at the most upstream opens may be received (flowed in). In addition, into a D side channel positioned at the most downstream side, not only a sample or a reagent solution but also an electrophoresis medium present in the first channel region further downstream than the first channel part where said opening of the D side channel positioned at the most downstream opens may be received (flowed in).

FIGS. 12 to 16 are a conceptual diagram of other solution introducing structure in the present invention.

FIGS. 12(a) to 12(i) show the cases that 2 kinds of solutions (for example, a sample and a reagent solution) are introduced, and the cases that each the openings of S/R side channels is arranged at inward part of the first channel in an axis direction of the 2 (the pair of) openings of the D side channels.

FIGS. 13(a) to 13(d) show the cases that 2 kinds of solutions (for example, a sample and a reagent solution) are introduced, and the cases that each the openings of S/R side channels is arranged just on the axis direction of any one one opening of the 2 (the pair of) openings of D side channels, (namely, it is opened on the first channel part at a coaxial part of either of the openings).

FIGS. 14(a) to 14(u) and 15(a) to 15(i) show the cases that 3 kinds of solutions (for example, a sample and 2 kinds of reagent solutions) are introduced, and the cases that each the openings of S/R side channels is arranged at inward part of the first channel in an axis direction of the 2 (the pair of) openings of the D side channels.

FIGS. 16(a) to 16(h) show the cases that 3 kinds of solutions (for example, a sample and 2 kinds of reagent solutions) are introduced, and the cases that each the openings of S/R side channels is arranged just on the axis direction of any one opening of the 2 (the pair of) openings of D side channels, (namely, it is opened on the first channel part at a coaxial part of either of the openings).

In this connection, the solution introducing structure of the present invention includes one wherein the structure shown by FIGS. 12 to 16 are reversed left and right, up and down or in 180 degree.

2. Micro Fluidic Device of the Present Invention

A micro fluidic device of the present invention is one having (incorporated) at least one solution introducing structure of the present invention described above within a substrate.

Namely, the micro fluidic device of the present invention is one comprising a main body structure arranged (formed) with at least a solution introducing structure of the present invention, as a micro fluidic element. The main body structure comprises exterior part or outer surface and inner part formed with a micro fluidic element such as a solution introducing structure of the present invention of whole of micro fluidic device.

In this connection, the micro fluidic device of the present invention may be one having a plurality of the same a solution introducing structures of the present invention in combination, within the same substrate, or may be one having a plurality of different a solution introducing structures of the present invention in combination.

A solution introducing structure of the present invention that the micro fluidic device of the present invention has is as described above, and preferable embodiments are also as described above.

In the micro fluidic device of the present invention addition, a reservoir (a well) for introducing a solution (a sample and/or a reagent solution) preferably be formed (arranged) in various side channels formed at the inner part (inside) of a main body structure. In this connection, "a reservoir" here means a well for storing various solutions (fluids), and usually a dimple holdable a certain amount of a solution (fluid), wherein it is opened at the exterior part or outer surface of a main body structure and the bottom thereof is communicated to a side channel formed at the inner part (inside) of a main body structure.

Namely, a S/R side channel in a solution introducing structure of the present invention preferably be connected (communicated) to a sample or reagent solution reservoir at the end part thereof, and a D side channel preferably be connected (communicated) to a waste reservoir. In this connection, into a sample or reagent solution reservoir, a sample or a reagent solution is put and supplied, and into a waste reservoir, a sample or a reagent solution (further an electrophoresis medium in certain cases) drawn into a D side channel for introducing into a main channel is stored.

Hereinafter, the sample or reagent solution reservoir may be abbreviated as a "S/R reservoir", and the waste reservoir may be abbreviated as a "W reservoir".

(1) Specific Structure

FIG. 17 is a conceptual diagram of a solution introducing structure in the micro fluidic device of the present invention in the case that each side channels are connected to the corresponding reservoir. Each 3 or more D side channels (2) has an opening (2-1) opened on a wall of the first channel (1) so as to be communicatable and said openings (2-1) are arranged in spaced relation to one another (with space) in an axis direction (from right to left in FIG. 17) of the first channel (1). In addition, the other end (the end opposite to the end opened at the first channel) of each D side channels (2) are connected to a W reservoir (4) so as to communicatable. On the other hand, each not less than 2 S/R side channels (3) has an opening (3-1) opened on the wall of the above-described first channel (1) at the different position (part) from the opening (2-1) of the D side channels (2), and each said openings (3-1) is arranged between adjacent 2 openings (2-1) of D side channels (2) (provided that each openings (3-1) of these not less than 2 S/R side channels (3) are each arranged at the different portion between different adjacent openings (2-1) of D side channels (2). In addition, the other end (the end opposite to the end opened at the first channel) of S/R side channels (3) are connected to a S/R reservoir (5) so as to communicatable.

Shape of the above-described reservoir is not especially limited and includes, for example, cylinder-like, conical (for example, head-cut body), cant cylinder-like, polygonal cylinder-like, pyramid-like (for example, head-cut body), polypyramid-like (for example, head-cut body), and the like, and other shape than these may also be allowed.

In this connection, these reservoirs may be connected to each side channel directly or via an access port. These reservoirs may be present at the exterior part of the device while being communicated to each side channel. A micro fluidic device of the present invention also includes such one as not having these reservoirs and having only an access port. In this connection, an access port here means a hole for communicating a side channel formed at the inner part (inside) of a main body structure and the exterior part or outer surface of a main body structure, in other words, a hole whose one end is opened at and communicated to a side channel, and the other end is opened at the exterior part or outer surface of a main body structure. In addition, it means a hole for communicating a reservoir and a side channel, when a reservoir is connected to a side channel via an access port.

Such a reservoirs and/or an access port also serve not only as an access point for introducing a solution into a channel of the device but also as a pressure port or electric access point for a channel of the device.

FIG. 18 is a conceptual diagram of a solution introducing structure in the micro fluidic device of the present invention in the case that each side channels are connected to the corresponding reservoir to be used for introducing 2 kinds of solutions (for example, a sample and a reagent solution). Each 3 D side channels of the first D side channel (2a), the second D side channel (2b) and the third D side channel (2c) has an opening (2-1a, 2-1b and 2-1c) opened on a wall of the first channel (1) so as to be communicatable and said openings (2-1a, 2-1b and 2-1c) are arranged in spaced relation to one another (with space) in an axis direction (from right to left in FIG. 18) of the first channel (1). In addition, each the other end (the end opposite to the end opened at the first channel) of each 3 D side channels (2a, 2b and 2c) are connected to a W reservoir (4a, 4b and 4c) so as to communicatable. On the other hand, each 2 S/R side channels of the first S/R side channel (3a) and the second S/R side channel (3b) has an opening (3-1a and 3-1b) opened on the wall of the above-described first channel (1) at the different position (part) from the openings (2-1a, 2-1b and 2-1c) of the 3 D side channels (2a 2b and 2c). Further, the opening (3-1a) of the first S/R side channel (3a) is arranged between the opening (2-1a) of the first D side channel (2a) and the opening (2-1b) of the second D side channel (2b) in an axis direction, namely the opening (3-1a) of the first S/R side channel (3a) is arranged at a part of the first channel (1) formed (sandwiched) by 2 (a pair of) the opening (2-1a) of the first D side channel (2a) and the opening (2-1b) of the second D side channel (2b); and the opening (3-1b) of the second S/R side channel (3b) is arranged between the opening (2-1b) of the second D side channel (2b) and the opening (2-1c) of the third D side channel (2c) in an axis direction, namely the opening (3-1b) of the second S/R side channel (3b) is arranged at a part of the first channel (1) formed (sandwiched) by 2 (a pair of) the opening (2-1b) of the second D side channel (2b) and the opening (2-1c) of the third D side channel (2c). In addition, each the other end (the end opposite to the end opened at the first channel) of the first S/R side channel (3a) and the second S/R side channel (3b) are connected to S/R reservoirs (5a and 5b) so as to communicatable.

FIG. 19 is a conceptual diagram of a solution introducing structure in the micro fluidic device of the present invention in the case that each side channels are connected to the corresponding reservoir to be used for introducing 3 kinds of solutions (for example, a sample and 2 kinds of reagent solutions). Each 4 D side channels of the first D side channel (2a), the second D side channel (2b), the third D side channel (2c) and the fourth D side channel (2d) has an opening (2-1a, 2-1b, 2-1c and 2-1d) opened on a wall of the first channel (1) so as to be communicatable and said openings (2-1a, 2-1b, 2-1c and 2-1d) are arranged in spaced relation to one another (with space) in an axis direction (from right to left in FIG. 19) of the first channel (1). In addition, each the other end (the end opposite to the end opened at the first channel) of each 4 D side channels (2a, 2b, 2c and 2d) are connected to a W reservoir (4a, 4b, 4c and 4d) so as to communicatable. On the other hand, each 3 S/R side channels of the first S/R side channel (3a), the second S/R side channel (3b) and the third S/R side channel (3c) has an opening (3-1a, 3-1b and 3-1c) opened on the wall of the above-described first channel (1) at the different position (part) from the openings (2-1a, 2-1b, 2-1c and 2-1d) of the above-described 4 D side channels (2a 2b, 2c and 2d). Further, the opening (3-1a) of the first S/R side channel (3a) is arranged between the opening (2-1a) of the first D side channel (2a) and the opening (2-1b) of the second D side channel (2b) in an axis direction, namely the opening (3-1a) of the first S/R side channel (3a) is arranged at a part of the first channel (1) formed (sandwiched) by 2 (a pair of) the opening (2-1a) of the first D side channel (2a) and the opening (2-1b) of the second D side channel; the opening (3-1b) of the second S/R side channel (3b) is arranged between the opening (2-1b) of the second D side channel (2b) and the opening (2-1c) of the third D side channel (2c) in an axis direction, namely the opening (3-1b) of the second side channel (3b) is arranged at a part of the first channel (1) formed (sandwiched) by 2 (a pair of) the opening (2-1b) of the second D side channel (2b) and the opening (2-1c) of the third D side channel (2c); and the opening (3-1c) of the third S/R side channel (3c) is arranged between the opening (2-1c) of the third D side channel (2c) and the opening (2-1d) of the fourth D side channel (2d) in an axis direction, namely the opening (3-1c) of the third S/R side channel (3c) is arranged at a part of the first channel (1) formed (sandwiched) by 2 (a pair of) the opening (2-1c) of the third D side channel (2c) and the opening (2-1d) of the fourth D side channel (2d). In addition, each the other end (the end opposite to the end opened at the first channel) of the first S/R side channel (3a), the second S/R side channel (3b) and the third S/R side channel (3c) are connected to S/R reservoirs (5a, 5b and 5c) so as to communicatable.

A solution introducing structure and a micro fluidic device of the present invention can be widely applied to the field of a microfluidics, such as a fluid system using various material transport mechanisms (for example, an electroosmotic flow material transport system, an electrokinetic material transport systems, a pressure drive system, and the like). Among others, a solution introducing structure and a micro fluidic device of the present invention are useful to an electrokinetic material transport systems using a capillary (a channel), in particular, an electrokinetic material transport systems utilizing electrophoresis (for example, electrophoresis such as a capillary electrophoresis method, a capillary chip electrophoresis method). In this connection, an electrophoresis method based on various principles (separation modes) can be used, for example, an isotachophoresis method (ITP), isoelectric focusing method (IF), a capillary zone electrophoresis method (CZE), micelle electrokinetic chromatography (MEKC), a capillary-gel electrophoresis method (CGE), and the like.

By using a solution introducing structure and a micro fluidic device of the present invention, 2 or more kinds of solutions (a sample or a reagent solution, and the like) can easily be introduced and arranged into the first channel (a main channel), and furthermore, these solutions can be reacted (mixed) in the first channel (a main channel), without mixing in advance outside the capillary (channel).

In particular, as is described later, by application of a solution introducing structure and a micro fluidic device of the present invention to an electrophoretic material transport system, 2 or more kinds of solutions (a sample or a reagent solution, and the like) for example, having viscosity different each other, can easily be introduced and arranged into the first channel (a main channel), and furthermore, these solutions can be electrophoretically reacted in the first channel (a main channel), without mixing in advance outside the capillary (channel). As a result, a reaction of 2 or more kinds of solutions (a sample or a reagent solution, and the like) can be carried out in a short time and highly efficiently and furthermore, easily and highly accurate separation of objective substances or highly sensitive analysis of objective substances is possible.

Therefore, the first channel of a solution introducing structure and a micro fluidic device of the present invention preferably have at least a region (reaction region) where a sample reacts with a reagent solution at one part thereof, and more preferably have at least a region (concentration and reaction region) where at least one kind of a CFS reacts with analyte or analogue thereof in a sample while concentrating said analyte or said analogue thereof in the sample and/or at least one kind of the CFS in the reagent solution. In addition, a region (separation region) where a complex between said analyte or said analogue thereof, and a CFS is separated from said CFS not involved in the formation of said complex, or said analogue not involved in the formation of said complex may further be comprised at downstream of such the reaction region (or the concentration and reaction region). In this connection, the reaction region or the concentration and reaction region, and the separation region may sequentially and directly be connected (sequential connection), or both may be connected (sequential connection) via a region or channel not having the above-described function (reaction, separation). In addition, these regions may be present at the first channel each independently, or a part of or whole of these may be present in overlapped state. In other words, the first channel of the present invention is enough to have the above-described region (function) as a result. In addition, length of the reaction region or the concentration and reaction region is not especially limited as long as they are sufficient to form a complex between an analyte or analogue thereof and a CFS, or they are sufficient to concentrate an analyte or an analogue thereof and/or a CFS, and form a complex between an analyte or analogue thereof and a CFS. For example, length is usually 0.1 mm to 100 cm, preferably 0.1 mm to 20 cm and more preferably 0.1 mm to 10 cm. Length of the separation region is not especially limited as long as they are sufficient to separate a complex between said analyte or said analogue thereof, and a CFS from said CFS not involved in the formation of said complex, or said analogue not involved in the formation of said complex. For example, length is usually 0.1 mm to 100 cm, preferably 0.1 mm to 20 cm and more preferably 0.1 mm to 10 cm.

In the above description, a reaction in the reaction region or the concentration and reaction region, and a separation in the separation region are carried out by a fluid system as described above, preferably by an electrophoretic material transport system utilizing electrophoresis (for example, electrophoresis such as a capillary electrophoresis method, a capillary chip electrophoresis method). In addition, when an electrophoresis method is used, these reaction and separation can use an electrophoresis method based on various principles (separation modes) such as ITP, IF, CZE, MEKC, CGE, and the like can be used.

As is described later, in the reaction or the concentration and reaction between a sample or a reagent solution, and separation, the same principle (separation mode) may be used or each different principle (separation mode) may be used.

In application of a solution introducing structure and a micro fluidic device of the present invention to an electrophoretic material transport system, and the like, filling the first channel (a main channel) with an electrophoresis medium as described later (for example, a leading buffer containing a leading ion, a trailing buffer containing a trailing ion, a high electric conductivity electrophoresis medium, an electrophoresis medium having alkaline range pH, an electrophoresis medium including a charged substance forming a micelle, a buffer solution for electrophoresis, said buffer solution for electrophoresis containing fillers, and the like) may sometimes be required.

In such cases, the first channel in a solution introducing structure and a micro fluidic device of the present invention preferably have an upstream reservoir at the end of the upstream side, and a downstream reservoir at the other end of the downstream side for introducing an electrophoresis medium into the first channel. In this connection, "an upstream reservoir" and "a downstream reservoir" here mean wells for storing the electrophoresis mediums, and usually a dimple holdable a certain amount of a solution (fluid), wherein it is opened at the exterior part or outer surface of a main body structure and the bottom thereof is communicated to a side channel formed at the inner part (inside) of a main body structure.

Namely, the first channel in a solution introducing structure and a micro fluidic device of the present invention preferably be connected (communicated) to the upstream reservoir at the end part of the upstream side and the downstream reservoir at the end part of the downstream side. In this connection, into the upstream reservoir, an electrophoresis medium is put and supplied, while into the downstream reservoir, an electrophoresis medium introduced into the first channel is stored.

FIG. 20 is a conceptual diagram of a solution introducing structure in the micro fluidic device of the present invention in the case that the first channel is connected to the upstream reservoir and the downstream reservoir, and each side channels are connected to the corresponding reservoir. The first channel (1) is connected each to the upstream reservoir (6) at the one end (for example, at the end of the upstream side. the right end in FIG. 20) and downstream reservoir (7) at the other end (for example, at the end of the downstream side. the left end in FIG. 20) so as to be communicated. Each 3 or more D side channels (2) has an opening (2-1) opened on a wall of the first channel (1) so as to be communicatable and said openings (2-1) are arranged in spaced relation to one another (with space) in an axis direction (from right to left in FIG. 20) of the first channel (1). In addition, the other end (the end opposite to the end opened at the first channel) of each D side channels (2) are connected to a W reservoir (4) so as to communicatable. On the other hand, each not less than 2 S/R side channels (3) has an opening (3-1) opened on the wall of the above-described first channel (1) at the different position (part) from the opening (2-1) of the D side channels (2), and each said openings (3-1) is arranged between adjacent 2 openings (2-1) of D side channels (2) (provided that each openings (3-1) of these not less than 2 S/R side channels (3) are each arranged at the different portion between different adjacent openings (2-1) of D side channels (2). In addition, the other end (the end opposite to the end opened at the first channel) of S/R side channels (3) are connected to a S/R reservoir (5) so as to communicatable.

FIG. 21 is a conceptual diagram of a solution introducing structure in the micro fluidic device of the present invention in the case that the first channel is connected to the upstream reservoir and the downstream reservoir, and each side channels are connected to the corresponding reservoir to be used for introducing 2 kinds of solutions (for example, a sample and a reagent solution). The first channel (1) is connected each to the upstream reservoir (6) at the one end (for example, at the end of the upstream side. the right end in FIG. 21) and downstream reservoir (7) at the other end (for example, at the end of the downstream side. the left end in FIG. 21) so as to be communicated. Each 3 D side channels of the first D side channel (2a), the second D side channel (2b) and the third D side channel (2c) has an opening (2-1a, 2-1b and 2-1c) opened on a wall of the first channel (1) so as to be communicatable and said openings (2-1a, 2-1b and 2-1c) are arranged in spaced relation to one another (with space) in an axis direction (from right to left in FIG. 21) of the first channel (1). In addition, each the other end (the end opposite to the end opened at the first channel) of each 3 D side channels (2a, 2b and 2c) are connected to a W reservoir (4a, 4b and 4c) so as to communicatable. On the other hand, each 2 S/R side channels of the first S/R side channel (3a) and the second S/R side channel (3b) has an opening (3-1a and 3-1b) opened on the wall of the above-described first channel (1) at the different position (part) from the openings (2-1a, 2-1b and 2-1c) of the 3 D side channels (2a 2b and 2c). Further, the opening (3-1a) of the first S/R side channel (3a) is arranged between the opening (2-1a) of the first D side channel (2a) and the opening (2-1b) of the second D side channel (2b) in an axis direction, namely the opening (3-1a) of the first S/R side channel (3a) is arranged at a part of the first channel (1) formed (sandwiched) by 2 (a pair of) the opening (2-1a) of the first D side channel (2a) and the opening (2-1b) of the second D side channel (2b); and the opening (3-1b) of the second S/R side channel (3b) is arranged between the opening (2-1b) of the second D side channel (2b) and the opening (2-1c) of the third D side channel (2c) in an axis direction, namely the opening (3-1b) of the second S/R side channel (3b) is arranged at a part of the first channel (1) formed (sandwiched) by 2 (a pair of) the opening (2-1b) of the second D side channel (2b) and the opening (2-1c) of the third D side channel (2c). In addition, each the other end (the end opposite to the end opened at the first channel) of the first S/R side channel (3a) and the second S/R side channel (3b) are connected to S/R reservoirs (5a and 5b) so as to communicatable.

FIG. 22 is a conceptual diagram of a solution introducing structure in the micro fluidic device of the present invention in the case that the first channel is connected to the upstream reservoir and the downstream reservoir, and each side channels are connected to the corresponding reservoir to be used for introducing 3 kinds of solutions (for example, a sample and 2 kinds of reagent solutions). The first channel (1) is connected each to the upstream reservoir (6) at the one end (for example, at the end of the upstream side. the right end in FIG. 22) and downstream reservoir (7) at the other end (for example, at the end of the downstream side. the left end in FIG. 22) so as to be communicated. Each 4 D side channels of the first D side channel (2a), the second D side channel (2b), the third D side channel (2c) and the fourth D side channel (2d) has an opening (2-1a, 2-1b, 2-1c and 2-1d) opened on a wall of the first channel (1) so as to be communicatable and said openings (2-1a, 2-1b, 2-1c and 2-1d) are arranged in spaced relation to one another (with space) in an axis direction (from right to left in FIG. 22) of the first channel (1). In addition, each the other end (the end opposite to the end opened at the first channel) of each 4 D side channels (2a, 2b, 2c and 2d) are connected to a W reservoir (4a, 4b, 4c and 4d) so as to communicatable. On the other hand, each 3 S/R side channels of the first S/R side channel (3a), the second S/R side channel (3b) and the third S/R side channel (3c) has an opening (3-1a, 3-1b and 3-1c) opened on the wall of the above-described first channel (1) at the different position (part) from the openings (2-1a, 2-1b, 2-1c and 2-1d) of the above-described 4 D side channels (2a 2b, 2c and 2d). Further, the opening (3-1a) of the first S/R side channel (3a) is arranged between the opening (2-1*a*) of the first D side channel (2*a*) and the opening (2-1*b*) of the second D side channel (2*b*) in an axis direction, namely the opening (3-1*a*) of the first S/R side channel (3*a*) is arranged at a part of the first channel (1) formed (sandwiched) by 2 (a pair of) the opening (2-1*a*) of the first D side channel (2*a*) and the opening (2-1*b*) of the second D side channel; the opening (3-1*b*) of the second S/R side channel (3*b*) is arranged between the opening (2-1*b*) of the second D side channel (2*b*) and the opening (2-1*c*) of the third D side channel (2*c*) in an axis direction, namely the opening (3-1*b*) of the second side channel (3*b*) is arranged at a part of the first channel (1) formed (sandwiched) by 2 (a pair of) the opening (2-1*b*) of the second D side channel (2*b*) and the opening (2-1*c*) of the third D side channel (2*c*); and the opening (3-1*c*) of the third S/R side channel (3*c*) is arranged between the opening (2-1*c*) of the third D side channel (2*c*) and the opening (2-1*d*) of the fourth D side channel (2*d*) in an axis direction, namely the opening (3-1*c*) of the third S/R side channel (3*c*) is arranged at apart of the first channel (1) formed (sandwiched) by 2 (a pair of) the opening (2-1*c*) of the third D side channel (2*c*) and the opening (2-1*d*) of the fourth D side channel (2*d*). In addition, each the other end (the end opposite to the end opened at the first channel) of the first S/R side channel (3*a*), the second S/R side channel (3*b*) and the third S/R side channel (3*c*) are connected to S/R reservoirs (5*a*, 5*b* and 5*c*) so as to communicatable.

Shape of the above-described upstream reservoir and downstream reservoir are not especially limited and includes, for example, cylinder-like, conical (for example, head-cut body), cant cylinder-like, polygonal cylinder-like, pyramid-like (for example, head-cut body), poly-pyramid-like (for example, head-cut body), and the like, and other shape than these may also be allowed.

In this connection, these upstream reservoir and downstream reservoir may be connected to first channel directly or via an access port. These upstream reservoir and downstream reservoir may be present at the exterior part of the device while being communicated to a first channel. A micro fluidic device of the present invention also includes such one as not having these upstream reservoir and downstream reservoir and having only an access port. In this connection, an access port here means a hole for communicating a first channel formed at the inner part (inside) of a main body structure and the exterior part or outer surface of a main body structure, in other words, a hole whose one end is opened at and communicated to a first channel, and the other end is opened at the exterior part or outer surface of a main body structure. In addition, it means a hole for communicating an upstream reservoir or downstream reservoir and a first channel, when an upstream reservoir or downstream reservoir is connected to a first channel via an access port.

In a solution introducing structure and micro fluidic device of the present invention, one or more side channels for introducing an electrophoresis medium (8) can be connected (communicated) to the first channel other than the S/R side channel as described above. The side channel for introducing an electrophoresis medium (8) here is a side channel for receiving an electrophoresis medium and material, inner diameter, length and preferable embodiments thereof are the same as in the side channel described above.

Hereinafter, a side channel for receiving an electrophoresis medium may be abbreviated as a "EM side channel".

As an example of using a EM side channel, a reaction or concentration and reaction between a sample or a reagent solution, and separation may be carried out using electrophoresis method based on each different principle (separation mode). Namely, in such cases, a solution introducing structure and micro fluidic device of the present invention having one or more kinds of EM side channels (if necessary, an access port, a electrophoresis medium reservoir) are particularly useful.

FIG. 23 is a conceptual diagram of a solution introducing structure and micro fluidic device of the present invention, having an EM side channel. The first channel (1) is connected each to the upstream reservoir (6) at the one end (for example, at the end of the upstream side. the right end in FIG. 23) and downstream reservoir (7) at the other end (for example, at the end of the downstream side. the left end in FIG. 23) so as to be communicated. Each 3 or more D side channels (2) has an opening (2-1) opened on a wall of the first channel (1) so as to be communicatable and said openings (2-1) are arranged in spaced relation to one another (with space) in an axis direction (from right to left in FIG. 23) of the first channel (1). In addition, the other end (the end opposite to the end opened at the first channel) of each D side channels (2) are connected to a W reservoir (4) so as to communicatable. On the other hand, each not less than 2 S/R side channels (3) has an opening (3-1) opened on the wall of the above-described first channel (1) at the different position (part) from the opening (2-1) of the D side channels (2), and each said openings (3-1) is arranged between adjacent 2 openings (2-1) of D side channels (2) (provided that each openings (3-1) of these not less than 2 S/R side channels (3) are each arranged at the different portion between different adjacent openings (2-1) of D side channels (2). In addition, the other end (the end opposite to the end opened at the first channel) of S/R side channels (3) are connected to a S/R reservoir (5) so as to communicatable. Furthermore, at the first channel region between a D side channel (2*n*) located at the most downstream side among the above-described 3 or more D side channels (2: 2*a*, 2*b*, 2*c*, . . . 2*n*) and the downstream reservoir (7), the EM side channel (8) is connected (communicated).

FIG. 23 shows the case wherein the EM side channel (8) is connected (communicated) at the first channel region between a D side channel (2*n*) located at the most downstream side among the above-described 3 or more D side channels (2: 2*a*, 2*b*, 2*c*, . . . 2*n*) and the downstream reservoir (7), however, a connection (communication) part (region) of a EM side channel (8) to the first channel (1) is not especially limited. It may be connected (communicated) at the end of the first channel (1), at the first channel region between a D side channel located at the most upstream side and an upstream reservoir, at the first channel region between two D side channels (2) [at the part of the first channel (1) formed (sandwiched) by 2 (a pair of) openings (2-1) of D side channels], or at the first channel region between two S/R side channels (3) [at the part of the first channel (1) formed (sandwiched) by 2 (a pair of) openings (3-1) of S/R side channels]. The connection (communication) at the first channel region between a D side channel located at the most downstream side among the above-described 3 or more D side channels and a downstream reservoir is preferable.

In addition, such a EM side channel (8) preferably be connected (communicated) to an electrophoresis medium reservoir (11) at the end thereof. In this connection, into the electrophoresis medium reservoir (11), an electrophoresis medium is put and supplied, and shape, preferable embodiments of the electrophoresis medium reservoir (11) are the same as in a S/R reservoir as described above.

In this connection, the electrophoresis medium reservoir (11) may be connected to the EM side channel directly or via an access port. The electrophoresis medium reservoir (11) may be present at the exterior part of the device while being communicated to the EM side channel. A micro fluidic device of the present invention also includes such one as not having the electrophoresis medium reservoir (11) and having only an access port. In this connection, an access port here means a hole for communicating a EM side channel (8) formed at the inner part (inside) of a main body structure and the exterior part or outer surface of a main body structure, in other words, a hole whose one end is opened at and communicated to a EM side channel, and the other end is opened at the exterior part or outer surface of a main body structure. In addition, it means a hole for communicating an electrophoresis medium reservoir and a EM side channel, when an electrophoresis medium reservoir is connected to a EM side channel via an access port.

Hereinafter, an electrophoresis medium reservoir may be abbreviated as a "EM reservoir".

In this connection, as is shown in FIG. 24, in the above description, in the case wherein the EM side channel (8) is connected (communicated) at the first channel region between a D side channel (2n) located at the most downstream side among 3 or more D side channels and the downstream reservoir (7), the first channel region (9a) between a D side channel (2a) located at the most upstream side among the above-described 3 or more D side channels (2: 2a, . . . 2n) and the D side channel (2n) located at the most downstream side; or the first channel region (9b) between a D side channel (2a) located at the most upstream side among the above-described 3 or more D side channels (2: 2a, . . . 2n) and the EM side channel (8) is a region (a reaction region) where a sample reacts with a reagent solution, or a region (a concentration and reaction region) where at least one kind of a CFS reacts with an analyte or an analogue in a sample while concentrating said analyte or said analogue thereof in the sample and/or at least one kind of the CFS in the reagent solution, and the first channel region (10) between the EM side channel (8) and the downstream reservoir (7) is a region (a separation region) where a complex between said analyte or said analogue thereof, and a CFS is separated from said substance binding to said analyte or said analogue thereof not involved in the formation of said complex, or said analogue not involved in the formation of said complex.

In addition, length of the reaction region (9a) or the concentration and reaction region (9b) is not especially limited as long as they are sufficient to form a complex between an analyte or analogue thereof and a CFS, or they are sufficient to concentrate an analyte or an analogue thereof and/or a CFS, and form a complex between an analyte or analogue thereof and a CFS. For example, length is usually 0.1 mm to 100 cm, preferably 0.1 mm to 20 cm and more preferably 0.1 mm to 10 cm. Length of the separation region (10) is not especially limited as long as they are sufficient to separate a complex between said analyte or said analogue thereof, and a CFS from said CFS not involved in the formation of said complex, or said analogue not involved in the formation of said complex. For example, length is usually 0.1 mm to 100 cm, preferably 0.1 mm to 20 cm and more preferably 0.1 mm to 10 cm.

A solution introducing structure and micro fluidic device of the present invention may have not only a EM side channel (if necessary an access port, a EM reservoir) but also a side channel for discharging an electrophoresis medium, a reservoir for discharging to be communicated to the end thereof, or an access port, and the like, further. In this connection, they may be suitably selected and arranged in accordance with the above-described a EM side channel, an access port, a EM reservoir, and the like.

A micro fluidic device of the present invention may further have various different channel layouts (for example, from a simple "T" or "cross" connection of 2 channels to a more complicated channel network) other than the above-described a solution introducing structure of the present invention, if necessary an access port and various reservoirs.

Therefore, a micro fluidic device of the present invention is one comprising a main body structure arranged with various micro fluidic elements such as a solution introducing structure of the present invention or various channels (layouts) as described above. The main body structure comprises exterior part or outer surface and inner part formed with various micro fluidic elements such as a solution introducing structure of the present invention of whole of micro fluidic device or various channels (layouts) as described above.

In addition, a micro fluidic device of the present invention may comprise an (upstream) electrode connected to an upstream side (for example, an upstream end part) of the first channel (1), an access port or the upstream reservoir (6) communicating thereto, and a (downstream) electrode connected to a downstream side (for example, a downstream end part) of the first channel (1), an access port or the downstream reservoir (7) communicating thereto, other than the above. In addition, it may also comprise an electrode connected to a EM side channel (8) (for example, the end part thereof), an access port or the EM reservoir (11) communicating thereto, and an electrode connected to a side channel for discharging an electrophoresis medium (for example, an end part thereof), an access port or the reservoir for discharging communicating thereto.

Furthermore, as described later, when introduction of a sample or a reagent solution is carried out electrically, it may also comprise an electrode connected to a D side channel (2) (for example, the end part thereof), an access port or a W reservoir (4) communicating thereto, and an electrode connected to a S/R side channel (3), an access port or a S/R reservoir (5) communicating thereto.

In this connection, each electrode is usually connected further to a control unit or voltage control device, so that it is operable.

In addition, when introduction of a sample or a reagent solution is carried out under increased and/or decreased pressure, each reservoir may also be connected to a pressure controllable unit.

A micro fluidic device of the present invention may be equipped with an IC tag to store information on a micro fluidic device and/or analysis.

As such an IC tag, any of a non-contact type IC (Integrated Circuit) tag such as an RF (Radio Frequency) tag, or a contact type IC tag may be used. In addition, as information on a micro fluidic device and/or analysis to be stored, for example, at least one selected from the following information is included:

(1) Information concerning display: unit, number of indication digits, reference value (range), and the like;

(2) Information concerning analysis: parameter for operating analysis device to carry out analysis [use amount of a sample, use amount of a reagent solution, the putting (application) place of a sample or a reagent solution to a micro fluidic device, the putting (application) timing of a sample or a reagent solution, measurement wavelength (the single wavelength, the dual-wavelength: the main wavelength and the sub-wavelength, excitation wavelength, fluorescent wavelength), reaction time, electrophoresis conditions (voltage, ampere, place of voltage application)], dilution condition (presence or absence of necessity for sample dilution, kind of a diluent and dilution rate), a calibration method, and reagent loading conditions (applied voltage, applied pressure), and the like;

(3) Information concerning analysis result: environment information [analysis device ID, analysis items, analysis state, parameters used in analysis, sample information (inspection results on kind, hue, background, viscosity of a sample), blank of a micro fluidic device in analysis (absorbance by a micro fluidic device only in analysis, fluorescence intensity, luminescence intensity), analysis results (practically measured values of a sample before correction, analysis values after correction, comparison results with reference value)], performance information (measurement blank values, information on calibration performed, information on measurement results on control), electrophoresis results (voltage, ampere, place of voltage application), and reagent loading results (applied voltage, applied pressure), and the like;

(4) Information concerning production: identifier of each micro fluidic device (production lot number, serial number), production date, guarantee period, and the like;

(5) Information concerning a reagent solution: calibration information (blank value, sensitivity, calibrator concentration in analysis, lot number of a calibrator, correction date, effective term, calibration history, lot number and serial number of a reagent solution used), linearity, repeatability, influence of coexistent substances, stability, threshold value data, and the like;

(6) Information concerning storage state: elapsed time since production date, data on temperature, humidity and vibration in storage of device and time required therefore), transportation state (data on temperature, humidity and vibration in transportation of device and time required therefore; and (7) Information concerning use state: date of the first use, elapsed time since the first use, date of the latest use, elapsed time since the latest use, use number, use time, total use time, effective period, use allowable or not, and the like.

In the above description, "a calibration method" is data concerning specific operation and conditions, which are indicated when the calibration is carried out. Specifically, for example, it includes a calibration method such as a K factor method, a linear line method, a multi-point calibration curve method, and an isozyme method; a calibration type (the type of calibration curve) such as a linear expression (a linear line), a quadratic expression, a spline curve and a Logit-log curve; the number of calibrators (standard solution) to be measured (for example, in a case of "2", 2 types of calibrators are used.); a concentration value of the calibrator (standard solution) to be measured; the measurement numbers (for example, in a case of "3", the measurement is carried out 3 times for one calibrator, and the measurement value is usually indicated as an average of n=3); and optional information, and the like. In this connection, the calibration is an operation to correct the measurement value using the device and the reagent, and the calibrator means the specimen to correct the measurement value, and is also called a standard solution. In order to confirm the correction result, it is necessary to measure the control as a specimen having the measurement value within a criterion range.

Rapid analysis can be attained by, for example, memorizing the information concerning analysis among the abovementioned informations by an IC tag. In this case, the following procedure can be taken:

Namely, a user of analysis device sets a sample to be analyzed and a reagent solution, along with micro fluidics device onto analysis device, and directs the device to start an analysis (pushes on a start button). Analysis device receives start direction of analysis by a user, and automatically starts and ends using information concerning analysis memorized by an IC tag.

In accordance with this procedure, input of information concerning analysis by a user of analysis device can be eliminated, and by only direction to start analysis (pushing a start button), suitable analysis corresponding to kinds of each sample or reagent solution can automatically be started and ended.

In addition, for example, by making an IC tag to memorize information concerning analysis result or use state, a management of a sample or a reagent solution, a micro fluidic device or an analysis device can simply (automatically) be carried out. In such a case, for example, the following procedure may be carried out:

Namely, after analysis is started using information concerning analysis memorized by an IC tag, as described above, a information concerning analysis result obtained by carrying out analysis is memorized by an IC tag connected (adhered) to a micro fluidic device of the present invention, and analysis is ended based on said information concerning analysis result and/or information concerning analysis.

When a micro fluidic device of the present invention is provided to the next analysis, by making an IC tag connected (adhered) to the micro fluidic device of the present invention to memorize information concerning analysis result, and by comparing thus memorized information concerning analysis result with information concerning analysis result to be obtained next time, correction of difference between devices or necessity of maintenance of micro fluidic device or analysis device can be specified based on a detection of presence or absence of effectiveness of analysis result to be obtained in the next time, presence or absence of abnormality, estimation of causes of abnormality or inter-device difference. In addition, by comparing information concerning analysis result obtained with information concerning threshold value data set in advance for the analysis result or information concerning analysis result to be obtained next time, presence or absence of effectiveness of analysis result to be obtained in the next time, presence or absence of abnormality, estimation of causes of abnormality, and the like are also possible.

In addition, by making memorized information concerning use state, replacement time of a micro fluidic device can be managed based on use number and use time, and the like.

Furthermore, even when analysis device is down from any cause and analysis should be carried out using another device, by making an IC tag attached on a micro fluidic device memorize the above-described information, comparison with past data maintained by a micro fluidic device becomes possible without input information drawn out not working device into new device.

In this connection, by registering information concerning analysis result not only by an IC tag of a micro fluidic device but also by a storage section of analysis result data, controlled by a remote computer, said analysis result can be utilized, for example, for management of other micro fluidic device relevant to the present micro fluidics device.

Furthermore, as is shown in WO2006/009251, by making an IC tag attached to a micro fluidic device of the present invention held information as described above, and by using analysis device suitably connected to a network, for example, management of micro fluidic device or analysis device and automation of effectiveness judgment of analysis become possible, and also order of a reagent solution or device maintenance becomes possible, which makes general analysis support possible.

(2) A Method for Production

Material of the substrate used in the present invention is not especially limited as long as it can realize the above-described solution introducing structure. As such material, any one generally used in this field and known itself may be used, including for example, silica-based compounds such as glass, quartz, silicon and polysilicon; resins such as polydimethylsiloxane (PDMS), polymethyl metacrylate (PMMA), polyurethane, polyvinyl chloride (PVC), polystyrene, polysulfone, polycarbonate, polymethylpentene, polypropylene, polyethylene, polyvinylidene fluoride, ABS (an acrylonitrile-butadiene-styrene copolymer), photosensitive resins, and other resins; metals; ceramics; combinations thereof; and the like.

Micro fluidic device of the present invention is generally such one as produced from a flat substrate made of material as described above, and being substantially flat or having at least one flat surface.

A method for producing a micro fluidic device of the present invention is not especially limited as long as a method formable a solution introducing structure of the present invention, if necessary various other micro fluidic elements such as the above-described access port, various reservoirs, various channels (layouts) in said substrate. Such a method includes micro production technology known itself, and it includes, for example, one piece molding such as a machining technique, an injection molding technique, compression molding technique, an embossing method, a laser melt removal technique, photolithography technique, dry etching (RIE, IE, IBE, plasma etching, laser etching, laser abrasion, blast fabrication, electric discharge machining, LIGA, electron beam etching, FAB), wet etching (chemical erosion), photo-fabrication, and ceramics paving; surface micro-machining wherein various substances are deposited by coating, vapor deposition or sputtering and then partially removed to form a micro-structure; a method for forming an opening part by one or more sheet-like substances (films, tapes, and the like) to form a channel; a method for forming by dropping and injecting a flow path material using an ink jet or a dispenser, and the like.

In this connection, in the above-described methods, a mask may be used to produce a micro fluidic device of the present invention. This mask has any design as long as finally formable a micro fluidic device of the present invention, and a plurality of masks may be used. The mask is usually designed in such shape as projection on a plane of a solution introducing structure (flow path) of the present invention (if necessary, an access port, various reservoirs and other micro fluidic elements). However, when fabrication is carried out at both sides of component material of a solution introducing structure (flow path) (if necessary, an access port, various reservoirs and other micro fluidic elements) to be adhered or when a solution introducing structure (flow path) (if necessary, an access port, various reservoirs and other micro fluidic elements) is formed using a plurality of parts, a plurality of masks may be used or direct fabrication is made partially without using a mask, therefore the mask has not necessarily such shape as projection of final solution introducing structure (flow path) (if necessary, an access port, various reservoirs and other micro fluidic elements). As a mask for electromagnetic wave shielding used in a photocurable resin, one made of quartz or glass coated with chromium, or one made of a resin film baked by laser are included.

The above-described mask may also be produced, for example, by drawing at least a part of the above-described a solution introducing structure (flow path) using a computer and suitable software, and then printing on a transparent resin film.

A micro fluidic device of the present invention can be produced, for example, by adhering the following 2 or more materials.

A solution introducing structure of the present invention, if necessary other micro fluidic element is formed on one surface of the first flat substrate, as a channel (well or dimple) in a surface thereof using the above-described micro production technique. Then, the second flat substrate of the same or different material is adhered so as to be overlapped on the first substrate to cover and seal a solution introducing structure of the present invention, if necessary other micro fluidic element, formed at the surface of the first substrate. By these processes, an inner part (inside) of a main body structure in the device is formed by the upper surface of the first substrate and the lower surface of the second substrate bound to said upper surface.

In this connection, to form the above-described reservoir and/or access port, usually, a hole is made on at least one of these substrates (for example, the second substrate), and arranged so that to be a reservoir and/or an access port to each channel in a solution introducing structure of the present invention, if necessary, other micro fluidics element, formed inside a main structure. In addition, the substrate is not limited to be 2 pieces, and device can also be produced by laminating an arbitrary plurality of pieces according to need.

In the above description, as a method for adhering 2 or more materials, adhesion by adhesives, resin bonding by a primer, diffusion bonding, anodic bonding, eutectic bonding, heat sealing, ultrasonic bonding, laser melting, adhesion by a solvent or dissolution solvent, adhesion by a pressure sensitive adhesive tape, adhesion by an adhesives tape, pressure bonding, bonding by a self-adsorbent, physical retaining, and intermeshing by concave-convex are included.

In addition, a micro fluidic device of the present invention can also be produced, for example, by forming a solution introducing structure (flow path) (if necessary, other micro fluidic element, a reservoir, an access port, and the like) including closed space created by one-piece molding such as photomolding.

Dimension (size), shape and thickness of a micro fluidic device of the present invention produced as described above are not especially limited. Generally, thickness of device is, as lower limit, usually not smaller than 20 μm, preferably not smaller than 40 μm, and as upper limit, usually not larger than 10 cm, preferably not larger than 5 cm, more preferably not larger than 1 cm, further preferably not larger than 0.5 cm, and particularly preferably not larger than 0.25 cm. Shape of device may be any one for example, polygon such as triangle, square, rectangle, and trapezoid; circle; eclipse; fan-like; and the like. Dimension (size) of device of the present invention is determined by number of a solution introducing structure of the present invention formed or number of analysis (samples), and length and width are usually in a range of 2 mm to 500 cm, preferably 5 mm to 100 mm, and more preferably 5 mm to 50 mm.

3. A Micro Fluidic System of the Present Invention

To operate a micro fluidic device of the present invention, usually, for example, an independent control unit (device) for transferring and driving (moving) a fluid in a channel of device is required. The control unit (device) can be incorporated in the micro fluidic itself, however, usually it is composed as a whole system so that detachable from a micro fluidic device of the present invention.

As such control unit (device), for example, pressurization and/or depressurization unit (device or mechanism) such as a pump and a switching manifold; pressure and/or vacuum supply source; voltage control unit (device); electric power supply source; computer for controlling these, interface for connecting these to a micro fluidic device of the present invention or computer; and the like are included. In addition, a whole system may include, a detector (for example, an optical detector such as an epifluorescent detector and an electrochemical detector, various sensors such as a conductivity sensor, a heat sensor, an IC heat sensor, a thermocouple, a thermistor) for monitoring progress of analysis in operation; interface for connecting these to a micro fluidic device of the present invention or a whole system, and the like, other than these.

4. A Method for Introducing a Sample and/or a Reagent Solution of the Present Invention By using a solution introducing structure or micro fluidic device of the present invention as described above, a plurality of solutions (a sample and/or a reagent solution) can be introduced in a channel, in particular, a channel of a micro fluidic device in highly accurate volume, in high amount and simply.

In addition, by using a solution introducing structure or micro fluidic device of the present invention, a plurality of solutions (a sample and/or a reagent solution) can be formed and arranged as each independent zone in a capillary (a first channel). In other words, between adjacent solutions of a plurality of solutions introduced in the capillary (the first channel) using a solution introducing structure or micro fluidic device of the present invention, liquid-liquid interface is formed and maintained when they are arranged.

In this connection, "interface" in the present invention means a boundary where 2 solutions are contacted, and does not necessarily mean completely no mixing, due to presence of diffusion from a practical standpoint.

A method for introducing a sample or a reagent solution of the present invention is not especially limited except that a solution introducing structure, a micro fluidic device or a micro fluidic system of the present invention as described above is used.

Namely, one of a sample and a reagent solution is separately supplied into each the above-described 2 or more S/R side channels (3) so that a sample or a reagent solution is present (introduced) in each of the S/R side channels (3). Then the above-described a sample and/or a reagent solution is each moved (transferred) to the 2 D side channels (2) adjacent to each S/R side channel in an axis direction, and said sample and/or said reagent solution is made present (introduced) in said S/R side channels (3), said 2 D side channels (2) and the first channel region between said 2 D side channels (2). By this procedure, a sample and a reagent solution are arranged as each independent (separate) zone in the first channel.

In this connection, a method for moving (transferring) a sample and/or a reagent solution present (introduced) in S/R side channel (3), to adjacent 2 D side channels (2), in other words, a method for introducing a sample and/or a reagent solution from S/R side channel (3), to the first channel (1), is not especially limited, and a method for moving (transferring) and introducing, known itself, can be used. As such a method, for example, a method for moving (transferring) and introducing a sample and/or a reagent solution into the first channel (1) electrically by application of voltage onto S/R side channels (3) [or an access port or a S/R reservoirs (5)]; a method for moving (transferring) and introducing a sample and/or a reagent solution into the first channel (1) by pressurization inside the S/R side channel (3) and/or by depressurization inside the D side channels (2); a method for moving (transferring) and introducing a sample and/or a reagent solution into the first channel (1) by using capillary phenomenon are included.

In addition, a method for making a sample and/or a reagent solution present (introducing a sample and/or a reagent solution) in the S/R side channels (3) is also not especially limited, and generally, it is carried out by the above-described method for moving (transferring) after dropping (putting) a sample or a reagent solution into the above-described access port or a S/R reservoir (5) connecting to the S/R side channels (3).

(1) A Specific Step

Specifically, a method for introducing a sample or a reagent solution of the present invention is, for example, one comprising the following steps:

(a) providing a micro fluidic device comprising at least one structure for introducing a sample or a reagent solution to a first channel (1) in a substrate, said the structure comprising;
  (i) the first channel (1);
  (ii) not less than 3 D side channels (2), each said D side channel (2) having a opening (2-1) opened on a wall of said first channel (1), and said openings (2-1) arranged in spaced relation to one another, wherein said D side channel (2) is connected to a W reservoir (4); and
  (iii) not less than 2 S/R side channels (3), each said S/R side channel (3) having a opening (3-1) opened on the wall of said first channel (1) at the different position (part) from said openings (2-1) of said D side channels (2), and each said opening (3-1) arranged between adjacent 2 openings (2-1) of D side channels (2), wherein each said opening (3-1) of these not less than 2 S/R side channels (3) are each arranged at the different portion between adjacent 2 openings (2-1) of D side channels (2), and S/R side channel (3) is connected to a S/R reservoir (5)[(a): a preparation step];

(b) putting a sample into at least one S/R reservoir (5) connecting to said S/R side channel (3);

(c) putting a reagent solution into at least one S/R reservoir (5) connecting to said S/R side channel (3), wherein said S/R reservoir (5) being different from one used in said step (b);

(d) introducing said sample in said S/R side channel (3) connected with said S/R reservoir (5) used in said step (b), 2 D side channels (2) adjacent to said S/R side channel (3) in an axis direction and a first channel region between said 2 D side channels (2), by moving said sample from said S/R reservoir (5) where said sample is put in said step (b) to said 2 D side channels (2) adjacent to said S/R side channel (3) connected with said S/R reservoir (5) in an axis direction, via said S/R side channel (3) connected with said S/R reservoir (5); and (e) introducing said reagent solution in said S/R side channel (3) connected with said S/R reservoir (5) used in said step (c), 2 D side channels (2) adjacent to said S/R side channel (3) in an axis direction and a first channel region between said 2 D side channels (2), by moving said reagent solution from said S/R reservoir (5) where said reagent solution is put in said step (c) to said 2 D side channels (2) adjacent to said S/R side channel (3) connected with said S/R reservoir (5) in an axis direction, via said S/R side channel (3) connected with said S/R reservoir (5) [(b) to (e): a introduction step].

In the above description, order of carrying out the steps (b) and (c) is not especially limited, and either of these steps may be carried out first or may simultaneously be carried out.

In addition, order of carrying out the steps (d) and (e) is not especially limited, however, usually these steps are simultaneously carried out.

In this connection, in the above description, embodiments, specific examples, preferable examples, and the like of a solution introducing structure, a micro fluidic device or a micro fluidic system of the present invention used in the preparation step (step (a)) are as described above. Generally, those usually having reservoirs (S/R reservoir, W reservoir) and/or access ports are used.

Introduction of a sample and/or a reagent solution is explained below in the case of pressurization and/or depressurization inside a channel.

The case of introducing 2 kinds of solutions (for example, a sample and a reagent solution) is explained in accordance with FIG. 25.

In the case of introducing solutions by pressurization, required force is applied, as appropriate, onto the first channel region (1b) at the downstream of a opening of a D side channel (2c) located at the most downstream side, the first channel region (1a) at the upstream of a opening of a D side channel (2a) located at the most upstream side, and 2 S/R side channels (3a and 3b). In addition, in the case of introducing solutions by depressurization, required force is depressurized, as appropriate, from 3 D side channels (2a, 2b and 2c).

By the above-described pressurization or depressurization, as shown in FIG. 8(a), the first sample or reagent solution supplied into the first S/R side channel (3a) passes through a crossing part between the first S/R side channel (3a) and the first channel (1), and further passes through each 2 crossing parts of a crossing part between the first channel (1) and the first D side channel (2a) and a crossing part between the first channel and the second D side channel (2b), and is transported to the first D side channel (2a) and the second D side channel (2b). The second sample or reagent solution supplied into the second S/R side channel (3b) passes through a crossing part between the second S/R side channel (3b) and the first channel (1), and further passes through each 2 crossing parts of a crossing part between the first channel (1) and the second D side channel (2b) and a crossing part between the first channel (1) and the third D side channel (2c), and is transported to the second D side channel (2b) and the third D side channel (2c). Then, as shown in FIG. 8(b), the first sample or reagent solution arranged at a part of the first channel (1) formed (sandwiched) by the opening (2-1a) of the first D side channel (2a) and the opening (2-1b) of the second D side channel (2b), and the second sample or reagent solution arranged at a part of the first channel (1) formed (sandwiched) by the opening (2-1b) of the second D side channel (2b) and the opening (2-1c) of the third D side channel (2c) are each transported to downstream side along the first channel. In this connection, into a first D side channel (2a) positioned at the most upstream side, not only the first sample or reagent solution but also an electrophoresis medium present in the first channel region further upstream than the first channel part wherein said opening (2-1a) of the first D side channel (2a) positioned at the most upstream opens may be received (flowed in). In addition, into a third D side channel (2c) positioned at the most downstream side, not only the second sample or reagent solution but also an electrophoresis medium present in the first channel region further downstream than the first channel part wherein said opening (2-1c) of the third D side channel (2c) positioned at the most downstream opens may be received (flowed in).

The case of introducing 3 kinds of solutions (for example, a sample and 2 kinds of reagent solutions) is explained in accordance with FIG. 26.

In the case of introducing solutions by pressurization, required force is applied, as appropriate, onto the first channel region (1b) at the downstream of a opening of a D side channel (2c) located at the most downstream side, the first channel region (1a) at the upstream of a opening of a D side channel (2a) located at the most upstream side, and 3 S/R side channels (3a, 3b and 3c). In addition, in the case of introducing solutions by depressurization, required force is depressurized, as appropriate, from 4 D side channels (2a, 2b, 2c and 2d).

By the above-described pressurization or depressurization, as shown in FIG. 10(a), the first sample or reagent solution supplied into the first S/R side channel (3a) passes through a crossing part between the first S/R side channel (3a) and the first channel (1), and further passes through each 2 crossing parts of a crossing part between the first channel (1) and the first D side channel (2a) and a crossing part between the first channel and the second D side channel (2b), and is transported to the first D side channel (2a) and the second D side channel (2b). The second sample or reagent solution supplied into the second S/R side channel (3b) passes through a crossing part between the second S/R side channel (3b) and the first channel (1), and further passes through each 2 crossing parts of a crossing part between the first channel (1) and the second D side channel (2b) and a crossing part between the first channel (1) and the third D side channel (2c), and is transported to the second D side channel (2b) and the third D side channel (2c). In addition, the third sample or reagent solution supplied into the third S/R side channel (3c) passes through a crossing part between the third S/R side channel (3c) and the first channel (1), and further passes through each 2 crossing parts of a crossing part between the first channel (1) and the third D side channel (2c) and a crossing part between the first channel (1) and the fourth D side channel (2d), and is transported to the third D side channel (2c) and the fourth D side channel (2d). Then, as shown in FIG. 10(b), the first sample or reagent solution arranged at a part of the first channel (1) formed (sandwiched) by the opening (2-1a) of the first D side channel (2a) and the opening (2-1b) of the second D side channel (2b), the second sample or reagent solution arranged at a part of the first channel (1) formed (sandwiched) by the opening (2-1b) of the second D side channel (2b) and the opening (2-1c) of the third D side channel (2c), and the third sample or reagent solution arranged at a part of the first channel (1) formed (sandwiched) by the opening (2-1c) of the third D side channel (2c) and the opening (2-1d) of the fourth D side channel (2d) are each transported to downstream side along the first channel. In this connection, into a first D side channel (2a) positioned at the most upstream side, not only the first sample or reagent solution but also an electrophoresis medium present in the first channel region further upstream than the first channel part wherein said opening (2-1a) of the first D side channel (2a) positioned at the most upstream opens may be received (flowed in). In addition, into a fourth D side channel (2d) positioned at the most downstream side, not only the third sample or reagent solution but also an electrophoresis medium present in the first channel region further downstream than the first channel part wherein said opening (2-1d) of the fourth D side channel (2d) positioned at the most downstream opens may be received (flowed in).

In the above description, force (pressure) to be applied (pressurization or depressurization) may be any level as long as enough to introduce specified a sample or a reagent solution into the first channel, and suitably be selected in a range usually used in this field. In addition, force (pressure) to be applied (pressurization or depressurization) depends on property of a sample or a reagent solution to be introduced and shape of a channel (the first channel, a D side channel, a S/R side channel, and the like), and may be the same or different at each application part.

5. Sample and Reagent Solution

In the present invention, a sample or a reagent solution is a solution as described later, and "2 or more kinds of a sample and/or a reagent solution" mean a plurality of solutions suitably selected from such a sample or a reagent solution.

(1) Sample

As a sample in the present invention, usually a solution containing an analyte or an analogue thereof (an analyte, a sample, an analogue, and a solution containing an analyte or an analogue) is included as shown below.

(a) Analyte

An analyte in the present invention includes, for example, a nucleotide chain (an oligonucleotide chain and a polynucleotide chain, etc.); a chromosome; a peptide chain (C-peptide and angiotensin I, etc.), protein [procalcitonin, immunoglobulin A (IgA), immunoglobulin E (IgE), immunoglobulin G (IgG), immunoglobulin M (IgM), immunoglobulin D (IgD), $\beta_2$-microglobulin, albumin, decomposition product thereof, and serum protein such as ferritin, etc.]; enzyme [an amylase (pancreatic type, salivary gland type and X-type, etc.), an alkaline phosphatase (hepatic, osseous, placental and small intestinal, etc.), an acid phosphatase (PAP, etc.), a γ-glutamyl transferase (renal, pancreatic and hepatic, etc.), a lipase (pancreatic type and gastric type, etc.), a creatine kinase (CK-1, CK-2 and mCK, etc.), a lactate dehydrogenase (LDH1 to LDH5, etc.), a glutamate oxaloacetate transaminase (ASTm and ASTs, etc.), a glutamate-pyruvate transaminase (ALTm and ALTs, etc.), a choline esterase (ChE1 to ChE5, etc.), a leucine aminopeptidase (C-LAP, AA and CAP, etc.), renin, a protein kinase and a tyrosine kinase, etc.]; microorganism such as bacteria (tuberculosis bacteria, pneumococcal organisms, diphtheria organisms, meningococcus, gonococcus, *staphylococcus, streptococcus*, enteric bacteria, coliform bacillus and *Helicobacter pylori*, etc.), viruses (rubella virus, herpes virus, hepatitis virus, ATL virus, AIDS virus, influenza virus, adenovirus, enterovirus, poliovirus, EB virus, HAV, HBV, HCV, HIV and HTLV, etc.), fungus (candida and *Cryptococcus*, etc.), spirochete (leptospire, *Treponema pallidum*, etc.), chlamydia and mycoplasma; protein, a peptide or a carbohydrate antigen derived from said microorganisms; various allergen causative of bronchospasm, allergic rhinitis and atopic dermatitis, etc. (allergen derived from the house dust, mites such as *Dermatophagoides farinae* and *Dermatophagoides pteronyssinus*, etc., pollen from cedar, cypress, *Pasupalum thunbergii*, ragweed, timothy, sweet vernal grass and rye, etc., an animal such as a cat, a dog or a crab, etc., food such as rice and egg white, etc., fungus, insect, wood, drug or chemical substance, etc.); lipids (lipoprotein, etc.); protease (trypsin, plasmin and serine protease, etc.); protein antigen tumor marker (PSA, PGI and PGII, etc.); a carbohydrate antigen [AFP (L1 to L3, etc.), hCG (hCG family, etc.), transferrin, IgG, thyroglobulin, Decay-accelerating factor (DAF), carcinoembryonic antigen (CEA, NCA, NCA-2 and NFA, etc.), CA19-9, PIVKA-II, CA125, prostate-specific antigen, a carbohydrate antigen tumor marker having a particular carbohydrate (sugar) chain produced by cancer cell and an ABO carbohydrate antigen, etc.]; carbohydrate (sugar) chain [hyaluronic acid, β-glucan and carbohydrate (sugar) chain contained in the above-described carbohydrate antigen, etc.]; a carbohydrate (sugar) chain binding protein (hyaluronic acid binding protein and β-glucan binding protein, etc.); lectin (concanavalin A, lentil lectin, kidney bean lectin, thorn apple lectin and wheat germ lectin, etc.); phospholipid (cardiolipin, etc.); lipopolysaccharide (endotoxin, etc.); chemical substances (hormones such as PTH, T3, T4, TSH, insulin, LH, FSH and prolactin, etc., an endocrine-disturbing chemicals such as tributyltin, nonyl phenol, 4-octyl phenol, di-n-butyl phthalate, dicyclohexyl phthalate, benzophenone, octachlorostyrene and di-2-ethylhexyl phthalate, etc.); a receptor (receptor for estrogen and TSH, etc.); a ligand (estrogen and TSH, etc.); and antibodies thereto, and the like.

Among the above-described, the method of the present invention is useful for analysis (quantitative determination) of glycoprotein having different carbohydrate (sugar) chain structure, a nucleotide chain (oligonucleotide chain and polynucleotide chain) and a peptide chain (including polypeptide), is especially useful for glycoprotein having different carbohydrate (sugar) chain structure. In this connection, as the carbohydrate (sugar) chain structure is known to be changed in a particular disease such as cancer, and reported its usefulness in the clinical laboratory (clinical chemistry), the glycoprotein having different carbohydrate (sugar) chain structure can be reassessed for its usefulness in the clinical laboratory (clinical chemistry) using the method of the present invention. In addition, the separation of a mutant type generated by minute mutation or substitution, etc. of a nucleotide chain (an oligonucleotide chain or a polynucleotide chain) or a peptide chain (including polypeptide), etc. from the wild type has been considered as an important analytical target in the field of molecular biology and molecular clinical laboratory (clinical chemistry), and therefore, by analyzing (determining quantity) these mutant type and/or wild type using the method of the present invention, the possibility of finding out some valuable factors and the like in the clinical laboratory (clinical chemistry) will be increased.

(b) Sample Containing Analyte

A sample containing an analyte of the present invention described above may be exemplified by the followings: samples derived from biological origin including body fluid such as serum, plasma, spinal fluid, synovial fluid, lymph fluid, etc., excretions such as urine, faces, etc., expectoration, purulent matter, dermal exfoliation, environmental samples such as food, beverage, tap water, seawater, water of lakes and marshes, river water, factory waste water, washings for semi-conductors, washings after washing of medical instruments, etc.; and their processed products reconstituted by dissolving in water or a buffer usually used in this field such as Tris buffer, phosphate buffer, Veronal buffer, borate buffer, Good's buffer, etc. In this connection, a sample relevant to the present invention encompasses one containing an analytes as described above produced by chemical synthesis.

(c) Analogue [an Analogue Labeled with a Labeling Substance, and an Analogue Bound with a Substance Capable of Changing Electrophoretic Mobility of an Analyte or an Analogue Thereof]

An analogue used in the present invention is a substance to which a CFS, binding to a target analyte for analysis in a sample, is bindable. In other words, an analogue is a substance having the same binding site as the binding site present in an analyte in said sample to which a CFS is bindable.

Such a substance includes, for example, the same one as an analyte in a sample, a target of an analysis; one wherein apart of structure of an analyte in a sample is modified, altered, denatured, removed, etc. (so-called an analogue); and the like. Examples of a substance are, for example, recombinant protein introduced with partial mutation at an analyte in a sample, a target of an analysis; peptide with partially modified peptide sequence of an analyte in a sample, a target of an analysis; a nucleotide chain with partially modified nucleotide sequence of an analyte in a sample, a target of an analysis; and the like. In this connection, specific examples of an analyte in a sample, a target of an analysis, are as described above.

In this connection, an analogue labeled with a labeling substance (hereinafter may be abbreviated as a labeled analogue) and an analogue bound with a substance capable of changing electrophoretic mobility of an analyte or an analogue thereof (hereinafter may be abbreviated as a reaction improvement analogue) used in the present invention are ones wherein a labeling substance or a substance capable of changing electrophoretic mobility of an analyte or an analogue thereof (hereinafter may be abbreviated as a reaction improvement substance) is bound to the above described substances, and specific examples and preferable embodiments of a labeling substance and a reaction improvement substance are as described later. In addition, a method for binding a labeling substance or a reaction improvement substance to the above-described substances may be in accordance with a similar method to a method for binding between a reaction improvement substance and a CFS or a method for labeling a CFS by a labeling substance, to be described later.

Use amount of an analogue (a labeled analogue or a reaction improvement analogue) is not simply described because of dependency on kinds of an analogue (a labeled analogue or a reaction improvement analogue) to be used, or kinds or use concentration of a CFS, and the like.

In more specifically, an analogue (a labeled analogue or a reaction improvement analogue) may be contained in a solution (for example, a solution containing an analyte and an analogue, a solution containing an analogue, a solution containing an analogue and a CFS), so that use amount of an analogue (a labeled analogue or a reaction improvement analogue) in a solution as described above is, as lower limit, usually not lower than 10 μM, preferably not lower than 1 nM and more preferably not lower than 100 nM, and as an upper limit, usually not higher than 10 μM, preferably not higher than 1 μM and more preferably not higher than 500 nM.

(d) Solution Containing Analyte or Analogue

"A solution containing an analyte or an analogue" in the present invention means a solution including an analyte (a sample including the analyte) or an analogue (a labeled analogue or a reaction improvement analogue) of the present invention, as described above.

Such a solution includes (a) a sample itself including an analyte, as described above, (b) a solution including a sample having an analyte and not less than one kind of CFSs (in other words, a solution including a complex between an analyte and not less than one kind of CFSs), (c) a solution containing an analogue (a labeled analogue or a reaction improvement analogue), (d) a solution including a sample having an analyte and an analogue (a labeled analogue or a reaction improvement analogue) (in other words, a solution including an analyte and an analogue), (e) a solution containing an analogue (a labeled analogue or a reaction improvement analogue) and not less than one kind of CFSs (in other words, a solution including a complex between an analogue and not less than one kind of CFSs), (f) a solution including a sample having an analyte, an analogue (a labeled analogue or a reaction improvement analogue) and not less than one kind of CFSs, and the like.

In this connection, as the above solution (b) or (e), for example, when 2 or more kinds of CFSs are used in the present invention, a solution containing a complex (an intermediate complex) between a part of CFSs among all of CFSs finally binding with an analyte or an analogue thereof (apart of the whole CFSs), and an analyte or an analogue thereof, in other words, a solution containing a complex (an intermediate complex) between CFS (s) fewer than CFSs composing a finally formed complex between an analyte or an analogue thereof and 2 or more kinds of CFSs, and an analyte or an analogue thereof is specifically included.

Namely, for example, when 2 kinds of CFSs are used, it is a solution containing a complex (an intermediate complex) between one kind of a CFS and an analyte or an analogue thereof. And for example, when 3 kinds of CFSs are used, it is a solution containing a complex (an intermediate complex) between one kind of a CFS and an analyte or an analogue thereof, and a solution containing a complex (an intermediate complex) between 2 kinds of CFSs and an analyte or an analogue thereof. (In this case, also when 4 or more kinds of CFSs are used, a way of thinking is the same as in theses cases.)

In more specifically, for example, as will be described later, when a CFS not bound with a labeling substance and a reaction improvement substance, and a CFS having property capable of forming a complex between an analyte or an analogue thereof and the substance, and capable of changing electrophoretic mobility of an analyte or an analogue thereof (hereinafter may be abbreviated as a reaction improvement CFS) are used in combination as a CFS, a solution containing a complex (an intermediate complex) between an analyte and said CFS, and a solution containing a complex (an intermediate complex) between an analyte and a reaction improvement CFS correspond to a solution (b) as described above; and when a CFS having property capable of forming a complex between an analyte or an analogue thereof and the substance, and labeled with a labeling substance (hereinafter may be abbreviated as a labeled CFS) and a reaction improvement CFS are used in combination as a CFS, a solution containing a complex (an intermediate complex) between an analyte and a labeled CFS, and a solution containing a complex (an intermediate complex) between an analyte and a reaction improvement CFS correspond to a solution (b) as described above. In addition, when a CFS not bound with a labeling substance and a reaction improvement substance, and a CFS labeled by a labeling substance, having property capable of forming a complex between an analyte or an analogue thereof and the substance, and capable of changing electrophoretic mobility of an analyte or an analogue thereof (hereinafter may be abbreviated as a labeled reaction improvement CFS) are used in combination as a CFS, a solution containing a complex (an intermediate complex) between an analyte and said CFS, and a solution containing a complex (an intermediate complex) between an analyte and a labeled reaction improvement CFS correspond to a solution (b) as described above.

In this connection, in the above description, usually, a solution including a sample having an analyte, and not less than one kind of CFSs is generally a reaction solution obtained by suitably mixing a sample including an analyte as described above (a CFS is not included) and a solution including a CFS as will be described later.

The above solution (e) includes, in more specifically, for example, when a labeled analogue or a reaction improvement analogue is used, and when 2 or more kinds of CFSs are used, a solution containing, similarly as described above, a complex (an intermediate complex) between a part of CFSs among all of CFSs finally binding with a labeled analogue or a reaction improvement analogue (a part of the whole CFSs), and a labeled analogue or a reaction improvement analogue, in other words, a solution containing a complex (an intermediate complex) between CFS (s) fewer than CFSs composing a finally formed complex between a labeled analogue or a reaction improvement analogue and 2 or more kinds of CFSs, and a labeled analogue or a reaction improvement analogue. In this connection, in the above description, usually, a solution containing an analogue (a labeled analogue or a reaction improvement analogue) is generally a reaction solution obtained by suitably mixing a solution including a labeled analogue or a reaction improvement analogue, and a solution including a CFS as will be described later.

In addition, as the above solution (d), for example, a solution containing an analyte in a sample, and an analogue labeled with a labeling substance (a labeled analogue) or an analogue bound with a reaction improvement substance (a reaction improvement analogue) is included. In this connection, a solution including a sample having an analyte and an analogue is usually and generally a mixed solution obtained by suitably mixing a sample including an analyte (a CFS is not contained) and a solution including an analogue.

As the above solution (f), in more specifically, for example, when a labeled analogue or a reaction improvement analogue is used, and when 2 or more kinds of CFSs are used, a solution containing, similarly as described above, a complex (an intermediate complex) between a part of CFSs among all of CFSs finally binding with an analyte and/or a labeled analogue (or a reaction improvement analogue), and an analyte and/or a labeled analogue (or a reaction improvement analogue) (a part of the whole CFSs), in other words, a solution containing a complex (an intermediate complex) between CFS(s) fewer than CFSs composing a finally formed complex between an analyte and/or a labeled analogue (or a reaction improvement analogue) and 2 or more kinds of CFSs, and an analyte and/or a labeled analogue (or a reaction improvement analogue). In this connection, a solution including a sample having an analyte, an analogue (a labeled analogue or a reaction improvement analogue) and not less than one kind of CFSs is usually and generally a reaction solution obtained by suitably mixing a sample having an analyte as described above, a solution containing a labeled analogue or a reaction improvement analogue, and at least one kind of solution containing not less than one kind of CFS.

In the above description, (a) a sample including an analyte is as described above. In addition, as a solution to be used for containing an analyte, an analogue, and the like in solutions (b) to (f), any one is used as long as not to inhibit formation of a complex between an analyte and a CFS, and/or a complex between an analogue (a labeled analogue or a reaction improvement analogue) and a CFS, and for example, water, a buffer solution, and the like are included.

As such a buffer solution, one having buffer action at a pH range of usually 5 to 11, and usually used in this field is included. Examples of the buffer solution include Tris buffer, Good's buffer, TE buffer, TAE buffer, TBE buffer, TBS buffer, a phosphate buffer, a borate buffer, and the like, and use concentration thereof is usually in a range of 1 mM to 2 M, and preferably 10 mM to 1 M, and pH is usually 5 to 11, preferably 5 to 10, more preferably 5.5 to 8.5, further preferably 6 to 8 and particularly preferably around 7.

(2) Reagent Solution

As a reagent solution in the present invention, usually as will be described below, a solution containing a CFS is included, but not limited thereto.

(a) CFS and a Solution Containing Thereof

In the present invention, "a substance formable a complex with an analyte or an analogue thereof (CFS)" means a substance having a property capable of forming a complex between a analyte or an analogue thereof and the CFS, namely, a complex containing the analyte or the analogue thereof and the CFS as constituent by binding with an analyte or the analogue thereof as the above described, or by binding with the analyte or the analogue thereof through other CFS.

Such CFS means the substance which binds with an analyte or an analogue thereof by interaction such as an "antigen"-"antibody" reaction, a "carbohydrate (sugar) chain"-"protein" reaction, "carbohydrate (sugar) chain"-"lectin" reaction, "enzyme"-"inhibitor" reaction, "protein"-"peptide chain" reaction or "chromosome or nucleotide chain"-"nucleotide chain" reaction, and the like. When one of the substances in the above-mentioned pairs is the analyte or the analogue thereof, the other is the CFS. For example, when an analyte or an analogue thereof is an "antigen", a CFS is an "antibody", and when an analyte or an analogue thereof is an "antibody", a CFS is an "antigen" (the same applied to the above other pairs). In more specifically, such a substance includes, for example, a nucleotide chain (an oligonucleotide chain and a polynucleotide chain, etc.); a chromosome; a peptide chain (C-peptide and angiotensin I, etc.), protein [procalcitonin, immunoglobulin A (IgA), immunoglobulin E (IgE), immunoglobulin G (IgG), immunoglobulin M (IgM), immunoglobulin D (IgD), $\beta_2$-microglobulin, albumin, decomposition product thereof, and serum protein such as ferritin, etc.]; enzyme [an amylase (pancreatic type, salivary gland type and X-type, etc.), an alkaline phosphatase (hepatic, osseous, placental and small intestinal, etc.), an acid phosphatase (PAP, etc.), a γ-glutamyl transferase (renal, pancreatic and hepatic, etc.), a lipase (pancreatic type and gastric type, etc.), a creatine kinase (CK-1, CK-2 and mCK, etc.), a lactate dehydrogenase (LDH1 to LDH5, etc.), a glutamate oxaloacetate transaminase (ASTm and ASTs, etc.), a glutamate-pyruvate transaminase (ALTm and ALTs, etc.), a choline esterase (ChE1 to ChE5, etc.), a leucine aminopeptidase (C-LAP, AA and CAP, etc.), renin, a protein kinase and a tyrosine kinase, etc.]; microorganism such as bacteria (tuberculosis bacteria, pneumococcal organisms, diphtheria organisms, meningococcus, gonococcus, *staphylococcus, streptococcus*, enteric bacteria, coliform bacillus and *Helicobacter pylori*, etc.), viruses (rubella virus, herpes virus, hepatitis virus, ATL virus, AIDS virus, influenza virus, adenovirus, enterovirus, poliovirus, EB virus, HAV, HBV, HCV, HIV and HTLV, etc.), fungus (candida and *Cryptococcus*, etc.), spirochete (leptospire, *Treponema pallidum*, etc.), chlamydia and mycoplasma; protein, a peptide or a carbohydrate antigen derived from said microorganisms; various allergen causative of bronchospasm, allergic rhinitis and atopic dermatitis, etc. (allergen derived from the house dust, mites such as *Dermatophagoides farinae* and *Dermatophagoides pteronyssinus*, etc., pollen from cedar, cypress, *Pasupalum thunbergii*, ragweed, timothy, sweet vernal grass and rye, etc., an animal such as a cat, a dog or a crab, etc., food such as rice and egg white, etc., fungus, insect, wood, drug or chemical substance, etc.); lipids (lipoprotein, etc.); protease (trypsin, plasmin and serine protease, etc.); protein antigen tumor marker (PSA, PGI and PGII, etc.); a carbohydrate antigen [AFP (L1 to L3, etc.), hCG (hCG family, etc.), transferrin, IgG, thyroglobulin, Decay-accelerating factor (DAF), carcinoembryonic antigen (CEA, NCA, NCA-2 and NFA, etc.), CA19-9, PIVKA-II, CA125, prostate-specific antigen, a carbohydrate antigen tumor marker having a particular carbohydrate (sugar) chain produced by cancer cell and an ABO carbohydrate antigen, etc.]; carbohydrate (sugar) chain [hyaluronic acid, β-glucan and carbohydrate (sugar) chain contained in the above-described carbohydrate antigen, etc.]; a carbohydrate (sugar) chain binding protein (hyaluronic acid binding protein and β-glucan binding protein, etc.); lectin (concanavalin A, lentil lectin, kidney bean lectin, thorn apple lectin and wheat germ lectin, etc.); phospholipid (cardiolipin, etc.); lipopolysaccharide (endotoxin, etc.); chemical substances (hormones such as PTH, T3, T4, TSH, insulin, LH, FSH and prolactin, etc., an endocrine-disturbing chemicals such as tributyltin, nonyl phenol, 4-octyl phenol, di-n-butyl phthalate, dicyclohexyl phthalate, benzophenone, octachlorostyrene and di-2-ethylhexyl phthalate, etc.); a receptor (receptor for estrogen and TSH, etc.); a ligand (estrogen and TSH, etc.); and antibodies thereto, and the like. In this connection, the antibody used in the present invention encompasses a decomposition product such as Fab and $F(ab')_2$ fragments and the like produced by degradation with a proteolytic enzyme (proteinase, etc.) such as papain or pepsin or by chemical degradation.

The CFS described above may be used alone or in combination with two or more kinds.

In this connection, when two or more kinds of the CFSs are used in combination (together), the binding site of each CFS is not especially limited as long as two or more kinds of the CFSs can form a complex with an analyte or an analogue thereof. The binding sites to be bound by such CFSs include, for example, a case when all of binding sites to be bound by two or more of the CFSs are present on the analyte or the analogue thereof [binding form (1)]; a case when the binding site to be bound by at least one kind of the CFS (for example, CFS A) among two or more of the CFSs is present only on the analyte or the analogue thereof, and the binding site to be bound by another at least one kind of the CFS (for example, complex binding substance B) is present on a site newly generated by the formation of a complex between an analyte or an analogue thereof and the CFS A [binding form (2)]; and a case when the binding site to be bound by at least one kind of the CFS (for example, CFS A) among two or more of the CFSs is present only on the analyte or the analogue thereof, and the binding site to be bound by another at least one kind of the CFS (for example, CFS B) is present only on the CFS A [binding form (3)]. Among these, it is preferable that the binding sites to be bound by each two or more of the CFSs are different. In this connection, in binding form (2), the substance having property to specifically binding to a newly generated site (a CFS) includes, for example, an antibody, a peptide chain and a nucleotide chain, and the like, which can recognize a complex between an analyte or an analogue thereof and a CFS, and capable of binding thereto are included.

As a CFS as described above, one which binds with an analyte or an analogue thereof by an "antigen"-"antibody" reaction or a "carbohydrate (sugar) chain"-"protein" reaction is preferable. Specifically, an antibody to an analyte or an analogue thereof, or an antigen bound with an analyte or an analogue thereof, or protein binding to an analyte or an analogue thereof is preferable, an antibody to an analyte or an analogue thereof, or protein binding to an analyte or an analogue thereof is more preferable.

A CFS as described above may be bound with a labeling substance and/or a substance capable of changing electrophoretic mobility (hereinafter, abbreviated as a reaction improvement substance) of an analyte or an analogue thereof and may result in (1) a CFS having property capable of forming a complex with an analyte or an analogue thereof and capable of changing electrophoretic mobility of an analyte or an analogue thereof (hereinafter, abbreviated as a reaction improvement CFS or a reaction improvement CFS), (2) a CFS having property capable of forming a complex with an analyte or an analogue thereof and labeled with a labeling substance (a labeled CFS), and (3) a CFS labeled with a labeling substance, having property capable of forming a complex with an analyte or an analogue thereof and capable of changing electrophoretic mobility of an analyte or an analogue thereof (a labeled reaction improvement CFS).

By using a CFS bound with a reaction improvement substance, electrophoretic mobility of a CFS can be changed, and arrangement order of a solution containing an analyte or an analogue thereof, and at least one kind of solution including not less than one kind of CFS, can arbitrarily be controlled, and efficiency in concentration of an analyte or an analogue thereof and/or a CFS, and a reaction of an analyte or an analogue thereof and a CFS (a complex formation reaction) can be enhanced.

In addition, by using a CFS bound with a labeling substance, an analyte in a sample can be measured (detected).

(a-1) A Reaction Improvement CFS

A reaction improvement CFS is one having property capable of forming a complex between an analyte or an analogue thereof and the substance, and capable of changing electrophoretic mobility of an analyte or an analogue thereof, in other words, one having property capable of generating difference in behavior (electrophoretic mobility) of said analyte or analogue thereof corresponding to electrophoresis operation by forming a complex with an analyte or an analogue thereof, and one capable of making electrophoretic mobility of a complex between an analyte or an analogue thereof and a reaction improvement CFS (or a complex between an analyte or an analogue thereof and a CFS other than a reaction improvement CFS) higher or lower than electrophoretic mobility (faster or slower than electrophoretic mobility) of an analyte or an analogue thereof itself (an analyte or an analogue thereof not bound with a reaction improvement CFS).

As such a reaction improvement CFS, the above-described CFSs bound with the following reaction improvement substances are general: For example, an inorganic metal oxide such as silica and alumina, etc.; a metal such as gold, titanium, iron and nickel, etc.; an inorganic metal oxide introduced with a functional group by an operation such as silane coupling treatment, etc.; organisms such as various microorganisms and eukaryote cells, etc.; polysaccharide such as agarose, cellulose and insoluble dextran, etc.; synthetic polymer compounds such as polystyrene latex, a styrene-butadiene copolymer, a styrene-methacrylic acid copolymer, an acrolein-ethyleneglycol dimethacrylate copolymer, styrene-styrenesulfonic acid latex, polyacrylamide, polyglycidyl methacrylate, polyacrolein coated particles, crosslinked polyacrylonitrile, acrylic acid or acrylate ester-based polymers, an acrylonitrile-butadiene copolymer, a vinyl chloride-acrylate ester copolymer and a poly vinyl acetate-acrylate copolymer, etc.; biomolecules such as erythrocyte, sugar, nucleic acid (polynucleotide such as RNA, DNA), protein, polypeptide and polyamino acid (polyglutamic acid, polyaspartic acid, polylysine, etc.); lipids; and the like.

However, for example, a reaction improvement substance may be bound to an analyte or an analogue thereof by a chemical binding method such as a method for introducing a functional group at the surface of a reaction improvement substance and subsequently binding to an analyte or an analogue thereof via this functional group; by a method for binding between a reaction improvement substance and an analyte or an analogue thereof via a linker; and the like. In this connection, in the above description, a reaction improvement substance is one having property capable of providing property as a reaction improvement CFS as described above to said CFS, by binding to a CFS. Namely, a reaction improvement substance is one having property capable of changing electrophoretic mobility of an analyte or an analogue thereof, in other words, one having property capable of generating difference in behavior (electrophoretic mobility) of said analyte or analogue thereof corresponding to electrophoresis operation, via a CFS, by forming a complex between an analyte or an analogue thereof and a CFS (or a complex among an analyte or an analogue thereof, a reaction improvement CFS and a CFS other than a reaction improvement CFS), and thus is capable of making electrophoretic mobility of a complex between an analyte or an analogue thereof and a reaction improvement CFS higher or lower than electrophoretic mobility (faster or slower than electrophoretic mobility) of an analyte or an analogue thereof itself or a complex between an analyte or analogue thereof not bound with a reaction improvement CFS and a CFS.

Among those, as a reaction improvement CFS, those obtained by binding nucleic acid (a nucleotide chain), protein, polypeptide or polyamino acid to a CFS as described above are preferable, and those obtained by binding nucleic acid (a nucleotide chain) or polyamino acid to a CFS are more preferable. In addition, as a reaction improvement substance, those including an antibody as a CFS are preferable, specifically, those obtained by binding nucleic acid (a nucleotide chain), protein, polypeptide or polyamino acid as a reaction improvement substance to an antibody as a CFS are preferable, and among others those obtained by binding nucleic acid (a nucleotide chain) or polyamino acid, as a reaction improvement substance, to an antibody as a CFS are particularly preferable.

To make binding of a reaction improvement substance to a CFS, namely, to prepare a reaction improvement CFS, any common method used in this field may be applied, for example, a known labeling method itself generally used in known EIA, RIA, FIA methods or a hybridization method themselves (for example, Ikagaku Jikken Koza (Experimental Manual in Medical Chemistry), vol. 8, edited by Yuichi Yamamura, $1^{st}$ Ed., Nakayama Shoten Co., Ltd., 1971; Zusetu (Illustrative Description) Fluorescent Antibodies, Akira Kawao, $1^{st}$ Ed., Softscience Co., Ltd., 1983; Enzyme Immunoassay, Eiji Ishikawa, Tadashi Kawai, Kiyoshi Miyai, $3^{rd}$ Ed., Igaku-Shoin Ltd., 1987; Molecular Cloning, A Laboratory Manual, $2^{nd}$ Ed., J. Sambrook, E. F. Fritsch, T. Maniatis, Cold Spring Harbor Laboratory Press; Handbook of Fluorescent Probe and Research Chemicals, $7^{th}$ Ed., Chapter 8, Molecular Probe Inc.; WO 2002/082083); or a common method utilizing a reaction between avidin (or streptavidin) and biotin.

In this connection, when a reaction improvement CFS is used as a CFS, combined use (parallel use) of a labeled CFS as described above is preferable. However, when a reaction improvement CFS itself is measurable (detectable) by any of a method, or enables to be labeled by a labeling substance, combined use of a labeled CFS is not necessary.

In addition, when a labeled CFS and a reaction improvement CFS are used in combination (are used parallely) as a CFS, and as long as a complex among 3 components of an analyte or an analogue thereof, a labeled CFS and a reaction improvement CFS, is formed, binding forms of these 3 components or binding sites of a labeled CFS and a reaction improvement CFS are not especially limited. Such binding forms include, for example, (1) so-called a sandwich complex wherein an analyte or an analogue thereof is sandwiched by a labeled CFS and a reaction improvement CFS, (2) a complex wherein a reaction improvement CFS or a labeled CFS is further bound at a binding site with an analyte or an analogue thereof and a labeled CFS or a reaction improvement CFS and (3) a complex wherein a reaction improvement CFS or a labeled CFS is further bound at a labeled CFS or a reaction improvement CFS bound with an analyte or an analogue thereof, and the like. In addition, said binding moieties include, for example, (1) the case when all of the binding sites of a labeled CFS and a reaction improvement CFS are present only on an analyte or an analogue thereof [binding form (1)], (2) the case when either of the binding sites of a labeled CFS or a reaction improvement CFS is present only on an analyte and an analogue thereof, and the other binding site is present at a new site generated by formation of a complex between an analyte and either of said labeled CFS and reaction improvement CFS [binding form (2)], (3) either of binding sites of a labeled CFS and a reaction improvement CFS is present only on an analyte or an analogue thereof, while the other binding site is present at only either of said labeled CFS and reaction improvement CFS [binding form (3)] and (4) the case of combinations thereof. Among those, a binding site of a labeled CFS, and a binding site of a reaction improvement CFS is preferably a different one. In this connection, in the above description (2), as one having property to specifically bind at a newly generated site (a labeled CFS and/or a reaction improvement CFS), for example, an antibody, a peptide chain, a nucleotide chain, and the like, which enable to recognize a complex between an analyte or an analogue thereof and a labeled CFS and/or a reaction improvement CFS, and bindable thereto are included.

(a-2) A Labeled CFS

A CFS as described above is generally one measurable (detectable) itself by any of a method, or enables to be labeled by a labeling substance. By using one having such property, an analyte or an analogue thereof in a sample can be measured (detected). In this connection, when an analyte or an analogue thereof itself is detectable by any of a method (for example, an enzyme, and the like), or an analyte or an analogue thereof is directly bindable to a labeling substance without using (not through) a CFS, an analyte or an analogue thereof in a sample can be measured (detected) even when said CFS may not have the above-described property. Examples of those detectable themselves by any of a method include an enzyme, a dye, a fluorescent substance, a luminescent substance, a substance having absorption at UV region, and the like.

Among those, as a CFS used in the present invention, a substance formable a complex with an analyte or an analogue thereof, and labeled by a labeling substance (a labeled CFS) is preferable.

As a labeling substance used in the present invention, any one used in this field such as an enzyme immunoassay (EIA), a radio immunoassay (RIA), a fluorescent immunoassay (FIA), a hybridization method, and the like, may be adopted. Such a labeling substance includes, for example, enzymes such as alkaline phosphatase (ALP), β-galactosidase (β-Gal), peroxidase (POD), microperoxidase, glucose oxidase (GOD), glucose-6-phosphate dehydrogenase (G6PDH), malate dehydrogenase and luciferase, etc.; dyes such as Coomassie brilliant blue R250, and methyl orange, etc.; radioactive isotopes such as $^{99m}$Tc, $^{131}$I, $^{125}$I, $^{14}$C, $^{3}$H, $^{32}$P and $^{35}$S, etc.; HiLyte type dyes such as HiLyte Fluor 488, HiLyte Fluor 555, HiLyte Fluor 647, HiLyte Fluor 680 and HiLyte Fluor 750, etc. (all of them are trade names of HiLyte Bioscience, Inc.); Alexa type dyes such as Alexa Fluor Dye 350, Alexa Fluor Dye 430, Alexa Fluor Dye 488, Alexa Fluor Dye 532, Alexa Fluor Dye 546, Alexa Fluor Dye 555, Alexa Fluor Dye 568, Alexa Fluor Dye 594, Alexa Fluor Dye 633, Alexa Fluor Dye 647, Alexa Fluor Dye 660, Alexa Fluor Dye 680, Alexa Fluor Dye 700 and Alexa Fluor Dye 750, etc. (all of them are trade names of Molecular Probes, Inc.); CyDye type dyes such as Cy3, Cy3.5, Cy5, Cy5.5 and Cy7, etc. (all of them are trade names of Amersham Biosciences, Inc.); fluorescent materials such as fluorescein, rhodamine, dansyl, fluorescamine, coumarin, naphthylamine, or derivatives thereof, rare-earth fluorescent dyes [combinations of a rare earth metal such as samarium (Sm), europium (Eu), terbium (Tb) or dysprosium (Dy) and a chelate compound such as 4,4'-bis (1",1",1",2",2",3",3"-heptafluoro-4",6"-hexanedione-6"-yl) chlorosulfo-O-terphenyl (BHHCT), 4,7-bis(chlorosulfonyl)-1,10-phenanthoroline-2,9-dicarboxylic acid (BCPDA), β-naphthyltrifluoroacetic acid (β-NTA), etc.], intercalator dyes [for example, acridine dyes such as acridine orange, etc.; ethidium compounds such as ethidium bromide, ethidium homodimer-1 (EthD-1), ethidium homodimer-2 (EthD-2), ethidium bromide monoazide (EMA) and dihydroethidium, etc.; iodine compounds such as propidium iodide, and hexidium iodide, etc.; 7-aminoactinomycin D (7-AAD); cyanine dimmer type dyes such as POPO-1, BOBO-1, YOYO-1, TOTO-1, JOJO-1, POPO-3, LOLO-1, BOBO-3, YOYO-3, and TOTO-3, etc. (all of them are trade names of Molecular Probes, Inc.); SYTOX type dyes such as SYBR Gold, SYBR Green I and SYBR Green II, SYTOX Green, SYTOX Blue, and SYTOX Orange, etc. (all of them are trade names of Molecular Probes, Inc.), and the like], one bound to a minor group of DNA double helix [for example, 4',6-diamidino-2-phenylindole (DAPI: trade name of Molecular Probes, Inc.), pentahydrate(bis-benzimido) (Hoechst 33258: trade name of Molecular Probes, Inc.), and trihydrochloride (Hoechst 33342: trade name of Molecular Probes, Inc.), etc.]; benzimido type dyes (Hoechst 34580: trade name of Molecular Probes, Inc.) and the like], one specifically bound to the sequence of adenine-thymine (A-T) [for example, acridine dyes such as 9-amino-6-chloro-2-methoxyacridine (ACMA), and bis(6-chloro-2-methoxy-9-acridinyl) spermine (acridine homodimer), etc., hydroxystilbamidine, and the like]; luminescent materials such as luciferin, isoluminal, luminal, and bis(2,4,6-trifluorophenyl)oxalate, etc.; material having absorption in ultra-violet region such as phenol, naphthol, anthracene, or derivatives thereof; substances having property as spin labeling agents represented by compounds having an oxyl group such as 4-amino-2,2,6,6-tetramethylpiperidine-1-oxyl, 3-amino-2,2,5,5-tetramethylpyrrolidine-1-oxyl, and 2,6-di-t-butyl-α-(3,5-di-t-butyl-4-oxo-2,5-cyclohexadine-1-ylidene)-p-tolyloxyl; and the like.

Labeling a CFS with a labeling substance may be carried out according to a method similar to a method for labeling a CFS with a labeling substance as described above, or a common method described in WO 2002/082083.

(a-3) A Labeled Reaction Improvement CFS

Furthermore, in the present invention, as a CFS, such a substance may also be used that is labeled by a labeling substance, formable a complex with an analyte or an analogue thereof, and capable of changing electrophoretic mobility of an analyte or an analogue thereof (a labeled reaction improvement CFS), namely, a reaction improvement CFS labeled by a labeling substance. In this connection, a labeling substance and a reaction improvement CFS are as described above, and also labeling a reaction improvement CFS with a labeling substance may be carried out according to a method similar to a method for labeling a CFS with a labeling substance as described above, or a common method described in WO 2002/082083.

(a-4) Combinations of CFSs

As described above, in the present invention, for example, the following various CFSs are used. In this connection, they may naturally be used in suitable combinations.

(a) A CFS not bound with a labeling substance and a reaction improvement substance
(b) A labeled CFS
(c) A reaction improvement CFS
(d) A labeled reaction improvement CFS
(e) A CFS not bound with a labeling substance and a reaction improvement substance and a reaction improvement CFS
(f) A labeled CFS and a reaction improvement CFS
(g) A CFS not bound with a labeling substance, and a reaction improvement substance, and a labeled reaction improvement CFS (a-5) A Solution Containing a CFS As a solution containing a CFS of the present invention, as described above, any one may be used as long as it does not inhibit formation of a complex between an analyte or an analogue thereof and said CFS. Such solution includes, for example, water, a buffer solution, and the like.

As such a buffer solution, any one may be used as long as it has buffer action usually in a pH range of 5 to 11, and does not inhibit formation of said complex formation reaction. Examples of the buffer solution are those usually used in this field such as Tris buffer, Good's buffer, TE buffer, TAE buffer, TBE buffer, TBS buffer, a phosphate buffer, a borate buffer, and the like. Use concentration of these buffers is usually 1 mM to 2 M, preferably 10 mM to 1 M, and pH is usually 5 to 11, preferably 5 to 10, more preferably 5.5 to 8.5, further preferably 6 to 8 and particularly preferably around 7. Concentration of a CFS contained in a solution as described above, namely use amount of a CFS is not simply described due to dependency on kinds of CFSs used, however, it is usually preferable that the CFS is present in the reaction solution (a solution containing an analyte or an analogue thereof and a CFS) at a concentration which is not lower than (preferably not lower than 2 times, more preferably not lower than 5 times) a concentration at which the CFS can bind to the whole of the analytes or analogues thereof of a concentration corresponding to the limit of measurement.

In addition, upper limit of the concentration is not especially limited, however, in view of economical efficiency, it is usually not higher than $10^{12}$ times (preferably not higher than $10^9$ times, more preferably not higher than $10^6$ times) a concentration at which the CFS can bind to the whole of the analytes or analogues thereof of a concentration corresponding to the limit of measurement.

In more specifically, a CFS may be contained in a solution as described above, so that concentration of a CFS in a solution containing an analyte or an analogue thereof and a CFS is, as lower limit, usually not lower than 10 pM, preferably not lower than 1 nM, and more preferably not lower than 100 nM, and as upper limit, usually not higher than 10 μM, preferably not higher than 1 μM and more preferably not higher than 500 nM.

(b) The Other Solutions

As the other solutions (reagent solutions), for example, liquids such as a solution containing a labeling substance, a solution containing reagents (an enzyme substrate, coupled enzymes, and the like) required for the measurement of a labeling substance (for example, an enzyme, a dye, luminescence, fluorescence, and the like), water, physiological saline, various buffer solutions, organic solvents, and the like are included.

In the above description, as a buffer solution, for example, those usually used in this field such as Tris buffer, Good's buffer, TE buffer, TAE buffer, TBE buffer, TBS buffer, a phosphate buffer, a borate buffer, and the like; for example, an electrophoresis medium as will be described later such as a leading buffer containing a leading ion, a trailing buffer containing a trailing ion, a high electric conductivity electrophoresis medium, an electrophoresis medium having alkaline range pH, an electrophoresis medium including a charged substance forming a micelle, a buffer solution for electrophoresis, said buffer solution for electrophoresis containing fillers, and the like are included. In addition, as a solution to be contained with a labeling substance or the above-described reagents, a similar buffer solution as described above is also included. In this connection, the concentration and pH of the buffer solution may be selected suitably from a range usually used in this field and are not specifically limited, however, the concentration is usually in a range of 1 mM to 2 M, and preferably 10 mM to 1 M, and pH is usually 5 to 11, preferably 5 to 10, more preferably 5.5 to 8.5, further preferably 6 to 8 and particularly preferably around 7.

6. A Method for Forming a Complex of the Present Invention

A method for forming a complex of the present invention is characterized in that (a) a solution (a sample) containing an analyte or an analogue thereof, and a solution (a reagent solution) containing a substance binding to said analyte or said analogue thereof (CFS) are introduced and arranged into each separate zone in a capillary (the first channel) by the method for introducing a sample and/or a reagent solution of the present invention as described above, and (b) an analyte or an analogue thereof in a sample and at least one kind of a CFS are reacted (contacted and reacted) while concentrating said analyte or said analogue thereof and/or at least one kind of the CFS electrophoretically to form a complex between said analyte or said analogue thereof and the CFS by applying a voltage onto said capillary (the first channel), without forming a complex between them by mixing these solutions in advance outside a capillary.

A method for forming a complex of the present invention is not especially limited except that a solution introducing structure, micro fluidic device or a micro fluidic system of the present invention as described above is used.

Namely, as described above, a method for introducing a sample and/or a reagent solution is carried out by using a solution introducing structure, micro fluidic device or a micro fluidic system of the present invention, to introduce and arrange a plurality of solutions (a sample and/or a reagent solution such as a solution containing an analyte or an analogue thereof, or a solution containing a CFS) in the capillary (the first channel) so that each independent zone is formed in a channel (the first channel). Then, an analyte or an analogue thereof and at least one kind of a CFS are reacted (contacted and reacted) while concentrating said analyte or said analogue thereof and/or at least one kind of the CFS electrophoretically to form a complex between said analyte or analogue thereof and the CFS by applying a voltage onto said capillary (the first channel) introduced and arranged with these solutions, without forming a complex between said analyte or analogue thereof and the CFS by mixing these solutions in advance outside a capillary.

Therefore, a method for forming a complex of the present invention is specifically, for example, one comprising the following steps:
(a) providing a micro fluidic device comprising at least one structure for introducing a sample or a reagent solution to a first channel (1) in a substrate, said the structure comprising;
  (i) the first channel (1);
  (ii) not less than 3 D side channels (2), each said D side channel (2) having a opening (2-1) opened on a wall of said first channel (1), and said openings (2-1) arranged in spaced relation to one another, wherein said D side channel (2) is connected to a W reservoir (4); and
  (iii) not less than 2 S/R side channels (3), each said S/R side channel (3) having a opening (3-1) opened on the wall of said first channel (1) at the different position (part) from said openings (2-1) of said D side channels (2), and each said opening (3-1) arranged between adjacent 2 openings (2-1) of D side channels (2), wherein each said opening (3-1) of these not less than 2 S/R side channels (3) are each arranged at the different portion between adjacent 2 openings (2-1) of D side channels (2), and S/R side channel (3) is connected to a S/R reservoir (5)[(a): a preparation step];
(b) putting a sample into at least one S/R reservoir (5) connecting to said S/R side channel (3);
(c) putting a reagent solution into at least one S/R reservoir (5) connecting to said S/R side channel (3), wherein said S/R reservoir (5) being different from one used in said step (b);
(d) introducing said sample in said S/R side channel (3) connected with said S/R reservoir (5) used in said step (b), 2 D side channels (2) adjacent to said S/R side channel (3) in an axis direction and a first channel region between said 2 D side channels (2), by moving said sample from said S/R reservoir (5) where said sample is put in said step (b) to said 2 D side channels (2) adjacent to said S/R side channel (3) connected with said S/R reservoir (5) in an axis direction, via said S/R side channel (3) connected with said S/R reservoir (5);
(e) introducing said reagent solution in said S/R side channel (3) connected with said S/R reservoir (5) used in said step (c), 2 D side channels (2) adjacent to said S/R side channel (3) in an axis direction and a first channel region between said 2 D side channels (2), by moving said reagent solution from said S/R reservoir (5) where said reagent solution is put in said step (c) to said 2 D side channels (2) adjacent to said S/R side channel (3) connected with said S/R reservoir (5) in an axis direction, via said S/R side channel (3) connected with said S/R reservoir (5) [(b) to (e): a introduction step]; and
(f) reacting an analyte or an analogue thereof in the sample with at least one kind of a CFS in the reagent solution while concentrating said analyte or said analogue thereof in the sample and/or at least one kind of the CFS in the reagent solution to form the complex between said analyte or said analogue thereof and the CFS, by applying a voltage to said first channel (1) [(f): concentration and reaction step].

In this connection, in the above description, embodiments, specific examples, preferable examples, and the like of an analyte, an analogue (a labeled analogue, a reaction improvement analogue), a solution containing an analyte or an analogue thereof, a sample containing an analyte, a CFS (a labeled CFS, a reaction improvement CFS, a labeled reaction improvement CFS), a solution containing thereof, a preparation step [a step (a)], a solution introducing structure, a micro fluidic device or a micro fluidic system used in a preparation step [a step (a)] are as described above. In general, as a solution introducing structure, a micro fluidic device or a micro fluidic system used in a method for forming a complex in the present invention, one usually having a reservoir (a S/R reservoir, a W reservoir) and/or an access port, an upstream reservoir and/or an access port, a downstream reservoir and/or or an access port are used. In addition, the first channel of a solution introducing structure and a micro fluidic device of the present invention preferably have at least a region (reaction region) where a sample reacts with a reagent solution at one part thereof, and more preferably have at least a region (concentration and reaction region) where at least one kind of a CFS reacts with analyte or analogue thereof in a sample while concentrating said analyte or said analogue thereof in the sample and/or at least one kind of the CFS in the reagent solution.

(1) An Introduction Step

A introduction step in a method for forming a complex of the present invention is as described above, and embodiments, specific examples, preferable example, and the like are also as described above.

However, because a method for forming a complex of the present invention is one to form a complex between an analyte or an analogue thereof, and a CFS, an introduction step in a method for forming a complex of the present invention may be rephrased that a step of arranging (i) a solution containing an analyte or an analogue thereof and (ii) at least one kind of solution containing not less than one kind of a CFS into the capillary (the first channel), so that by applying a voltage to said capillary (the first channel) the complex between said analyte or said analogue thereof and the CFS is formed without mixing these solutions in advance.

An introduction step in a method for forming a complex of the present invention is a step of introducing and arranging a solution containing an analyte or an analogue thereof, and at least one kind of solution containing CFS into a capillary (the first channel), so that a complex between an analyte or an analogue thereof and a CFS is formed, without mixing these solutions in advance outside a capillary, and by applying a voltage onto the capillary (the first channel), namely by carrying out a step (f) of the present invention as described later.

Here, "so that a complex between an analyte or an analogue thereof and a CFS is formed, by applying a voltage onto a capillary" means to form a complex between an analyte or an analogue thereof and a CFS by contacting the analyte or analogue thereof with the CFS, not by (not depending on) molecular diffusion and by utilization of the phenomenon that when a solution containing a substance with higher electrophoretic mobility (faster electrophoretic speed) is arranged at upstream of a solution containing a substance with lower electrophoretic mobility (slow electrophoretic speed) and electrophoresis is carried out, a substance with higher electrophoretic mobility (faster electrophoretic speed) in a solution overtakes a substance with lower electrophoretic mobility (slow electrophoretic speed).

Namely, the present invention aims at forming a complex between (1) an analyte or an analogue thereof, or a complex between an analyte or an analogue thereof, and a certain CFS, and (2) at least one kind of a CFS (note: a CFS different from one described above) in a capillary (a first channel) by applying a voltage onto a capillary (a first channel). In other words, the present invention includes not only the case that a complex between an analyte or an analogue thereof, and all of CFSs is formed only in a capillary (a first channel), but also such a case is also included, for example, that when 2 or more kinds of CFSs are used, a complex (an intermediate complex) between an analyte or an analogue thereof, and a part of CFSs among 2 or more kinds of CFSs is formed in advance outside a capillary, or in a capillary (a first channel) without application of a voltage, and subsequently said intermediate complex and residual not less than one kind of CFSs are made reacted (contacted and reacted) in a capillary (a first channel) by applying a voltage onto a capillary (a first channel), to form a complex between the intermediate complex formed in advance, and the residual not less than one kind of CFSs.

For example, when 2 kinds of CFSs are used, such a case is naturally included that (1) a complex (an intermediate complex) between an analyte or an analogue thereof and one kind of a CFS, and a complex between said intermediate complex and a residual one kind of a CFS is formed in a capillary (a first channel) by applying a voltage onto a capillary (a first channel), and such a case is also included that (2) an intermediate complex between an analyte or an analogue thereof, and a kind of a CFS is formed in advance outside a capillary, or in a capillary (a first channel) without application of a voltage, and subsequently said intermediate complex and a residual one kind of a CFS is formed in a capillary (a first channel) by applying a voltage onto a capillary (a first channel) In addition, for example, when 3 kinds of CFSs are used, the case is naturally included that (1) a complex (an intermediate complex 1) between an analyte or an analogue thereof and one kind of a CFS (a CFS-1), a complex (an intermediate complex 2) between said intermediate complex 1 and the residual one kind of a CFS (a CFS-2), and a complex between the intermediate complex 2 and residual one kind of a CFS (a CFS-3) are formed in a capillary (a first channel) by applying a voltage onto a capillary (a first channel), and such cases are also included that (2) an intermediate complex 1 between an analyte or an analogue thereof, and a CFS-1 is formed in advance outside a capillary, or in a capillary (a first channel) without application of a voltage, and then an intermediate complex 2 between said intermediate complex 1 and a CFS-2, along with a complex between said intermediate complex 2 and a CFS-3 are formed in a capillary (a first channel) by applying a voltage onto a capillary (a first channel); or (3) an intermediate complex 1 between an analyte or an analogue thereof and a CFS-1, and an intermediate complex 2 between said intermediate complex 1 and a CFS-2 are formed in advance outside a capillary, or in a capillary (a first channel) without application of a voltage, and then, a complex between said intermediate complex 2 and a CFS-3 is formed in a capillary (a first channel) by applying a voltage onto a capillary (a first channel). (In this connection, the cases when 4 or more kinds of CFSs are used are considered by the same way of thinking.)

Therefore, in the present invention, "without mixing solutions in advance" means no mixing of a solution containing an analyte or an analogue thereof, and at least one kind of a solution containing a CFS in advance, but does not necessarily mean exclusion of any mixing of a solution containing an analyte or an analogue thereof, and at least one kind of a solution containing a CFS in advance (in other words, it does not mean never to do to mix some of a sample including an analyte and all solutions containing the CFSs, along with if necessary, a solution containing analogues).

In the present invention, a direction toward which a complex between an analyte or an analogue thereof, and not less than one kind of CFSs, finally formed and measured, or a free analogue finally measured, when voltage is applied, moves is defined as "downstream" side, and the opposite direction is defined as "upstream" side (the same hereinafter).

In addition, in the present invention, "electrophoretic speed (of an analyte or an analogue thereof, a CFS, and the like are subjected to electrophoresis) is "slow" or "electrophoretic mobility (of an analyte or an analogue thereof, a CFS, and the like are subjected to electrophoresis) is low" means not only the case when electrophoretic speed is slow (electrophoretic mobility is low) than those of at least not less than one kind other substances, but also means movement in a direction opposite to the direction of at least not less than one kind other substances.

(a) Arrangement Order

Arrangement order of a solution containing an analyte or an analogue thereof, and at least one kind of solution containing not less than one kind of CFS is not especially limited, as long as it is an order formable a complex between an analyte or an analogue thereof, and a CFS by applying a voltage onto a capillary (a first channel).

In Tables 1-1 to 1-5, relations between arrangement order of a solution containing an analyte or an analogue thereof and at least one kind of solution containing not less than one kind of CFS, and electrophoretic mobility (electrophoretic speed) of an analyte or an analogue thereof, and a CFS are shown, however, the present invention is by no means limited thereto.

In this connection, in Tables 1-1 to 1-5, the cases when from one kind to 3 kinds of CFSs are used are shown, however, the same way of thinking as in Tables 1-1 to 1-5 is applied in suitable arrangement, also in the case when 4 or more kinds of CFSs are used.

In Tables 1-1 to 1-5, Ana represents an analyte or an analogue thereof, CFS-1 represents a first CFS, CFS-2 represents a second CFS, and CFS-3 represents a third CFS. In addition, in Tables 1-1 to 1-5, arrangement order A in a capillary (a first channel) is a zone of a solution arranged at the most upstream side, among a solution containing an analyte or an analogue thereof, and at least one kind of solution containing not less than one kind of CFS, B is a zone of a solution arranged at the downstream side of zone A, C is a zone of a solution arranged at the downstream side of zone B, and D is a zone of a solution arranged at the downstream side of zone C. In this connection, the arrangement orders (A to D) in said capillary (a first channel) is only the orders among a solution containing an analyte or an analogue thereof, at least one kind of solution containing not less than one kind of CFS, and such arrangement may naturally be allowed that a solution, and the like, other than said solutions is arranged at further downstream side of said solution arranged at the most downstream side among these, or at further upstream side of said solution arranged at the most upstream side.

TABLE 1-1

| Pattern | Arrangement order in capillary (Upstream→Downstream) | | | | Relationship of Electorophoretic Mobility between Ana and CFS |
|---|---|---|---|---|---|
| | A | B | C | D | |
| 1 | Solution containing Ana | Solution containing CFS-1 | — | — | Ana > CFS-1 |
| 2 | Solution containing CFS-1 | Solution containing Ana | — | — | Ana < CFS-1 |
| 3 | Solution containing Ana | Solution containing CFS-1 | Solution containing CFS-2 | — | (1) Ana > CFS-1; (Ana/CFS-1)complex > CFS-2 However, (Ana/CFS-1)complex is formed prior to (Ana/CFS-2)complex. |
| 4 | | | | | (2) CFS-1 > Ana > CFS-2; (Ana/CFS-2)complex > CFS-1 However, (Ana/CFS-2)complex is formed prior to (Ana/CFS-1)complex. |
| 5 | Solution containing CFS-1 | Solution containing Ana | Solution containing CFS-2 | — | (1) Ana < CFS-1; (Ana/CFS-1)complex > CFS-2 However, (Ana/CFS-1)complex is formed prior to (Ana/CFS-2)complex. |
| 6 | | | | | (2) Ana > CFS-2; (Ana/CFS-2)complex < CFS-1 However, (Ana/CFS-2)complex is formed prior to (Ana/CFS-1)complex. |
| 7 | Solution containing CFS-1 | Solution containing CFS-2 | Solution containing Ana | — | (1) CFS-2 < CFS-1; Ana < CFS-1 (Ana/CFS-1)complex < CFS-2 However, (Ana/CFS-1)complex is formed prior to (Ana/CFS-2)complex. |
| 8 | | | | | (2) Ana < CFS-2; (Ana/CFS-2)complex < CFS-1 However, (Ana/CFS-2)complex is formed prior to (Ana/CFS-1)complex. |

TABLE 1-2

| 9 | Solution containing Ana | Solution containing CFS-1 | Solution containing CFS-2 | Solution containing CFS-3 | (1) Ana > CFS-1; (Ana/CFS-1)complex > CFS-2; (Ana/CFS-1/CFS-2)complex > CFS-3 However, (Ana/CFS-1)complex is formed prior to (Ana/CFS-2)complex and (Ana/CFS-3)complex, (Ana/CFS-1/CFS-2)complex is formed prior to(Ana/CFS-1/CFS-3)complex. |
|---|---|---|---|---|---|
| 10 | | | | | (2) Ana > CFS-1; CFS-2 > (Ana/CFS-1)complex > CFS-3; (Ana/CFS-1/CFS-3)complex > CFS-2 However, (Ana/CFS-1)complex is formed prior to (Ana/CFS-2)complex and (Ana/CFS-3)complex, (Ana/CFS-1/CFS-3)complex is formed prior to (Ana/CFS-1/CFS-2)complex. |

TABLE 1-2-continued

| | | |
|---|---|---|
| 11 | | (3) CFS-1 > Ana > CFS-2;<br>(Ana/CFS-2)complex > CFS-1;<br>(Ana/CFS-2/CFS-1)complex > CFS-3<br>However, (Ana/CFS-2)complex is<br>formed prior to (Ana/CFS-1)complex<br>and (Ana/CFS-3)complex,<br>(Ana/CFS-2/CFS-1)complex is formed<br>prior to (Ana/CFS-2/CFS-3)complex. |
| 12 | | (4) CFS-1 > Ana > CFS-2;<br>CFS-1 > (Ana/CFS-2)complex > CFS-3;<br>(Ana/CFS-2/CFS-3)complex > CFS-1<br>However, (Ana/CFS-2)complex is<br>formed prior to (Ana/CFS-1)complex<br>and (Ana/CFS-3)complex,<br>(Ana/CFS-2/CFS-3)complex is formed<br>prior to(Ana/CFS-2/CFS-1)complex. |
| 13 | | (5) CFS-1,CFS-2 > Ana > CFS-3;<br>(Ana/CFS-3)complex > CFS-1;<br>(Ana/CFS-3/CFS-1)complex > CFS-2<br>However, (Ana/CFS-3)complex is<br>formed prior to (Ana/CFS-1)complex<br>and (Ana/CFS-2)complex,<br>(Ana/CFS-3/CFS-1)complex is formed<br>prior to (Ana/CFS-3/CFS-2)complex. |
| 14 | | (6) CFS-1, CFS-2 > Ana > CFS-3;<br>CFS-1 > (Ana/CFS-3)complex > CFS-2;<br>(Ana/CFS-3/CFS-2)complex > CFS-1<br>However, (Ana/CFS-3)complex is<br>formed prior to (Ana/CFS-1)complex<br>and (Ana/CFS-2)complex,<br>(Ana/CFS-3/CFS-2)) complex is formed<br>prior to (Ana/CFS-3/CFS-1)complex. |

TABLE 1-3

| | | | | | |
|---|---|---|---|---|---|
| 15 | Solution containing CFS-1 | Solution containing Ana | Solution containing CFS-2 | Solution containing CFS-3 | (1) Ana < CFS-1;<br>(Ana/CFS-1)complex > CFS-2;<br>(Ana/CFS-1/CFS-2)complex > CFS-3<br>However, (Ana/CFS-1)complex is<br>formed prior to (Ana/CFS-2)complex<br>and (Ana/CFS-3)complex,<br>(Ana/CFS-1/CFS-2)complex is formed<br>prior to (Ana/CFS-1/CFS-3)complex. |
| 16 | | | | | (2) Ana < CFS-1;<br>CFS-2 > (Ana/CFS-1)complex > CFS-3;<br>(Ana/CFS-1/CFS-2)complex > CFS-3<br>However, (Ana/CFS-1)complex is<br>formed prior to (Ana/CFS-2)complex<br>and (Ana/CFS-3)complex,<br>(Ana/CFS-1/CFS-3)complex is formed<br>prior to(Ana/CFS-1/CFS-2)complex. |
| 17 | | | | | (3) Ana > CFS-2;<br>(Ana/CFS-2)complex < CFS-1;<br>(Ana/CFS-2/CFS-1)complex > CFS-3<br>However, (Ana/CFS-2)complex is<br>formed prior to (Ana/CFS-1)complex<br>and (Ana/CFS-3)complex,<br>(Ana/CFS-2/CFS-1)complex is formed<br>prior to (Ana/CFS-2/CFS-3)complex. |
| 18 | | | | | (4) Ana > CFS-2;<br>(Ana/CFS-2)complex > CFS-3;<br>(Ana/CFS-2/CFS-3)complex < CFS-1<br>However, (Ana/CFS-2)complex is<br>formed prior to (Ana/CFS-1)complex<br>and (Ana/CFS-3)complex,<br>(Ana/CFS-2/CFS-3)complex is formed<br>prior to (Ana/CFS-2/CFS-1)complex. |
| 19 | | | | | (5) CFS-2 > Ana > CFS-3;<br>(Ana/CFS-3)complex < CFS-1;<br>(Ana/CFS-3/CFS-1)complex > CFS-2<br>However, (Ana/CFS-3)complex is<br>formed prior to (Ana/CFS-1)complex<br>and (Ana/CFS-2)complex,<br>(Ana/CFS-3/CFS-1)complex is formed<br>prior to (Ana/CFS-3/CFS-2)complex. |
| 20 | | | | | (6) CFS-2 > Ana > CFS-3;<br>(Ana/CFS-3)complex > CFS-2; |

TABLE 1-3-continued (Ana/CFS-3/CFS-2)complex < CFS-1
However, (Ana/CFS-3)complex is
formed prior to (Ana/CFS-1)complex
and (Ana/CFS-2)complex,
(Ana/CFS-3/CFS-2)complex is formed
prior to (Ana/CFS-3/CFS-1)complex.

TABLE 1-4

| | | | | | |
|---|---|---|---|---|---|
| 21 | Solution containing CFS-1 | Solution containing CFS-2 | Solution containing Ana | Solution containing CFS-3 | (1) CFS-2 < CFS-1;<br>Ana < CFS-1;<br>(Ana/CFS-1)complex < CFS-2;<br>(Ana/CFS-1 /CFS-2)complex > CFS-3<br>However, (Ana/CFS-1)complex is<br>formed prior to (Ana/CFS-2)complex<br>and (Ana/CFS-3)complex,<br>(Ana/CFS-1/CFS-2)complex is formed<br>prior to(Ana/CFS-1/CFS-3)complex. |
| 22 | | | | | (2) CFS-2 < CFS-1;<br>Ana < CFS-1;<br>(Ana/CFS-1)complex > CFS-3;<br>(Ana/CFS-1/CFS-3)complex < CFS-2<br>However, (Ana/CFS-1)complex is<br>formed prior to (Ana/CFS-2)complex<br>and (Ana/CFS-3)complex,<br>(Ana/CFS-1/CFS-3)complex is formed<br>prior to (Ana/CFS-1/CFS-2)complex. |
| 23 | | | | | (3) Ana < CFS-2;<br>(Ana/CFS-2)complex < CFS-1;<br>(Ana/CFS-2/CFS-1)complex > CFS-3<br>However, (Ana/CFS-2)complex is<br>formed prior to (Ana/CFS-1)complex<br>and (Ana/CFS-3)complex,<br>(Ana/CFS-2/CFS-1)complex is formed<br>prior to (Ana/CFS-2/CFS-3)complex. |
| 24 | | | | | (4) Ana < CFS-2:<br>(Ana/CFS-2)complex > CFS-3;<br>(Ana/CFS-2/CFS-3)complex > CFS-1<br>However, (Ana/CFS-2)complex is<br>formed prior to (Ana/CFS-1)complex<br>and (Ana/CFS-3)complex,<br>(Ana/CFS-2/CFS-3)complex is formed<br>prior to (Ana/CFS-2/CFS-1) complex. |
| 25 | | | | | (5) Ana > CFS-3;<br>CFS-1 > CFS-2;<br>(Ana/CFS-3)complex < CFS-1;<br>(Ana/CFS-3/CFS-1)complex < CFS-2<br>However, (Ana/CFS-3)complex is<br>formed prior to (Ana/CFS-1)complex<br>and (Ana/CFS-2)complex,<br>(Ana/CFS-3/CFS-1)complex is formed<br>prior to (Ana/CFS-3/CFS-2)complex. |
| 26 | | | | | (6) Ana > CFS-3;<br>(Ana/CFS-3)complex < CFS-2;<br>(Ana/CFS-3/CFS-2)complex < CFS-1<br>However, (Ana/CFS-3)complex is<br>formed prior to (Ana/CFS-1)complex<br>and (Ana/CFS-2)complex,<br>(Ana/CFS-3/CFS-2)complex is formed<br>prior to (Ana/CFS-3/CFS-1)complex. |

TABLE 1-5

| | | | | | |
|---|---|---|---|---|---|
| 27 | Solution containing CFS-1 | Solution containing CFS-2 | Solution containing CFS-3 | Solution containing Ana | (1) CFS-1 > CFS-2, CFS-3, Ana;<br>CFS-2 > CFS-3;<br>(Ana/CFS-1)complex < CFS-2;<br>(Ana/CFS-1/CFS-2)complex < CFS-3<br>However, (Ana/CFS-1)complex is<br>formed prior to (Ana/CFS-2)complex<br>and (Ana/CFS-3)complex,<br>(Ana/CFS-1/CFS-2)complex is formed<br>prior to (Ana/CFS-1/CFS-3)complex. |
| 28 | | | | | (2) CFS-1 > CFS-2, CFS-3, Ana;<br>(Ana/CFS-1)complex < CFS-3;<br>(Ana/CFS-1/CFS-3)complex < CFS-2 |

TABLE 1-5-continued

| | |
|---|---|
| 29 | However, (Ana/CFS-1)complex is formed prior to (Ana/CFS-2)complex and (Ana/CFS-3)complex, (Ana/CFS-1/CFS-3)complex is formed prior to (Ana/CFS-1/CFS-2)complex. (3) CFS-2 > CFS-1, CFS-3, Ana; CFS-1 > CFS-3; (Ana/CFS-2)complex < CFS-1; (Ana/CFS-2/CFS-1)complex < CFS-3 However, (Ana/CFS-2)complex is formed prior to (Ana/CFS-1)complex and (Ana/CFS-3)complex, (Ana/CFS-2/CFS-1)complex is formed i prior to (Ana/CFS-2/CFS-3)complex. |
| 30 | (4) CFS-2 > CFS-1, CFS-3, Ana; (Ana/CFS-2)complex < CFS-1; (Ana/CFS-2/CFS-3)complex < CFS-1 However, (Ana/CFS-2)complex is formed prior to (Ana/CFS-1)complex and (Ana/CFS-3)complex, (Ana/CFS-2/CFS-3)complex is formed prior to (Ana/CFS-2/CFS-1)complex. |
| 31 | (5) CFS-3 > Ana; CFS-1 > CFS-3; (Ana/CFS-3)complex < CFS-1; (Ana/CFS-3/CFS-1)complex < CFS-2 However, (Ana/CFS-3)complex is formed prior to (Ana/CFS-1)complex and (Ana/CFS-2)complex, (Ana/CFS-3/CFS-1)complex is formed prior to (Ana/CFS-3/CFS-2)complex. |
| 32 | (6) CFS-3 > Ana; (Ana/CFS-3)complex < CFS-2; (Ana/CFS-3/CFS-2)complex < CFS-1 However, (Ana/CFS-3)complex is formed prior to (Ana/CFS-1)complex and (Ana/CFS-2)complex, (Ana/CFS-3/CFS-2)complex is formed prior to (Ana/CFS-3/CFS-1)complex. |

In Tables 1-1 to 1-5, "formed prior to" means that the former complex is formed substantially before the latter complex is formed, but does not exclude when a part of the former complex and the latter complex are formed simultaneously or in reversed order, for example, in the following case.
(1) The case that by adjacently placing each zone (zone of a solution containing an analyte or an analogue thereof, zone of solutions containing CFSs) and by molecular diffusion generated at the vicinity of liquid-liquid interface between each zone among these, a part of the former complex and the latter complex are formed simultaneously or in reversed order.
(2) The case that from the relation of electrophoretic speed of an analyte or an analogue thereof and not less than one kind of CFSs, a part of the former complex and the latter complex are formed simultaneously or in reversed order.
(3) The case that because at least one kind of a CFS among an analyte or an analogue thereof and not less than one kind of CFSs move in a direction opposite from those of other substances, a part of the former complex and the latter complex are formed simultaneously or in reversed order.
In such cases, a solution containing an analyte or an analogue thereof, and solutions containing CFSs may suitably be arranged by the same way of thinking as in Tables 1-1 to 1-5.

In addition, for the case when 2 or more kinds of CFSs are used, among the cases in Tables 1-1 to 1-5, such a case is shown that all of CFSs (a CFS-1 to -3) bind to an analyte or an analogue thereof, namely all of the binding sites of 2 or more kinds of CFSs are present only at an analyte or an analogue thereof [binding form (1): a sandwich complex with Ana sandwiched by CFS-1 and CFS-2]. The following other cases may be understood as follows: A case, for example, a CFS-1 in 2 kinds of CFSs (a CFS-1 and -2) binds to an analyte or an analogue thereof, and a CFS-2 binds to new sites generated by formation of a complex between an analyte or an analogue thereof, and a CFS-1, in other words, binding sites of at least one kind of a CFS (for example, a CFS A) among 2 or more kinds of CFSs are present only on an analyte or an analogue thereof, and binding sites of other at least one kind of a CFS (for example, a CFS B) are present at new sites generated by formation of a complex between an analyte or an analogue thereof, and a CFS A, [binding form (2)]; or a case, for example, a CFS-1 in 2 kinds of CFSs (a CFS-1 and -2) binds to an analyte or an analogue thereof, and a CFS-2 binds to a CFS-1 bound with an analyte or an analogue thereof, in other words, binding sites of at least one kind of a CFS (for example, a CFS A) among 2 or more kinds of CFSs are present only on an analyte or an analogue thereof, and binding sites of other at least one kind of a CFS (for example, a CFS B) are present only on a CFS A, [binding form (3)]; are the cases when a sandwich complex of CFS-1, sandwiched by Ana and CFS-2, is formed in the binding form (1) [an analyte or an analogue thereof in the case of using 2 kinds of CFSs in Tables 1-1 to 1-5 is alternatively read as a CFS-1, and a CFS-1 in Tables 1-1 to 1-5 is alternatively read as an analyte or an analogue thereof]. In addition, in such cases as 3 kinds or more CFSs are used in the above-described binding forms (2) and (3), or such cases as the above-described binding forms (1) to (3) are suitably combined, a solution containing an analyte or an analogue thereof, and solutions containing CFSs may suitably be arranged by the same way of thinking as in Tables 1-1 to 1-5 and the above.

In this connection, in carrying out the present invention in a competitive method using an analogue of an analyte, any of the following arrangements may also be adopted; An analyte in a sample (namely, a sample including an analyte) and an analogue [for example, an analogue labeled by a labeling substance (a labeled analogue), and an analogue bound with a reaction improvement substance (a reaction improvement analogue)], are simultaneously present in the same solution and introduced and arranged into a capillary (a first channel) as one solution zone (namely, a zone of a solution including a sample including an analyte and an analogue); a sample including an analyte, and a solution containing an analogue (for example, a labeling analogue or a reaction improvement analogue) are introduced and arranged into a capillary (a first channel) as each separate zone (solution); or a solution containing an analyte in a sample (namely, a sample including an analyte) and not less than one kind of CFSs, and a solution including an analogue (for example, a labeled analogue or a reaction improvement analogue) are introduced and arranged into a capillary (a first channel) as each separate zone (solution).

In this connection, in the above-described competitive method, to arrange, in a capillary (a first channel), (1) a solution including a sample having an analyte and a labeled analogue (a solution containing an analyte and an analogue), along with at least one kind of solution containing not less than one kind of CFS (a CFS, a reaction improvement CFS and combinations thereof); or (2) a sample including an analyte (a solution containing an analyte or an analogue thereof), along with a solution containing a labeled analogue and at least one kind of solution containing not less than one kind of CFS (a CFS, a reaction improvement CFS and combinations thereof); or (3) a solution including a sample having an analyte and not less than one kind of CFSs (a CFS, a reaction improvement CFS and combinations thereof), along with a solution containing a labeled analogue; so that a complex A between said analyte and CFS, and a complex B between said labeled analogue and CFS are formed by applying a voltage onto a capillary (a first channel), arrangement order of these solutions may be determined, in accordance with arrangement order of a solution including an analyte or an analogue thereof, and at least one kind of solution containing not less than one kind of CFS, as explained above, by consideration on electrophoretic mobility of an analyte, a labeled analogue and a CFS. In addition, to arrange, in a capillary (a first channel), (1) a solution including a sample having an analyte and a reaction improvement analogue (a solution containing an analyte and an analogue), along with a solution containing not less than one kind of a CFS having property capable of forming a complex with an analyte or an analogue thereof and labeled with a labeling substance (hereinafter, abbreviated as a labeled binding substance or a labeled CFS); or (2) a sample including an analyte (a solution containing an analyte or an analogue), along with a solution including a reaction improvement analogue and a solution containing not less than one kind of labeled CFSs; or (3) a solution including a sample having an analyte and not less than one kind of labeled CFSs, along with a solution containing a reaction improvement analogue; so that a complex A between said analyte and labeled CFS, and a complex B between said reaction improvement analogue and labeled CFS are formed by applying a voltage onto a capillary (a first channel), arrangement order of these solutions may be determined, in accordance with arrangement order of a solution containing an analyte or an analogue thereof, and at least one kind of solution containing not less than one kind of CFS, as explained above, by consideration on electrophoretic mobility of an analyte, a reaction improvement analogue and a labeled CFS.

In addition, a solution containing an analyte or an analogue thereof, and at least one kind of solution containing not less than one kind of CFS are not necessarily made adjacent, and liquid such as water, a physiological salt solution, various buffer solutions, an organic solvent, and the like may be inserted between these solutions. In this connection, as such a buffer solution, any one not inhibit formation of a complex between an analyte or an analogue thereof and not less than one kind of CFSs, can be used, including buffers usually used in this field, for example, Tris buffer, Good's buffer, TE buffer, TAE buffer, TBE buffer, TBS buffer, a phosphate buffer, a borate buffer, and the like.

In this connection, a solution containing an analyte or an analogue thereof, and at least one kind of solution containing not less than one kind of CFS, along with if necessary, the liquids, are formed and arranged as each separate zone in a capillary. In other words, between a solution containing an analyte or an analogue thereof, and at least one kind of solution containing not less than one kind of CFS, along with if necessary, between the solution containing an analyte or analogue thereof and the liquid or between the at least one kind of solution containing not less than one kind of CFS and the liquid, liquid-liquid interface is formed and maintained at the time these solutions, and if necessary, the liquids are arranged.

In an introduction step in the method for forming a complex of the present invention, a method for introducing a solution containing an analyte or an analogue thereof, and at least one kind of solution containing not less than one kind of CFS into a capillary (a first channel) is as mentioned above.

In addition, a method for introducing the following: A sample containing an analyte; a solution including a sample having an analyte and a labeled analogue or a reaction improvement analogue (a solution containing an analyte or an analogue); a solution containing an analyte and not less than one kind of CFSs (for example, a CFS, a labeled CFS, a reaction improvement CFS, combinations thereof); a solution including a labeled analogue; or a solution including a reaction improvement analogue; into a capillary is the same as a method for introducing a solution containing an analyte or an analogue thereof, and at least one kind of solution containing not less than one kind of CFS into a capillary, as described above.

(2) A Concentration and Reaction Step

A concentration and reaction step in the method for forming a complex of the present invention is a step of reacting (contacting and reacting) said analyte or said analogue thereof with the CFS while concentrating said analyte or said analogue thereof and/or at least one kind of the CFSs by applying a voltage to said capillary (said first channel) before uniformly mixing the plurality of solutions (a solution containing an analyte or an analogue thereof and at least one kind of solution containing not less than one kind of CFS) introduced into said capillary (said first channel) by the introduction step to form the complex between said analyte or said analogue thereof and the CFS. In other words, this step is a step of reacting (contacting and reacting) said analyte or analogue thereof and CFS while concentrating said analyte or analogue thereof and/or CFS electrophoretically to form a complex between said analyte or analogue thereof and CFS, not by (not depending on) molecular diffusion.

"Before solutions (a solution containing an analyte or an analogue thereof and at least one kind of solution containing not less than one kind of CFS) are uniformly mixed" means "before each zone (liquid-liquid interface) of a solution containing an analyte or an analogue thereof and a solution including not less than one kind of CFS, along with if necessary the liquid, arranged into a capillary (a first channel) by a step (1) of the present invention, are uniformly mixed by molecular".

In this connection, in the present invention, "interface" means, boundary where a solution containing an analyte or an analogue thereof, and solutions including not less than one kind of CFSs are contacting, or if necessary boundary where the solution containing an analyte or analogue thereof and the liquid are contacting or boundary where the solution including not less than one kind of CFSs and the liquid are contacting, and said interface does not necessarily mean completely no mixing, due to presence of diffusion from a practical standpoint.

In addition, in a competitive method using an analogue of an analyte, and when a labeled analogue is used, the above-described term means "before uniformly mixing the following zones (liquid-liquid interface) arranged into a capillary (a first channel) by a introduction step, by molecular diffusion"; (1) an each zone (liquid-liquid interface) of a solution including a sample having an analyte and a labeled analogue (a solution containing an analyte and an analogue) along with a solution containing not less than one kind of CFS (a CFS, a reaction improvement CFS, combinations thereof), and if necessary the liquid; (2) an each zone (liquid-liquid interface) of a sample containing an analyte, a solution containing a labeled analogue and a solution containing not less than one kind of CFS (a CFS, a reaction improvement CFS, combinations thereof), and if necessary the liquid; or (3) an each zone (liquid-liquid interface) of a solution including a sample having an analyte and not less than one kind of CFSs (a CFS, a reaction improvement CFS, combinations thereof) and a solution containing a labeled analogue, and if necessary the liquid.

In a competitive method using an analogue of analyte, when a reaction improvement analogue is used, the above-described term means "before uniformly mixing the following zones (liquid-liquid interface) by molecular diffusion"; (1) an each zone (liquid-liquid interface) of a solution including a sample having an analyte and a reaction improvement analogue (a solution containing an analyte and an analogue) along with a solution containing not less than one kind of labeled CFSs, and if necessary the liquid; (2) an each zone (liquid-liquid interface) of a sample containing an analyte, a solution containing a reaction improvement analogue and a solution containing not less than one kind of labeled CFSs, and if necessary the liquid; or (3) an each zone (liquid-liquid interface) of a solution including a sample having an analyte and not less than one kind of CFSs (a CFS, a labeled CFS, combinations thereof) and a solution containing a reaction improvement analogue, and if necessary the liquid.

In this connection, "interface" also has the same meaning as above.

(a) Concentration

In a concentration and reaction step, "concentrating an analyte or an analogue thereof, and/or at least one kind of a CFS by applying a voltage onto a capillary (a first channel)" means that at least one kind among an analyte or an analogue thereof and not less than one kind of CFSs gather in band-like (plug-like) on application of a voltage onto a capillary (a first channel). In other words, it means that said substances gather on application of a voltage onto a capillary (a first channel) so that such a portion is generated wherein concentration of said substance becomes higher than that of a substance in a zone arranged in an introduction step, namely it means that an analyte or an analogue thereof and/or a CFS gather on application of a voltage onto a capillary (a first channel), and a portion is generated wherein concentration of an analyte or an analogue thereof and/or concentration of a CFS becomes higher than that of an analyte or an analogue and/or that of a CFS in a solution zone (for example, a zone of a solution containing an analyte or an analogue thereof, a zone of a solution containing a CFS) arranged in an introduction step.

In this connection, as for level (degree) of concentration in the present invention, concentration of an analyte or an analogue thereof and/or at least one kind of a CFS at an gathered part (band-like) of said substance on application of a voltage onto a capillary (a first channel), relative to concentration of an analyte or an analogue thereof and/or at least one kind of a CFS in a zone arranged by an introduction step is, as lower limit, usually not lower than 1.5 times, preferably not lower than 5 times, more preferably not lower than 10 times, and further preferably not lower than 25 times, and upper limit is not especially limited, however usually not higher than $10^7$ times, preferably not higher than $10^6$ times and more preferably not higher than $10^5$ times.

(b) A Contact Reaction

In addition, in the present invention, "reacting (contacting and reacting) said analyte or analogue thereof with CFS" means that, as described above, reaction (contact and reaction) between an analyte or an analogue thereof and a CFS is occurred not by (not depending on) molecular diffusion and by the phenomenon that a substance having higher electrophoretic mobility (faster electrophoretic speed) among an analyte or an analogue thereof and not less than one kind of CFSs overtakes a substance having lower electrophoretic mobility (slow electrophoretic speed), by utilization of the fact that when electrophoresis carried out under the condition that a solution containing a substance having higher electrophoretic mobility (faster electrophoretic speed) is arranged at upstream of a solution containing a substance having lower electrophoretic mobility (slow electrophoretic speed), a substance having higher electrophoretic mobility (faster electrophoretic speed) in a solution overtakes a substance having lower electrophoretic mobility (slow electrophoretic speed).

Namely, in a concentration and reaction step of the present invention, an analyte or an analogue thereof in a solution, and a CFS in a solution are made react (contact and react) by movement electrophoretically, without mixing by (depending on) molecular diffusion generated by standing still a solution containing an analyte or an analogue thereof and a solution including not less than one kind of CFS, along with if necessary the liquid, arranged in a capillary (a first channel), or also not by physical mixing thereof in a capillary (a first channel).

As described above, a concentration and reaction step of the present invention forms a complex between said analyte or analogue thereof and CFS by migrating an analyte or analogue thereof in a solution and a CFS in a solution electrophoretically and reacting (contacting and reacting) them while concentrating an analyte or analogue thereof and/or a CFS electrophoretically, before a solution containing an analyte or an analogue thereof and a solution containing CFS, along with if necessary the liquid, are uniformly mixed by molecular diffusion, and further without uniformly mixing these physically in a capillary (a first channel), in other words, with maintaining a liquid-liquid interface between these adjacent solutions and if necessary between the liquid and the solution.

In the present invention, "reacting (contacting and reacting) said analyte or analogue thereof with CFS while concentrating said analyte or analogue thereof and/or at least one kind of CFS by applying a voltage to a capillary (a first channel)" means the following both cases: (1) the case that the above-mentioned concentration of an analyte or an analogue thereof and/or a CFS, and reaction (contact and reaction) of an analyte or an analogue thereof and a CFS are simultaneously carried out; or (2) the case that after substantial completion of the above-mentioned concentration of an analyte or an analogue thereof and/or a CFS, reaction (contact and reaction) of an analyte or an analogue thereof and a CFS is carried out. Therefore, the term includes the cases other than the case that concentration of an analyte or an analogue thereof and/or a CFS is carried out after substantial completion of reaction (contact and reaction) between an analyte or an analogue thereof and a CFS.

(a) Condition

In other words, a concentration and reaction step of the present invention can be carried out by applying a voltage onto said capillary (said first channel) under condition that a complex between said analyte or analogue thereof and CFS can be formed by reacting (contacting and reacting) said analyte or analogue thereof and CFS while concentrating said analyte or analogue thereof and/or at least one kind of CFS as described above by applying a voltage onto said capillary (said channel) as described above, before a solution containing an analyte or an analogue thereof and a solution containing CFS are uniformly mixed.

Such conditions are specifically those used in so-called an electrophoresis concentration method for concentration of substances in a capillary.

An electrophoresis concentration method includes, for example, methods using difference in electrophoretic mobility in a capillary such as (1) Field Amplification Sample Stacking Method (FASS) [US-A-2003-0057092 A1; Weiss, D. J., Saunders, K., Lunte, C. E. *Electrophoresis* 2001, 22, 59-65; Britz-McKibbin, P., Bebault, G. M., Chen, D. D. Y. *Anal Chem.* 2000, 72, 1729-1735; Ross, D., Locascio, L. E. *Anal Chem.* 2002, 71, 5137-5145, and the like]; (2) Field Amplification Sample Injection Method (FASI) [Chien, R. L et al. *J. Chromatogr.* 1991, 559, 141-148, and the like]; (3) Isotachophoresis (ITP) [Everaerts, F. M., Geurts, M. Mikkers, F. E. P., Verheggen, T. P. E. M *J Chromatogr.* 1976, 119, 129-155; Mikkers, F. E. P., Everaerts, F. M., Peek, J. A. F. *J. Chromatogr.* 1979, 168, 293-315; Mikkers, F. E. P., Everaerts, F. M., Peek, J. A. F. *J. Chromatogr.* 1979, 168, 317-332; Hirokawa, T, Okamoto, H. Ikuta, N., and Gas, B., *Analytical Sciences* 2001, Vol. 17 Supplement i185, and the like]; (4) Isoelectric Focusing method (IF) [Wehr T, et al., *Am. Biotechnol. Lab.* 1990, 8, 22 Kilar F. et al., *Electrophoresis* 1989, 10, 23-29, and the like]; (5) Large-volume sample stacking method (LVSS) [Siri, N. et al., J. Chormatogr. B, (2003), 793, 151-157, and the like]; (6) pH junction method (pH-mediated stacking) [P. Britz-McKibbin et al., 2000, *Anal. Chem.,* 72, 1242, P. Britz-McKibbin et al., 2002, *Anal. Chem.,* 74, 3736]; (7) Sweeping method (stacking micellar electrokinetic chromatography) [J. P. Quirino et al., 1998, *Science,* 282, 465, J. P. Quirino et al., 1999, *Anal. Chem.,* 71, 1638, Y. Sera et al., 2001*, Electrophoresis,* 22, 3509]; and the like, however, not limited thereto.

Among the electrophoresis condensation methods described above, for example, ITP, FASS are preferable, and ITP is particularly preferable.

In this connection, ITP is based on principle that an objective substance can be concentrated when the objective substance is sandwiched between an electrophoresis medium (a leading buffer) including a leading ion having faster electrophoretic speed than that of an objective substance, and an electrophoresis medium (a trailing buffer) including a trailing ion having slow electrophoretic speed than that of an objective substance and subjected to electrophoresis.

Therefore, in carrying out a concentration and reaction step of the present invention by ITP, at least a an electrophoresis medium (leading buffer) including an leading ion having faster electrophoretic speed than that of an analyte or an analogue thereof and/or not less than one kind of CFSs, and an electrophoresis medium (a trailing buffer) including a trailing ion having slow electrophoretic speed than that of an analyte or an analogue thereof and/or not less than one kind of CFSs are necessary, and these components are also included in "condition that an analyte or an analogue thereof and/or at least not less than one kind of CFSs are concentrated" of the present invention.

In this connection, a leading buffer is arranged further downstream side of a solution arranged at the most downstream side of a capillary (a first channel), among a solution containing an analyte or an analogue thereof, and at least one kind of solution containing not less than one kind of CFS, and a trailing buffer is arranged further upstream side of a solution arranged at the most upstream side of a capillary (a first channel), among a solution containing an analyte or an analogue thereof, and at least one kind of solution containing not less than one kind of CFS.

In the above description, as a leading ion, any ion having faster electrophoretic speed than that of an analyte or an analogue thereof and/or not less than one kind of CFSs may be used, and suitably be selected from those usually used in this field. Such ion includes, for example, $Cl^-$, and the like. In addition, use concentration of a leading ion may also suitably be selected from a range usually used in this field. Use concentration is, for example, usually 1 µM to 10 M, preferably 100 µM to 1 M, and more preferably 1 mM to 500 mM.

Also a leading buffer including such a leading ion is used by suitably selected from one usually used in this field, and for example, Good's buffer, Tris buffer, a borate buffer, a phosphate buffer, a histidine buffer, an imidazole buffer, a glycine buffer, and the like are included. Use concentration and pH thereof may suitably be selected from those usually used in this field, and use concentration is usually 1 µM to 10 M, preferably 100 µM to 1 M, and more preferably 1 mM to 500 mM, and pH is usually 2 to 12, preferably 4 to 10 and more preferably 6 to 9.

In the above description, as a trailing ion, any ion having slow electrophoretic speed than that of an analyte or an analogue thereof and/or not less than one kind of CFSs may be used, and suitably be selected from one usually used in this field. Such ion includes, including, for example, Good's buffer such as HEPES, TAPS, MES, MOPS, and the like, an amino acid such as glycine, threonine and the like. In addition, use concentration of a trailing ion may also suitably be selected from a range usually used in this field. Use concentration is, for example, usually 1 µM to 10 M, preferably 100 µM to 1 M, and more preferably 1 mM to 500 mM.

Also a trailing buffer including such a trailing ion is used by suitably selected from one usually used in this field, and for example, Good's buffer, Tris buffer, a borate buffer, a phosphate buffer, a histidine buffer, an imidazole buffer, a glycine buffer, and the like are included. Use concentration and pH thereof may suitably be selected from those usually used in this field, and use concentration is usually 1 µM to 10 M, preferably 100 µM to 1 M, and more preferably 1 mM to 500 mM, and pH is usually 2 to 12, preferably 4 to 10 and more preferably 6 to 9.

In this connection, the above-described conditions (a leading ion, a leading buffer, a trailing ion, a trailing buffer, and the like), other reagents, operation methods, other conditions, and the like can be selected according to the description in the above-described references, and the like.

FASS, FASI and LVSS are based on principle that electrophoretic mobility of an objective substance is decreased and an objective substance is concentrated, when an objective substance reaches interface between a medium wherein an objective substance is present, and a medium having higher electric conductivity than that of a medium wherein an objective substance is present.

Therefore, when a concentration and reaction step of the present invention is carried out by FASS, LVSS or FASI, at least one kind of a solution among a solution containing an analyte or an analogue thereof, and at least one kind of solution containing not less than one kind of CFS is required to have higher electric conductivity than that of other at least one kind of a the solutions; or an electrophoresis medium (high electric conductivity electrophoresis medium) having higher electric conductivity than that of a solution containing an analyte or an analogue thereof, and/or at least one kind of solution containing not less than one kind of CFS is required to be separately used, and these components are also included in "condition that an analyte or an analogue thereof and/or not less than one kind of CFSs are concentrated" of the present invention.

In this connection, a high electric conductivity electrophoresis medium is arranged at further downstream side of a solution arranged at the most downstream in a capillary (a first channel), among a solution containing an analyte or an analogue thereof, and at least one kind of solution containing not less than one kind of CFS.

In addition, a high electric conductivity electrophoresis medium may be any one as long as having higher salt concentration than that of a solution containing an analyte or an analogue thereof, and/or at least one kind of solution containing not less than one kind of CFS, and is used by suitably be selected from one usually used in this field. Such high electric conductivity electrophoresis medium includes, for example, an electrophoresis medium containing NaCl, KCl, and the like. As an electrophoresis medium, for example, Good's buffer, Tris buffer, a borate buffer, a phosphate buffer, a histidine buffer, an imidazole buffer, a glycine buffer, and the like are included. Use concentration and pH thereof may suitably be selected from those usually used in this field, and use concentration is usually 1 µM to 10 M, preferably 100 µM to 1 M, and more preferably 1 mM to 500 mM, and pH is usually 2 to 12, preferably 4 to 10 and more preferably 6 to 9.

In this connection, the above-described conditions (high electric conductivity electrophoresis medium, and the like), other reagents, operation methods, other conditions, and the like can suitably be selected according to the description in the above-described references, and the like.

IF is based on principle that an objective substance is concentrated by filling a capillary (channel) with a solution of amphoteric substances having various isoelectric points, then forming pH gradient in a capillary (channel) by applying a voltage, and when an objective substance reaches pH region corresponding to an isoelectric point.

Therefore, in the case when a concentration and reaction step of the present invention is carried out by IF, at least an electrophoresis medium formable pH gradient in a capillary (a first channel) is required, and this component is also included in "condition to make an analyte or an analogue thereof and/or at least one kind of CFSs concentrated" of the present invention.

In the above description, as an electrophoresis medium formable pH gradient in a capillary (a first channel), any one formable pH gradient in a capillary by applying a voltage is used by suitably selecting from one usually used in this field. As such an electrophoresis medium formable pH gradient in a capillary, for example, an electrophoresis medium containing a substance formable pH gradient in a capillary, such as ampholyte is included. As such an electrophoresis medium, for example, Good's buffer, Tris buffer, a borate buffer, a phosphate buffer, a histidine buffer, an imidazole buffer, a glycine buffer, and the like are included. Use concentration and pH thereof also may suitably be selected from those usually used in this field, and use concentration is usually 1 µM to 10 M, preferably 100 µM to 1 M, and more preferably 1 mM to 500 mM.

In this connection, the above-described conditions (an electrophoresis medium containing a substance formable pH gradient in a capillary, and the like), other reagents, operation methods, other conditions, and the like can be selected according to the description in the above-described references, and the like.

A pH junction method is one for carrying out concentration of an objective substance contained in a sample at the boundary surface between a sample and an alkaline electrophoresis medium by forming an acidic or a weak acidic sample region (zone) in the alkaline electrophoresis medium.

Therefore, in the case when a concentration and reaction step of the present invention is carried out by a pH junction method, at least an electrophoresis medium having more alkaline range pH than that of a solution including a sample is required, and this component is also included in "condition to make an analyte or an analogue thereof and/or not less than one kind of CFSs concentrated" of the present invention.

In the above description, as an electrophoresis medium having alkaline range pH, any one formable a boundary surface with different pH, between a solution including a sample and said electrophoresis medium in a capillary by applying a voltage is used by suitably selected from one usually used in this field. As such an electrophoresis medium, for example, Good's buffer such as HEPES, TAPS, MES, MOPS, and the like, a borate buffer, a phosphate buffer, a histidine buffer, an imidazole buffer, a glycine buffer, and the like are included. Use concentration and pH thereof may suitably be selected from those usually used in this field, and use concentration is usually 1 µM to 10 M, preferably 100 µM to 1 M, and more preferably 1 mM to 500 mM, and pH is usually 7 to 11, preferably 7 to 10 and more preferably 7 to 9.

In this connection, the above-described conditions (an electrophoresis medium having alkaline range pH, and the like), other reagents, operation methods, other conditions, and the like can be selected according to the description in the above-described references, and the like.

A sweeping method is based on the following principle: Namely, an electrophoresis medium including a charged substance forming a micelle is arranged at the upstream side of a solution zone including an objective substance. By applying a voltage here, the micelle formed overtakes an objective substance and forms a micelle complex with an objective substance. When the micelle complex reaches interface between a medium wherein an objective substance is present, and a medium having higher electric conductivity than that of a medium wherein an objective substance is present, electrophoretic speed of an objective substance is decreased and thus an objective substance is concentrated.

Therefore, when a concentration and reaction step of the present invention is carried out by a sweeping method, at least one kind of a solution among a solution containing an analyte or an analogue thereof and at least one kind of solution containing not less than one kind of CFS is required to have high electric conductivity than that of other at least one kind of a the solutions; or an electrophoresis medium (high electric conductivity electrophoresis medium) having higher electric conductivity than that of a solution containing an analyte or an analogue thereof and/or at least one kind of solution containing not less than one kind of CFS is required to separately be used; and an electrophoresis medium including a charged substance forming a micelle with higher electrophoretic speed than that of an analyte or an analogue thereof and/or not less than one kind of CFSs, and having lower electric conductivity than that of a solution (or an electrophoresis medium) having higher electric conductivity is required; and these components are also included in "condition to make an analyte or an analogue thereof and/or not less than one kind of CFSs concentrated" of the present invention.

In this connection, a high electric conductivity electrophoresis medium is arranged further downstream side of a solution arranged at the most downstream side of a capillary (a first channel), among a solution containing an analyte or an analogue thereof, and at least one kind of solution containing not less than one kind of CFS, and an electrophoresis medium including a charged substance forming a micelle is arranged further upstream side of a solution arranged at the most upstream side of a capillary, among a solution containing an analyte or an analogue thereof, and at least one kind of solution containing not less than one kind of CFS.

In the above description, as a charged substance forming a micelle, any charged substance may be used as long as having faster electrophoretic speed than that of an analyte or an analogue thereof and/or not less than one kind of CFSs, and suitably be selected from one usually used in this field. Such charged substance includes, for example, a surfactant such as SDS, and the like. In addition, use concentration of said charged substance may also suitably be selected from a range usually used in this field, and the amount over critical micelle concentration is used, and, in more specifically, use concentration of said charged substance is for example, usually 1 µM to 10 M, preferably 100 µM to 1 M, and more preferably 1 mM to 500 mM.

Also an electrophoresis medium is used by suitably selected from one usually used in this field, and, for example, Good's buffer, Tris buffer, a borate buffer, a phosphate buffer, a histidine buffer, an imidazole buffer, a glycine buffer, and the like are included. Use concentration and pH thereof may suitably be selected from those usually used in this field, and use concentration is usually 1 µM to 10 M, preferably 100 µM to 1 M, and more preferably 1 mM to 500 mM, and pH is usually 2 to 12, preferably 4 to 10 and more preferably 6 to 9.

In this connection, the above-described conditions [a charged substance forming a micelle, an electrophoresis medium, and the like], other reagents, operation methods, other conditions, and the like can suitably be selected according to the description in the above-described references, and the like.

(d) Applied Voltage

Applied voltage in a concentration and reaction step may be in a range wherein an analyte or analogue thereof and/or a CFS is sufficiently concentrated, and a complex between an analyte or an analogue thereof and a CFS is sufficiently formed, and may suitably be selected from that usually used in this field. In more specifically, voltage is applied, so that electric field intensity is in the following range: as lower limit, usually not lower than 5 V/cm, preferably not lower than 10 V/cm, more preferably not lower than 50 V/cm, further preferably not lower than 500 V/cm, and particularly preferably not lower than 1000 V/cm, and as upper limit, usually not higher than 10000 V/cm, preferably not higher than 5000 V/cm, more preferably not higher than 2000 V/cm.

In addition, other reaction conditions (for example, pH, temperature, time, and the like) preferably be in a range not to inhibit concentration of an analyte or analogue thereof and/or a CFS, and formation of a complex between an analyte or an analogue thereof and a CFS.

Specifically, although not to simply be described because of dependency on property of an analyte or an analogue thereof and a CFS, lower limit of pH is usually not lower than 2, preferably not lower than 5, and upper limit of pH is usually not higher than 10, and preferably not higher than 9; and lower limit of temperature is usually not lower than 0° C., preferably not lower than 5° C., and more preferably not lower than 10° C., and upper limit of temperature is usually not higher than 50° C., preferably not higher than 40° C., and more preferably not higher than 30° C. Reaction time depends on binding constant of a CFS to be used to an analyte or an analogue thereof, and relatively low binding constant requires relatively long reaction time but relatively high binding constant requires relatively short reaction time. In more specifically, for example, lower limit is usually not shorter than 1 minute, preferably not shorter than 3 minutes and more preferably not shorter than 5 minutes; and upper limit is usually not longer than 24 hours, preferably not longer than 12 hours, more preferably not longer than 1 hour and further preferably not longer than 30 minutes.

(e) An Electrophoresis Medium

A concentration and reaction step of the present invention is usually carried out in a state that the above-mentioned capillary (first channel) is filled with an electrophoresis medium. As an electrophoresis medium, a buffer solution for electrophoresis or said buffer solution for electrophoresis containing fillers, and the like are included. In this connection, an electrophoresis medium may be used alone or in combination with two or more kinds. In addition, as a method for introducing an electrophoresis medium into a capillary (a first channel) includes a method for introducing a solution containing an analyte or an analogue thereof, and a solution containing CFS into a capillary (a first channel) as described above. And any one of the following timings of introduction of an electrophoresis medium into a capillary (a first channel) may be adopted: (1) before the introduction of a solution containing an analyte or an analogue thereof, and/or at least one kind of solution containing not less than one kind of CFS into a capillary (a first channel); (2) simultaneously with the introduction of a solution containing an analyte or an analogue thereof, and/or at least one kind of solution containing not less than one kind of CFS into a capillary (a first channel); and (3) after the introduction of a solution containing an analyte or an analogue thereof, and/or at least one kind of solution containing not less than one kind of CFS into a capillary (a first channel).

Such a buffer solution for electrophoresis is not especially limited as long as it is usually used in this field. Examples of a buffer solution for electrophoresis are, for example, the buffer solutions etc. usually used in the field of a hybridization method, an immunization, and the like such as Tris buffer, a phosphate buffer, Veronal buffer, a borate buffer, Good's buffer, SSC buffer, TBE buffer, TAE buffer, and the like. Concentration of these buffer solutions is usually 0.1 mM to 10 M, preferably 1 mM to 5 M, and more preferably 5 mM to 1M. In addition, any pH of said buffer solution may be used as long as not to give bad effect on separation of substances, and is usually 2 to 13, preferably 4 to 11 and more preferably 5 to 9. In this connection, these buffer solutions may be used alone or in combination with two or more kinds.

Fillers (polymers) filled in a capillary (a first channel) are not especially limited as long as they are usually used in this field. Examples of fillers are, for example, polyethers such as polyethylene oxide (polyethylene glycol), polypropylene oxide; polyalkylene imines such as polyethylene imine; polyacrylic acid polymers such as polyacrylic acid, polyacrylate esters, and poly(methyl acrylate); polyamide-based polymers such as polyacrylamide, polymethacrylamide; polymethacrylic acid-based polymers such as polymethacrylic acid, polymethacrylate esters and poly(methyl methacrylate); polyvinyl-based polymers such as polyvinyl acetate, polyvinyl pyrrolidone and polyvinyl oxazolidone; water-soluble hydroxyl polymers such as pullulan, elsinan, xanthan, dextran and guar gum; water-soluble cellulosic compounds such as methyl cellulose, hydroxyethyl cellulose and hydroxypropyl cellulose; derivatives thereof, and copolymers having a plurality of kinds of monomer unites composing these polymers, and the like. In this connection, these fillers may be used alone or in combination with two or more kinds.

Molecular weight of the fillers as described above is usually 500 Da to 6000 kDa, preferably 1 to 1000 kDa and more preferably 50 to 500 kDa.

Use concentration of the fillers as described above may suitably be selected from a range usually used in this field, and is usually 0.01 to 40% (w/v), preferably 0.01 to 20% (w/v), and more preferably 0.1 to 10% (w/v).

In this connection, viscosity of a buffer solution for electrophoresis when the above-described fillers are added thereto, is usually 1 to 1000 centipoises, preferably 1 to 200 centipoises, and more preferably 1 to 10 centipoises.

(3) A Specific Method for Forming a Complex

Modes for carrying out the methods for forming a complex of the present invention are specifically shown below.

(3-1) A Case when a CFS not Bound with a Labeling Substance and a Reaction Improvement Substance are Used.

(a) A micro fluidic device comprising at least one structure for introducing a sample or a reagent solution to a first channel (1) in a substrate is provided, said the structure comprising;

(i) the first channel (1);
   (ii) not less than 3 D side channels (2), each said D side channel (2) having a opening (2-1) opened on a wall of said first channel (1), and said openings (2-1) arranged in spaced relation to one another, wherein said D side channel (2) is connected to a W reservoir (4); and
   (iii) not less than 2 S/R side channels (3), each said S/R side channel (3) having a opening (3-1) opened on the wall of said first channel (1) at the different position (part) from said openings (2-1) of said D side channels (2), and each said opening (3-1) arranged between adjacent 2 openings (2-1) of D side channels (2), wherein each said opening (3-1) of these not less than 2 S/R side channels (3) are each arranged at the different portion between adjacent 2 openings (2-1) of D side channels (2), and S/R side channel (3) is connected to a S/R reservoir (5).

(b) A solution containing an analyte [for example, (i) a sample including an analyte, (ii) a solution including a sample having an analyte, and not less than one kind of CFSs] is put into one of the S/R reservoir (5) connecting to said S/R side channel (3).

(c) A solution containing not less than one kind of CFS is put into at least one of the other S/R reservoir (5) connecting to said S/R side channel (3), wherein said S/R reservoir (5) being different from one used in said step (b).

(d) Then, said solution containing an analyte [for example, (i) a sample including an analyte, (ii) a solution including a sample having an analyte, and not less than one kind of CFSs] is introduced in said S/R side channel (3) connected with said S/R reservoir (5) used in said step (b), 2 D side channels (2) adjacent to said S/R side channel (3) in an axis direction and a first channel region between said 2 D side channels (2), by moving said solution containing an analyte [for example, (i) a sample including an analyte, (ii) a solution including a sample having an analyte, and not less than one kind of CFSs] from said S/R reservoir (5) where said solution containing an analyte [for example, (i) a sample including an analyte, (ii) a solution including a sample having an analyte, and not less than one kind of CFSs] is put in said step (b) to said 2 D side channels (2) adjacent to said S/R side channel (3) connected with said S/R reservoir (5) in an axis direction, via said S/R side channel (3) connected with said S/R reservoir (5).

(e) Said solution containing not less than one kind of CFS is introduced in said S/R side channel (3) connected with said S/R reservoir (5) used in said step (c), 2 D side channels (2) adjacent to said S/R side channel (3) in an axis direction and a first channel region between said 2 D side channels (2), by moving said solution containing not less than one kind of CFS from said S/R reservoir (5) where said solution containing not less than one kind of CFS is put in said step (c) to said 2 D side channels (2) adjacent to said S/R side channel (3) connected with said S/R reservoir (5) in an axis direction, via said S/R side channel (3) connected with said S/R reservoir (5). By the steps (d) and (e), the solution containing an analyte [for example, (i) a sample including an analyte, (ii) a solution including a sample having an analyte, and not less than one kind of CFSs] and the solution containing not less than one kind of CFS are introduced and arranged into a first channel, so that a zone of the solution containing an analyte [for example, (i) a sample including an analyte, (ii) a solution including a sample having an analyte, and not less than one kind of CFSs], and a zone of the solution including not less than one kind of CFSs are separately formed (so that liquid-liquid interface is formed), and a complex between said analyte and CFS is formed on application of a voltage onto said channel, without mixing these solutions in advance outside a channel.

(f) Said analyte is electrophoretically contacted and reacted with said CFS while concentrating said analyte and/or at least one kind of the CFSs by applying a voltage to said channel before uniformly mixing these solutions, not by (not depending on) molecular diffusion and without physically mixing, to form the complex between said analyte and the CFS.

In addition, in the described above, "concentrating said analyte and/or at least one kind of CFSs by applying a voltage onto a channel" means that, as similarly described above, said analyte and/or at least one kind of CFS gather in band-like (plug-like) on application of a voltage onto a channel. In other words, it means that said substances gather on application of a voltage onto a channel so that such a portion is generated wherein concentration of said substances becomes higher than that of a substance in a zone arranged in an introduction step [the steps (b) to (e)], namely it means that an analyte and/or at least one kind of a CFS gather on application of a voltage onto a channel, and a portion is generated wherein concentration of an analyte and/or concentration of not less than one kind of CFSs becomes higher than that of an analyte and/or not less than one kind of CFSs in a solution zone [for example, a zone of a solution containing an analyte (for example, (i) a sample including an analyte, (ii) a solution including a sample having an analyte, and not less than one kind of CFSs) and a zone of a solution containing not less than one kind of CFS] arranged in an introduction step [the steps (b) to (e)].

(3-2) A Case when a Labeled CFS is Used.

(a) The same micro fluidic device as the above-described step (a) in the case (3-1) of "(3) a specific method for forming a complex" is provided.

(b) A solution containing an analyte [for example, (i) a sample including an analyte, (ii) a solution including a sample having an analyte, and not less than one kind of CFSs] is put into one of the S/R reservoir (5) connecting to said S/R side channel (3).

(c) A solution containing not less than one kind of labeled CFSs is put into at least one of the other S/R reservoir (5) connecting to said S/R side channel (3), wherein said S/R reservoir (5) being different from one used in said step (b).

(d) Then, said solution containing an analyte [for example, (i) a sample including an analyte, (ii) a solution including a sample having an analyte, and not less than one kind of CFSs] is introduced in said S/R side channel (3) connected with said S/R reservoir (5) used in said step (b), 2 D side channels (2) adjacent to said S/R side channel (3) in an axis direction and a first channel region between said 2 D side channels (2), by moving said solution containing an analyte [for example, (i) a sample including an analyte, (ii) a solution including a sample having an analyte, and not less than one kind of CFSs] from said S/R reservoir (5) where said solution containing an analyte [for example, (i) a sample including an analyte, (ii) a solution including a sample having an analyte, and not less than one kind of CFSs] is put in said step (b) to said 2 D side channels (2) adjacent to said S/R side channel (3) connected with said S/R reservoir (5) in an axis direction, via said S/R side channel (3) connected with said S/R reservoir (5).

(e) Said solution containing not less than one kind of labeled CFSs is introduced in said S/R side channel (3) connected with said S/R reservoir (5) used in said step (c), 2 D side channels (2) adjacent to said S/R side channel (3) in an axis direction and a first channel region between said 2 D side channels (2), by moving said solution containing not less than one kind of labeled CFSs from said S/R reservoir (5) where said solution containing not less than one kind of labeled CFSs is put in said step (c) to said 2 D side channels (2) adjacent to said S/R side channel (3) connected with said S/R reservoir (5) in an axis direction, via said S/R side channel (3) connected with said S/R reservoir (5). By the steps (d) and (e), the solution containing an analyte [for example, (i) a sample including an analyte, (ii) a solution including a sample having an analyte, and not less than one kind of CFSs] and the solution containing not less than one kind of labeled CFSs are introduced and arranged into a channel so that a zone of the solution containing an analyte [for example, (i) a sample including an analyte, (ii) solutions including a sample having an analyte, and not less than one kind of CFSs], and a zone of the solution containing not less than one kind of labeled CFSs are separately formed (so that liquid-liquid interface is formed), and a complex between said analyte and labeled CFS is formed on application of a voltage onto a channel, without mixing these solutions in advance outside a channel.

(f) Said analyte is electrophoretically contacted and reacted with said labeled CFS while concentrating said analyte and/or at least one kind of said labeled CFS by applying a voltage onto said channel before uniformly mixing these solutions, not by (not depending on) molecular diffusion and without physically mixing, to form the complex between said analyte and labeled CFS.

In addition, in the described above, "concentrating said analyte and/or at least one kind of labeled CFSs by applying a voltage onto a channel" means that, as similarly described above, said analyte and/or at least one kind of labeled CFS to gather in band-like (plug-like) on application of a voltage onto a channel. In other words, it means that said substances gather on application of a voltage onto a channel so that such a portion is generated wherein concentration of said substances becomes higher than that of a substance in a zone arranged in an introduction step [the steps (b) to (e)], namely, it means that an analyte and/or at least one kind of a labeled CFS gather on application of a voltage onto a channel, and a portion is generated wherein concentration of an analyte and/or concentration of at least one kind of a labeled CFS becomes higher than that of an analyte and/or at least one kind of a labeled CFS in a solution zone [for example, a zone of a solution containing an analyte (for example, (i) a sample including an analyte, (ii) a solution including a sample having an analyte, and not less than one kind of CFSs) and a zone of a solution containing not less than one kind of labeled CFSs] arranged in an introduction step [the steps (b) to (e)].

(3-3) A Case when a Reaction Improvement CFS is Used.

(a) The same micro fluidic device as the above-described step (a) in the case (3-1) of "(3) a specific method for forming a complex" is provided.

(b) A solution containing an analyte [for example, (i) a sample including an analyte, (ii) a solution including a sample having an analyte, and not less than one kind of CFSs (ex. a labeled CFS)] is put into one of the S/R reservoir (5) connecting to said S/R side channel (3).

(c) A solution containing not less than one kind of reaction improvement CFSs is put into at least one of the other S/R reservoir (5) connecting to said S/R side channel (3), wherein said S/R reservoir (5) being different from one used in said step (b).

(d) Then, said solution containing an analyte [for example, (i) a sample including an analyte, (ii) a solution including a sample having an analyte, and not less than one kind of CFSs (ex. a labeled CFS)] is introduced in said S/R side channel (3) connected with said S/R reservoir (5) used in said step (b), 2 D side channels (2) adjacent to said S/R side channel (3) in an axis direction and a first channel region between said 2 D side channels (2), by moving said solution containing an analyte [for example, (i) a sample including an analyte, (ii) a solution including a sample having an analyte, and not less than one kind of CFSs (ex. a labeled CFS)] from said S/R reservoir (5) where said solution containing an analyte [for example, (i) a sample including an analyte, (ii) a solution including a sample having an analyte, and not less than one kind of CFSs (ex. a labeled CFS)] is put in said step (b) to said 2 D side channels (2) adjacent to said S/R side channel (3) connected with said S/R reservoir (5) in an axis direction, via said S/R side channel (3) connected with said S/R reservoir (5).

(e) Said solution containing not less than one kind of reaction improvement CFSs is introduced in said S/R side channel (3) connected with said S/R reservoir (5) used in said step (c), 2 D side channels (2) adjacent to said S/R side channel (3) in an axis direction and a first channel region between said 2 D side channels (2), by moving said solution containing not less than one kind of reaction improvement CFSs from said S/R reservoir (5) where said solution containing not less than one kind of reaction improvement CFSs is put in said step (c) to said 2 D side channels (2) adjacent to said S/R side channel (3) connected with said S/R reservoir (5) in an axis direction, via said S/R side channel (3) connected with said S/R reservoir (5). By the steps (d) and (e), the solution containing an analyte [for example, (i) a sample including an analyte, (ii) a solution including a sample having an analyte, and not less than one kind of CFSs (ex. a labeled CFS)] and the solution containing not less than one kind of reaction improvement CFSs are introduced and arranged into a channel so that a zone of the solution containing an analyte [for example, (i) a sample including an analyte, (ii) a solution including a sample having an analyte, and not less than one kind of CFSs (ex. a labeled CFS)], and a zone of the solution including not less than one kind of reaction improvement CFSs are separately formed (so that liquid-liquid interface is formed), and a complex between said analyte and reaction improvement CFS is formed on application of a voltage onto a channel, without mixing these solutions in advance outside a channel.

(f) Said analyte is electrophoretically contacted and reacted with said reaction improvement CFS while concentrating said analyte and/or at least one kind of the reaction improvement CFS by applying a voltage onto said channel before uniformly mixing these solutions, not by (not depending on) molecular diffusion and without physically mixing, to form the complex between said analyte and reaction improvement CFS.

In addition, in the described above, "concentrating said analyte and/or at least one kind of reaction improvement CFSs by applying a voltage onto a channel" means that, as similarly described above, said analyte and/or at least one kind of reaction improvement CFS gather in band-like (plug-like) on application of a voltage onto a channel. In other words, it means that said substances gather on application of a voltage onto a channel so that such a portion is generated wherein concentration of said substances becomes higher than that of a substance in a zone arranged in an introduction step [the steps (b) to (e)], namely, it means that an analyte and/or at least one kind of a reaction improvement CFS gather on application of a voltage onto a channel, and a portion is generated wherein concentration of an analyte and/or concentration of not less than one kind of reaction improvement CFSs becomes higher than that of an analyte and/or not less than one kind of reaction improvement CFSs in a solution zone [for example, a solution zone containing an analyte (for example, (i) a sample including an analyte, (ii) a solution including a sample having an analyte, and not less than one kind of CFSs) and a zone of a solution containing not less than one kind of reaction improvement CFSs] arranged in an introduction step [the steps (b) to (e)].

(3-4) A Case when a Labeled Reaction Improvement CFS is Used.

(a) The same micro fluidic device as the above-described step (a) in the case (3-1) of "(3) a specific method for forming a complex" is provided.

(b) A solution containing an analyte [for example, (i) a sample including an analyte, (ii) a solution including a sample having an analyte, and not less than one kind of CFSs] is put into one of the S/R reservoir (5) connecting to said S/R side channel (3).

(c) A solution containing not less than one kind of labeled reaction improvement CFSs is put into at least one of the other S/R reservoir (5) connecting to said S/R side channel (3), wherein said S/R reservoir (5) being different from one used in said step (b).

(d) Then, said solution containing an analyte [for example, (i) a sample including an analyte, (ii) a solution including a sample having an analyte, and not less than one kind of CFSs] is introduced in said S/R side channel (3) connected with said S/R reservoir (5) used in said step (b), 2 D side channels (2) adjacent to said S/R side channel (3) in an axis direction and a first channel region between said 2 D side channels (2), by moving said solution containing an analyte [for example, (i) a sample including an analyte, (ii) a solution including a sample having an analyte, and not less than one kind of CFSs] from said S/R reservoir (5) where said solution containing an analyte [for example, (i) a sample including an analyte, (ii) a solution including a sample having an analyte, and not less than one kind of CFSs] is put in said step (b) to said 2 D side channels (2) adjacent to said S/R side channel (3) connected with said S/R reservoir (5) in an axis direction, via said S/R side channel (3) connected with said S/R reservoir (5).

(e) Said solution containing not less than one kind of labeled reaction improvement CFSs is introduced in said S/R side channel (3) connected with said S/R reservoir (5) used in said step (c), 2 D side channels (2) adjacent to said S/R side channel (3) in an axis direction and a first channel region between said 2 D side channels (2), by moving said solution containing not less than one kind of labeled reaction improvement CFSs from said S/R reservoir (5) where said solution containing not less than one kind of labeled reaction improvement CFSs is put in said step (c) to said 2 D side channels (2) adjacent to said S/R side channel (3) connected with said S/R reservoir (5) in an axis direction, via said S/R side channel (3) connected with said S/R reservoir (5). By the steps (d) and (e), the solution containing an analyte [for example, (i) a sample including an analyte, (ii) a solution including a sample having an analyte, and not less than one kind of CFSs] and the solution containing not less than one kind of labeled reaction improvement CFSs are introduced and arranged into a channel so that a zone of the solution containing an analyte [for example, (i) a sample including an analyte, (ii) a solution including a sample having an analyte, and not less than one kind of CFSs], and a zone of a solution including not less than one kind labeled reaction improvement CFSs are separately formed (so that liquid-liquid interface is formed), and a complex between said analyte and labeled reaction improvement CFS is formed on application of a voltage onto said channel, without mixing these solutions in advance outside a channel.

(f) Said analyte is electrophoretically contacted and reacted with said labeled reaction improvement CFS while concentrating said analyte and/or at least one kind of a labeled reaction improvement CFS by applying a voltage onto said channel before uniformly mixing these solutions, not by (not depending on) molecular diffusion and without physically mixing, to form the complex between said analyte and labeled reaction improvement CFS.

In addition, in the described above, "concentrating said analyte and/or at least one kind of labeled reaction improvement CFS by applying a voltage onto a channel" means that, as similarly described above, said analyte and/or at least one kind of labeled reaction improvement CFS gather in band-like (plug-like) on application of a voltage onto a channel. In other words, it means that said substances gather on application of a voltage onto a channel so that such a portion is generated wherein concentration of said substances becomes higher than a substance in a zone arranged in an introduction step [the steps (b) to (e)], namely, it means that an analyte and/or at least one kind of a labeled reaction improvement CFS gather on application of a voltage onto a channel, and a portion is generated wherein concentration of an analyte and/or concentration of not less than one kind of labeled reaction improvement CFSs becomes higher than that of an analyte and/or not less than one kind of labeled reaction improvement CFSs in a solution zone [for example, a zone of a solution containing an analyte (for example, (i) a sample including an analyte, (ii) a solution including a sample having an analyte, and not less than one kind of CFSs) and a zone of a solution containing not less than one kind of labeled reaction improvement CFSs] arranged in an introduction step [the steps (b) to (e)].

(3-5) A Case when a CFS not Bound with a Labeling Substance and a Reaction Improvement Substance, and a Reaction Improvement CFS are Used.

(a) The same micro fluidic device as the above-described step (a) in the case (3-1) of "(3) a specific method for forming a complex" is provided.

(b) A solution containing an analyte [for example, (i) a sample including an analyte, (ii) a solution including a sample having an analyte, and not less than one kind of CFSs] is put into one of the S/R reservoir (5) connecting to said S/R side channel (3).

(c) A solution containing not less than one kind of a CFS is put into at least one of the other S/R reservoir (5) connecting to said S/R side channel (3), wherein said S/R reservoir (5) being different from one used in said step (b).

(d) A solution containing not less than one kind of a reaction improvement CFS is put into at least one of the other S/R reservoir (5) connecting to said S/R side channel (3), wherein said S/R reservoir (5) being different from one used in said steps (b) and (c).

(e) Then, said solution containing an analyte [for example, (i) a sample including an analyte, (ii) a solution including a sample having an analyte, and not less than one kind of CFSs] is introduced in said S/R side channel (3) connected with said S/R reservoir (5) used in said step (b), 2 D side channels (2) adjacent to said S/R side channel (3) in an axis direction and a first channel region between said 2 D side channels (2), by moving said solution containing an analyte [for example, (i) a sample including an analyte, (ii) a solution including a sample having an analyte, and not less than one kind of CFSs] from said S/R reservoir (5) where said solution containing an analyte [for example, (i) a sample including an analyte, (ii) a solution including a sample having an analyte, and not less than one kind of CFSs] is put in said step (b) to said 2 D side channels (2) adjacent to said S/R side channel (3) connected with said S/R reservoir (5) in an axis direction, via said S/R side channel (3) connected with said S/R reservoir (5).

(f) Said solution containing not less than one kind of a CFS is introduced in said S/R side channel (3) connected with said S/R reservoir (5) used in said step (c), 2 D side channels (2) adjacent to said S/R side channel (3) in an axis direction and a first channel region between said 2 D side channels (2), by moving said solution containing not less than one kind of a CFS from said S/R reservoir (5) where said solution containing not less than one kind of a CFS is put in said step (c) to said 2 D side channels (2) adjacent to said S/R side channel (3) connected with said S/R reservoir (5) in an axis direction, via said S/R side channel (3) connected with said S/R reservoir (5).

(g) Said solution containing not less than one kind of a reaction improvement CFS is introduced in said S/R side channel (3) connected with said S/R reservoir (5) used in said step (d), 2 D side channels (2) adjacent to said S/R side channel (3) in an axis direction and a first channel region between said 2 D side channels (2), by moving said solution containing not less than one kind of a reaction improvement CFS from said S/R reservoir (5) where said solution containing not less than one kind of a reaction improvement CFS is put in said step (d) to said 2 D side channels (2) adjacent to said S/R side channel (3) connected with said S/R reservoir (5) in an axis direction, via said S/R side channel (3) connected with said S/R reservoir (5). By the steps (e) to (g), the solution containing an analyte [for example, (i) a sample including an analyte, (ii) a solution including a sample having an analyte, and not less than one kind of CFSs], the solution containing not less than one kind of a CFS and the solution containing not less than one kind of a reaction improvement CFS are introduced and arranged into a channel so that a zone of the solution containing an analyte [for example, (i) a sample including an analyte, (ii) a solution including a sample having an analyte, and not less than one kind of CFSs], a zone of the solution including not less than one kind of CFSs, and a zone of the solution including not less than one kind of reaction improvement CFSs are separately formed (so that liquid-liquid interface is formed), and a complex between said analyte, CFS and reaction improvement CFS is formed on application of a voltage onto a channel, without mixing these solutions in advance outside a channel.

(h) Said analyte is electrophoretically contacted and reacted with said CFS and reaction improvement CFS while concentrating at least one selected from said analyte, not less than one kind of CFS and not less than one kind of reaction improvement CFS by applying a voltage onto said channel before uniformly mixing these solutions, not by (not depending on) molecular diffusion and without physically mixing, to form the complex between said analyte, CFS and reaction improvement CFS.

In addition, in the described above, "concentrating at least one selected from said analyte not less than one kind of CFS and not less than one kind of reaction improvement CFS, by applying a voltage onto a channel" means that, as similarly described above, at least one selected from said analyte, not less than one kind of CFS and not less than one kind of reaction improvement CFS gather in band-like (plug-like) on application of a voltage onto a channel. In other words, it means that said substances gather on application of a voltage onto a channel so that such a portion is generated wherein concentration of said substances becomes higher than that of a substance in a zone arranged in an introduction step [the steps (b) to (g)], namely, it means that at least one selected from an analyte, not less than one kind of CFS and not less than one kind of reaction improvement CFS gather on application of a voltage onto a channel, and a portion is generated wherein concentration of an analyte, concentration of not less than one kind of a CFS or concentration of not less than one kind of a reaction improvement CFS becomes higher than that of an analyte, not less than one kind of a CFS or not less than one kind of a reaction improvement CFS in a solution zone [for example, a zone of a solution containing an analyte (for example, (i) a sample including an analyte, (ii) a solution including a sample having an analyte, and not less than one kind of CFSs), a zone of a solution including not less than one kind of CFSs and a zone of a solution including not less than one kind of reaction improvement CFSs] arranged in an introduction step [the steps (b) to (g)].

(3-6) A Case when a Labeled CFS and a Reaction Improvement CFS are Used.

(a) The same micro fluidic device as the above-described step (a) in the case (3-1) of "(3) a specific method for forming a complex" is provided.

(b) A solution containing an analyte [for example, (i) a sample including an analyte, (ii) a solution including a sample having an analyte, and not less than one kind of CFSs] is put into one of the S/R reservoir (5) connecting to said S/R side channel (3).

(c) A solution containing not less than one kind of a labeled CFS is put into at least one of the other S/R reservoir (5) connecting to said S/R side channel (3), wherein said S/R reservoir (5) being different from one used in said step (b).

(d) A solution containing not less than one kind of a reaction improvement CFS is put into at least one of the other S/R reservoir (5) connecting to said S/R side channel (3), wherein said S/R reservoir (5) being different from one used in said steps (b) and (c).

(e) Then, said solution containing an analyte [for example, (i) a sample including an analyte, (ii) a solution including a sample having an analyte, and not less than one kind of CFSs] is introduced in said S/R side channel (3) connected with said S/R reservoir (5) used in said step (b), 2 D side channels (2) adjacent to said S/R side channel (3) in an axis direction and a first channel region between said 2 D side channels (2), by moving said solution containing an analyte [for example, (i) a sample including an analyte, (ii) a solution including a sample having an analyte, and not less than one kind of CFSs] from said S/R reservoir (5) where said solution containing an analyte [for example, (i) a sample including an analyte, (ii) a solution including a sample having an analyte, and not less than one kind of CFSs] is put in said step (b) to said 2 D side channels (2) adjacent to said S/R side channel (3) connected with said S/R reservoir (5) in an axis direction, via said S/R side channel (3) connected with said S/R reservoir (5).

(f) Said solution containing not less than one kind of a labeled CFS is introduced in said S/R side channel (3) connected with said S/R reservoir (5) used in said step (c), 2 D side channels (2) adjacent to said S/R side channel (3) in an axis direction and a first channel region between said 2 D side channels (2), by moving said solution containing not less than one kind of a labeled CFS from said S/R reservoir (5) where said solution containing not less than one kind of a labeled CFS is put in said step (c) to said 2 D side channels (2) adjacent to said S/R side channel (3) connected with said S/R reservoir (5) in an axis direction, via said S/R side channel (3) connected with said S/R reservoir (5).

(g) Said solution containing not less than one kind of a reaction improvement CFS is introduced in said S/R side channel (3) connected with said S/R reservoir (5) used in said step (d), 2 D side channels (2) adjacent to said S/R side channel (3) in an axis direction and a first channel region between said 2 D side channels (2), by moving said solution containing not less than one kind of a reaction improvement CFS from said S/R reservoir (5) where said solution containing not less than one kind of a reaction improvement CFS is put in said step (d) to said 2 D side channels (2) adjacent to said S/R side channel (3) connected with said S/R reservoir (5) in an axis direction, via said S/R side channel (3) connected with said S/R reservoir (5). By the steps (e) to (g), the solution containing an analyte [for example, (i) a sample including an analyte, (ii) a solution including a sample having an analyte, and not less than one kind of CFSs], the solution containing not less than one kind of a labeled CFS and the a solution containing not less than one kind of a reaction improvement CFS are introduced and arranged into a channel so that a zone of the solution containing an analyte [for example, (i) a sample including an analyte, (ii) a solution including a sample having an analyte, and not less than one kind of CFSs], a zone of the solution containing not less than one kind of labeled CFSs, and a zone of the solution containing not less than one kind of reaction improvement CFSs are separately formed (so that liquid-liquid interface is formed), and a complex between said analyte, labeled CFS and reaction improvement CFS is formed on application of a voltage onto a channel, without mixing these solutions in advance outside a channel.

(h) Said analyte is electrophoretically contacted and reacted with said labeled CFS and reaction improvement CFS while concentrating at least one selected from said analyte, not less than one kind of labeled CFS and not less than one kind of reaction improvement CFS by applying a voltage onto said channel before uniformly mixing these solutions, not by (not depending on) molecular diffusion and without physically mixing, to form the complex between said analyte, labeled CFS and reaction improvement CFS.

In addition, in the described above, "concentrating at least one selected from said analyte, not less than one kind of labeled CFS and not less than one kind of reaction improvement CFS, by applying a voltage onto a channel" means that, as similarly described above, at least one selected from said analyte, not less than one kind of labeled CFS and not less than one kind of reaction improvement CFS gather in band-like (plug-like) on application of a voltage onto a channel. In other words, it means that said substances gather on application of a voltage onto a channel so that such a portion is generated wherein concentration of said substances becomes higher than a substance in a zone arranged in an introduction step [the steps (b) to (g)], namely, it means that at least one selected from an analyte, not less than one kind of labeled CFS and not less than one kind of reaction improvement CFS gather on application of a voltage onto a channel, and a portion is generated wherein concentration of an analyte, concentration of not less than one kind of a labeled CFS or concentration of not less than one kind of a reaction improvement CFS becomes higher than that of an analyte, not less than one kind of a labeled CFS or not less than one kind of a reaction improvement CFS in a solution zone [for example, a zone of a solution containing an analyte (for example, (i) a sample including an analyte, (ii) a solution including a sample having an analyte, and not less than one kind of CFSs), a zone of a solution including not less than one kind of a labeled CFS, and a zone of a solution including not less than one kind of a reaction improvement CFS] arranged in an introduction step [the steps (b) to (g)].

(3-7) A Case when a CFS not Bound with a Labeling Substance and a Reaction Improvement Substance, and a Labeled Reaction Improvement CFS are Used.

(a) The same micro fluidic device as the above-described step (a) in the case (3-1) of "(3) a specific method for forming a complex" is provided.

(b) A solution containing an analyte [for example, (i) a sample including an analyte, (ii) a solution including a sample having an analyte, and not less than one kind of CFSs] is put into one of the S/R reservoir (5) connecting to said S/R side channel (3).

(c) A solution containing not less than one kind of a CFS is put into at least one of the other S/R reservoir (5) connecting to said S/R side channel (3), wherein said S/R reservoir (5) being different from one used in said step (b).

(d) A solution containing not less than one kind of a labeled reaction improvement CFS is put into at least one of the other S/R reservoir (5) connecting to said S/R side channel (3), wherein said S/R reservoir (5) being different from one used in said steps (b) and (c).

(e) Then, said solution containing an analyte [for example, (i) a sample including an analyte, (ii) a solution including a sample having an analyte, and not less than one kind of CFSs] is introduced in said S/R side channel (3) connected with said S/R reservoir (5) used in said step (b), 2 D side channels (2) adjacent to said S/R side channel (3) in an axis direction and a first channel region between said 2 D side channels (2), by moving said solution containing an analyte [for example, (i) a sample including an analyte, (ii) a solution including a sample having an analyte, and not less than one kind of CFSs] from said S/R reservoir (5) where said solution containing an analyte [for example, (i) a sample including an analyte, (ii) a solution including a sample having an analyte, and not less than one kind of CFSs] is put in said step (b) to said 2 D side channels (2) adjacent to said S/R side channel (3) connected with said S/R reservoir (5) in an axis direction, via said S/R side channel (3) connected with said S/R reservoir (5).

(f) Said solution containing not less than one kind of a CFS is introduced in said S/R side channel (3) connected with said S/R reservoir (5) used in said step (c), 2 D side channels (2) adjacent to said S/R side channel (3) in an axis direction and a first channel region between said 2 D side channels (2), by moving said solution containing not less than one kind of a CFS from said S/R reservoir (5) where said solution containing not less than one kind of a CFS is put in said step (c) to said 2 D side channels (2) adjacent to said S/R side channel (3) connected with said S/R reservoir (5) in an axis direction, via said S/R side channel (3) connected with said S/R reservoir (5).

(g) Said solution containing not less than one kind of a labeled reaction improvement CFS is introduced in said S/R side channel (3) connected with said S/R reservoir (5) used in said step (d), 2 D side channels (2) adjacent to said S/R side channel (3) in an axis direction and a first channel region between said 2 D side channels (2), by moving said solution containing not less than one kind of a labeled reaction improvement CFS from said S/R reservoir (5) where said solution containing not less than one kind of a labeled reaction improvement CFS is put in said step (d) to said 2 D side channels (2) adjacent to said S/R side channel (3) connected with said S/R reservoir (5) in an axis direction, via said S/R side channel (3) connected with said S/R reservoir (5). By the steps (e) to (g), the solution containing an analyte [for example, (i) a sample including an analyte, (ii) a solution including a sample having an analyte, and not less than one kind of CFSs], the solution containing not less than one kind of a CFS and the solution containing not less than one kind of a labeled reaction improvement CFS are introduced and arranged into a channel so that a zone of a solution containing an analyte [for example, (i) a sample including an analyte, (ii) a solution including a sample having an analyte, and not less than one kind of CFSs], a zone of the solution including not less than one kind of CFSs, and a zone of the solution containing not less than one kind labeled reaction improvement CFSs are separately formed (so that liquid-liquid interface is formed), and a complex between said analyte, CFS and labeled reaction improvement CFS is formed on application of a voltage onto a channel, without mixing these solutions in advance outside a channel.

(h) Said analyte is electrophoretically contacted and reacted with said CFS and labeled reaction improvement CFS while concentrating at least one selected from said analyte, not less than one kind of CFS and not less than one kind of labeled reaction improvement CFS by applying a voltage onto said channel before uniformly mixing these solutions, not by (not depending on) molecular diffusion and without physically mixing, to form the complex between said analyte, CFS and labeled reaction improvement CFS.

In addition, in the described above, "concentrating at least one selected from said analyte, not less than one kind of CFS and not less than one kind of labeled reaction improvement CFS, by applying a voltage onto a channel" means that, as similarly described above, at least one selected from said analyte, not less than one kind of CFS and not less than one kind of labeled reaction improvement CFS gather in band-like (plug-like) on application of a voltage onto a channel. In other words, it means that said substances gather on application of a voltage onto a channel so that such a portion is generated wherein concentration of said substances becomes higher than a substance in a zone arranged in an introduction step [the steps (b) to (g)], namely, it means that at least one selected from an analyte, not less than one kind of CFS and not less than one kind of labeled reaction improvement CFS gather on application of a voltage onto a channel, and a portion is generated wherein concentration of an analyte, concentration of not less than one kind of a CFS or concentration of not less than one kind of a labeled reaction improvement CFS becomes higher than that of an analyte, not less than one kind of a CFS or not less than one kind of a labeled reaction improvement CFS in a solution zone [for example, a zone of solution containing an analyte (for example, (i) a sample including an analyte, (ii) a solution including a sample having an analyte, and not less than one kind of CFSs), a zone of a solution including not less than one kind of CFSs and a zone of a solution containing not less than one kind labeled reaction improvement CFSs] arranged in an introduction step [the steps (b) to (g)].

A method for forming a complex of the present invention can also be used in so-called a competitive method. The procedure in carrying it out in a competitive method is as follows:

(3-8) A Case when a Labeled Analogue and a CFS are Used. (The Use of a Solution Including Both an Analyte and an Analogue.)

(a) The same micro fluidic device as the above-described step (a) in the case (3-1) of "(3) a specific method for forming a complex" is provided.

(b) A solution including a sample having an analyte and a labeled analogue (or a solution including a sample having an analyte, a labeled analogue and not less than one kind of CFSs) is put into one of the S/R reservoir (5) connecting to said S/R side channel (3).

(c) A solution containing not less than one kind of CFSs is put into at least one of the other S/R reservoir (5) connecting to said S/R side channel (3), wherein said S/R reservoir (5) being different from one used in said step (b).

(d) Then, said solution including a sample having an analyte and a labeled analogue (or a solution including a sample having an analyte, a labeled analogue and not less than one kind of CFSs) is introduced in said S/R side channel (3) connected with said S/R reservoir (5) used in said step (b), 2 D side channels (2) adjacent to said S/R side channel (3) in an axis direction and a first channel region between said 2 D side channels (2), by moving said solution including a sample having an analyte and a labeled analogue (or a solution including a sample having an analyte, a labeled analogue and not less than one kind of CFSs) from said S/R reservoir (5) where said solution including a sample having an analyte and a labeled analogue (or a solution including a sample having an analyte, a labeled analogue and not less than one kind of CFSs) is put in said step (b) to said 2 D side channels (2) adjacent to said S/R side channel (3) connected with said S/R reservoir (5) in an axis direction, via said S/R side channel (3) connected with said S/R reservoir (5).

(e) Said solution containing not less than one kind of CFSs is introduced in said S/R side channel (3) connected with said S/R reservoir (5) used in said step (c), 2 D side channels (2) adjacent to said S/R side channel (3) in an axis direction and a first channel region between said 2 D side channels (2), by moving said solution containing not less than one kind of CFSs from said S/R reservoir (5) where said solution containing not less than one kind of CFSs is put in said step (c) to said 2 D side channels (2) adjacent to said S/R side channel (3) connected with said S/R reservoir (5) in an axis direction, via said S/R side channel (3) connected with said S/R reservoir (5). By the steps (d) and (e), the solution including a sample having an analyte and a labeled analogue (or a solution including a sample having an analyte, a labeled analogue and not less than one kind of CFSs) and the a solution containing not less than one kind of CFSs are introduced and arranged into a channel so that a zone of the solution including a sample having an analyte and a labeled analogue (or the solution including a sample having an analyte, a labeled analogue and not less than one kind of CFSs), and a zone of the solution including not less than one kind of CFSs are separately formed (so that liquid-liquid interface is formed), and a complex A between said analyte and CFS and a complex B between said labeled analogue and CFS are formed on application of a voltage onto a channel, without mixing these solutions in advance outside a channel.

(f) Said analyte and labeled analogue are electrophoretically contacted and reacted with said CFS (namely, said analyte is electrophoretically contacted and reacted with said CFS, and said labeled analogue electrophoretically contacted and reacted with said CFS) while concentrating said analyte and labeled analogue and/or not less than one kind of a CFS by applying a voltage onto said channel before uniformly mixing these solutions, not by (not depending on) molecular diffusion and without physically mixing, to form the complex A between said analyte and CFS and a complex B between said labeled analogue and CFS.

In addition, in the described above, "concentrating said analyte and labeled analogue, and/or not less than one kind of a CFS, by applying a voltage onto a channel" means that, as similarly described above, said analyte and labeled analogue and/or not less than one kind of CFS gather in band-like (plug-like) on application of a voltage onto a channel. In other words, it means that said substances gather on application of a voltage onto a channel so that such a portion is generated wherein concentration of said substances becomes higher than a substance in a zone arranged in an introduction step [the steps (b) to (e)], namely, it means that an analyte and a labeled analogue, and/or not less than one kind of a CFS gather on application of a voltage onto a channel, and a portion is generated wherein concentration of an analyte and a labeled analogue, and/or concentration of a CFS becomes higher than that of an analyte and a labeled analogue, and/or not less than one kind of a CFS in a solution zone [for example, a zone of a solution including a sample having an analyte and a labeled analogue (or a solution including a sample having an analyte, a labeled analogue and not less than one kind of CFSs), a zone of a solution containing CFS] arranged in a an introduction step [the steps (b) to (e)].

(3-9) A Case when a Labeled Analogue and a Reaction Improvement CFS are Used. (The Use of a Solution Including Both an Analyte and an Analogue.)

(a) The same micro fluidic device as the above-described step (a) in the case (3-1) of "(3) a specific method for forming a complex" is provided.

(b) A solution including a sample having an analyte and a labeled analogue (or a solution including a sample having an analyte, a labeled analogue and not less than one kind of CFSs) is put into one of the S/R reservoir (5) connecting to said S/R side channel (3).

(c) A solution containing not less than one kind of reaction improvement CFSs is put into at least one of the other S/R reservoir (5) connecting to said S/R side channel (3), wherein said S/R reservoir (5) being different from one used in said step (b).

(d) Then, said solution including a sample having an analyte and a labeled analogue (or a solution including a sample having an analyte, a labeled analogue and not less than one kind of CFSs) is introduced in said S/R side channel (3) connected with said S/R reservoir (5) used in said step (b), 2 D side channels (2) adjacent to said S/R side channel (3) in an axis direction and a first channel region between said 2 D side channels (2), by moving said solution including a sample having an analyte and a labeled analogue (or a solution including a sample having an analyte, a labeled analogue and not less than one kind of CFSs) from said S/R reservoir (5) where said solution including a sample having an analyte and a labeled analogue (or a solution including a sample having an analyte, a labeled analogue and not less than one kind of CFSs) is put in said step (b) to said 2 D side channels (2) adjacent to said S/R side channel (3) connected with said S/R reservoir (5) in an axis direction, via said S/R side channel (3) connected with said S/R reservoir (5).

(e) Said solution containing not less than one kind of reaction improvement CFSs is introduced in said S/R side channel (3) connected with said S/R reservoir (5) used in said step (c), 2 D side channels (2) adjacent to said S/R side channel (3) in an axis direction and a first channel region between said 2 D side channels (2), by moving said solution containing not less than one kind of reaction improvement CFSs from said S/R reservoir (5) where said solution containing not less than one kind of reaction improvement CFSs is put in said step (c) to said 2 D side channels (2) adjacent to said S/R side channel (3) connected with said S/R reservoir (5) in an axis direction, via said S/R side channel (3) connected with said S/R reservoir (5). By the steps (d) and (e), the solution including a sample having an analyte and a labeled analogue (or a solution including a sample having an analyte, a labeled analogue and not less than one kind of CFSs) and the solution containing not less than one kind of reaction improvement CFSs are introduced and arranged into a channel so that a zone of the solution including a sample having an analyte and a labeled analogue (or the solution including a sample having an analyte, a labeled analogue and not less than one kind of CFSs), and a zone of the solution including not less than one kind of reaction improvement CFSs are separately formed (so that liquid-liquid interface is formed), and a complex A between said analyte and reaction improvement CFS and a complex B between said labeled analogue and reaction improvement CFS are formed on application of a voltage onto a channel, without mixing these solutions in advance outside a channel.

(f) Said analyte and labeled analogue are electrophoretically contacted and reacted with said reaction improvement CFS (namely, said analyte is electrophoretically contacted and reacted with said reaction improvement CFS, and said labeled analogue is electrophoretically contacted and reacted with said reaction improvement CFS) while concentrating said analyte and labeled analogue and/or not less than one kind of said reaction improvement CFS by applying a voltage onto said channel before uniformly mixing these solutions, not by (not depending on) molecular diffusion and without physically mixing, to form the complex A between said analyte and reaction improvement CFS and a complex B between said labeled analogue and reaction improvement CFS.

In addition, in the described above, "concentrating said analyte and labeled analogue, and/or not less than one kind of reaction improvement CFS, by applying a voltage onto a channel" means that, as similarly described above, said analyte and labeled analogue and/or not less than one kind of reaction improvement CFS gather in band-like (plug-like) on application of a voltage onto a channel. In other words, it means that said substances gather on application of a voltage onto a channel so that such a portion is generated wherein concentration of said substances becomes higher than a substance in a zone arranged in an introduction step [the steps (b) to (e)], namely, it means that an analyte and a labeled analogue, and/or not less than one kind of reaction improvement CFS gather on application of a voltage onto a channel, and a portion is generated wherein concentration of an analyte and a labeled analogue, and/or concentration of a reaction improvement CFS becomes higher than that of an analyte and a labeled analogue, and/or not less than one kind of a reaction improvement CFS in a solution zone [for example, a zone of a solution including a sample having an analyte and a labeled analogue (or a solution including a sample having an analyte, a labeled analogue and not less than one kind of CFSs), a zone of a solution including reaction improvement CFSs] arranged in an introduction step [the steps (b) to (e)].

(3-10) A Case when a Labeled Analogue, a CFS and a Reaction Improvement CFS are Used. (The Use of a Solution Including Both an Analyte and an Analogue.)

(a) The same micro fluidic device as the above-described step (a) in the case (3-1) of "(3) a specific method for forming a complex" is provided.

(b) A solution including a sample having an analyte and a labeled analogue (or a solution including a sample having an analyte, a labeled analogue and not less than one kind of CFSs) is put into one of the S/R reservoir (5) connecting to said S/R side channel (3).

(c) A solution including not less than one kind of a CFS is put into at least one of the other S/R reservoir (5) connecting to said S/R side channel (3), wherein said S/R reservoir (5) being different from one used in said step (b).

(d) A solution including not less than one kind of a reaction improvement CFS is put into at least one of the other S/R reservoir (5) connecting to said S/R side channel (3), wherein said S/R reservoir (5) being different from one used in said steps (b) and (c).

(e) Then, said solution including a sample having an analyte and a labeled analogue (or a solution including a sample having an analyte, a labeled analogue and not less than one kind of CFSs) is introduced in said S/R side channel (3) connected with said S/R reservoir (5) used in said step (b), 2 D side channels (2) adjacent to said S/R side channel (3) in an axis direction and a first channel region between said 2 D side channels (2), by moving said solution including a sample having an analyte and a labeled analogue (or a solution including a sample having an analyte, a labeled analogue and not less than one kind of CFSs) from said S/R reservoir (5) where said solution including a sample having an analyte and a labeled analogue (or a solution including a sample having an analyte, a labeled analogue and not less than one kind of CFSs) is put in said step (b) to said 2 D side channels (2) adjacent to said S/R side channel (3) connected with said S/R reservoir (5) in an axis direction, via said S/R side channel (3) connected with said S/R reservoir (5).

(f) Said solution including not less than one kind of a CFS is introduced in said S/R side channel (3) connected with said S/R reservoir (5) used in said step (c), 2 D side channels (2) adjacent to said S/R side channel (3) in an axis direction and a first channel region between said 2 D side channels (2), by moving said solution including not less than one kind of a CFS from said S/R reservoir (5) where said solution including not less than one kind of a CFS is put in said step (c) to said 2 D side channels (2) adjacent to said S/R side channel (3) connected with said S/R reservoir (5) in an axis direction, via said S/R side channel (3) connected with said S/R reservoir (5).

(g) Said solution including not less than one kind of a reaction improvement CFS is introduced in said S/R side channel (3) connected with said S/R reservoir (5) used in said step (d), 2 D side channels (2) adjacent to said S/R side channel (3) in an axis direction and a first channel region between said 2 D side channels (2), by moving said solution including not less than one kind of a reaction improvement CFS from said S/R reservoir (5) where said solution including not less than one kind of a reaction improvement CFS is put in said step (d) to said 2 D side channels (2) adjacent to said S/R side channel (3) connected with said S/R reservoir (5) in an axis direction, via said S/R side channel (3) connected with said S/R reservoir (5). By the steps (e) to (g), the solution including a sample having an analyte and a labeled analogue (or a solution including a sample having an analyte, a labeled analogue and not less than one kind of CFSs), the solution including not less than one kind of a CFS and the solution including not less than one kind of a reaction improvement CFS are introduced and arranged into a channel so that a zone of the solution including a sample having an analyte and a labeled analogue (or the solution including a sample having an analyte, a labeled analogue and not less than one kind of CFSs), a zone of the solution including not less than one kind of CFSs and a zone of the solution including not less than one kind of reaction improvement CFSs are separately formed (so that liquid-liquid interface is formed), and a complex A between said analyte, CFS and reaction improvement CFS and a complex B between said labeled analogue, CFS and reaction improvement CFS are formed on application of a voltage onto a channel, without mixing these solutions in advance outside a channel.

(h) Said analyte and labeled analogue are electrophoretically contacted and reacted with said CFS and reaction improvement CFS (namely, said analyte is electrophoretically contacted and reacted with said CFS and reaction improvement CFS, and said labeled analogue is electrophoretically contacted and reacted with said CFS and reaction improvement CFS) while concentrating at least one selected from said analyte and labeled analogue, not less than one kind of a CFS and not less than one kind of a reaction improvement CFS by applying a voltage onto said channel before uniformly mixing these solutions, not by (not depending on) molecular diffusion and without physically mixing, to form the complex A between said analyte, CFS and reaction improvement CFS and a complex B between said labeled analogue, CFS and reaction improvement CFS.

In addition, in the described above, "concentrating at least one selected from said analyte and labeled analogue, not less than one kind of CFS and not less than one kind of reaction improvement CFS, by applying a voltage onto a channel" means that, as similarly described above, at least one selected from said analyte and labeled analogue, not less than one kind of CFS and not less than one kind of reaction improvement CFS gather in band-like (plug-like) on application of a voltage onto a channel. In other words, it means that said substances gather on application of a voltage onto a channel so that such a portion is generated wherein concentration of said substances becomes higher than a substance in a zone arranged in an introduction step [the steps (b) to (g)], namely, it means that at least one selected from an analyte and labeled analogue, not less than one kind of CFS and not less than one kind of reaction improvement CFS gather on application of a voltage onto a channel, and a portion is generated wherein concentration of an analyte and a labeled analogue, concentration of not less than one kind of a CFS or concentration of not less than one kind of a reaction improvement CFS becomes higher than that of an analyte and a labeled analogue, not less than one kind of a CFS or not less than one kind of a reaction improvement CFS in a solution zone [for example, a zone of a solution including an analyte and a labeled analogue (or a solution including a sample having an analyte, a labeled analogue and not less than one kind of CFSs), a zone of a solution including not less than one kind of CFSs, and a zone of a solution including not less than one kind of reaction improvement CFSs] arranged in an introduction step [the steps (b) to (g)].

(3-11) A Case when a Reaction Improvement Analogue and a Labeled CFS are Used. (The Use of a Solution Including Both an Analyte and an Analogue.)

(a) The same micro fluidic device as the above-described step (a) in the case (3-1) of "(3) a specific method for forming a complex" is provided.

(b) A solution containing sample having an analyte and reaction improvement analogue (or a solution including a sample having an analyte, a reaction improvement analogue and not less than one kind of CFSs) is put into one of the S/R reservoir (5) connecting to said S/R side channel (3).

(c) A solution including not less than one kind of labeled CFSs is put into at least one of the other S/R reservoir (5) connecting to said S/R side channel (3), wherein said S/R reservoir (5) being different from one used in said step (b).

(d) Then, said solution containing sample having an analyte and reaction improvement analogue (or a solution including a sample having an analyte, a reaction improvement analogue and not less than one kind of CFSs) is introduced in said S/R side channel (3) connected with said S/R reservoir (5) used in said step (b), 2 D side channels (2) adjacent to said S/R side channel (3) in an axis direction and a first channel region between said 2 D side channels (2), by moving said solution containing sample having an analyte and reaction improvement analogue (or a solution including a sample having an analyte, a reaction improvement analogue and not less than one kind of CFSs) from said S/R reservoir (5) where said solution containing sample having an analyte and reaction improvement analogue (or a solution including a sample having an analyte, a reaction improvement analogue and not less than one kind of CFSs) is put in said step (b) to said 2 D side channels (2) adjacent to said S/R side channel (3) connected with said S/R reservoir (5) in an axis direction, via said S/R side channel (3) connected with said S/R reservoir (5).

(e) Said solution including not less than one kind of labeled CFSs is introduced in said S/R side channel (3) connected with said S/R reservoir (5) used in said step (c), 2 D side channels (2) adjacent to said S/R side channel (3) in an axis direction and a first channel region between said 2 D side channels (2), by moving said solution including not less than one kind of labeled CFSs from said S/R reservoir (5) where said solution including not less than one kind of labeled CFSs is put in said step (c) to said 2 D side channels (2) adjacent to said S/R side channel (3) connected with said S/R reservoir (5) in an axis direction, via said S/R side channel (3) connected with said S/R reservoir (5). By the steps (d) and (e), the solution containing sample having an analyte and reaction improvement analogue (or a solution including a sample having an analyte, a reaction improvement analogue and not less than one kind of CFSs) and the a solution including not less than one kind of labeled CFSs are introduced and arranged into a channel so that a zone of a solution including the sample having an analyte and a reaction improvement analogue (or the solution including a sample having an analyte, a reaction improvement analogue and not less than one kind of CFSs), and a zone of the solution including not less than one kind of labeled CFSs are separately formed (so that liquid-liquid interface is formed), and a complex A between said analyte and labeled CFS and a complex B between said reaction improvement analogue and labeled CFS are formed on application of a voltage onto a channel, without mixing these solutions in advance outside a channel.

(f) Said analyte and reaction improvement analogue are electrophoretically contacted and reacted with said labeled CFS (namely, said analyte is electrophoretically contacted and reacted with said labeled CFS, and said reaction improvement analogue is electrophoretically contacted and reacted with said labeled CFS) while concentrating said analyte and reaction improvement analogue and/or not less than one kind of labeled CFS by applying a voltage onto said channel, before uniformly mixing these solutions, not by (not depending on) molecular diffusion and without physically mixing, to form the complex A between said analyte and labeled CFS and the complex B between said reaction improvement analogue and labeled CFS.

In addition, in the described above, "concentrating said analyte and reaction improvement analogue and/or not less than one kind of labeled CFS, by applying a voltage onto a channel" means that, as similarly described above, said analyte and reaction improvement analogue and/or not less than one kind of labeled CFS gather in band-like (plug-like) on application of a voltage onto a channel. In other words, it means that said substances gather on application of a voltage onto a channel so that such a portion is generated wherein concentration of said substances becomes higher than a substance in a zone arranged in an introduction step [the steps (b) to (e)], namely, it means that an analyte and reaction improvement analogue and/or not less than one kind of labeled CFS gather on application of a voltage onto a channel, and a portion is generated wherein concentration of an analyte and a reaction improvement analogue and/or concentration of not less than one kind of a labeled CFS becomes higher than that of an analyte and a reaction improvement analogue, and/or not less than one kind of a labeled CFS in a solution zone [for example, a zone of a solution including an analyte and a reaction improvement analogue (or a solution including a sample having an analyte, a reaction improvement analogue and not less than one kind of CFSs), a solution including not less than one kind of labeled CFSs] arranged in an introduction step [the steps (b) to (e)]

(3-12) A Case when a Labeled Analogue and a CFS are Used. (The Use of Two Separate Solutions of a Solution Including an Analyte and a Solution Containing an Analogue.)

(a) The same micro fluidic device as the above-described step (a) in the case (3-1) of "(3) a specific method for forming a complex" is provided.

(b) A solution including a sample having an analyte, and not less than one kind of CFSs is put into one of the S/R reservoir (5) connecting to said S/R side channel (3).

(c) A solution containing a labeled analogue is put into at least one of the other S/R reservoir (5) connecting to said S/R side channel (3), wherein said S/R reservoir (5) being different from one used in said step (b).

(d) Then, said solution including a sample having an analyte, and not less than one kind of CFSs is introduced in said S/R side channel (3) connected with said S/R reservoir (5) used in said step (b), 2 D side channels (2) adjacent to said S/R side channel (3) in an axis direction and a first channel region between said 2 D side channels (2), by moving said solution including a sample having an analyte, and not less than one kind of CFSs from said S/R reservoir (5) where said solution including a sample having an analyte, and not less than one kind of CFSs is put in said step (b) to said 2 D side channels (2) adjacent to said S/R side channel (3) connected with said S/R reservoir (5) in an axis direction, via said S/R side channel (3) connected with said S/R reservoir (5).

(e) Said solution containing a labeled analogue is introduced in said S/R side channel (3) connected with said S/R reservoir (5) used in said step (c), 2 D side channels (2) adjacent to said S/R side channel (3) in an axis direction and a first channel region between said 2 D side channels (2), by moving said solution containing a labeled analogue from said S/R reservoir (5) where said solution containing a labeled analogue is put in said step (c) to said 2 D side channels (2) adjacent to said S/R side channel (3) connected with said S/R reservoir (5) in an axis direction, via said S/R side channel (3) connected with said S/R reservoir (5). By the steps (d) and (e), the solution including a sample having an analyte, and not less than one kind of CFSs, and the a solution containing a labeled analogue are introduced and arranged into a channel so that a zone of a solution including a sample having an analyte, and not less than one kind of CFSs, and a zone of a solution including a labeled analogue are separately formed (so that liquid-liquid interface is formed), and a complex B between said labeled analogue and CFS is formed on application of a voltage onto a channel, without mixing these solutions in advance outside a channel.

(f) Said labeled analogue is electrophoretically contacted and reacted with CFS (namely, said labeled analogue is electrophoretically contacted and reacted with said CFS not involved in the formation of a complex (complex A) with said analyte in the said solution including a sample having an analyte, and not less than one kind of CFSs) while concentrating said labeled analogue and/or said CFS not involved in the formation of a complex A by applying a voltage onto said channel before uniformly mixing these solutions, not by (not depending on) molecular diffusion and without physically mixing, to form the complex B between said labeled analogue and CFS.

In addition, in the described above, "concentrating said labeled analogue and/or said CFS not involved in the formation of a complex A, by applying a voltage onto a channel" means that, as similarly described above, said labeled analogue and/or said CFS not involved in the formation of a complex A gather in band-like (plug-like) on application of a voltage onto a channel. In other words, it means that said substances gather on application of a voltage onto a channel so that such a portion is generated wherein concentration of said substances becomes higher than a substance in a zone arranged in an introduction step [the steps (b) to (e)], namely, it means that said labeled analogue and/or said CFS not involved in the formation of a complex A gather on application of a voltage onto a channel, and a portion is generated wherein concentration of a concentration of a labeled analogue and/or a concentration of a CFS not involved in the formation of a complex A becomes higher than that of a labeled analogue and/or a CFS not involved in the formation of a complex A in a solution zone [for example, a zone of a solution including a sample having an analyte, and not less than one kind of CFSs, and a zone of a solution including a labeled analogue] arranged in an introduction step [the steps (b) to (e)].

(3-13) A Case when a Labeled Analogue and a Reaction Improvement CFS are Used. (The Use of Two Separate Solutions of a Solution Including an Analyte and a Solution Containing an Analogue.)

(a) The same micro fluidic device as the above-described step (a) in the case (3-1) of "(3) a specific method for forming a complex" is provided.

(b) A solution including a sample having an analyte, and not less than one kind of reaction improvement CFSs is put into one of the S/R reservoir (5) connecting to said S/R side channel (3).

(c) A solution containing a labeled analogue is put into at least one of the other S/R reservoir (5) connecting to said S/R side channel (3), wherein said S/R reservoir (5) being different from one used in said step (b).

(d) Then, said solution including a sample having an analyte, and not less than one kind of reaction improvement CFSs is introduced in said S/R side channel (3) connected with said S/R reservoir (5) used in said step (b), 2 D side channels (2) adjacent to said S/R side channel (3) in an axis direction and a first channel region between said 2 D side channels (2), by moving said solution including a sample having an analyte, and not less than one kind of reaction improvement CFSs from said S/R reservoir (5) where said solution including a sample having an analyte, and not less than one kind of reaction improvement CFSs is put in said step (b) to said 2 D side channels (2) adjacent to said S/R side channel (3) connected with said S/R reservoir (5) in an axis direction, via said S/R side channel (3) connected with said S/R reservoir (5).

(e) Said solution containing a labeled analogue is introduced in said S/R side channel (3) connected with said S/R reservoir (5) used in said step (c), 2 D side channels (2) adjacent to said S/R side channel (3) in an axis direction and a first channel region between said 2 D side channels (2), by moving said solution containing a labeled analogue from said S/R reservoir (5) where said solution containing a labeled analogue is put in said step (c) to said 2 D side channels (2) adjacent to said S/R side channel (3) connected with said S/R reservoir (5) in an axis direction, via said S/R side channel (3) connected with said S/R reservoir (5). By the steps (d) and (e), the solution including a sample having an analyte, and not less than one kind of reaction improvement CFSs, and the solution containing a labeled analogue are introduced and arranged into a channel so that a zone of a solution including a sample having an analyte, and not less than one kind of reaction improvement CFSs, and a zone of a solution including a labeled analogue are separately formed (so that liquid-liquid interface is formed), and a complex B between said labeled analogue and reaction improvement CFS is formed on application of a voltage onto a channel, without mixing these solutions in advance outside a channel.

(f) Said labeled analogue is electrophoretically contacted and reacted with said reaction improvement CFS (namely, said labeled analogue is electrophoretically contacted and reacted with said reaction improvement CFS not involved in the formation of a complex (complex A) with said analyte in the said solution including a sample having an analyte, and not less than one kind of reaction improvement CFS) while concentrating said labeled analogue and/or said reaction improvement CFS not involved in the formation of a complex A by applying a voltage onto said channel before uniformly mixing these solutions, not by (not depending on) molecular diffusion and without physically mixing, to form the complex B between said labeled analogue and reaction improvement CFS.

In addition, in the described above, "concentrating said labeled analogue and/or said reaction improvement CFS not involved in the formation of a complex A, by applying a voltage onto a channel" means that, as similarly described above, said labeled analogue and/or said reaction improvement CFS not involved in the formation of a complex A gather in band-like (plug-like) on application of a voltage onto a channel. In other words, it means that said substances gather on application of a voltage onto a channel so that such a portion is generated wherein concentration of said substances becomes higher than a substance in a zone arranged in an introduction step [the steps (b) to (e)], namely, it means that a labeled analogue and/or a reaction improvement CFS not involved in the formation of a complex A gather on application of a voltage onto a channel, and a portion is generated wherein concentration of a labeled analogue and/or concentration of a reaction improvement CFS not involved in the formation of a complex A becomes higher than that of a labeled analogue and/or a reaction improvement CFS not involved in the formation of a complex A in a solution zone [for example, a zone of a solution including a sample having an analyte, and not less than one kind of reaction improvement CFSs, and a zone of a solution including a labeled analogue] arranged in an introduction step [the steps (b) to (e)].

(3-14) A Case when a Labeled Analogue, a CFS and a Reaction Improvement CFS are Used. (The Use of Two Separate Solutions of a Solution Including an Analyte and a Solution Containing an Analogue.)

(a) The same micro fluidic device as the above-described step (a) in the case (3-1) of "(3) a specific method for forming a complex" is provided.

(b) A solution including a sample having an analyte and not less than one kind of a CFS (or not less than one kind of a reaction improvement CFS) is put into one of the S/R reservoir (5) connecting to said S/R side channel (3).

(c) A solution containing a labeled analogue is put into at least one of the other S/R reservoir (5) connecting to said S/R side channel (3), wherein said S/R reservoir (5) being different from one used in said step (b).

(d) A solution containing not less than one kind of a reaction improvement CFS (or not less than one kind of a CFS) is put into at least one of the other S/R reservoir (5) connecting to said S/R side channel (3), wherein said S/R reservoir (5) being different from one used in said steps (b) and (c).

(e) Then, said solution including a sample having an analyte and not less than one kind of a CFS (or not less than one kind of a reaction improvement CFS) is introduced in said S/R side channel (3) connected with said S/R reservoir (5) used in said step (b), 2 D side channels (2) adjacent to said S/R side channel (3) in an axis direction and a first channel region between said 2 D side channels (2), by moving said solution including a sample having an analyte and not less than one kind of a CFS (or not less than one kind of a reaction improvement CFS) from said S/R reservoir (5) where said solution including a sample having an analyte and not less than one kind of a CFS (or not less than one kind of a reaction improvement CFS) is put in said step (b) to said 2 D side channels (2) adjacent to said S/R side channel (3) connected with said S/R reservoir (5) in an axis direction, via said S/R side channel (3) connected with said S/R reservoir (5).

(f) Said solution containing a labeled analogue is introduced in said S/R side channel (3) connected with said S/R reservoir (5) used in said step (c), 2 D side channels (2) adjacent to said S/R side channel (3) in an axis direction and a first channel region between said 2 D side channels (2), by moving said solution containing a labeled analogue from said S/R reservoir (5) where said solution containing a labeled analogue is put in said step (c) to said 2 D side channels (2) adjacent to said S/R side channel (3) connected with said S/R reservoir (5) in an axis direction, via said S/R side channel (3) connected with said S/R reservoir (5).

(g) Said solution containing not less than one kind of a reaction improvement CFS (or not less than one kind of a CFS) is introduced in said S/R side channel (3) connected with said S/R reservoir (5) used in said step (d), 2 D side channels (2) adjacent to said S/R side channel (3) in an axis direction and a first channel region between said 2 D side channels (2), by moving said solution containing not less than one kind of a reaction improvement CFS (or not less than one kind of a CFS) from said S/R reservoir (5) where said solution containing not less than one kind of a reaction improvement CFS (or not less than one kind of a CFS) is put in said step (d) to said 2 D side channels (2) adjacent to said S/R side channel (3) connected with said S/R reservoir (5) in an axis direction, via said S/R side channel (3) connected with said S/R reservoir (5). By the steps (e) to (g), the solution including a sample having an analyte and not less than one kind of a CFS (or not less than one kind of a reaction improvement CFS), the solution containing a labeled analogue and the solution containing not less than one kind of a reaction improvement CFS (or not less than one kind of a CFS) are introduced and arranged into a channel so that a zone of the solution including a sample having an analyte and at least one kind of a CFS (or not less than one kind of a reaction improvement CFS), a zone of the solution including a labeled analogue and a zone of a solution including not less than one kind of a reaction improvement CFS (or not less than one kind of a CFS) are separately formed (so that liquid-liquid interface is formed), and a complex A between said analyte, CFS and reaction improvement CFS and a complex B between said labeled analogue, CFS and reaction improvement CFS are formed on application of a voltage onto a channel, without mixing these solutions in advance outside a channel.

(h) Said analyte and labeled analogue are electrophoretically contacted and reacted with said CFS and reaction improvement CFS [namely, a complex between said analyte and CFS (or reaction improvement CFS) in said solution (a) is electrophoretically contacted and reacted with said reaction improvement CFS (or CFS) in said solution (c), and said labeled analogue is electrophoretically contacted and reacted with said CFS (or reaction improvement CFS) not involved in the formation of said complex with said analyte in said solution (a) and said reaction improvement CFS (or CFS) in said solution (c)] while concentrating at least one selected from the complex A between said analyte and not less than one kind of CFS (or not less than one kind of reaction improvement CFS), labeled analogue, and not less than one kind of reaction improvement CFS (or not less than one kind of CFS) by applying a voltage onto said channel before uniformly mixing these solutions, not depending on molecular diffusion and without physically mixing, to form the complex A between said analyte, CFS and reaction improvement CFS and the complex B between said labeled analogue, CFS and reaction improvement CFS.

In addition, in the described above, "concentrating at least one selected from said complex between said analyte and not less than one kind of a CFS (or not less than one kind of a reaction improvement CFS), said labeled analogue, and not less than one kind of a reaction improvement CFS (or not less than one kind of a CFS), by applying a voltage onto a channel" means that, as similarly described above, at least one selected from said complex between said analyte and not less than one kind of a CFS (or not less than one kind of a reaction improvement CFS), said labeled analogue, and not less than one kind of a reaction improvement CFS (or not less than one kind of a CFS) gather in band-like (plug-like) on application of a voltage onto a channel. In other words, it means that said substances gather on application of a voltage onto a channel so that such a portion is generated wherein concentration of said substances becomes higher than a substance in a zone arranged in an introduction step [the steps (b) to (g)], namely, it means that at least one selected from a complex between said analyte and not less than one kind of a CFS (or not less than one kind of a reaction improvement CFS), a labeled analogue, and not less than one kind of a reaction improvement CFS (or not less than one kind of a CFS) gather on application of a voltage onto a channel, and a portion is generated wherein concentration of a complex between said analyte and not less than one kind of a CFS (or not less than one kind of a reaction improvement CFS), concentration of a labeled analogue or concentration of not less than one kind of a reaction improvement CFS (or not less than one kind of a CFS) becomes higher than that of a complex between said analyte and at least one kind of a CFS (or not less than one kind of a reaction improvement CFS), a labeled analogue, or not less than one kind of a reaction improvement CFS (or not less than one kind of a CFS) in a solution zone [for example, a zone of a solution including a sample having an analyte and not less than one kind of a CFS (or not less than one kind of a reaction improvement CFS), a zone of a solution including a labeled analogue and a zone of a solution including not less than one kind of reaction improvement CFSs (or not less than one kind of a CFS)] arranged in an introduction step [the steps (b) to (g)].

(3-15) A Case when a Reaction Improvement Analogue and a Labeled CFS are Used. (The Use of Two Separate Solutions of a Solution Including an Analyte and a Solution Containing an Analogue.)

(a) The same micro fluidic device as the above-described step (a) in the case (3-1) of "(3) a specific method for forming a complex" is provided.

(b) A solution including a sample having an analyte, and not less than one kind of labeled CFSs is put into one of the S/R reservoir (5) connecting to said S/R side channel (3).

(c) A solution containing a reaction improvement analogue is put into at least one of the other S/R reservoir (5) connecting to said S/R side channel (3), wherein said S/R reservoir (5) being different from one used in said step (b).

(d) Then, said solution including a sample having an analyte, and not less than one kind of labeled CFSs is introduced in said S/R side channel (3) connected with said S/R reservoir (5) used in said step (b), 2 D side channels (2) adjacent to said S/R side channel (3) in an axis direction and a first channel region between said 2 D side channels (2), by moving said solution including a sample having an analyte, and not less than one kind of labeled CFSs from said S/R reservoir (5) where said solution including a sample having an analyte, and not less than one kind of labeled CFSs is put in said step (b) to said 2 D side channels (2) adjacent to said S/R side channel (3) connected with said S/R reservoir (5) in an axis direction, via said S/R side channel (3) connected with said S/R reservoir (5).

(e) Said solution containing a reaction improvement analogue is introduced in said S/R side channel (3) connected with said S/R reservoir (5) used in said step (c), 2 D side channels (2) adjacent to said S/R side channel (3) in an axis direction and a first channel region between said 2 D side channels (2), by moving said solution containing a reaction improvement analogue from said S/R reservoir (5) where said solution containing a reaction improvement analogue is put in said step (c) to said 2 D side channels (2) adjacent to said S/R side channel (3) connected with said S/R reservoir (5) in an axis direction, via said S/R side channel (3) connected with said S/R reservoir (5). By the steps (d) and (e), the solution including a sample having an analyte, and not less than one kind of labeled CFSs, and the solution containing a reaction improvement analogue are introduced and arranged into a channel so that a zone of a solution including a sample having an analyte, and not less than one kind of labeled CFSs, and a zone of a solution including a reaction improvement analogue are separately formed (so that liquid-liquid interface is formed), and a complex B between said reaction improvement analogue and labeled CFS is formed on application of a voltage onto a channel, without mixing these solutions in advance outside a channel.

(f) Said reaction improvement analogue is electrophoretically contacted and reacted with labeled CFS (namely, said reaction improvement analogue is electrophoretically contacted and reacted with said labeled CFS not involved in the formation of a complex (complex A) with said analyte in the said solution including a sample having an analyte, and not less than one kind of labeled CFSs) while concentrating said reaction improvement analogue and/or said labeled CFS not involved in the formation of a complex A by applying a voltage onto said channel before uniformly mixing these solutions, not by (not depending on) molecular diffusion and without physically mixing, to form the complex B between said reaction improvement analogue and labeled CFS.

In addition, in the described above, "concentrating a reaction improvement analogue and/or a labeled CFS not involved in the formation of a complex A, by applying a voltage onto a channel" means that, as similarly described above, a reaction improvement analogue and/or a labeled CFS not involved in the formation of a complex A gather in band-like (plug-like) on application of a voltage onto a channel. In other words, it means that said substances gather on application of a voltage onto a channel so that such a portion is generated wherein concentration of said substances becomes higher than a substance in a zone arranged in an introduction step [the steps (b) to (e)], namely, it means that said reaction improvement analogue and/or said labeled CFS not involved in the formation of a complex A gather on application of a voltage onto a channel, and a portion is generated wherein concentration of concentration of a reaction improvement analogue and/or concentration of a labeled CFS not involved in the formation of a complex A becomes higher than that of a reaction improvement analogue and/or a labeled CFS not involved in the formation of a complex A in a solution zone [for example, a zone of a solution including an analyte, and not less than one kind of labeled CFSs, and a zone of a solution including a reaction improvement analogue] arranged in an introduction step [the steps (b) to (e)].

(3-16) A Case when a Labeled Reaction Improvement Analogue, and a CFS not Bound with a Labeling Substance and a Reaction Improvement Substance are Used. (The Use of a Solution Including Both an Analyte and an Analogue.)

(a) The same micro fluidic device as the above-described step (a) in the case (3-1) of "(3) a specific method for forming a complex" is provided.

(b) A solution including a sample having an analyte and a labeled reaction improvement analogue (or a solution including a sample having an analyte, a labeled reaction improvement analogue and not less than one kind of CFSs) is put into one of the S/R reservoir (5) connecting to said S/R side channel (3).

(c) A solution containing not less than one kind of CFS not bound with a labeling substance and a reaction improvement substance is put into at least one of the other S/R reservoir (5) connecting to said S/R side channel (3), wherein said S/R reservoir (5) being different from one used in said step (b).

(d) Then, said solution including a sample having an analyte and a labeled reaction improvement analogue (or a solution including a sample having an analyte, a labeled reaction improvement analogue and not less than one kind of CFSs) is introduced in said S/R side channel (3) connected with said S/R reservoir (5) used in said step (b), 2 D side channels (2) adjacent to said S/R side channel (3) in an axis direction and a first channel region between said 2 D side channels (2), by moving said solution including a sample having an analyte and a labeled reaction improvement analogue (or a solution including a sample having an analyte, a labeled reaction improvement analogue and not less than one kind of CFSs) from said S/R reservoir (5) where said solution including a sample having an analyte and a labeled reaction improvement analogue (or a solution including a sample having an analyte, a labeled reaction improvement analogue and not less than one kind of CFSs) is put in said step (b) to said 2 D side channels (2) adjacent to said S/R side channel (3) connected with said S/R reservoir (5) in an axis direction, via said S/R side channel (3) connected with said S/R reservoir (5).

(e) Said solution containing not less than one kind of CFS not bound with a labeling substance and a reaction improvement substance is introduced in said S/R side channel (3) connected with said S/R reservoir (5) used in said step (c), 2 D side channels (2) adjacent to said S/R side channel (3) in an axis direction and a first channel region between said 2 D side channels (2), by moving said solution containing not less than one kind of CFS not bound with a labeling substance and a reaction improvement substance from said S/R reservoir (5) where said solution containing not less than one kind of CFS not bound with a labeling substance and a reaction improvement substance is put in said step (c) to said 2 D side channels (2) adjacent to said S/R side channel (3) connected with said S/R reservoir (5) in an axis direction, via said S/R side channel (3) connected with said S/R reservoir (5). By the steps (d) and (e), the solution including a sample having an analyte and a labeled reaction improvement analogue (or a solution including a sample having an analyte, a labeled reaction improvement analogue and not less than one kind of CFSs) and the a solution containing not less than one kind of CFS not bound with a labeling substance and a reaction improvement substance are introduced and arranged into a channel so that a zone of the solution including a sample having an analyte and a labeled reaction improvement analogue (or the solution including a sample having an analyte, a labeled reaction improvement analogue and not less than one kind of CFSs), and a zone of the solution including not less than one kind of CFS not bound with a labeling substance and a reaction improvement substance are separately formed (so that liquid-liquid interface is formed), and a complex A between said analyte and CFS not bound with a labeling substance and a reaction improvement substance and a complex B between said labeled reaction improvement analogue and CFS not bound with a labeling substance and a reaction improvement substance are formed on application of a voltage onto a channel, without mixing these solutions in advance outside a channel.

(f) Said analyte and labeled reaction improvement analogue are electrophoretically contacted and reacted with said CFS not bound with a labeling substance and a reaction improvement substance (namely, said analyte is electrophoretically contacted and reacted with said CFS not bound with a labeling substance and a reaction improvement substance, and said labeled reaction improvement analogue electrophoretically contacted and reacted with said CFS not bound with a labeling substance and a reaction improvement substance) while concentrating said analyte and labeled reaction improvement analogue and/or not less than one kind of a CFS not bound with a labeling substance and a reaction improvement substance by applying a voltage onto said channel before uniformly mixing these solutions, not by (not depending on) molecular diffusion and without physically mixing, to form the complex A between said analyte and CFS not bound with a labeling substance and a reaction improvement substance and a complex B between said labeled reaction improvement analogue and CFS not bound with a labeling substance and a reaction improvement substance.

In addition, in the described above, "concentrating said analyte and labeled reaction improvement analogue, and/or not less than one kind of a CFS not bound with a labeling substance and a reaction improvement substance, by applying a voltage onto a channel" means that, as similarly described above, said analyte and labeled reaction improvement analogue and/or not less than one kind of CFS not bound with a labeling substance and a reaction improvement substance gather in band-like (plug-like) on application of a voltage onto a channel. In other words, it means that said substances gather on application of a voltage onto a channel so that such a portion is generated wherein concentration of said substances becomes higher than a substance in a zone arranged in an introduction step [the steps (b) to (e)], namely, it means that an analyte and a labeled reaction improvement analogue, and/or not less than one kind of a CFS not bound with a labeling substance and a reaction improvement substance gather on application of a voltage onto a channel, and a portion is generated wherein concentration of an analyte and a labeled reaction improvement analogue, and/or concentration of a CFS not bound with a labeling substance and a reaction improvement substance becomes higher than that of an analyte and a labeled reaction improvement analogue, and/or not less than one kind of a CFS not bound with a labeling substance and a reaction improvement substance in a solution zone [for example, a zone of a solution including a sample having an analyte and a labeled reaction improvement analogue (or a solution including a sample having an analyte, a labeled reaction improvement analogue and not less than one kind of CFSs), a zone of a solution containing CFS not bound with a labeling substance and a reaction improvement substance] arranged in a an introduction step [the steps (b) to (e)].

(3-17) A Case when a Labeled Reaction Improvement Analogue, and a CFS not Bound with a Labeling Substance and a Reaction Improvement Substance are Used. (The Use of Two Separate Solutions of a Solution Including an Analyte and a Solution Containing an Analogue.)

(a) The same micro fluidic device as the above-described step (a) in the case (3-1) of "(3) a specific method for forming a complex" is provided.

(b) A solution including a sample having an analyte, and not less than one kind of CFS not bound with a labeling substance and a reaction improvement substance is put into one of the S/R reservoir (5) connecting to said S/R side channel (3).

(c) A solution containing a labeled reaction improvement analogue is put into at least one of the other S/R reservoir (5) connecting to said S/R side channel (3), wherein said S/R reservoir (5) being different from one used in said step (b).

(d) Then, said solution including a sample having an analyte, and not less than one kind of CFS not bound with a labeling substance and a reaction improvement substance is introduced in said S/R side channel (3) connected with said S/R reservoir (5) used in said step (b), 2 D side channels (2) adjacent to said S/R side channel (3) in an axis direction and a first channel region between said 2 D side channels (2), by moving said solution including a sample having an analyte, and not less than one kind of CFS not bound with a labeling substance and a reaction improvement substance from said S/R reservoir (5) where said solution including a sample having an analyte, and not less than one kind of CFS not bound with a labeling substance and a reaction improvement substance is put in said step (b) to said 2 D side channels (2) adjacent to said S/R side channel (3) connected with said S/R reservoir (5) in an axis direction, via said S/R side channel (3) connected with said S/R reservoir (5).

(e) Said solution containing a labeled reaction improvement analogue is introduced in said S/R side channel (3) connected with said S/R reservoir (5) used in said step (c), 2 D side channels (2) adjacent to said S/R side channel (3) in an axis direction and a first channel region between said 2 D side channels (2), by moving said solution containing a labeled reaction improvement analogue from said S/R reservoir (5) where said solution containing a labeled reaction improvement analogue is put in said step (c) to said 2 D side channels (2) adjacent to said S/R side channel (3) connected with said S/R reservoir (5) in an axis direction, via said S/R side channel (3) connected with said S/R reservoir (5). By the steps (d) and (e), the solution including a sample having an analyte, and not less than one kind of CFS not bound with a labeling substance and a reaction improvement substance, and the solution containing a labeled reaction improvement analogue are introduced and arranged into a channel so that a zone of a solution including a sample having an analyte, and not less than one kind of CFS not bound with a labeling substance and a reaction improvement substance, and a zone of a solution including a labeled reaction improvement analogue are separately formed (so that liquid-liquid interface is formed), and a complex B between said labeled reaction improvement analogue and labeled CFS is formed on application of a voltage onto a channel, without mixing these solutions in advance outside a channel.

(f) Said labeled reaction improvement analogue is electrophoretically contacted and reacted with CFS not bound with a labeling substance and a reaction improvement substance (namely, said labeled reaction improvement analogue is electrophoretically contacted and reacted with said CFS not bound with a labeling substance and a reaction improvement substance not involved in the formation of a complex (complex A) with said analyte in the said solution including a sample having an analyte, and not less than one kind of CFS not bound with a labeling substance and a reaction improvement substance) while concentrating said labeled reaction improvement analogue and/or said CFS not bound with a labeling substance and a reaction improvement substance not involved in the formation of a complex A by applying a voltage onto said channel before uniformly mixing these solutions, not by (not depending on) molecular diffusion and without physically mixing, to form the complex B between said labeled reaction improvement analogue and CFS not bound with a labeling substance and a reaction improvement substance.

In addition, in the described above, "concentrating a labeled reaction improvement analogue and/or a CFS not bound with a labeling substance and a reaction improvement substance not involved in the formation of a complex A, by applying a voltage onto a channel" means that, as similarly described above, a labeled reaction improvement analogue and/or a CFS not bound with a labeling substance and a reaction improvement substance not involved in the formation of a complex A gather in band-like (plug-like) on application of a voltage onto a channel. In other words, it means that said substances gather on application of a voltage onto a channel so that such a portion is generated wherein concentration of said substances becomes higher than a substance in a zone arranged in an introduction step [the steps (b) to (e)], namely, it means that said labeled reaction improvement analogue and/or said CFS not bound with a labeling substance and a reaction improvement substance, not involved in the formation of a complex A gather on application of a voltage onto a channel, and a portion is generated wherein concentration of concentration of a labeled reaction improvement analogue and/or concentration of a CFS not bound with a labeling substance and a reaction improvement substance, not involved in the formation of a complex A becomes higher than that of a labeled reaction improvement analogue and/or a CFS not bound with a labeling substance and a reaction improvement substance, not involved in the formation of a complex A in a solution zone [for example, a zone of a solution including an analyte, and not less than one kind of CFS not bound with a labeling substance and a reaction improvement substance, and a zone of a solution including a labeled reaction improvement analogue] arranged in an introduction step [the steps (b) to (e)].

In the above-described methods (3-1) to (3-17), as for level (degree) of concentration of a substance to be concentrated [for example, an analyte, a CFS, a labeled CFS, a reaction improvement CFS, a labeled reaction improvement CFS, a labeled analogue, a reaction improvement analogue, a complex between an analyte and a CFS, a complex between an analyte and a reaction improvement substance, a complex between an analyte and a labeled CFS, a complex between a labeled analogue and CFS and a complex between a reaction improvement analogue and CFS, etc.], concentration of a substance [for example, an analyte, a CFS, a labeled CFS, a reaction improvement CFS, a labeled reaction improvement CFS, a labeled analogue, a reaction improvement analogue, a complex between an analyte and a CFS, a complex between an analyte and a reaction improvement substance, a complex between an analyte and a labeled CFS, a complex between a labeled analogue and CFS and a complex between a reaction improvement analogue and CFS, etc.] at an gathered part (in band-like) of said substance on application of a voltage onto a channel, relative to concentration of an substance [for example, an analyte, a CFS, a labeled CFS, a reaction improvement CFS, a labeled reaction improvement CFS, a labeled analogue, a reaction improvement analogue, a complex between an analyte and a CFS, a complex between an analyte and a reaction improvement substance, a complex between an analyte and a labeled CFS, a complex between a labeled analogue and CFS and a complex between a reaction improvement analogue and CFS, etc.] in a solution zone arranged by an introduction step is, as lower limit, usually not lower than 1.5 times, preferably not lower than 5 times, more preferably not lower than 10 times, and further preferably not lower than 25 times, and upper limit is not especially limited, however usually not higher than $10^7$ times, preferably not higher than $10^6$ times and more preferably not higher than $10^5$ times.

In addition, in the above-described methods (3-1) to (3-17), "contacted while concentrating" means, similarly as described above, both cases when concentration and contact are simultaneously carried out, and a case when contact is carried out after concentration is substantially completed, and therefore encompasses so-called all the cases other than a case when concentration is carried out after contact is substantially completed.

In the above-described methods (3-1) to (3-17), a concentration and reaction step can be carried out, similarly as described above, before a solution arranged in a channel by an introduction step is uniformly mixed under conditions enabling concentration, contacting and formation of a complex, by applying a voltage onto said channel.

Specific examples, preferable embodiments, and the like of such conditions are as described above, and for example, the above concentration and reaction step may be carried out in accordance with the above-described method for concentration, in suitable consideration of electrophoretic mobility of an analyte, a CFS, a labeled CFS, a reaction improvement CFS, a labeled reaction improvement CFS, a labeled analogue, a reaction improvement analogue, a complex composed of 2 or more kinds thereof, to be used, or electric conductivity of solutions including these.

In addition, applied voltage and other reaction conditions (for example, pH, temperature, time, etc.), and the like in a concentration and reaction step may also suitably be determined from a range as described above, in consideration of an analyte, a CFS, a labeled CFS, a reaction improvement CFS, a labeled reaction improvement CFS, a labeled analogue, a reaction improvement analogue, a complex composed of 2 or more kinds thereof, solutions including these, and the like.

7. A Method for Separation of the Present Invention

A method for separation of the present invention features in electrical separation of a complex between an analyte or an analogue thereof and not less than one kind of CFSs, formed by a method for formation of a complex of the present invention as described above, and a CFS not involved in formation of said complex or an analogue not involved in formation of said complex.

Namely, the features is that a complex between an analyte or an analogue thereof and a CFS in a solution, formed by each react (contact and react) by electrophoretically moving (migrating) in a capillary (a first channel) in a step of concentrating and reacting of the present invention, and a CFS not involved in formation of said complex or an analogue not involved in formation of said complex are further electrophoretically moved (migrated) and are separated.

A method for separation of the present invention may be carried out in accordance with a known method itself except in electrically separating a complex between an analyte or an analogue thereof and not less than one kind of CFSs formed by a method for formation of a complex of the present invention, using a structure for introducing solutions, micro fluidics device or a micro fluidics system of the present invention as described above, and a CFS not involved in formation of said complex or an analogue not involved in formation of said complex, in a known method itself for separating a substance by electric movement (migration) using, for example, a capillary, and as for material and reagents to be used also, those used in known methods themselves may be used.

Namely, as described above, a method for introducing a sample and/or a reagent solution is carried out by using a solution introducing structure, micro fluidic device or a micro fluidic system of the present invention, to introduce and arrange a plurality of solutions (a sample and/or a reagent solution such as a solution containing an analyte or an analogue thereof, or a solution containing a CFS) in the capillary (the first channel) so that each independent zone is formed in a channel (the first channel). Then, an analyte or an analogue thereof and at least one kind of a CFS are reacted (contacted and reacted) while concentrating said analyte or said analogue thereof and/or at least one kind of the CFS electrophoretically to form a complex between said analyte or analogue thereof and the CFS by applying a voltage onto said capillary (the first channel) introduced and arranged with these solutions, without forming a complex between said analyte or analogue thereof and the CFS by mixing these solutions in advance outside a capillary. Subsequently, a complex between an analyte or an analogue thereof and a CFS in a solution, formed by each react (contact and react) by electrophoretically moving (migrating) in a capillary (a first channel), and a CFS not involved in formation of said complex or an analogue not involved in formation of said complex are further electrophoretically moved (migrated) and are separated.

Therefore, a method for separating of the present invention is specifically, for example, one comprising the following steps:

(a) providing a micro fluidic device comprising at least one structure for introducing a sample or a reagent solution to a first channel (1) in a substrate, said the structure comprising;
 (i) the first channel (1);
 (ii) not less than 3 D side channels (2), each said D side channel (2) having a opening (2-1) opened on a wall of said first channel (1), and said openings (2-1) arranged in spaced relation to one another, wherein said D side channel (2) is connected to a W reservoir (4); and
 (iii) not less than 2 S/R side channels (3), each said S/R side channel (3) having a opening (3-1) opened on the wall of said first channel (1) at the different position (part) from said openings (2-1) of said D side channels (2), and each said opening (3-1) arranged between adjacent 2 openings (2-1) of D side channels (2), wherein each said opening (3-1) of these not less than 2 S/R side channels (3) are each arranged at the different portion between adjacent 2 openings (2-1) of D side channels (2), and S/R side channel (3) is connected to a S/R reservoir (5)[(a): a preparation step];

(b) putting a sample into at least one S/R reservoir (5) connecting to said S/R side channel (3);

(c) putting a reagent solution into at least one S/R reservoir (5) connecting to said S/R side channel (3), wherein said S/R reservoir (5) being different from one used in said step (b);

(d) introducing said sample in said S/R side channel (3) connected with said S/R reservoir (5) used in said step (b), 2 D side channels (2) adjacent to said S/R side channel (3) in an axis direction and a first channel region between said 2 D side channels (2), by moving said sample from said S/R reservoir (5) where said sample is put in said step (b) to said 2 D side channels (2) adjacent to said S/R side channel (3) connected with said S/R reservoir (5) in an axis direction, via said S/R side channel (3) connected with said S/R reservoir (5);

(e) introducing said reagent solution in said S/R side channel (3) connected with said S/R reservoir (5) used in said step (c), 2 D side channels (2) adjacent to said S/R side channel (3) in an axis direction and a first channel region between said 2 D side channels (2), by moving said reagent solution from said S/R reservoir (5) where said reagent solution is put in said step (c) to said 2 D side channels (2) adjacent to said S/R side channel (3) connected with said S/R reservoir (5) in an axis direction, via said S/R side channel (3) connected with said S/R reservoir (5) [(b) to (e): a introduction step];

(f) reacting an analyte or an analogue thereof in the sample with at least one kind of a CFS in the reagent solution while concentrating said analyte or said analogue thereof in the sample and/or at least one kind of the CFS in the reagent solution to form the complex between said analyte or said analogue thereof and the CFS, by applying a voltage to said first channel (1) [(f): concentration and reaction step]; and (g) separating said complex betwee said analyte or said analogue thereof and the CFS, and CFS not involved in the formation of said complex or said analogue not involved in the formation of said complex, by further applying a voltage to said first channel (1) [(g): separation step].

In this connection, in the above description, embodiments, specific examples, preferable examples, and the like of an analyte, an analogue (a labeled analogue, a reaction improvement analogue), a solution containing an analyte or an analogue thereof, a sample containing an analyte, a CFS (a labeled CFS, a reaction improvement CFS, a labeled reaction improvement CFS), a solution containing thereof, a preparation step [a step (a)], a solution introducing structure, a micro fluidic device or a micro fluidic system used in a preparation step [a step (a)] a introduction step, a concentration and reaction step are as described above.

In general, as a solution introducing structure, a micro fluidic device or a micro fluidic system used in a method for forming a complex in the present invention, one usually having a reservoir (a S/R reservoir, a W reservoir) and/or an access port, an upstream reservoir and/or an access port, a downstream reservoir and/or an access port are used. In addition, the first channel of a solution introducing structure and a micro fluidic device of the present invention preferably have at least a region (reaction region) where a sample reacts with a reagent solution at one part thereof, in particular, at least a region (concentration and reaction region) where at least one kind of a CFS reacts with analyte or analogue thereof in a sample while concentrating said analyte or said analogue thereof in the sample and/or at least one kind of the CFS in the reagent solution, and further have a region (separation region) where a complex between said analyte or said analogue thereof, and a substance binding to said analyte or said analogue thereof is separated from said substance binding to said analyte or said analogue thereof not involved in the formation of said complex, or said analogue not involved in the formation of said complex, at the downstream of said reaction region or said concentration and reaction region.

(1) A Separation Step

As described above, a complex between an analyte or an analogue thereof and a CFS, obtained by the introduction step and the concentration and reaction step of the present invention, and a CFS not involved in formation of said complex or an analogue not involved in formation of said complex, are separated in a capillary (a first channel), by further electrical movement (migration).

A method for separation of the present invention is for separation of a complex between an analyte or an analogue thereof and a CFS, and a CFS not involved in formation of said complex or an analogue not involved in formation of said complex, and in more specifically, (1) for separation of a complex between said analyte and CFS, and a CFS not involved in formation of said complex, by further electrical movement (migration); or (2) for separation of a complex between said analogue and CFS, and an analogue not involved in formation of said complex or a complex between said analyte and CFS not involved in formation of said complex, by further electrical movement (migration).

For example, when a method for separation of the present invention is used in a non-competitive method (for example, methods (3-1) to (3-7) to be described later, and the like), and when a CFS including a labeling substance (a labeled CFS or a labeled reaction improvement CFS) is used, separation of at least a CFS including a labeling substance not involved (free labeling substances) in formation of a complex between an analyte and a CFS, and a complex including an analyte is enough. Though separation of a CFS not including a labeling substance, from said complex is not necessarily required, separation of said complex and all of the CFSs not involved (free CFSs) in formation of a complex is preferable.

In addition, for example, when a method for separation of the present invention is used in a competitive method (for example, methods (3-8) to (3-17) to be described later, and the like), and when a labeled analogue is used, separation of at least a (final) complex between a labeled analogue and (all of the) CFSs, and a labeled analogue not involved (free labeled analogue) in formation of said complex is enough. Separation of a complex between an analyte and a CFS, and a (final) complex between a labeled analogue and (all of the) CFSs is not necessarily required. In addition, when a reaction improvement analogue is used, separation of at least a complex between a reaction improvement analogue and a labeled CFS, and a complex between an analyte and a labeled CFS is enough.

A separation step of the present invention may be carried out using a method which enables to sufficiently separate a complex between an analyte or an analogue thereof and a CFS, and a CFS not involved in formation of said complex or an analogue not involved in formation of said complex. As such a method, a known electrophoresis method itself and usually used in this field can be used.

Specifically, electrophoresis methods based on various principles (separation modes) can be used. Examples of such method are ITP, IF, as described above; so-called a capillary zone electrophoresis method (CZE) for separation of an objective substance by moving each substance in different speed depending on intensity of a charge thereof, wherein a capillary is fundamentally filled with only a buffer solution for electrophoresis, [Reference: H. Hisamoto et al., Chem. Commun., (2001), 2662, and the like]; so-called a micelle electro kinetic chromatography (MEKC) using a charged substance forming an ionic micelle, and separating a objective substance by interaction with said micelle, [Reference: S. Terabe, Trends Anal. Chem., (1989), 8, 129, and the like]; so-called a capillary gel electrophoresis method (CGE) for separating an objective substance by using a filler such as a polymer having molecular sieve effect, and by charge of a molecule and size of a molecule inducing interaction with a polymer, [Reference: S. Hjerten, J. Chromatogr., (1987), 397, 409, and the like].

In this connection, in the present invention, reagents, and the like used in an electrophoresis method as described above can be used, as appropriate. In addition, these reagents, an operation method in separation, conditions, and the like can suitably be selected in accordance with the description in references, as described above, and the like.

As an electrophoresis method used in a separation step of the present invention, any of an electrophoresis method based on the same principle (separation mode) as in a concentration method used in a concentration and reaction step, or an electrophoresis method based on different principle (separation mode) as in a concentration method used in a concentration and reaction step may be used.

In this connection, when use of an electrophoresis method based on the same principle (separation mode) as in a concentration and reaction step provides insufficient separation of a complex between an analyte or an analogue thereof and a CFS, and a CFS not involved in formation of said complex or an analogue not involved in formation of said complex, use of an electrophoresis method based on different principle (separation mode) as in a concentration method used in a concentration and reaction step to carry out a separation step of the present invention is desirable.

In such a case, execution of ITP, FASS, and the like in a concentration and reaction step, and subsequently CZE, and the like in a separation step is particularly preferable.

As described above, when separation modes are changed between a concentration and reaction step, and a separation step, a solution introducing structure and a micro fluidic device of the present invention having one or more kinds of EM side channels (if necessary, an access port, a electrophoresis medium reservoir), in particular, a solution introducing structure and a micro fluidic device or a micro fluidic system shown in FIG. 23, is particularly useful.

Therefore, a method for separating of the present invention, when such a solution introducing structure, a micro fluidic device or a micro fluidic system is used, specifically includes the following steps:

(a) providing a micro fluidic device comprising at least one structure for introducing a sample or a reagent solution to a first channel (1) in a substrate, said structure comprising;
  (i) the first channel (1), said first channel (1) having an upstream reservoir (6) at the end of the upstream side thereof and a downstream reservoir (7) at the other end of the downstream side thereof,
  (ii) not less than 3 D side channels (2), each said D side channel (2) having a opening (2-1) opened on a wall of said first channel (1), and said openings (2-1) arranged in spaced relation to one another, wherein said D side channel (2) is connected to a W reservoir (4);
  (iii) not less than 2 S/R side channels (3), each said S/R side channel (3) having a opening (3-1) opened on the wall of said first channel (1) at the different position (part) from said openings (2-1) of said D side channels (2), and each said opening (3-1) arranged between adjacent 2 openings (2-1) of D side channels (2), wherein each said opening (3-1) of these not less than 2 S/R side channels (3) are each arranged at the different portion between adjacent 2 openings (2-1) of D side channels (2), and S/R side channel (3) is connected to a S/R reservoir (5), (iv) a EM side channel (8) communicating with the first channel region between a D side channel (2n) located at the most downstream among said not less than 3 D side channels (2) and a downstream reservoir (7), and said EM side channel (8) connecting to an EM reservoir (11);

(b) putting a sample into at least one S/R reservoir (5) connecting to said S/R side channel (3);

(c) putting a reagent solution into at least one S/R reservoir (5) connecting to said S/R side channel (3), wherein said S/R reservoir (5) being different from one used in said step (b);

(d) introducing said sample in said S/R side channel (3) connected with said S/R reservoir (5) used in said step (b), 2 D side channels (2) adjacent to said S/R side channel (3) in an axis direction and a first channel region between said 2 D side channels (2), by moving said sample from said S/R reservoir (5) where said sample is put in said step (b) to said 2 D side channels (2) adjacent to said S/R side channel (3) connected with said S/R reservoir (5) in an axis direction, via said S/R side channel (3) connected with said reservoir (5);

(e) introducing said reagent solution in said S/R side channel (3) connected with said S/R reservoir (5) used in said step (c), 2 D side channels (2) adjacent to said S/R side channel (3) in an axis direction and a first channel region between said 2 D side channels (2), by moving said reagent solution from said S/R reservoir (5) where said reagent solution is put in said step (c) to said 2 D side channels (2) adjacent to said S/R side channel (3) connected with said S/R reservoir (5) in an axis direction, via said S/R side channel (3) connected with said S/R reservoir (5);

(f) reacting an analyte or an analogue thereof in a sample with at least one kind of a CFS in the reagent solution while concentrating said analyte or said analogue thereof in the sample and/or at least one kind of the CFS in the reagent solution to form the complex between said analyte or said analogue thereof and the CFS, at a first channel region (9a) between a D side channel (2a) located at the most upstream among said not less than 3 D side channels (2) and a D side channel (2n) located at the most downstream among said not less than 3 D side channels (2), or a first channel region (9b) between a D side channel (2a) located at the most upstream among said not less than 3 D side channels (2) and said EM side channel (8) by applying a voltage to said upstream reservoir (6) part at the end of said upstream side of said first channel (1) and said downstream reservoir (7) part at the other end of said downstream side of said first channel (1); and (g) separating said complex between said analyte or said analogue thereof and the CFS, and said CFS not involved in the formation of said complex or said analogue not involved in the formation of said complex, by applying a voltage to said EM reservoir (11) part connecting to said EM side channel (8) and said downstream reservoir (7) part.

As described above, in a separation method of the present invention, the following 2 cases are included: (i) react (contact and react) of said analyte or analogue thereof and CFS is conducted while concentrating an analyte or an analogue thereof and/or at least one kind of a CFS, to form a complex between said analyte or analogue thereof and CFS by a concentration and reaction step [in other words, react (contact and react) of said analyte or analogue thereof and CFS is conducted by applying a voltage onto said capillary (said first channel) under such condition as an analyte or an analogue thereof and/or at least one kind of a CFS are concentrated, to form a complex between said analyte or analogue thereof and CFS], and subsequently by using the same separation mode without changing applied voltage (in other words, while applying a voltage with the same intensity under the same condition as in a concentration and reaction step), said complex and CFS not involved in formation of said complex or analogue not involved in formation of said complex are separated by further electric moving (migrating); (ii) or react (contact and react) of said analyte or analogue thereof and CFS is conducted while concentrating an analyte or an analogue thereof and/or at least one kind of a CFS, to form a complex between said analyte or analogue thereof and CFS by a concentration and reaction step [in other words, react (contact and react) of said analyte or analogue thereof and CFS is conducted by applying a voltage onto said capillary (said first channel) under such condition as an analyte or an analogue thereof and/or at least one kind of a CFS are concentrated, to form a complex between said analyte or analogue thereof and CFS], and subsequently by using different separation mode and/or different applied voltage [in other words, by changing condition (separation mode used) from that in a concentration and reaction step and/or intensity of voltage to be applied], said complex and a CFS not involved in formation of said complex or an analogue not involved in formation of said complex are separated by further electric moving (migrating).

(2) Condition

As for applied voltage in a separation step, any range may be adopted as long as a complex between an analyte or an analogue thereof and a CFS, and a CFS not involved in formation of said complex or an analogue not involved in formation of said complex are sufficiently separated, and it is suitably selected from a range usually used in this field. In more specifically, the voltage is applied so that electric field intensity is in a range of usually, as lower limit, not lower than 5 V/cm, preferably not lower than 10 V/cm, more preferably not lower than 50 V/cm, further preferably not lower than 500 V/cm, particularly preferably not lower than 1000 V/cm, and as upper limit, usually not higher than 10000 V/cm, preferably not higher than 5000 V/cm, and more preferably not higher than 2000 V/cm. In this connection, as described above, applied voltage in a step (3) may be the same as or different from that in a step (2).

In addition, other separation conditions (for example, pH, temperature, time, and the like) may be any range as long as a complex of an analyte or an analogue thereof and a CFS, and a CFS not involved in formation of said complex or an analogue not involved in formation of said complex are sufficiently separated, and it is suitably selected in accordance with a known method itself usually used in this field.

Specifically, although not simply described due to dependency on property of an analyte or an analogue thereof and a CFS, however, lower limit of the pH is usually not lower than 2, preferably not lower than 4, and more preferably not lower than 5, and upper limit is not higher than 13, preferably not higher than 11 and more preferably not higher than 9. Lower limit of the temperature is usually not lower than 0° C., preferably not lower than 5° C. and more preferably not lower than 10° C., and upper limit is usually not higher than 90° C., preferably not higher than 80° C., more preferably not higher than 50° C., further preferably not higher than 40° C., and particularly preferably not higher than 30° C. In addition, lower limit of the time is usually not shorter than 1 minute, preferably not shorter than 2 minutes and more preferably not shorter than 3 minutes, and upper limit is not longer than 20 minutes and more preferably not longer than 10 minutes.

As described above, a separation step is carried out in a capillary, and as such a capillary, the same one as used in a concentration and reaction step is included, and material and inner diameter of the capillary are also as described above.

In addition, a separation step of the present invention is carried out usually in a state that an electrophoresis medium such as a buffer solution for electrophoresis or said buffer solution for electrophoresis containing fillers, is filled in a capillary (a first channel) (in separation region) as described above. In this connection, a specific example, use concentration, pH, molecular weight, viscosity, an introduction method into a capillary (a first channel), introduction timing, and the like of an electrophoresis medium are the same as described above.

In this connection, as described above, when a separation step of the present invention is carried out using an electrophoresis method based on different principle (separation mode) from that in a concentration method used in a concentration and reaction step, an electrophoresis medium used in a concentration and reaction step, and an electrophoresis medium used in a separation step are not required to be the same, and a different electrophoresis medium may be used by suitable selection thereof.

In this connection, a concentration and reaction step and a separation step of the present invention are usually carried out using the same capillary (in the same capillary). Namely, a capillary used in a separation method of the present invention has at least a part enabling to carry out a introduction step of the present invention, a part enabling to carry out a concentration and reaction step of the present invention, and a part enabling to carry out a separation step of the present invention. These parts may be present each independently in a capillary (a first channel), or a part of or all of these parts may be present in overlapped state. In other words, as a result, a capillary (a first channel) used in a separation method of the present invention is one, which enables to arrange in a capillary (a first channel) (a) a solution containing an analyte or an analogue thereof and (b) a solution containing not less than one kind of substances formable a complex (a CFS) with said analyte or analogue thereof, so that by applying a voltage onto said capillary (a first channel) the complex between said analyte or analogue thereof and CFS is formed without mixing these solutions in advance, and enables to react (contact and react) said analyte or analogue thereof and CFS while concentrating said analyte or analogue thereof and/or at least one kind of CFS by applying a voltage onto said capillary (a first channel), before uniformly mixing these solutions, to form the complex between said analyte or analogue thereof and CFS, and further enables to separate said complex and a CFS not involved in formation of said complex or an analogue not involved in formation of said complex, by further electrical movement (migration).

(3) Specific Method for Separating

Modes for carrying out the methods for separation of the present invention are specifically shown below.

(3-1) A Case when a CFS not Bound with a Labeling Substance and a Reaction Improvement Substance are Used.

(a) A micro fluidic device comprising at least one structure for introducing a sample or a reagent solution to a first channel (1) in a substrate is provided, said structure comprising;

(i) the first channel (1), said first channel (1) having an upstream reservoir (6) at the end of the upstream side thereof and a downstream reservoir (7) at the other end of the downstream side thereof, (ii) not less than 3 D side channels (2), each said D side channel (2) having a opening (2-1) opened on a wall of said first channel (1), and said openings (2-1) arranged in spaced relation to one another, wherein said D side channel (2) is connected to a W reservoir (4);

(iii) not less than 2 S/R side channels (3), each said S/R side channel (3) having a opening (3-1) opened on the wall of said first channel (1) at the different position (part) from said openings (2-1) of said D side channels (2), and each said opening (3-1) arranged between adjacent 2 openings (2-1) of D side channels (2), wherein each said opening (3-1) of these not less than 2 S/R side channels (3) are each arranged at the different portion between adjacent 2 openings (2-1) of D side channels (2), and S/R side channel (3) is connected to a S/R reservoir (5), (iv) a EM side channel (8) communicating with the first channel region between a D side channel (2n) located at the most downstream among said not less than 3 D side channels (2) and a downstream reservoir (7), and said EM side channel (8) connecting to an EM reservoir (11);

(b) A solution containing an analyte [for example, (i) a sample including an analyte, (ii) a solution including a sample having an analyte, and not less than one kind of CFSs] is put into one of the S/R reservoir (5) connecting to said S/R side channel (3).

(c) A solution containing not less than one kind of CFSs is put into at least one of the other S/R reservoir (5) connecting to said S/R side channel (3), wherein said S/R reservoir (5) being different from one used in said step (b).

(d) Then, said solution containing an analyte [for example, (i) a sample including an analyte, (ii) a solution including a sample having an analyte, and not less than one kind of CFSs] is introduced in said S/R side channel (3) connected with said S/R reservoir (5) used in said step (b), 2 D side channels (2) adjacent to said S/R side channel (3) in an axis direction and a first channel region between said 2 D side channels (2), by moving said solution containing an analyte [for example, (i) a sample including an analyte, (ii) a solution including a sample having an analyte, and not less than one kind of CFSs] from said S/R reservoir (5) where said solution containing an analyte [for example, (i) a sample including an analyte, (ii) a solution including a sample having an analyte, and not less than one kind of CFSs] is put in said step (b) to said 2 D side channels (2) adjacent to said S/R side channel (3) connected with said S/R reservoir (5) in an axis direction, via said S/R side channel (3) connected with said S/R reservoir (5).

(e) Said solution containing not less than one kind of CFSs is introduced in said S/R side channel (3) connected with said S/R reservoir (5) used in said step (c), 2 D side channels (2) adjacent to said S/R side channel (3) in an axis direction and a first channel region between said 2 D side channels (2), by moving said solution containing not less than one kind of CFSs from said S/R reservoir (5) where said solution containing not less than one kind of CFSs is put in said step (c) to said 2 D side channels (2) adjacent to said S/R side channel (3) connected with said S/R reservoir (5) in an axis direction, via said S/R side channel (3) connected with said S/R reservoir (5). By the steps (d) and (e), the solution containing an analyte [for example, (i) a sample including an analyte, (ii) a solution including a sample having an analyte, and not less than one kind of CFSs] and the solution containing not less than one kind of CFSs are introduced and arranged into a first channel, so that a zone of the solution containing an analyte [for example, (i) a sample including an analyte, (ii) a solution including a sample having an analyte, and not less than one kind of CFSs], and a zone of the solution including not less than one kind of CFSs are separately formed (so that liquid-liquid interface is formed), and a complex between said analyte and CFS is formed on application of a voltage onto said channel, without mixing these solutions in advance outside a channel.

(f) Said analyte is electrophoretically contacted and reacted with said CFS while concentrating said analyte and/or at least one kind of the CFSs by applying a voltage to said upstream reservoir (6) part at the end of said upstream side of said first channel (1) and said downstream reservoir (7) part at the other end of said downstream side of said first channel (1) before uniformly mixing these solutions, not by (not depending on) molecular diffusion and without physically mixing, to form the complex between said analyte and the CFS at a first channel region (9*a*) between a D side channel (2*a*) located at the most upstream among said not less than 3 D side channels (2) and a D side channel (2*n*) located at the most downstream among said not less than 3 D side channels (2), or a first channel region (9*b*) between a D side channel (2*a*) located at the most upstream among said not less than 3 D side channels (2) and said EM side channel (8).

(g) Said complex between said analyte and the CFS, and said CFS not involved in the formation of said complex are separated, by applying a voltage to said EM reservoir (11) part connecting to said EM side channel (8) and said downstream reservoir (7) part.

(3-2) A Case when a Labeled CFS is Used.

(a) The same micro fluidic device as the above-described step (a) in the case (3-1) of "(3) a specific method for separating" is provided.

(b) A solution containing an analyte [for example, (i) a sample including an analyte, (ii) a solution including a sample having an analyte, and not less than one kind of CFSs] is put into one of the S/R reservoir (5) connecting to said S/R side channel (3).

(c) A solution containing not less than one kind of labeled CFSs is put into at least one of the other S/R reservoir (5) connecting to said S/R side channel (3), wherein said S/R reservoir (5) being different from one used in said step (b).

(d) Then, said solution containing an analyte [for example, (i) a sample including an analyte, (ii) a solution including a sample having an analyte, and not less than one kind of CFSs] is introduced in said S/R side channel (3) connected with said S/R reservoir (5) used in said step (b), 2 D side channels (2) adjacent to said S/R side channel (3) in an axis direction and a first channel region between said 2 D side channels (2), by moving said solution containing an analyte [for example, (i) a sample including an analyte, (ii) a solution including a sample having an analyte, and not less than one kind of CFSs] from said S/R reservoir (5) where said solution containing an analyte [for example, (i) a sample including an analyte, (ii) a solution including a sample having an analyte, and not less than one kind of CFSs] is put in said step (b) to said 2 D side channels (2) adjacent to said S/R side channel (3) connected with said S/R reservoir (5) in an axis direction, via said S/R side channel (3) connected with said S/R reservoir (5).

(e) Said solution containing not less than one kind of labeled CFSs is introduced in said S/R side channel (3) connected with said S/R reservoir (5) used in said step (c), 2 D side channels (2) adjacent to said S/R side channel (3) in an axis direction and a first channel region between said 2 D side channels (2), by moving said solution containing not less than one kind of labeled CFSs from said S/R reservoir (5) where said solution containing not less than one kind of labeled CFSs is put in said step (c) to said 2 D side channels (2) adjacent to said S/R side channel (3) connected with said S/R reservoir (5) in an axis direction, via said S/R side channel (3) connected with said S/R reservoir (5). By the steps (d) and (e), the solution containing an analyte [for example, (i) a sample including an analyte, (ii) a solution including a sample having an analyte, and not less than one kind of CFSs] and the solution containing not less than one kind of labeled CFSs are introduced and arranged into a channel so that a zone of the solution containing an analyte [for example, (i) a sample including an analyte, (ii) solutions including a sample having an analyte, and not less than one kind of CFSs], and a zone of the solution containing not less than one kind of labeled CFSs are separately formed (so that liquid-liquid interface is formed), and a complex between said analyte and labeled CFS is formed on application of a voltage onto a channel, without mixing these solutions in advance outside a channel.

(f) Said analyte is electrophoretically contacted and reacted with said labeled CFS while concentrating said analyte and/or at least one kind of said labeled CFS by applying a voltage to said upstream reservoir (6) part at the end of said upstream side of said first channel (1) and said downstream reservoir (7) part at the other end of said downstream side of said first channel (1) before uniformly mixing these solutions, not by (not depending on) molecular diffusion and without physically mixing, to form the complex between said analyte and labeled CFS at a first channel region (9*a*) between a D side channel (2*a*) located at the most upstream among said not less than 3 D side channels (2) and a D side channel (2*n*) located at the most downstream among said not less than 3 D side channels (2), or a first channel region (9*b*) between a D side channel (2*a*) located at the most upstream among said not less than 3 D side channels (2) and said EM side channel (8).

(g) Said complex between said analyte and labeled CFS, and said labeled CFS not involved in the formation of said complex are separated, by applying a voltage to said EM reservoir (11) part connecting to said EM side channel (8) and said downstream reservoir (7) part.

(3-3) A Case when a Reaction Improvement CFS is Used.

(a) The same micro fluidic device as the above-described step (a) in the case (3-1) of "(3) a specific method for separating" is provided.

(b) A solution containing an analyte [for example, (i) a sample including an analyte, (ii) a solution including a sample having an analyte, and not less than one kind of CFSs (ex. a labeled CFS)] is put into one of the S/R reservoir (5) connecting to said S/R side channel (3).

(c) A solution containing not less than one kind of reaction improvement CFSs is put into at least one of the other S/R reservoir (5) connecting to said S/R side channel (3), wherein said S/R reservoir (5) being different from one used in said step (b).

(d) Then, said solution containing an analyte [for example, (i) a sample including an analyte, (ii) a solution including a sample having an analyte, and not less than one kind of CFSs (ex. a labeled CFS)] is introduced in said S/R side channel (3) connected with said S/R reservoir (5) used in said step (b), 2 D side channels (2) adjacent to said S/R side channel (3) in an axis direction and a first channel region between said 2 D side channels (2), by moving said solution containing an analyte [for example, (i) a sample including an analyte, (ii) a solution including a sample having an analyte, and not less than one kind of CFSs (ex. a labeled CFS)] from said S/R reservoir (5) where said solution containing an analyte [for example, (i) a sample including an analyte, (ii) a solution including a sample having an analyte, and not less than one kind of CFSs (ex. a labeled CFS)] is put in said step (b) to said 2 D side channels (2) adjacent to said S/R side channel (3) connected with said S/R reservoir (5) in an axis direction, via said S/R side channel (3) connected with said S/R reservoir (5).

(e) Said solution containing not less than one kind of reaction improvement CFSs is introduced in said S/R side channel (3) connected with said S/R reservoir (5) used in said step (c), 2 D side channels (2) adjacent to said S/R side channel (3) in an axis direction and a first channel region between said 2 D side channels (2), by moving said solution containing not less than one kind of reaction improvement CFSs from said S/R reservoir (5) where said solution containing not less than one kind of reaction improvement CFSs is put in said step (c) to said 2 D side channels (2) adjacent to said S/R side channel (3) connected with said S/R reservoir (5) in an axis direction, via said S/R side channel (3) connected with said S/R reservoir (5). By the steps (d) and (e), the solution containing an analyte [for example, (i) a sample including an analyte, (ii) a solution including a sample having an analyte, and not less than one kind of CFSs (ex. a labeled CFS)] and the solution containing not less than one kind of reaction improvement CFSs are introduced and arranged into a channel so that a zone of the solution containing an analyte [for example, (i) a sample including an analyte, (ii) a solution including a sample having an analyte, and not less than one kind of CFSs (ex. a labeled CFS)], and a zone of the solution including not less than one kind of reaction improvement CFSs are separately formed (so that liquid-liquid interface is formed), and a complex between said analyte and reaction improvement CFS is formed on application of a voltage onto a channel, without mixing these solutions in advance outside a channel.

(f) Said analyte is electrophoretically contacted and reacted with said reaction improvement CFS while concentrating said analyte and/or at least one kind of the reaction improvement CFS by applying a voltage to said upstream reservoir (6) part at the end of said upstream side of said first channel (1) and said downstream reservoir (7) part at the other end of said downstream side of said first channel (1) before uniformly mixing these solutions, not by (not depending on) molecular diffusion and without physically mixing, to form the complex between said analyte and reaction improvement CFS at a first channel region (9a) between a D side channel (2a) located at the most upstream among said not less than 3 D side channels (2) and a D side channel (2n) located at the most downstream among said not less than 3 D side channels (2), or a first channel region (9b) between a D side channel (2a) located at the most upstream among said not less than 3 D side channels (2) and said EM side channel (8).

(g) Said complex between said analyte and reaction improvement CFS, and said reaction improvement CFS not involved in the formation of said complex are separated, by applying a voltage to said EM reservoir (11) part connecting to said EM side channel (8) and said downstream reservoir (7) part.

(3-4) A Case when a Labeled Reaction Improvement CFS is Used.

(a) The same micro fluidic device as the above-described step (a) in the case (3-1) of "(3) a specific method for separating" is provided.

(b) A solution containing an analyte [for example, (i) a sample including an analyte, (ii) a solution including a sample having an analyte, and not less than one kind of CFSs] is put into one of the S/R reservoir (5) connecting to said S/R side channel (3).

(c) A solution containing not less than one kind of labeled reaction improvement CFSs is put into at least one of the other S/R reservoir (5) connecting to said S/R side channel (3), wherein said S/R reservoir (5) being different from one used in said step (b).

(d) Then, said solution containing an analyte [for example, (i) a sample including an analyte, (ii) a solution including a sample having an analyte, and not less than one kind of CFSs] is introduced in said S/R side channel (3) connected with said S/R reservoir (5) used in said step (b), 2 D side channels (2) adjacent to said S/R side channel (3) in an axis direction and a first channel region between said 2 D side channels (2), by moving said solution containing an analyte [for example, (i) a sample including an analyte, (ii) a solution including a sample having an analyte, and not less than one kind of CFSs] from said S/R reservoir (5) where said solution containing an analyte [for example, (i) a sample including an analyte, (ii) a solution including a sample having an analyte, and not less than one kind of CFSs] is put in said step (b) to said 2 D side channels (2) adjacent to said S/R side channel (3) connected with said S/R reservoir (5) in an axis direction, via said S/R side channel (3) connected with said S/R reservoir (5).

(e) Said solution containing not less than one kind of labeled reaction improvement CFSs is introduced in said S/R side channel (3) connected with said S/R reservoir (5) used in said step (c), 2 D side channels (2) adjacent to said S/R side channel (3) in an axis direction and a first channel region between said 2 D side channels (2), by moving said solution containing not less than one kind of labeled reaction improvement CFSs from said S/R reservoir (5) where said solution containing not less than one kind of labeled reaction improvement CFSs is put in said step (c) to said 2 D side channels (2) adjacent to said S/R side channel (3) connected with said S/R reservoir (5) in an axis direction, via said S/R side channel (3) connected with said S/R reservoir (5). By the steps (d) and (e), the solution containing an analyte [for example, (i) a sample including an analyte, (ii) a solution including a sample having an analyte, and not less than one kind of CFSs] and the solution containing not less than one kind of labeled reaction improvement CFSs are introduced and arranged into a channel so that a zone of the solution containing an analyte [for example, (i) a sample including an analyte, (ii) a solution including a sample having an analyte, and not less than one kind of CFSs], and a zone of a solution including not less than one kind labeled reaction improvement CFSs are separately formed (so that liquid-liquid interface is formed), and a complex between said analyte and labeled reaction improvement CFS is formed on application of a voltage onto said channel, without mixing these solutions in advance outside a channel.

(f) Said analyte is electrophoretically contacted and reacted with said labeled reaction improvement CFS while concentrating said analyte and/or at least one kind of a labeled reaction improvement CFS by applying a voltage to said upstream reservoir (6) part at the end of said upstream side of said first channel (1) and said downstream reservoir (7) part at the other end of said downstream side of said first channel (1) before uniformly mixing these solutions, not by (not depending on) molecular diffusion and without physically mixing, to form the complex between said analyte and labeled reaction improvement CFS at a first channel region (9a) between a D side channel (2a) located at the most upstream among said not less than 3 D side channels (2) and a D side channel (2n) located at the most downstream among said not less than 3 D side channels (2), or a first channel region (9b) between a D side channel (2a) located at the most upstream among said not less than 3 D side channels (2) and said EM side channel (8).

(g) Said complex between said analyte and labeled reaction improvement CFS, and said labeled reaction improvement CFS not involved in the formation of said complex are separated, by applying a voltage to said EM reservoir (11) part connecting to said EM side channel (8) and said downstream reservoir (7) part.

(3-5) A Case when a CFS not Bound with a Labeling Substance and a Reaction Improvement Substance, and a Reaction Improvement CFS are Used.

(a) The same micro fluidic device as the above-described step (a) in the case (3-1) of "(3) a specific method for separating" is provided.

(b) A solution containing an analyte [for example, (i) a sample including an analyte, (ii) a solution including a sample having an analyte, and not less than one kind of CFSs] is put into one of the S/R reservoir (5) connecting to said S/R side channel (3).

(c) A solution containing not less than one kind of a CFS is put into at least one of the other S/R reservoir (5) connecting to said S/R side channel (3), wherein said S/R reservoir (5) being different from one used in said step (b).

(d) A solution containing not less than one kind of a reaction improvement CFS is put into at least one of the other S/R reservoir (5) connecting to said S/R side channel (3), wherein said S/R reservoir (5) being different from one used in said steps (b) and (c).

(e) Then, said solution containing an analyte [for example, (i) a sample including an analyte, (ii) a solution including a sample having an analyte, and not less than one kind of CFSs] is introduced in said S/R side channel (3) connected with said S/R reservoir (5) used in said step (b), 2 D side channels (2) adjacent to said S/R side channel (3) in an axis direction and a first channel region between said 2 D side channels (2), by moving said solution containing an analyte [for example, (i) a sample including an analyte, (ii) a solution including a sample having an analyte, and not less than one kind of CFSs] from said S/R reservoir (5) where said solution containing an analyte [for example, (i) a sample including an analyte, (ii) a solution including a sample having an analyte, and not less than one kind of CFSs] is put in said step (b) to said 2 D side channels (2) adjacent to said S/R side channel (3) connected with said S/R reservoir (5) in an axis direction, via said S/R side channel (3) connected with said S/R reservoir (5).

(f) Said solution containing not less than one kind of a CFS is introduced in said S/R side channel (3) connected with said S/R reservoir (5) used in said step (c), 2 D side channels (2) adjacent to said S/R side channel (3) in an axis direction and a first channel region between said 2 D side channels (2), by moving said solution containing not less than one kind of a CFS from said S/R reservoir (5) where said solution containing not less than one kind of a CFS is put in said step (c) to said 2 D side channels (2) adjacent to said S/R side channel (3) connected with said S/R reservoir (5) in an axis direction, via said S/R side channel (3) connected with said S/R reservoir (5).

(g) Said solution containing not less than one kind of a reaction improvement CFS is introduced in said S/R side channel (3) connected with said S/R reservoir (5) used in said step (d), 2 D side channels (2) adjacent to said S/R side channel (3) in an axis direction and a first channel region between said 2 D side channels (2), by moving said solution containing not less than one kind of a reaction improvement CFS from said S/R reservoir (5) where said solution containing not less than one kind of a reaction improvement CFS is put in said step (d) to said 2 D side channels (2) adjacent to said S/R side channel (3) connected with said S/R reservoir (5) in an axis direction, via said S/R side channel (3) connected with said S/R reservoir (5). By the steps (e) to (g), the solution containing an analyte [for example, (i) a sample including an analyte, (ii) a solution including a sample having an analyte, and not less than one kind of CFSs], the solution containing not less than one kind of a CFS and the solution containing not less than one kind of a reaction improvement CFS are introduced and arranged into a channel so that a zone of the solution containing an analyte [for example, (i) a sample including an analyte, (ii) a solution including a sample having an analyte, and not less than one kind of CFSs], a zone of the solution including not less than one kind of CFSs, and a zone of the solution including not less than one kind of reaction improvement CFSs are separately formed (so that liquid-liquid interface is formed), and a complex between said analyte, CFS and reaction improvement CFS is formed on application of a voltage onto a channel, without mixing these solutions in advance outside a channel.

(h) Said analyte is electrophoretically contacted and reacted with said CFS and reaction improvement CFS while concentrating at least one selected from said analyte, not less than one kind of CFS and not less than one kind of reaction improvement CFS by applying a voltage to said upstream reservoir (6) part at the end of said upstream side of said first channel (1) and said downstream reservoir (7) part at the other end of said downstream side of said first channel (1) before uniformly mixing these solutions, not by (not depending on) molecular diffusion and without physically mixing, to form the complex between said analyte, CFS and reaction improvement CFS at a first channel region (9a) between a D side channel (2a) located at the most upstream among said not less than 3 D side channels (2) and a D side channel (2n) located at the most downstream among said not less than 3 D side channels (2), or a first channel region (9b) between a D side channel (2a) located at the most upstream among said not less than 3 D side channels (2) and said EM side channel (8).

(i) Said complex between said analyte, CFS and reaction improvement CFS, and said CFS not involved in the formation of said complex, and if necessary said reaction improvement CFS not involved in the formation of said complex are separated, by applying a voltage to said EM reservoir (11) part connecting to said EM side channel (8) and said downstream reservoir (7) part.

(3-6) A Case when a Labeled CFS and a Reaction Improvement CFS are Used.

(a) The same micro fluidic device as the above-described step (a) in the case (3-1) of "(3) a specific method for separating" is provided.

(b) A solution containing an analyte [for example, (i) a sample including an analyte, (ii) a solution including a sample having an analyte, and not less than one kind of CFSs] is put into one of the S/R reservoir (5) connecting to said S/R side channel (3).

(c) A solution containing not less than one kind of a labeled CFS is put into at least one of the other S/R reservoir (5) connecting to said S/R side channel (3), wherein said S/R reservoir (5) being different from one used in said step (b).

(d) A solution containing not less than one kind of a reaction improvement CFS is put into at least one of the other S/R reservoir (5) connecting to said S/R side channel (3), wherein said S/R reservoir (5) being different from one used in said steps (b) and (c).

(e) Then, said solution containing an analyte [for example, (i) a sample including an analyte, (ii) a solution including a sample having an analyte, and not less than one kind of CFSs] is introduced in said S/R side channel (3) connected with said S/R reservoir (5) used in said step (b), 2 D side channels (2) adjacent to said S/R side channel (3) in an axis direction and a first channel region between said 2 D side channels (2), by moving said solution containing an analyte [for example, (i) a sample including an analyte, (ii) a solution including a sample having an analyte, and not less than one kind of CFSs] from said S/R reservoir (5) where said solution containing an analyte [for example, (i) a sample including an analyte, (ii) a solution including a sample having an analyte, and not less than one kind of CFSs] is put in said step (b) to said 2 D side channels (2) adjacent to said S/R side channel (3) connected with said S/R reservoir (5) in an axis direction, via said S/R side channel (3) connected with said S/R reservoir (5).

(f) Said solution containing not less than one kind of a labeled CFS is introduced in said S/R side channel (3) connected with said S/R reservoir (5) used in said step (c), 2 D side channels (2) adjacent to said S/R side channel (3) in an axis direction and a first channel region between said 2 D side channels (2), by moving said solution containing not less than one kind of a labeled CFS from said S/R reservoir (5) where said solution containing not less than one kind of a labeled CFS is put in said step (c) to said 2 D side channels (2) adjacent to said S/R side channel (3) connected with said S/R reservoir (5) in an axis direction, via said S/R side channel (3) connected with said S/R reservoir (5).

(g) Said solution containing not less than one kind of a reaction improvement CFS is introduced in said S/R side channel (3) connected with said S/R reservoir (5) used in said step (d), 2 D side channels (2) adjacent to said S/R side channel (3) in an axis direction and a first channel region between said 2 D side channels (2), by moving said solution containing not less than one kind of a reaction improvement CFS from said S/R reservoir (5) where said solution containing not less than one kind of a reaction improvement CFS is put in said step (d) to said 2 D side channels (2) adjacent to said S/R side channel (3) connected with said S/R reservoir (5) in an axis direction, via said S/R side channel (3) connected with said S/R reservoir (5). By the steps (e) to (g), the solution containing an analyte [for example, (i) a sample including an analyte, (ii) a solution including a sample having an analyte, and not less than one kind of CFSs], the solution containing not less than one kind of a labeled CFS and the a solution containing not less than one kind of a reaction improvement CFS are introduced and arranged into a channel so that a zone of the solution containing an analyte [for example, (i) a sample including an analyte, (ii) a solution including a sample having an analyte, and not less than one kind of CFSs], a zone of the solution containing not less than one kind of labeled CFSs, and a zone of the solution containing not less than one kind of reaction improvement CFSs are separately formed (so that liquid-liquid interface is formed), and a complex between said analyte, labeled CFS and reaction improvement CFS is formed on application of a voltage onto a channel, without mixing these solutions in advance outside a channel.

(h) Said analyte is electrophoretically contacted and reacted with said labeled CFS and reaction improvement CFS while concentrating at least one selected from said analyte, not less than one kind of labeled CFS and not less than one kind of reaction improvement CFS by applying a voltage to said upstream reservoir (6) part at the end of said upstream side of said first channel (1) and said downstream reservoir (7) part at the other end of said downstream side of said first channel (1) before uniformly mixing these solutions, not by (not depending on) molecular diffusion and without physically mixing, to form the complex between said analyte, labeled CFS and reaction improvement CFS at a first channel region (9a) between a D side channel (2a) located at the most upstream among said not less than 3 D side channels (2) and a D side channel (2n) located at the most downstream among said not less than 3 D side channels (2), or a first channel region (9b) between a D side channel (2a) located at the most upstream among said not less than 3 D side channels (2) and said EM side channel (8).

(i) Said complex between said analyte, labeled CFS and reaction improvement CFS, and said labeled CFS not involved in the formation of said complex, and if necessary said reaction improvement CFS not involved in the formation of said complex are separated, by applying a voltage to said EM reservoir (11) part connecting to said EM side channel (8) and said downstream reservoir (7) part.

(3-7) A Case when a CFS not Bound with a Labeling Substance and a Reaction Improvement Substance, and a Labeled Reaction Improvement CFS are Used.

(a) The same micro fluidic device as the above-described step (a) in the case (3-1) of "(3) a specific method for separating" is provided.

(b) A solution containing an analyte [for example, (i) a sample including an analyte, (ii) a solution including a sample having an analyte, and not less than one kind of CFSs] is put into one of the S/R reservoir (5) connecting to said S/R side channel (3).

(c) A solution containing not less than one kind of a CFS is put into at least one of the other S/R reservoir (5) connecting to said S/R side channel (3), wherein said S/R reservoir (5) being different from one used in said step (b).

(d) A solution containing not less than one kind of a labeled reaction improvement CFS is put into at least one of the other S/R reservoir (5) connecting to said S/R side channel (3), wherein said S/R reservoir (5) being different from one used in said steps (b) and (c).

(e) Then, said solution containing an analyte [for example, (i) a sample including an analyte, (ii) a solution including a sample having an analyte, and not less than one kind of CFSs] is introduced in said S/R side channel (3) connected with said S/R reservoir (5) used in said step (b), 2 D side channels (2) adjacent to said S/R side channel (3) in an axis direction and a first channel region between said 2 D side channels (2), by moving said solution containing an analyte [for example, (i) a sample including an analyte, (ii) a solution including a sample having an analyte, and not less than one kind of CFSs] from said S/R reservoir (5) where said solution containing an analyte [for example, (i) a sample including an analyte, (ii) a solution including a sample having an analyte, and not less than one kind of CFSs] is put in said step (b) to said 2 D side channels (2) adjacent to said S/R side channel (3) connected with said S/R reservoir (5) in an axis direction, via said S/R side channel (3) connected with said S/R reservoir (5).

(f) Said solution containing not less than one kind of a CFS is introduced in said S/R side channel (3) connected with said S/R reservoir (5) used in said step (c), 2 D side channels (2) adjacent to said S/R side channel (3) in an axis direction and a first channel region between said 2 D side channels (2), by moving said solution containing not less than one kind of a CFS from said S/R reservoir (5) where said solution containing not less than one kind of a CFS is put in said step (c) to said 2 D side channels (2) adjacent to said S/R side channel (3) connected with said S/R reservoir (5) in an axis direction, via said S/R side channel (3) connected with said S/R reservoir (5).

(g) Said solution containing not less than one kind of a labeled reaction improvement CFS is introduced in said S/R side channel (3) connected with said S/R reservoir (5) used in said step (d), 2 D side channels (2) adjacent to said S/R side channel (3) in an axis direction and a first channel region between said 2 D side channels (2), by moving said solution containing not less than one kind of a labeled reaction improvement CFS from said S/R reservoir (5) where said solution containing not less than one kind of a labeled reaction improvement CFS is put in said step (d) to said 2 D side channels (2) adjacent to said S/R side channel (3) connected with said S/R reservoir (5) in an axis direction, via said S/R side channel (3) connected with said S/R reservoir (5). By the steps (e) to (g), the solution containing an analyte [for example, (i) a sample including an analyte, (ii) a solution including a sample having an analyte, and not less than one kind of CFSs], the solution containing not less than one kind of a CFS and the solution containing not less than one kind of a labeled reaction improvement CFS are introduced and arranged into a channel so that a zone of a solution containing an analyte [for example, (i) a sample including an analyte, (ii) a solution including a sample having an analyte, and not less than one kind of CFSs], a zone of the solution including not less than one kind of CFSs, and a zone of the solution containing not less than one kind labeled reaction improvement CFSs are separately formed (so that liquid-liquid interface is formed), and a complex between said analyte, CFS and labeled reaction improvement CFS is formed on application of a voltage onto a channel, without mixing these solutions in advance outside a channel.

(h) Said analyte is electrophoretically contacted and reacted with said CFS and labeled reaction improvement CFS while concentrating at least one selected from said analyte, not less than one kind of CFS and not less than one kind of labeled reaction improvement CFS by applying a voltage to said upstream reservoir (6) part at the end of said upstream side of said first channel (1) and said downstream reservoir (7) part at the other end of said downstream side of said first channel (1) before uniformly mixing these solutions, not by (not depending on) molecular diffusion and without physically mixing, to form the complex between said analyte, CFS and labeled reaction improvement CFS at a first channel region (9*a*) between a D side channel (2*a*) located at the most upstream among said not less than 3 D side channels (2) and a D side channel (2*n*) located at the most downstream among said not less than 3 D side channels (2), or a first channel region (9*b*) between a D side channel (2*a*) located at the most upstream among said not less than 3 D side channels (2) and said EM side channel (8).

(i) Said complex between said analyte, CFS and labeled reaction improvement CFS, and said labeled CFS not involved in the formation of said complex, and if necessary said CFS not involved in the formation of said complex are separated, by applying a voltage to said EM reservoir (11) part connecting to said EM side channel (8) and said downstream reservoir (7) part.

A method for separating of the present invention can also be used in so-called a competitive method. The procedure in carrying it out in a competitive method is as follows:
(3-8) A Case when a Labeled Analogue and a CFS are Used. (The Use of a Solution Including Both an Analyte and an Analogue.)

(a) The same micro fluidic device as the above-described step (a) in the case (3-1) of "(3) a specific method for separating" is provided.

(b) A solution including a sample having an analyte and a labeled analogue (or a solution including a sample having an analyte, a labeled analogue and not less than one kind of CFSs) is put into one of the S/R reservoir (5) connecting to said S/R side channel (3).

(c) A solution containing not less than one kind of CFSs is put into at least one of the other S/R reservoir (5) connecting to said S/R side channel (3), wherein said S/R reservoir (5) being different from one used in said step (b).

(d) Then, said solution including a sample having an analyte and a labeled analogue (or a solution including a sample having an analyte, a labeled analogue and not less than one kind of CFSs) is introduced in said S/R side channel (3) connected with said S/R reservoir (5) used in said step (b), 2 D side channels (2) adjacent to said S/R side channel (3) in an axis direction and a first channel region between said 2 D side channels (2), by moving said solution including a sample having an analyte and a labeled analogue (or a solution including a sample having an analyte, a labeled analogue and not less than one kind of CFSs) from said S/R reservoir (5) where said solution including a sample having an analyte and a labeled analogue (or a solution including a sample having an analyte, a labeled analogue and not less than one kind of CFSs) is put in said step (b) to said 2 D side channels (2) adjacent to said S/R side channel (3) connected with said S/R reservoir (5) in an axis direction, via said S/R side channel (3) connected with said S/R reservoir (5).

(e) Said solution containing not less than one kind of CFSs is introduced in said S/R side channel (3) connected with said S/R reservoir (5) used in said step (c), 2 D side channels (2) adjacent to said S/R side channel (3) in an axis direction and a first channel region between said 2 D side channels (2), by moving said solution containing not less than one kind of CFSs from said S/R reservoir (5) where said solution containing not less than one kind of CFSs is put in said step (c) to said 2 D side channels (2) adjacent to said S/R side channel (3) connected with said S/R reservoir (5) in an axis direction, via said S/R side channel (3) connected with said S/R reservoir (5). By the steps (d) and (e), the solution including a sample having an analyte and a labeled analogue (or a solution including a sample having an analyte, a labeled analogue and not less than one kind of CFSs) and the a solution containing not less than one kind of CFSs are introduced and arranged into a channel so that a zone of the solution including a sample having an analyte and a labeled analogue (or the solution including a sample having an analyte, a labeled analogue and not less than one kind of CFSs), and a zone of the solution including not less than one kind of CFSs are separately formed (so that liquid-liquid interface is formed), and a complex A between said analyte and CFS and a complex B between said labeled analogue and CFS are formed on application of a voltage onto a channel, without mixing these solutions in advance outside a channel.

(f) Said analyte and labeled analogue are electrophoretically contacted and reacted with said CFS (namely, said analyte is electrophoretically contacted and reacted with said CFS, and said labeled analogue electrophoretically contacted and reacted with said CFS) while concentrating said analyte and labeled analogue and/or not less than one kind of a CFS by applying a voltage to said upstream reservoir (6) part at the end of said upstream side of said first channel (1) and said downstream reservoir (7) part at the other end of said downstream side of said first channel (1) before uniformly mixing these solutions, not by (not depending on) molecular diffusion and without physically mixing, to form the complex A between said analyte and CFS and a complex B between said labeled analogue and CFS at a first channel region (9*a*) between a D side channel (2*a*) located at the most upstream among said not less than 3 D side channels (2) and a D side channel (2*n*) located at the most downstream among said not less than 3 D side channels (2), or a first channel region (9*b*) between a D side channel (2*a*) located at the most upstream among said not less than 3 D side channels (2) and said EM side channel (8).

(g) Said complex B and said labeled analogue not involved in the formation of said complex B are separated, by applying a voltage to said EM reservoir (11) part connecting to said EM side channel (8) and said downstream reservoir (7) part.

(3-9) A Case when a Labeled Analogue and a Reaction Improvement CFS are Used. (The Use of a Solution Including Both an Analyte and an Analogue.)

(a) The same micro fluidic device as the above-described step (a) in the case (3-1) of "(3) a specific method for separating" is provided.

(b) A solution including a sample having an analyte and a labeled analogue (or a solution including a sample having an analyte, a labeled analogue and not less than one kind of CFSs) is put into one of the S/R reservoir (5) connecting to said S/R side channel (3).

(c) A solution containing not less than one kind of reaction improvement CFSs is put into at least one of the other S/R reservoir (5) connecting to said S/R side channel (3), wherein said S/R reservoir (5) being different from one used in said step (b).

(d) Then, said solution including a sample having an analyte and a labeled analogue (or a solution including a sample having an analyte, a labeled analogue and not less than one kind of CFSs) is introduced in said S/R side channel (3) connected with said S/R reservoir (5) used in said step (b), 2 D side channels (2) adjacent to said S/R side channel (3) in an axis direction and a first channel region between said 2 D side channels (2), by moving said solution including a sample having an analyte and a labeled analogue (or a solution including a sample having an analyte, a labeled analogue and not less than one kind of CFSs) from said S/R reservoir (5) where said solution including a sample having an analyte and a labeled analogue (or a solution including a sample having an analyte, a labeled analogue and not less than one kind of CFSs) is put in said step (b) to said 2 D side channels (2) adjacent to said S/R side channel (3) connected with said S/R reservoir (5) in an axis direction, via said S/R side channel (3) connected with said S/R reservoir (5).

(e) Said solution containing not less than one kind of reaction improvement CFSs is introduced in said S/R side channel (3) connected with said S/R reservoir (5) used in said step (c), 2 D side channels (2) adjacent to said S/R side channel (3) in an axis direction and a first channel region between said 2 D side channels (2), by moving said solution containing not less than one kind of reaction improvement CFSs from said S/R reservoir (5) where said solution containing not less than one kind of reaction improvement CFSs is put in said step (c) to said 2 D side channels (2) adjacent to said S/R side channel (3) connected with said S/R reservoir (5) in an axis direction, via said S/R side channel (3) connected with said S/R reservoir (5). By the steps (d) and (e), the solution including a sample having an analyte and a labeled analogue (or a solution including a sample having an analyte, a labeled analogue and not less than one kind of CFSs) and the solution containing not less than one kind of reaction improvement CFSs are introduced and arranged into a channel so that a zone of the solution including a sample having an analyte and a labeled analogue (or the solution including a sample having an analyte, a labeled analogue and not less than one kind of CFSs), and a zone of the solution including not less than one kind of reaction improvement CFSs are separately formed (so that liquid-liquid interface is formed), and a complex A between said analyte and reaction improvement CFS and a complex B between said labeled analogue and reaction improvement CFS are formed on application of a voltage onto a channel, without mixing these solutions in advance outside a channel.

(f) Said analyte and labeled analogue are electrophoretically contacted and reacted with said reaction improvement CFS (namely, said analyte is electrophoretically contacted and reacted with said reaction improvement CFS, and said labeled analogue is electrophoretically contacted and reacted with said reaction improvement CFS) while concentrating said analyte and labeled analogue and/or not less than one kind of said reaction improvement CFS by applying a voltage to said upstream reservoir (6) part at the end of said upstream side of said first channel (1) and said downstream reservoir (7) part at the other end of said downstream side of said first channel (1) before uniformly mixing these solutions, not by (not depending on) molecular diffusion and without physically mixing, to form the complex A between said analyte and reaction improvement CFS and a complex B between said labeled analogue and reaction improvement CFS at a first channel region (9a) between a D side channel (2a) located at the most upstream among said not less than 3 D side channels (2) and a D side channel (2n) located at the most downstream among said not less than 3 D side channels (2), or a first channel region (9b) between a D side channel (2a) located at the most upstream among said not less than 3 D side channels (2) and said EM side channel (8).

(g) Said complex B and said labeled analogue not involved in the formation of said complex B are separated, by applying a voltage to said EM reservoir (11) part connecting to said EM side channel (8) and said downstream reservoir (7) part.

(3-10) A Case when a Labeled Analogue, a CFS and a Reaction Improvement CFS are Used. (The Use of a Solution Including Both an Analyte and an Analogue.)

(a) The same micro fluidic device as the above-described step (a) in the case (3-1) of "(3) a specific method for separating" is provided.

(b) A solution including a sample having an analyte and a labeled analogue (or a solution including a sample having an analyte, a labeled analogue and not less than one kind of CFSs) is put into one of the S/R reservoir (5) connecting to said S/R side channel (3).

(c) A solution including not less than one kind of a CFS is put into at least one of the other S/R reservoir (5) connecting to said S/R side channel (3), wherein said S/R reservoir (5) being different from one used in said step (b).

(d) A solution including not less than one kind of a reaction improvement CFS is put into at least one of the other S/R reservoir (5) connecting to said S/R side channel (3), wherein said S/R reservoir (5) being different from one used in said steps (b) and (c).

(e) Then, said solution including a sample having an analyte and a labeled analogue (or a solution including a sample having an analyte, a labeled analogue and not less than one kind of CFSs) is introduced in said S/R side channel (3) connected with said S/R reservoir (5) used in said step (b), 2 D side channels (2) adjacent to said S/R side channel (3) in an axis direction and a first channel region between said 2 D side channels (2), by moving said solution including a sample having an analyte and a labeled analogue (or a solution including a sample having an analyte, a labeled analogue and not less than one kind of CFSs) from said S/R reservoir (5) where said solution including a sample having an analyte and a labeled analogue (or a solution including a sample having an analyte, a labeled analogue and not less than one kind of CFSs) is put in said step (b) to said 2 D side channels (2) adjacent to said S/R side channel (3) connected with said S/R reservoir (5) in an axis direction, via said S/R side channel (3) connected with said S/R reservoir (5).

(f) Said solution including not less than one kind of a CFS is introduced in said S/R side channel (3) connected with said S/R reservoir (5) used in said step (c), 2 D side channels (2) adjacent to said S/R side channel (3) in an axis direction and a first channel region between said 2 D side channels (2), by moving said solution including not less than one kind of a CFS from said S/R reservoir (5) where said solution including not less than one kind of a CFS is put in said step (c) to said 2 D side channels (2) adjacent to said S/R side channel (3) connected with said S/R reservoir (5) in an axis direction, via said S/R side channel (3) connected with said S/R reservoir (5).

(g) Said solution including not less than one kind of a reaction improvement CFS is introduced in said S/R side channel (3) connected with said S/R reservoir (5) used in said step (d), 2 D side channels (2) adjacent to said S/R side channel (3) in an axis direction and a first channel region between said 2 D side channels (2), by moving said solution including not less than one kind of a reaction improvement CFS from said S/R reservoir (5) where said solution including not less than one kind of a reaction improvement CFS is put in said step (d) to said 2 D side channels (2) adjacent to said S/R side channel (3) connected with said S/R reservoir (5) in an axis direction, via said S/R side channel (3) connected with said S/R reservoir (5). By the steps (e) to (g), the solution including a sample having an analyte and a labeled analogue (or a solution including a sample having an analyte, a labeled analogue and not less than one kind of CFSs), the solution including not less than one kind of a CFS and the solution including not less than one kind of a reaction improvement CFS are introduced and arranged into a channel so that a zone of the solution including a sample having an analyte and a labeled analogue (or the solution including a sample having an analyte, a labeled analogue and not less than one kind of CFSs), a zone of the solution including not less than one kind of CFSs and a zone of the solution including not less than one kind of reaction improvement CFSs are separately formed (so that liquid-liquid interface is formed), and a complex A between said analyte, CFS and reaction improvement CFS and a complex B between said labeled analogue, CFS and reaction improvement CFS are formed on application of a voltage onto a channel, without mixing these solutions in advance outside a channel.

(h) Said analyte and labeled analogue are electrophoretically contacted and reacted with said CFS and reaction improvement CFS (namely, said analyte is electrophoretically contacted and reacted with said CFS and reaction improvement CFS, and said labeled analogue is electrophoretically contacted and reacted with said CFS and reaction improvement CFS) while concentrating at least one selected from said analyte and labeled analogue, not less than one kind of a CFS and not less than one kind of a reaction improvement CFS by applying a voltage to said upstream reservoir (6) part at the end of said upstream side of said first channel (1) and said downstream reservoir (7) part at the other end of said downstream side of said first channel (1) before uniformly mixing these solutions, not by (not depending on) molecular diffusion and without physically mixing, to form the complex A between said analyte, CFS and reaction improvement CFS and a complex B between said labeled analogue, CFS and reaction improvement CFS at a first channel region (9a) between a D side channel (2a) located at the most upstream among said not less than 3 D side channels (2) and a D side channel (2n) located at the most downstream among said not less than 3 D side channels (2), or a first channel region (9b) between a D side channel (2a) located at the most upstream among said not less than 3 D side channels (2) and said EM side channel (8).

(i) Said complex B and said labeled analogue not involved in the formation of said complex B are separated, by applying a voltage to said EM reservoir (11) part connecting to said EM side channel (8) and said downstream reservoir (7) part.

(3-11) A Case when a Reaction Improvement Analogue and a Labeled CFS are Used. (The Use of a Solution Including Both an Analyte and an Analogue.)

(a) The same micro fluidic device as the above-described step (a) in the case (3-1) of "(3) a specific method for separating" is provided.

(b) A solution containing sample having an analyte and reaction improvement analogue (or a solution including a sample having an analyte, a reaction improvement analogue and not less than one kind of CFSs) is put into one of the S/R reservoir (5) connecting to said S/R side channel (3).

(c) A solution including not less than one kind of labeled CFSs is put into at least one of the other S/R reservoir (5) connecting to said S/R side channel (3), wherein said S/R reservoir (5) being different from one used in said step (b).

(d) Then, said solution containing sample having an analyte and reaction improvement analogue (or a solution including a sample having an analyte, a reaction improvement analogue and not less than one kind of CFSs) is introduced in said S/R side channel (3) connected with said S/R reservoir (5) used in said step (b), 2 D side channels (2) adjacent to said S/R side channel (3) in an axis direction and a first channel region between said 2 D side channels (2), by moving said solution containing sample having an analyte and reaction improvement analogue (or a solution including a sample having an analyte, a reaction improvement analogue and not less than one kind of CFSs) from said S/R reservoir (5) where said solution containing sample having an analyte and reaction improvement analogue (or a solution including a sample having an analyte, a reaction improvement analogue and not less than one kind of CFSs) is put in said step (b) to said 2 D side channels (2) adjacent to said S/R side channel (3) connected with said S/R reservoir (5) in an axis direction, via said S/R side channel (3) connected with said S/R reservoir (5).

(e) Said solution including not less than one kind of labeled CFSs is introduced in said S/R side channel (3) connected with said S/R reservoir (5) used in said step (c), 2 D side channels (2) adjacent to said S/R side channel (3) in an axis direction and a first channel region between said 2 D side channels (2), by moving said solution including not less than one kind of labeled CFSs from said S/R reservoir (5) where said solution including not less than one kind of labeled CFSs is put in said step (c) to said 2 D side channels (2) adjacent to said S/R side channel (3) connected with said S/R reservoir (5) in an axis direction, via said S/R side channel (3) connected with said S/R reservoir (5). By the steps (d) and (e), the solution containing sample having an analyte and reaction improvement analogue (or a solution including a sample having an analyte, a reaction improvement analogue and not less than one kind of CFSs) and the a solution including not less than one kind of labeled CFSs are introduced and arranged into a channel so that a zone of a solution including the sample having an analyte and a reaction improvement analogue (or the solution including a sample having an analyte, a reaction improvement analogue and not less than one kind of CFSs), and a zone of the solution including not less than one kind of labeled CFSs are separately formed (so that liquid-liquid interface is formed), and a complex A between said analyte and labeled CFS and a complex B between said reaction improvement analogue and labeled CFS are formed on application of a voltage onto a channel, without mixing these solutions in advance outside a channel.

(f) Said analyte and reaction improvement analogue are electrophoretically contacted and reacted with said labeled CFS (namely, said analyte is electrophoretically contacted and reacted with said labeled CFS, and said reaction improvement analogue is electrophoretically contacted and reacted with said labeled CFS) while concentrating said analyte and reaction improvement analogue and/or not less than one kind of labeled CFS by applying a voltage to said upstream reservoir (6) part at the end of said upstream side of said first channel (1) and said downstream reservoir (7) part at the other end of said downstream side of said first channel (1) before uniformly mixing these solutions, not by (not depending on) molecular diffusion and without physically mixing, to form the complex A between said analyte and labeled CFS and the complex B between said reaction improvement analogue and labeled CFS at a first channel region (9*a*) between a D side channel (2*a*) located at the most upstream among said not less than 3 D side channels (2) and a D side channel (2*n*) located at the most downstream among said not less than 3 D side channels (2), or a first channel region (9*b*) between a D side channel (2*a*) located at the most upstream among said not less than 3 D side channels (2) and said EM side channel (8).

(g) Said complex B and said complex A are separated by applying a voltage to said EM reservoir (11) part connecting to said EM side channel (8) and said downstream reservoir (7) part.

(3-12) A Case when a Labeled Analogue and a CFS are Used. (The Use of Two Separate Solutions of a Solution Including an Analyte and a Solution Containing an Analogue.)

(a) The same micro fluidic device as the above-described step (a) in the case (3-1) of "(3) a specific method for separating" is provided.

(b) A solution including a sample having an analyte, and not less than one kind of CFSs is put into one of the S/R reservoir (5) connecting to said S/R side channel (3).

(c) A solution containing a labeled analogue is put into at least one of the other S/R reservoir (5) connecting to said S/R side channel (3), wherein said S/R reservoir (5) being different from one used in said step (b).

(d) Then, said solution including a sample having an analyte, and not less than one kind of CFSs is introduced in said S/R side channel (3) connected with said S/R reservoir (5) used in said step (b), 2 D side channels (2) adjacent to said S/R side channel (3) in an axis direction and a first channel region between said 2 D side channels (2), by moving said solution including a sample having an analyte, and not less than one kind of CFSs from said S/R reservoir (5) where said solution including a sample having an analyte, and not less than one kind of CFSs is put in said step (b) to said 2 D side channels (2) adjacent to said S/R side channel (3) connected with said S/R reservoir (5) in an axis direction, via said S/R side channel (3) connected with said S/R reservoir (5).

(e) Said solution containing a labeled analogue is introduced in said S/R side channel (3) connected with said S/R reservoir (5) used in said step (c), 2 D side channels (2) adjacent to said S/R side channel (3) in an axis direction and a first channel region between said 2 D side channels (2), by moving said solution containing a labeled analogue from said S/R reservoir (5) where said solution containing a labeled analogue is put in said step (c) to said 2 D side channels (2) adjacent to said S/R side channel (3) connected with said S/R reservoir (5) in an axis direction, via said S/R side channel (3) connected with said S/R reservoir (5). By the steps (d) and (e), the solution including a sample having an analyte, and not less than one kind of CFSs, and the a solution containing a labeled analogue are introduced and arranged into a channel so that a zone of a solution including a sample having an analyte, and not less than one kind of CFSs, and a zone of a solution including a labeled analogue are separately formed (so that liquid-liquid interface is formed), and a complex B between said labeled analogue and CFS is formed on application of a voltage onto a channel, without mixing these solutions in advance outside a channel.

(f) Said labeled analogue is electrophoretically contacted and reacted with CFS (namely, said labeled analogue is electrophoretically contacted and reacted with said CFS not involved in the formation of a complex (complex A) with said analyte in the said solution including a sample having an analyte, and not less than one kind of CFSs) while concentrating said labeled analogue and/or said CFS not involved in the formation of a complex A by applying a voltage to said upstream reservoir (6) part at the end of said upstream side of said first channel (1) and said downstream reservoir (7) part at the other end of said downstream side of said first channel (1) before uniformly mixing these solutions, not by (not depending on) molecular diffusion and without physically mixing, to form the complex B between said labeled analogue and CFS at a first channel region (9*a*) between a D side channel (2*a*) located at the most upstream among said not less than 3 D side channels (2) and a D side channel (2*n*) located at the most downstream among said not less than 3 D side channels (2), or a first channel region (9*b*) between a D side channel (2*a*) located at the most upstream among said not less than 3 D side channels (2) and said EM side channel (8).

(g) Said complex B and said labeled analogue not involved in the formation of said complex B are separated, by applying a voltage to said EM reservoir (11) part connecting to said EM side channel (8) and said downstream reservoir (7) part.

(3-13) A Case when a Labeled Analogue and a Reaction Improvement CFS are Used. (The Use of Two Separate Solutions of a Solution Including an Analyte and a Solution Containing an Analogue.)

(a) The same micro fluidic device as the above-described step (a) in the case (3-1) of "(3) a specific method for separating" is provided.

(b) A solution including a sample having an analyte, and not less than one kind of reaction improvement CFSs is put into one of the S/R reservoir (5) connecting to said S/R side channel (3).

(c) A solution containing a labeled analogue is put into at least one of the other S/R reservoir (5) connecting to said S/R side channel (3), wherein said S/R reservoir (5) being different from one used in said step (b).

(d) Then, said solution including a sample having an analyte, and not less than one kind of reaction improvement CFSs is introduced in said S/R side channel (3) connected with said S/R reservoir (5) used in said step (b), 2 D side channels (2) adjacent to said S/R side channel (3) in an axis direction and a first channel region between said 2 D side channels (2), by moving said solution including a sample having an analyte, and not less than one kind of reaction improvement CFSs from said S/R reservoir (5) where said solution including a sample having an analyte, and not less than one kind of reaction improvement CFSs is put in said step (b) to said 2 D side channels (2) adjacent to said S/R side channel (3) connected with said S/R reservoir (5) in an axis direction, via said S/R side channel (3) connected with said S/R reservoir (5).

(e) Said solution containing a labeled analogue is introduced in said S/R side channel (3) connected with said S/R reservoir (5) used in said step (c), 2 D side channels (2) adjacent to said S/R side channel (3) in an axis direction and a first channel region between said 2 D side channels (2), by moving said solution containing a labeled analogue from said S/R reservoir (5) where said solution containing a labeled analogue is put in said step (c) to said 2 D side channels (2) adjacent to said S/R side channel (3) connected with said S/R reservoir (5) in an axis direction, via said S/R side channel (3)

connected with said S/R reservoir (5). By the steps (d) and (e), the solution including a sample having an analyte, and not less than one kind of reaction improvement CFSs, and the solution containing a labeled analogue are introduced and arranged into a channel so that a zone of a solution including a sample having an analyte, and not less than one kind of reaction improvement CFSs, and a zone of a solution including a labeled analogue are separately formed (so that liquid-liquid interface is formed), and a complex B between said labeled analogue and reaction improvement CFS is formed on application of a voltage onto a channel, without mixing these solutions in advance outside a channel.

(f) Said labeled analogue is electrophoretically contacted and reacted with said reaction improvement CFS (namely, said labeled analogue is electrophoretically contacted and reacted with said reaction improvement CFS not involved in the formation of a complex (complex A) with said analyte in the said solution including a sample having an analyte, and not less than one kind of reaction improvement CFS) while concentrating said labeled analogue and/or said reaction improvement CFS not involved in the formation of a complex A by applying a voltage to said upstream reservoir (6) part at the end of said upstream side of said first channel (1) and said downstream reservoir (7) part at the other end of said downstream side of said first channel (1) before uniformly mixing these solutions, not by (not depending on) molecular diffusion and without physically mixing, to form the complex B between said labeled analogue and reaction improvement CFS at a first channel region (9a) between a D side channel (2a) located at the most upstream among said not less than 3 D side channels (2) and a D side channel (2n) located at the most downstream among said not less than 3 D side channels (2), or a first channel region (9b) between a D side channel (2a) located at the most upstream among said not less than 3 D side channels (2) and said EM side channel (8).

(g) Said complex B and said labeled analogue not involved in the formation of said complex B are separated, by applying a voltage to said EM reservoir (11) part connecting to said EM side channel (8) and said downstream reservoir (7) part.

(3-14) A Case when a Labeled Analogue, a CFS and a Reaction Improvement CFS are Used. (The Use of Two Separate Solutions of a Solution Including an Analyte and a Solution Containing an Analogue.)

(a) The same micro fluidic device as the above-described step (a) in the case (3-1) of "(3) a specific method for separating" is provided.

(b) A solution including a sample having an analyte and not less than one kind of a CFS (or not less than one kind of a reaction improvement CFS) is put into one of the S/R reservoir (5) connecting to said S/R side channel (3).

(c) A solution containing a labeled analogue is put into at least one of the other S/R reservoir (5) connecting to said S/R side channel (3), wherein said S/R reservoir (5) being different from one used in said step (b).

(d) A solution containing not less than one kind of a reaction improvement CFS (or not less than one kind of a CFS) is put into at least one of the other S/R reservoir (5) connecting to said S/R side channel (3), wherein said S/R reservoir (5) being different from one used in said steps (b) and (c).

(e) Then, said solution including a sample having an analyte and not less than one kind of a CFS (or not less than one kind of a reaction improvement CFS) is introduced in said S/R side channel (3) connected with said S/R reservoir (5) used in said step (b), 2 D side channels (2) adjacent to said S/R side channel (3) in an axis direction and a first channel region between said 2 D side channels (2), by moving said solution including a sample having an analyte and not less than one kind of a CFS (or not less than one kind of a reaction improvement CFS) from said S/R reservoir (5) where said solution including a sample having an analyte and not less than one kind of a CFS (or not less than one kind of a reaction improvement CFS) is put in said step (b) to said 2 D side channels (2) adjacent to said S/R side channel (3) connected with said S/R reservoir (5) in an axis direction, via said S/R side channel (3) connected with said S/R reservoir (5).

(f) Said solution containing a labeled analogue is introduced in said S/R side channel (3) connected with said S/R reservoir (5) used in said step (c), 2 D side channels (2) adjacent to said S/R side channel (3) in an axis direction and a first channel region between said 2 D side channels (2), by moving said solution containing a labeled analogue from said S/R reservoir (5) where said solution containing a labeled analogue is put in said step (c) to said 2 D side channels (2) adjacent to said S/R side channel (3) connected with said S/R reservoir (5) in an axis direction, via said S/R side channel (3) connected with said S/R reservoir (5).

(g) Said solution containing not less than one kind of a reaction improvement CFS (or not less than one kind of a CFS) is introduced in said S/R side channel (3) connected with said S/R reservoir (5) used in said step (d), 2 D side channels (2) adjacent to said S/R side channel (3) in an axis direction and a first channel region between said 2 D side channels (2), by moving said solution containing not less than one kind of a reaction improvement CFS (or not less than one kind of a CFS) from said S/R reservoir (5) where said solution containing not less than one kind of a reaction improvement CFS (or not less than one kind of a CFS) is put in said step (d) to said 2 D side channels (2) adjacent to said S/R side channel (3) connected with said S/R reservoir (5) in an axis direction, via said S/R side channel (3) connected with said S/R reservoir (5). By the steps (e) to (g), the solution including a sample having an analyte and not less than one kind of a CFS (or not less than one kind of a reaction improvement CFS), the solution containing a labeled analogue and the solution containing not less than one kind of a reaction improvement CFS (or not less than one kind of a CFS) are introduced and arranged into a channel so that a zone of the solution including a sample having an analyte and at least one kind of a CFS (or not less than one kind of a reaction improvement CFS), a zone of the solution including a labeled analogue and a zone of a solution including not less than one kind of a reaction improvement CFS (or not less than one kind of a CFS) are separately formed (so that liquid-liquid interface is formed), and a complex A between said analyte, CFS and reaction improvement CFS and a complex B between said labeled analogue, CFS and reaction improvement CFS are formed on application of a voltage onto a channel, without mixing these solutions in advance outside a channel.

(h) Said analyte and labeled analogue are electrophoretically contacted and reacted with said CFS and reaction improvement CFS [namely, a complex between said analyte and CFS (or reaction improvement CFS) in said solution (a) is electrophoretically contacted and reacted with said reaction improvement CFS (or CFS) in said solution (c), and said labeled analogue is electrophoretically contacted and reacted with said CFS (or reaction improvement CFS) not involved in the formation of said complex with said analyte in said solution (a) and said reaction improvement CFS (or CFS) in said solution (c)] while concentrating at least one selected from the complex A between said analyte and not less than one kind of CFS (or not less than one kind of reaction improvement CFS), labeled analogue, and not less than one kind of reaction improvement CFS (or not less than one kind of CFS) by applying a voltage to said upstream reservoir (6) part at the end of said upstream side of said first channel (1) and said downstream reservoir (7) part at the other end of said downstream side of said first channel (1) before uniformly mixing these solutions, not depending on molecular diffusion and without physically mixing, to form the complex A between said analyte, CFS and reaction improvement CFS and the complex B between said labeled analogue, CFS and reaction improvement CFS at a first channel region (9a) between a D side channel (2a) located at the most upstream among said not less than 3 D side channels (2) and a D side channel (2n) located at the most downstream among said not less than 3 D side channels (2), or a first channel region (9b) between a D side channel (2a) located at the most upstream among said not less than 3 D side channels (2) and said EM side channel (8).

(i) Said complex B and said labeled analogue not involved in the formation of said complex B are separated, by applying a voltage to said EM reservoir (11) part connecting to said EM side channel (8) and said downstream reservoir (7) part.

(3-15) A Case when a Reaction Improvement Analogue and a Labeled CFS are Used. (The Use of Two Separate Solutions of a Solution Including an Analyte and a Solution Containing an Analogue.)

(a) The same micro fluidic device as the above-described step (a) in the case (3-1) of "(3) a specific method for separating" is provided.

(b) A solution including a sample having an analyte, and not less than one kind of labeled CFSs is put into one of the S/R reservoir (5) connecting to said S/R side channel (3).

(c) A solution containing a reaction improvement analogue is put into at least one of the other S/R reservoir (5) connecting to said S/R side channel (3), wherein said S/R reservoir (5) being different from one used in said step (b).

(d) Then, said solution including a sample having an analyte, and not less than one kind of labeled CFSs is introduced in said S/R side channel (3) connected with said S/R reservoir (5) used in said step (b), 2 D side channels (2) adjacent to said S/R side channel (3) in an axis direction and a first channel region between said 2 D side channels (2), by moving said solution including a sample having an analyte, and not less than one kind of labeled CFSs from said S/R reservoir (5) where said solution including a sample having an analyte, and not less than one kind of labeled CFSs is put in said step (b) to said 2 D side channels (2) adjacent to said S/R side channel (3) connected with said S/R reservoir (5) in an axis direction, via said S/R side channel (3) connected with said S/R reservoir (5).

(e) Said solution containing a reaction improvement analogue is introduced in said S/R side channel (3) connected with said S/R reservoir (5) used in said step (c), 2 D side channels (2) adjacent to said S/R side channel (3) in an axis direction and a first channel region between said 2 D side channels (2), by moving said solution containing a reaction improvement analogue from said S/R reservoir (5) where said solution containing a reaction improvement analogue is put in said step (c) to said 2 D side channels (2) adjacent to said S/R side channel (3) connected with said S/R reservoir (5) in an axis direction, via said S/R side channel (3) connected with said S/R reservoir (5). By the steps (d) and (e), the solution including a sample having an analyte, and not less than one kind of labeled CFSs, and the solution containing a reaction improvement analogue are introduced and arranged into a channel so that a zone of a solution including a sample having an analyte, and not less than one kind of labeled CFSs, and a zone of a solution including a reaction improvement analogue are separately formed (so that liquid-liquid interface is formed), and a complex B between said reaction improvement analogue and labeled CFS is formed on application of a voltage onto a channel, without mixing these solutions in advance outside a channel.

(f) Said reaction improvement analogue is electrophoretically contacted and reacted with labeled CFS (namely, said reaction improvement analogue is electrophoretically contacted and reacted with said labeled CFS not involved in the formation of a complex (complex A) with said analyte in the said solution including a sample having an analyte, and not less than one kind of labeled CFSs) while concentrating said reaction improvement and/or said labeled CFS not involved in the formation of a complex A analogue by applying a voltage to said upstream reservoir (6) part at the end of said upstream side of said first channel (1) and said downstream reservoir (7) part at the other end of said downstream side of said first channel (1) before uniformly mixing these solutions, not by (not depending on) molecular diffusion and without physically mixing, to form the complex B between said reaction improvement analogue and labeled CFS at a first channel region (9a) between a D side channel (2a) located at the most upstream among said not less than 3 D side channels (2) and a D side channel (2n) located at the most downstream among said not less than 3 D side channels (2), or a first channel region (9b) between a D side channel (2a) located at the most upstream among said not less than 3 D side channels (2) and said EM side channel (8).

(g) Said complex B and said complex A are separated, by applying a voltage to said EM reservoir (11) part connecting to said EM side channel (8) and said downstream reservoir (7) part.

(3-16) A Case when a Labeled Reaction Improvement Analogue, and a CFS not Bound with a Labeling Substance and a Reaction Improvement Substance are Used. (The Use of a Solution Including Both an Analyte and an Analogue.)

(a) The same micro fluidic device as the above-described step (a) in the case (3-1) of "(3) a specific method for separating" is provided.

(b) A solution including a sample having an analyte and a labeled reaction improvement analogue (or a solution including a sample having an analyte, a labeled reaction improvement analogue and not less than one kind of CFSs) is put into one of the S/R reservoir (5) connecting to said S/R side channel (3).

(c) A solution containing not less than one kind of CFS not bound with a labeling substance and a reaction improvement substance is put into at least one of the other S/R reservoir (5) connecting to said S/R side channel (3), wherein said S/R reservoir (5) being different from one used in said step (b).

(d) Then, said solution including a sample having an analyte and a labeled reaction improvement analogue (or a solution including a sample having an analyte, a labeled reaction improvement analogue and not less than one kind of CFSs) is introduced in said S/R side channel (3) connected with said S/R reservoir (5) used in said step (b), 2 D side channels (2) adjacent to said S/R side channel (3) in an axis direction and a first channel region between said 2 D side channels (2), by moving said solution including a sample having an analyte and a labeled reaction improvement analogue (or a solution including a sample having an analyte, a labeled reaction improvement analogue and not less than one kind of CFSs) from said S/R reservoir (5) where said solution including a sample having an analyte and a labeled reaction improvement analogue (or a solution including a sample having an analyte, a labeled reaction improvement analogue and not less than one kind of CFSs) is put in said step (b) to said 2 D side channels (2) adjacent to said S/R side channel (3) connected with said S/R reservoir (5) in an axis direction, via said S/R side channel (3) connected with said S/R reservoir (5).

(e) Said solution containing not less than one kind of CFS not bound with a labeling substance and a reaction improvement substance is introduced in said S/R side channel (3) connected with said S/R reservoir (5) used in said step (c), 2 D side channels (2) adjacent to said S/R side channel (3) in an axis direction and a first channel region between said 2 D side channels (2), by moving said solution containing not less than one kind of CFS not bound with a labeling substance and a reaction improvement substance from said S/R reservoir (5) where said solution containing not less than one kind of CFS not bound with a labeling substance and a reaction improvement substance is put in said step (c) to said 2 D side channels (2) adjacent to said S/R side channel (3) connected with said S/R reservoir (5) in an axis direction, via said S/R side channel (3) connected with said S/R reservoir (5). By the steps (d) and (e), the solution including a sample having an analyte and a labeled reaction improvement analogue (or a solution including a sample having an analyte, a labeled reaction improvement analogue and not less than one kind of CFSs) and the a solution containing not less than one kind of CFS not bound with a labeling substance and a reaction improvement substance are introduced and arranged into a channel so that a zone of the solution including a sample having an analyte and a labeled reaction improvement analogue (or the solution including a sample having an analyte, a labeled reaction improvement analogue and not less than one kind of CFSs), and a zone of the solution including not less than one kind of CFS not bound with a labeling substance and a reaction improvement substance are separately formed (so that liquid-liquid interface is formed), and a complex A between said analyte and CFS not bound with a labeling substance and a reaction improvement substance and a complex B between said labeled reaction improvement analogue and CFS not bound with a labeling substance and a reaction improvement substance are formed on application of a voltage onto a channel, without mixing these solutions in advance outside a channel.

(f) Said analyte and labeled reaction improvement analogue are electrophoretically contacted and reacted with said CFS not bound with a labeling substance and a reaction improvement substance (namely, said analyte is electrophoretically contacted and reacted with said CFS not bound with a labeling substance and a reaction improvement substance, and said labeled reaction improvement analogue electrophoretically contacted and reacted with said CFS not bound with a labeling substance and a reaction improvement substance) while concentrating said analyte and labeled reaction improvement analogue and/or not less than one kind of a CFS not bound with a labeling substance and a reaction improvement substance by applying a voltage to said upstream reservoir (6) part at the end of said upstream side of said first channel (1) and said downstream reservoir (7) part at the other end of said downstream side of said first channel (1) before uniformly mixing these solutions, not by (not depending on) molecular diffusion and without physically mixing, to form the complex A between said analyte and CFS not bound with a labeling substance and a reaction improvement substance and a complex B between said labeled reaction improvement analogue and CFS not bound with a labeling substance and a reaction improvement substance at a first channel region (9a) between a D side channel (2a) located at the most upstream among said not less than 3 D side channels (2) and a D side channel (2n) located at the most downstream among said not less than 3 D side channels (2), or a first channel region (9b) between a D side channel (2a) located at the most upstream among said not less than 3 D side channels (2) and said EM side channel (8).

(g) Said complex B and said complex A are separated, by applying a voltage to said EM reservoir (11) part connecting to said EM side channel (8) and said downstream reservoir (7) part.

(3-17) A Case when a Labeled Reaction Improvement Analogue, and a CFS not Bound with a Labeling Substance and a Reaction Improvement Substance are Used. (The Use of Two Separate Solutions of a Solution Including an Analyte and a Solution Containing an Analogue.)

(a) The same micro fluidic device as the above-described step (a) in the case (3-1) of "(3) a specific method for separating" is provided.

(b) A solution including a sample having an analyte, and not less than one kind of CFS not bound with a labeling substance and a reaction improvement substance is put into one of the S/R reservoir (5) connecting to said S/R side channel (3).

(c) A solution containing a labeled reaction improvement analogue is put into at least one of the other S/R reservoir (5) connecting to said S/R side channel (3), wherein said S/R reservoir (5) being different from one used in said step (b).

(d) Then, said solution including a sample having an analyte, and not less than one kind of CFS not bound with a labeling substance and a reaction improvement substance is introduced in said S/R side channel (3) connected with said S/R reservoir (5) used in said step (b), 2 D side channels (2) adjacent to said S/R side channel (3) in an axis direction and a first channel region between said 2 D side channels (2), by moving said solution including a sample having an analyte, and not less than one kind of CFS not bound with a labeling substance and a reaction improvement substance from said S/R reservoir (5) where said solution including a sample having an analyte, and not less than one kind of CFS not bound with a labeling substance and a reaction improvement substance is put in said step (b) to said 2 D side channels (2) adjacent to said S/R side channel (3) connected with said S/R reservoir (5) in an axis direction, via said S/R side channel (3) connected with said S/R reservoir (5).

(e) Said solution containing a labeled reaction improvement analogue is introduced in said S/R side channel (3) connected with said S/R reservoir (5) used in said step (c), 2 D side channels (2) adjacent to said S/R side channel (3) in an axis direction and a first channel region between said 2 D side channels (2), by moving said solution containing a labeled reaction improvement analogue from said S/R reservoir (5) where said solution containing a labeled reaction improvement analogue is put in said step (c) to said 2 D side channels (2) adjacent to said S/R side channel (3) connected with said S/R reservoir (5) in an axis direction, via said S/R side channel (3) connected with said S/R reservoir (5). By the steps (d) and (e), the solution including a sample having an analyte, and not less than one kind of CFS not bound with a labeling substance and a reaction improvement substance, and the solution containing a labeled reaction improvement analogue are introduced and arranged into a channel so that a zone of a solution including a sample having an analyte, and not less than one kind of CFS not bound with a labeling substance and a reaction improvement substance, and a zone of a solution including a labeled reaction improvement analogue are separately formed (so that liquid-liquid interface is formed), and a complex B between said labeled reaction improvement analogue and labeled CFS is formed on application of a voltage onto a channel, without mixing these solutions in advance outside a channel.

(f) Said labeled reaction improvement analogue is electrophoretically contacted and reacted with CFS not bound with a labeling substance and a reaction improvement substance (namely, said labeled reaction improvement analogue is electrophoretically contacted and reacted with said CFS not bound with a labeling substance and a reaction improvement substance not involved in the formation of a complex (complex A) with said analyte in the said solution including a sample having an analyte, and not less than one kind of CFS not bound with a labeling substance and a reaction improvement substance) while concentrating said labeled reaction improvement analogue and/or said CFS not bound with a labeling substance and a reaction improvement substance not involved in the formation of a complex A by applying a voltage to said upstream reservoir (6) part at the end of said upstream side of said first channel (1) and said downstream reservoir (7) part at the other end of said downstream side of said first channel (1) before uniformly mixing these solutions, not by (not depending on) molecular diffusion and without physically mixing, to form the complex B between said labeled reaction improvement analogue and CFS not bound with a labeling substance and a reaction improvement substance at a first channel region (9a) between a D side channel (2a) located at the most upstream among said not less than 3 D side channels (2) and a D side channel (2n) located at the most downstream among said not less than 3 D side channels (2), or a first channel region (9b) between a D side channel (2a) located at the most upstream among said not less than 3 D side channels (2) and said EM side channel (8).

(g) Said complex B and said complex A are separated, by applying a voltage to said EM reservoir (11) part connecting to said EM side channel (8) and said downstream reservoir (7) part.

8. A Method for Measuring of the Present Invention

By measuring the amount of a complex between an analyte or an analogue thereof and a CFS, and the amount of a CFS not involved in formation of said complex or an analogue not involved in formation of said complex, which are separated by a method for separation of the present invention, by a method corresponding to property of, for example, a labeling substance in a complex, or a labeling substance in a CFS or analogue thereof not involved in formation of a complex, the amount of an analyte present in a sample can be determined simply, in high sensitivity and in a short time.

Therefore, a method for measuring of the present invention features in comprising the following steps:

(a) providing a micro fluidic device comprising at least one structure for introducing a sample or a reagent solution to a first channel (1) in a substrate, said the structure comprising;
  (i) the first channel (1);
  (ii) not less than 3 D side channels (2), each said D side channel (2) having a opening (2-1) opened on a wall of said first channel (1), and said openings (2-1) arranged in spaced relation to one another, wherein said D side channel (2) is connected to a W reservoir (4); and
  (iii) not less than 2 S/R side channels (3), each said S/R side channel (3) having a opening (3-1) opened on the wall of said first channel (1) at the different position (part) from said openings (2-1) of said D side channels (2), and each said opening (3-1) arranged between adjacent 2 openings (2-1) of D side channels (2), wherein each said opening (3-1) of these not less than 2 S/R side channels (3) are each arranged at the different portion between adjacent 2 openings (2-1) of D side channels (2), and S/R side channel (3) is connected to a S/R reservoir (5)[(a): a preparation step];

(b) putting a sample into at least one S/R reservoir (5) connecting to said S/R side channel (3);

(c) putting a reagent solution into at least one S/R reservoir (5) connecting to said S/R side channel (3), wherein said S/R reservoir (5) being different from one used in said step (b);

(d) introducing said sample in said S/R side channel (3) connected with said S/R reservoir (5) used in said step (b), 2 D side channels (2) adjacent to said S/R side channel (3) in an axis direction and a first channel region between said 2 D side channels (2), by moving said sample from said S/R reservoir (5) where said sample is put in said step (b) to said 2 D side channels (2) adjacent to said S/R side channel (3) connected with said S/R reservoir (5) in an axis direction, via said S/R side channel (3) connected with said S/R reservoir (5);

(e) introducing said reagent solution in said S/R side channel (3) connected with said S/R reservoir (5) used in said step (c), 2 D side channels (2) adjacent to said S/R side channel (3) in an axis direction and a first channel region between said 2 D side channels (2), by moving said reagent solution from said S/R reservoir (5) where said reagent solution is put in said step (c) to said 2 D side channels (2) adjacent to said S/R side channel (3) connected with said S/R reservoir (5) in an axis direction, via said S/R side channel (3) connected with said S/R reservoir (5) [(b) to (e): a introduction step];

(f) reacting an analyte or an analogue thereof in the sample with at least one kind of a CFS in the reagent solution while concentrating said analyte or said analogue thereof in the sample and/or at least one kind of the CFS in the reagent solution to form the complex between said analyte or said analogue thereof and the CFS, by applying a voltage to said first channel (1) [(f): concentration and reaction step];

(g) separating said complex between said analyte or said analogue thereof and the CFS, and CFS not involved in the formation of said complex or said analogue not involved in the formation of said complex, by further applying a voltage to said first channel (1) [(g): separation step]; and (h) measuring the amount of thus separated complex between said analyte or said analogue thereof and the CFS, the amount of said CFS not involved in the formation of said complex, or the amount of said analogue not involved in the formation of said complex to determine the amount of said analyte or said analogue thereof in a sample based on the result [(h) measurement step].

In this connection, in the above description, embodiments, specific examples, preferable examples, and the like of an analyte, an analogue (a labeled analogue, a reaction improvement analogue), a solution containing an analyte or an analogue thereof, a sample containing an analyte, a CFS (a labeled CFS, a reaction improvement CFS, a labeled reaction improvement CFS), a solution containing thereof, a preparation step [a step (a)], a solution introducing structure, a micro fluidic device or a micro fluidic system used in a preparation step [a step (a)] a introduction step, a concentration and reaction step, a separation step are as described above.

In general, as a solution introducing structure, a micro fluidic device or a micro fluidic system used in a method for measuring in the present invention, one usually having a reservoir (a S/R reservoir, a W reservoir) and/or an access port, an upstream reservoir and/or an access port, a downstream reservoir and/or an access port are used. In addition, the first channel of a solution introducing structure and a micro fluidic device of the present invention preferably have at least a region (reaction region) where a sample reacts with a reagent solution at one part thereof, in particular, at least a region (concentration and reaction region) where at least one kind of a CFS reacts with analyte or analogue thereof in a sample while concentrating said analyte or said analogue thereof in the sample and/or at least one kind of the CFS in the reagent solution, and further have a region (separation region) where a complex between said analyte or said analogue thereof, and a substance binding to said analyte or said analogue thereof is separated from said substance binding to said analyte or said analogue thereof not involved in the formation of said complex, or said analogue not involved in the formation of said complex, at the downstream of said reaction region or said concentration and reaction region.

A method for measuring of the present invention is for measuring the amount of a complex between an analyte or an analogue thereof and a CFS, or the amount of a CFS not involved in formation of said complex or the amount of an analogue not involved in formation of said complex, which are separated by a separation step of the present invention as described above, and for determining the amount of an analyte, based on the results, and in more specifically, (1) for measuring the amount of a complex between an analyte and a CFS, or the amount of a CFS not involved in formation of said complex, which are separated by a separation step of the present invention, and for determining the amount of an analyte, based on the results; or (2) for measuring the amount of a complex between an analogue and a CFS, or the amount of an analogue not involved in formation of said complex, or the amount of a complex between an analyte and a CFS, which are separated, and for determining the amount of an analyte, based on the results.

A method for measuring of the present invention is applicable to any of a non-competitive method or a competitive method.

Namely, when a method for measuring of the present invention is carried out by a non-competitive method, for example, it may be carried out as follows:
(1) By a introduction step of the present invention, (a) A solution containing an analyte [for example, (i) a sample including an analyte, (ii) a solution including a sample having an analyte, and not less than one kind of CFSs] and (b) at least one kind of solution containing not less than one kind of CFS (a CFS, a labeled CFS, a reaction improvement CFS, a labeled reaction improvement CFS, combinations thereof) are arranged into a capillary (a first channel), so that by applying a voltage to said capillary (said first channel) the complex between said analyte and the CFS [(analyte-CFS) complex, (analyte-labeled CFS) complex, (analyte-reaction improvement CFS) complex, (analyte-labeled reaction improvement CFS) complex, (CFS-analyte-reaction improvement CFS) complex, (labeled CFS-analyte-reaction improvement CFS) complex, (CFS-analyte-labeled reaction improvement CFS) complex, and combinations thereof, etc.] is formed, without mixing these solutions in advance;
(2) by a concentration and reaction step of the present invention, said analyte is reacted (contacted and reacted) with said CFS while concentrating said analyte and/or at least one kind of the CFSs by applying a voltage to said capillary (said first channel) before uniformly mixing these solutions to form the complex between said analyte and the CFS;
(3) by a separation step of the present invention, said complex and a CFS not involved in formation of said complex are separated by further electrical movement (migration); and
(4) the amount of separated complex or the amount of a CFS not involved in formation of said complex is measured to determine the amount of an analyte in a sample based on the result.

In addition, when a method for measuring of the present invention is carried out by a competitive method, for example, it may be carried out as follows:
(1) By an introduction step of the present invention, (i) (a) a sample including an analyte (or a solution including a sample having an analyte, and not less than one kind of CFSs), (b) a solution containing a labeled analogue labeled by a labeling substance (or a solution including a labeled analogue and not less than one kind of CFSs), and (c) at least one kind of solution containing not less than one kind of CFS (a CFS, a reaction improvement CFS, combinations thereof), or (ii) (a) a solution including a sample having an analyte, and a labeled analogue (or a solution including a sample having an analyte, a labeled analogue and not less than one kind of CFSs), and (b) at least one kind of solution containing not less than one kind of CFS (a CFS, a reaction improvement CFS, combinations thereof), or (iii) (a) a solution including a sample having an analyte, and not less than one kind of CFSs (a CFS, a reaction improvement CFS, combinations thereof), and (b) a solution containing a labeled analogue (or a solution including a labeled analogue and not less than one kind of CFSs), are arranged into a capillary (a first channel), so that by applying a voltage to said capillary (said first channel) a complex B between said labeled analogue and CFS [(labeled analogue-CFS) complex, (labeled analogue-reaction improvement CFS) complex, (CFS-labeled analogue-reaction improvement CFS) complex, and combinations thereof, etc.] is formed, or a complex A between said analyte and CFS [(analyte-CFS) complex, (analyte-reaction improvement CFS) complex, (CFS-analyte-reaction improvement CFS) complex, and combinations thereof, etc.] and such Complex B are formed, without mixing these solutions in advance;
(2) by a concentration and reaction step of the present invention, (i) said labeled analogue is reacted (contacted and reacted) with said CFS [namely, said labeled analogue is reacted (contacted and reacted) with a CFS not involved in the formation of a complex (complex A) including said analyte] or (ii) said analyte and labeled analogue are reacted (contacted and reacted) with said CFS [namely, said analyte is reacted (contacted and reacted) with said CFS and said labeled analogue is contacted with said CFS] while concentrating at least one of said analyte, said labeled analogue and not less than one kind of CFSs before uniformly mixing these solutions, to form the complex B between said labeled analogue and CFS or to form the complex A between said analyte and CFS and the complex B;
(3) by a separation step of the present invention, said complex B, and a labeled analogue not involved in formation of said complex B are separated by further electrical movement (migration); and
(4) the amount of separated complex B, or the amount of said labeled analogue not involved in formation of said complex B is measured to determine the amount of an analyte in a sample based on the result.

In addition, when a method for measuring of the present invention is carried out by a competitive method, for example, it may also be carried out as follows:
(1) By an introduction step of the present invention, (i) (a) a sample including an analyte (or a solution including a sample having an analyte, and not less than one kind of CFSs), (b) a solution containing a analogue bound with a reaction improvement substance (a reaction improvement analogue) (or a solution including a reaction improvement analogue and not less than one kind of CFSs) or a analogue bound with a labeled reaction improvement substance (a labeled reaction improvement analogue) (or a solution including a labeled reaction improvement analogue and not less than one kind of CFSs), and (c) at least one kind of solution containing not less than one kind of CFS (a CFS, a labeled CFS, combinations thereof), or (ii) (a) a solution including a sample having an analyte, and a reaction improvement analogue or a labeled reaction improvement analogue [or a solution including a sample having an analyte, a reaction improvement analogue or a labeled reaction improvement analogue, and not less than one kind of CFSs], and (b) at least one kind of solution containing not less than one kind of CFS (a CFS, a labeled CFS, combinations thereof), or (iii) (a) a solution including a sample having an analyte, and not less than one kind of CFSs (a CFS, a labeled CFS, combinations thereof), and (b) a solution containing a reaction improvement analogue or a labeled reaction improvement analogue [or a solution including a reaction improvement analogue or a labeled reaction improvement analogue, and not less than one kind of CFSs], are arranged into a capillary (a first channel), so that by applying a voltage to said capillary (said first channel) a complex B between said reaction improvement analogue and labeled CFS (or a complex B between said labeled reaction improvement analogue and CFS) is formed, or a complex A between said analyte and labeled CFS (or a complex A between said analyte and CFS) and such Complex B are formed, without mixing these solutions in advance;

(2) by a concentration and reaction step of the present invention, (i) said reaction improvement analogue (or said labeled reaction improvement analogue) is reacted (contacted and reacted) with said labeled CFS (or said CFS) [namely, said reaction improvement analogue (or a labeled reaction improvement analogue) is reacted (contacted and reacted) with a labeled CFS (or a CFS) not involved in the formation of a complex (complex A) including said analyte] or (ii) said analyte and reaction improvement analogue (or labeled reaction improvement analogue) are reacted (contacted and reacted) with said labeled CFS (or CFS) [namely, said analyte is reacted (contacted and reacted) with said labeled CFS (or CFS) and said reaction improvement analogue (or labeled reaction improvement analogue) is reacted (contacted and reacted) with said labeled CFS (or CFS)] while concentrating at least one of said analyte, said reaction improvement analogue (or labeled reaction improvement analogue) and not less than one kind of labeled CFS (or CFS) before uniformly mixing these solutions, to form the complex B between said reaction improvement analogue and labeled CFS (or a complex B between said labeled reaction improvement analogue and CFS) or to form the complex A between said analyte and labeled CFS (or a complex A between said analyte and CFS) and the complex B;

(3) by a separation step of the present invention, said complex B and complex A are separated by further electrical movement (migration); and (4) the amount of separated complex B or the amount of separated complex A is measured to determine the amount of an analyte in a sample based on the result.

In this connection, an analogue (a labeled analogue, a reaction improvement analogue or a labeled reaction improvement analogue) is used by (i) co-presence with an analyte in a sample (namely, a sample including an analyte) as a solution including a labeled analogue, a reaction improvement analogue or a labeled reaction improvement analogue and an analyte (a solution containing an analyte and an analogue); or (2) without co-presence with an analyte in a sample (namely, a sample including an analyte) and separately from a solution containing an analyte, as a solution containing an analogue.

(1) A Measurement Step

In a measurement step of the present invention, the amount of a complex or the amount of a CFS not involved in formation of said complex or the amount of an analogue not involved in formation of said complex, which are separated, may be measured, for example, by a method corresponding to property of a labeling substance in said complex, or a labeling substance in a CFS not involved in formation of said complex or a labeling substance in an analogue not involved in formation of said complex, and based on measurement results of said labeling substance. Namely, in a non-competitive method, the amount of a complex between an analyte and a CFS, or the amount of a CFS not involved in formation of said complex, which are separated, may be determined, for example, by a method corresponding to property of a labeling substance in said complex, or labeling substance in CFS not involved in formation of said complex, and based on the result of measurement of said labeling substance. In a competitive method, the amount of a complex B or the amount of a labeled analogue not involved in formation of said complex B (or the amount of a complex B or the amount of a complex A), which are separated, may be determined, by a method corresponding to property of a labeling substance in said complex B, or a labeling substance in a labeled analogue not involved in formation of said complex B (or a labeling substance in a complex A), and based on the measurement result of said labeling substance.

Measurement of a labeling substance may be carried out in accordance with each specified method corresponding to a kind of a labeling substance. For example, when said property is enzyme activity, measurement of a labeling substance may be carried out in accordance with a common method such as EIA or a hybridization method [for example, a method described in "Enzyme immunoassay method, protein, nucleic acid, enzyme, separate vol., No. 31, Edited by T. Kitagawa, T. Nannbara, A. Tuji, 51 to 63, KYORITSU SHUPPAN Co., Ltd., published on Sep. 10, 1987", etc.]; when said property is radioactivity, measurement of a labeling substance may be carried out by using suitably selected measuring instrument such as a liquid immersion type GM counter, a liquid scintillation counter, and a well-type scintillation counter, depending on kind and intensity of radiation ray emitted by said radioactive substance in accordance with a common method such as RIA or a hybridization method, [for example, Medical Chemistry Experimental Course, vol. 8, Edited by U. Yamamura, $1^{st}$ Ed., published by Nakayama Bookstore in 1971; Biochemistry Experimental Course 2, A Tracer Experiment Method (part 2), A. Takemura, H, Honjo, 501 to 525, published by TOKYO KAGAKU DOJIN Co., Ltd. on Feb. 25, 1977]; when said property is fluorescence, measurement of a labeling substance may be carried out in accordance with a common method such as FIA or a hybridization method using measuring instrument such as fluorospectrometer or a confocal laser scanning microscope [a method described in, for example, "Illustration Explanation, Fluorescent antibody, A. Kawao, $1^{st}$ Ed, published by Softscience Co., Ltd., 1983"; "Medical Chemistry Experimental Course, vol. 2, Chemistry of nucleic acid III, M. Saneyoshi, 299 to 318, published by TOKYO KAGAKU DOJIN Co., Ltd. on Dec. 15, 1977"]; when said property is luminescence, measurement of a labeling substance may be carried out in accordance with a common method using measuring instrument such as a photon-counter [for example, a method described in "Enzyme immunoassay method, protein, nucleic acid, enzyme, separate vol., No. 31, Edited by T. Kitagawa, T. Nannbara, A. Tuji, 252 to 263, KYORITSU SHUPPAN Co., Ltd., published on Sep. 10, 1987"]; further when said property is UV absorption, measurement of a labeling substance may be carried out in accordance with a common method using measuring instrument such as a spectrometer; when said property is color phenomenon, measurement of a labeling substance may be carried out in accordance with a common method using measuring instrument such as a spectrometer or a microscope; when said property is spin, measurement of a labeling substance may be carried out in accordance with a common method using electron spin resonance instrument [for example, a method described in "Enzyme immunoassay method, protein, nucleic acid, enzyme, separate vol., No. 31, Edited by T. Kitagawa, T. Nannbara, A. Tuji, 264 to 271, KYORITSU SHUPPAN Co., Ltd., published on Sep. 10, 1987", etc.].

In addition, for determination of the amount of an analyte present in a sample, based on measured amount of a complex or amount of a CFS not involved in formation of said complex or amount of an analogue not involved in formation of said complex, namely the amount of a labeling substance in a complex or amount of a labeling substance in a CFS not involved in formation of said complex or a labeling substance in an analogue not involved in formation of said complex, for example, a calibration curve or an internal standard, and the like may be used, and for example, it may be carried out as follows:

[The Case for Using a Calibration Curve]

In a non-competitive method, determination of the amount of an analyte present in a sample based on the measured amount of a complex or the amount of a CFS not involved in formation of said complex, namely the amount of a labeling substance in a complex or the amount of a labeling substance in a CFS not involved in formation of said complex, obtained as above, can be carried out, for example, by preparing a calibration curve showing relation between the amount of an analyte and the amount of a labeling substance in a complex or the amount of a labeling substance in a CFS not involved in formation of said complex, obtained by measurement with a similar method using a sample containing a known concentration of an analyte, and by applying the amount of a labeling substance obtained by measurement of a sample containing an analyte to said calibration curve. In addition, in a competitive method, determination of the amount of an analyte present in a sample based on the amount of a complex B or the amount of a labeled analogue (or a labeled reaction improvement analogue) not involved in formation of said complex B (or the amount of a complex B or the amount of complex A), namely the amount of a labeling substance in a complex B or the amount of a labeling substance in a labeled analogue (or a labeled reaction improvement analogue) not involved in formation of said complex B (or the amount of a labeling substance in a complex A), obtained as above, can be carried out, for example, by preparing a calibration curve showing relation between the amount of an analyte, and the amount of a labeling substance in a complex B or the amount of a labeling substance in a labeled analogue (or a labeled reaction improvement analogue) not involved in formation of said complex B (or the amount of a labeling substance in a complex A), obtained by measurement with a similar method using a sample containing a known concentration of an analyte, and by applying the amount of a labeling substance obtained by measurement of a sample containing an analyte to said calibration curve.

[The Case for Using an Internal Standard]

In addition, by the addition of a known concentration of a detectable substance as an internal standard into a sample, and by comparing the amount of said substance added as internal standard, with the amount of a complex not involved in formation of said complex, or the amount of a CFS or the amount of an analogue not involved in formation of said complex [namely, the amount of a labeling substance in a complex or the amount of a labeling substance in a CFS not involved in formation of said complex, or the amount of a labeling substance in a complex B or the amount of a labeling substance in a labeled analogue (or a labeled reaction improvement analogue) not involved in formation of said complex B (or the amount of a labeling substance in a complex B or the amount of a labeling substance in a complex A)], the relative amount of an analyte in a sample may be calculated. Namely, the amount of an analyte in a sample may relatively be calculated based on the known addition amount of said internal standard and the ratio determined by comparing the peak of the internal standard measured and detected with the peak of the complex measured and detected simultaneously with the internal standard, the peak of the CFSs not involved in formation of said complex measured and detected simultaneously with the internal standard or the peak of the analogue not involved in formation of said complex measured and detected simultaneously with the internal standard.

By using an internal standard it is possible to correct the error among electrophoresis equipment (device). Furthermore, by using a known mobility of a substance as an internal standard, the correction of objective peak mobility using mobility of a peak of an internal standard becomes also possible.

A detectable substance (internal standard) is a substance can be detected and having a different mobility from the complex, the CFSs not involved in formation of said complex or the analogue not involved in formation of said complex, measured and detected at the same time (migrated at different portion from them). Such detectable substances (internal standards) include, for example, peptide, protein, nucleic acid (DNA, RNA), an amino acid, sugar, a sugar chain, etc., labeled with the above described labeling substance; and a fluorescent substance, etc.

In addition, in the present invention, when an enzyme is used as a labeling substance, and the like, substrates or other coupling enzymes of said enzyme may be required to measure activity of said enzyme. In such a case, for example, these substrates or other coupling enzymes may be arranged in a capillary at the downstream side of a solution including a complex or a CFS not involved in formation of said complex or an analogue not involved in formation of said complex [namely, a complex between an analyte and a CFS or a CFS not involved in formation of said complex, or a complex B or a labeled analogue (or a labeled reaction improvement analogue) not involved in formation of said complex B (or a complex B or a complex A)], separated by a separation step of the present invention, at least before carrying out a measurement step of the present invention. It is preferable that in a introduction step of the present invention a solution including these substrates or other coupling enzymes is arranged at further downstream side of the solution (zone) arranged at the most downstream side among a solution (zone) including an analyte or analogue thereof and a solution (zone) including not less than one kind of CFS, and an introduction step, a concentration and reaction step, a separation step and a measurement step of the present invention are carried out. Such solution may be used alone or in combination with two or more kinds.

In addition, when an intercalator dye is used as a labeling substance, in an introduction step of the present invention said intercalator dye is not required to be introduced and arranged in a capillary with a solution containing an analyte or an analogue thereof, and a solution including not less than one kind of CFS. And also, in a concentration and reaction step of the present invention said intercalator dye is not required to make contact with an analyte or an analogue thereof and a CFS. It is only necessary to carry out at least a separation step of the present invention in the presence of said intercalator dye. In such a case, specifically, for example, said intercalator dye may be contained in an electrophoresis medium and/or buffer solution used in a separation step of the present invention. Among others, in the present invention, it is preferable that a concentration and reaction step and a separation step of the present invention are carried out in the presence of said intercalator dye. In this case, said intercalator dye may be contained in an electrophoresis medium and/or buffer solution used in a concentration and reaction step and in a separation step of the present invention.

(2) Use of a Charged Polymer

In the present invention, it is preferable that a concentration and reaction step is carried out in the presence of a charged polymer.

Namely, (i) by making react (contact and react) of an analyte or an analogue thereof, and a CFS in the presence of a charged polymer to form a complex between said analyte or analogue thereof and CFS, or (ii) by making react (contact and react) of an analyte, an analogue (a labeled analogue or a labeled reaction improvement analogue) and a CFS in the presence of a charged polymer to form a complex A between said analyte and CFS, and a complex B between said labeled analogue and CFS; or (iii) by making react (contact and react) of an analyte, a reaction improvement analogue (or a labeled reaction improvement analogue) and a labeled CFS (or CFS) in the presence of a charged polymer to form a complex A between said analyte and labeled CFS (or CFS) and a complex B between said reaction improvement analogue (or a labeled reaction improvement analogue) and labeled CFS (or CFS), effect of a co-present substance in a sample (particularly in a serum sample) having bad effect on analysis can be reduced. Specifically, for example, (i) by making react (contact and react) of an analyte and CFS in the presence of a charged polymer, a complex between said analyte and CFS [(analyte-CFS) complex, (analyte-labeled CFS) complex, (analyte-reaction improvement CFS) complex, (analyte-labeled reaction improvement CFS) complex, (CFS-analyte-reaction improvement CFS) complex, (labeled CFS-analyte-reaction improvement CFS) complex, (CFS-analyte-labeled reaction improvement CFS) complex, and combinations thereof, etc.] is formed; or (ii) by making react (contact and react) of an analyte, a labeled analogue (or a labeled reaction improvement analogue) and a CFS in the presence of a charged polymer [namely, by making contact of said analyte and CFS, and said labeling analogue (or a labeled reaction improvement analogue) and CFS], a complex A between said analyte and said CFS [(analyte-CFS) complex, (analyte-reaction improvement CFS) complex, (CFS-analyte-reaction improvement CFS) complex, and combinations thereof, etc.] and a complex B between said labeled analogue (or a labeled reaction improvement analogue) and CFS [(labeled analogue-CFS) complex, (labeled analogue-reaction improvement CFS) complex, (CFS-labeled analogue-reaction improvement CFS) complex, (CFS-labeled reaction improvement analogue) complex and combinations thereof, etc.] are formed; or (iii) by making react (contact and react) of an analyte, a reaction improvement analogue (or a labeled reaction improvement analogue) and a labeled CFS (a CFS) [namely, by making react (contact and react) of said analyte and labeled CFS(CFS), and said reaction improvement analogue (or a labeled reaction improvement analogue) and labeled CFS(CFS)] in the presence of a charged polymer, a complex A between said analyte and said labeled CFS (or CFS) and a complex B between said reaction improvement analogue (or a labeled reaction improvement analogue) and said labeled CFS (or CFS) are formed.

As a charged polymer used in the present invention, one having the opposite charge (plus or minus) from that of a co-present substance in a sample is used. In addition, a charged polymer having the same charge as that of a CFS used is preferable.

As such a charged polymer, polyanionic polymers and polycationic polymers are included.

Polyanionic polymers include, polysaccharides such as heparin, heparin sulfate, chondroitin sulfate, dextran sulfate, polytungstic acid, tungstophosphoric acid, hyaluronic acid, dermatan sulfate and polyanethole sulfate, etc.; polynucleotides such as DNA (plasmid DNA, calf thymus DNA, salmon sperm DNA, DNA bound with cellulose and synthetic DNA, etc.), and RNA, etc.; polypeptides such as polyamino acids (polyaspartic acid, polyglutamic acid, etc.), a synthetic polypeptide, etc.; synthetic polymer compounds such as poly-dldC, polyvinyl sulfate, polyacrylic acid, etc.; ceramics such as glass particle, colloidal glass, glass milk, etc.; and complexes thereof; and the like.

In addition, polycationic polymers include, polysaccharides such as chitosan, derivatives thereof, etc.; polypeptides such as polylysine, polyhistidine, polyarginine, protamine, histone, ornithine, etc.; synthetic polymer compounds such as polyallyl amine, polyethylene imine, polyvinyl amine, etc.; polyamines such as spermine, spermidine, etc.; cationic lipid; ceramics; complexes thereof; and the like.

Among them, an anionic polysaccharide is preferable, and heparin sulfate is particularly preferable.

The above-described charged polymers may be used alone or in suitable combination with two or more kinds.

A method for making the above described charged polymers present in carrying out a concentration and reaction step is not especially limited as long as formation of a complex can finally be carried out in the presence of a charged polymer.

Such a method includes, for example, a method for making a charged polymer co-present in an electrophoresis medium to be filled in a capillary as described above; a method for making a charged polymer co-present in a solution containing an analyte or an analogue thereof, and/or in a solution containing CFS; and the like.

Among these, the charged polymer is co-present preferably in a solution (zone) other than the solution (zone) containing an analyte, more preferably in at least one solution (zone) arranged adjacently upstream side or downstream side of the solution (zone) containing an analyte.

Use amount of the above-described charged polymer is not simply be described due to dependency on the kind of the charged polymer used, however, for example, concentration in an electrophoresis medium to be filled in a channel is, as lower limit, usually not lower than 0.01% (w/v), preferably not lower than 0.05% (w/v), and more preferably not lower than 0.5% (w/v), and as upper limit, usually not higher than 50% (w/v), preferably not higher than 10% (w/v) and further preferably not higher than 5% (w/v), and among others about 1% (w/v) is particularly preferable. In addition, concentration in a solution containing an analyte or an analogue thereof or in a solution containing a CFS is, as lower limit, usually not lower than 0.001% (w/v), preferably not lower than 0.01% (w/v), more preferably not lower than 0.02% (w/v), and further preferably not lower than 0.025% (w/v), and as upper limit, usually not higher than 10% (w/v), preferably not higher than 5% (w/v), more preferably not higher than 1% (w/v) and further preferably not higher than 0.05% (w/v).

(3) A Specific Method for Measuring

Embodiments of a method for measuring of the present invention are specifically shown below.

(3-1) A Non-Competitive Method

For example, a non-competitive method is as follows.

(3-1-1) A case when a CFS not bound with a labeling substance and a reaction improvement substance are used.

In this case, for example, it may be carried out as the following [method A] or [method B].

[Method A; The Case for Using a Calibration Curve]:

(a) The same preparation step [the step (a)] as the above-described in the case (3-1) of "(3) a specific method for separating" is carried out.

(b) to (e) The same introduction steps [the steps (b) to (e)] as the above-described in the case (3-1) of "(3) a specific method for separating" is carried out.

(f) The same concentration and reaction step [the step (f)] as the above-described in the case (3-1) of "(3) a specific method for separating" is carried out.

(g) The same separation step [the step (g)] as the above-described in the case (3-1) of "(3) a specific method for separating" is carried out.

(h) The amount of a CFS contained in the separated complex or the amount of a CFS not involved in formation of said complex is measured by a method corresponding to property (kind) of a CFS, and the amount of an analyte in a sample is calculated by applying the measurement result (measurement value) to a calibration curve showing relation between the amount of an analyte, and the amount of a CFS contained in the separated complex or the amount of a CFS not involved in formation of said complex, obtained by a similar method using a sample containing a known concentration of an analyte.

[Method B; The Case for Using an Internal Standard]:

A known concentration of a detectable substance as an internal standard is added to at least one of a solution containing an analyte and a solution containing CFS in the above-described [method A], and the above-described steps (a) to (g) are carried out using that solution containing the internal standard. The amount of a CFS contained in the separated complex or the amount of a CFS not involved in formation of said complex is measured by a method corresponding to property (kind) of a CFS, and the amount of an analyte in a sample is calculated by comparing the measurement result (measurement value) with the amount of said substance added as internal standard. In more specifically, the amount of the analyte in the sample is relatively calculated by measuring the amount of the CFSs contained in the separated complex or the amount of the CFSs not involved in formation of said complex, by a method corresponding to property (kind) of a CFS, and further the amount of the internal standard added is measured by a method corresponding to property (kind) of the internal standard, and by comparing these resultant measurement values to determine the ratio, and then based on the ratio and the known addition amount of said internal standard.

(3-1-2) A Case when a Labeled CFS is Used.

In this case, for example, it may be carried out as the following [method A] or [method B].

[Method A; The Case for Using a Calibration Curve]:

(a) The same preparation step [the step (a)] as the above-described in the case (3-2) of "(3) a specific method for separating" is carried out.

(b) to (e) The same introduction steps [the steps (b) to (e)] as the above-described in the case (3-2) of "(3) a specific method for separating" is carried out.

(f) The same concentration and reaction step [the step (f)] as the above-described in the case (3-2) of "(3) a specific method for separating" is carried out.

(g) The same separation step [the step (g)] as the above-described in the case (3-2) of "(3) a specific method for separating" is carried out.

(h) The amount of a labeling substance contained in the separated complex or the amount of a labeling substance contained in a labeled CFS not involved in formation of said complex is measured by a method corresponding to property (kind) of a labeling substance, and the amount of an analyte in a sample is calculated by applying the measurement result (measurement value) to a calibration curve showing relation between the amount of an analyte, and the amount of a labeling substance contained in the separated complex or the amount of a labeling substance contained in a labeled CFS not involved in formation of said complex, obtained by a similar method using a sample containing a known concentration of an analyte.

[Method B; The Case for Using an Internal Standard]:

A known concentration of a detectable substance as an internal standard is added to at least one of a solution containing an analyte and a solution containing a labeled CFS in the above-described [method A], and the above-described steps (a) to (g) are carried out using that solution containing the internal standard. The amount of a labeling substance contained in the separated complex or the amount of a labeling substance contained in a labeled CFS not involved in formation of said complex is measured by a method corresponding to property (kind) of a labeling substance, and the amount of an analyte in a sample is calculated by comparing the measurement result (measurement value) with the amount of said substance added as internal standard. In more specifically, the amount of the analyte in the sample is relatively calculated by measuring the amount of the labeling substance contained in the separated complex or the amount of the labeling substance contained in the labeling CFS not involved in formation of said complex, by a method corresponding to property (kind) of the labeling substance, and further the amount of the internal standard added is measured by a method corresponding to property (kind) of the internal standard, and by comparing these resultant measurement values to determine the ratio, and then based on the ratio and the known addition amount of said internal standard.

(3-1-3) A Case when a Reaction Improvement CFS is Used.

In this case, for example, it may be carried out as the following [method A] or [method B].

[Method A; The Case for Using a Calibration Curve]:

(a) The same preparation step [the step (a)] as the above-described in the case (3-3) of "(3) a specific method for separating" is carried out.

(b) to (e) The same introduction steps [the steps (b) to (e)] as the above-described in the case (3-3) of "(3) a specific method for separating" is carried out.

(f) The same concentration and reaction step [the step (f)] as the above-described in the case (3-3) of "(3) a specific method for separating" is carried out.

(g) The same separation step [the step (g)] as the above-described in the case (3-3) of "(3) a specific method for separating" is carried out.

(h) The amount of a reaction improvement CFS contained in the separated complex or the amount of a reaction improvement CFS not involved in formation of said complex is measured by a method corresponding to property (kind) of a reaction improvement CFS, and the amount of an analyte in a sample is calculated by applying the measurement result (measurement value) to a calibration curve showing relation between the amount of an analyte, and the amount of a reaction improvement CFS contained in the separated complex or the amount of a reaction improvement CFS not involved in formation of said complex, obtained by a similar method using a sample containing a known concentration of an analyte.

[Method B; The Case for Using an Internal Standard]:

A known concentration of a detectable substance as an internal standard is added to at least one of a solution containing an analyte and a solution containing a reaction improvement CFS in the above-described [method A], and the above-described steps (a) to (g) are carried out using that solution containing the internal standard. The amount of a reaction improvement CFS contained in the separated complex or the amount of a reaction improvement CFS not involved in formation of said complex is measured by a method corresponding to property (kind) of a reaction improvement CFS, and the amount of an analyte in a sample is calculated by comparing the measurement result (measurement value) with the amount of said substance added as internal standard. In more specifically, the amount of the analyte in the sample is relatively calculated by measuring the amount of the reaction improvement CFS contained in the separated complex or the amount of the reaction improvement CFS not involved in formation of said complex, by a method corresponding to property (kind) of the reaction improvement CFS, and further the amount of the internal standard added is measured by a method corresponding to property (kind) of the internal standard, and by comparing these resultant measurement values to determine the ratio, and then based on the ratio and the known addition amount of said internal standard.

(3-1-4) A Case when a Labeled Reaction Improvement CFS is Used.

In this case, for example, it may be carried out as the following [method A] or [method B].

[Method A; The Case for Using a Calibration Curve]:

(a) The same preparation step [the step (a)] as the above-described in the case (3-4) of "(3) a specific method for separating" is carried out.

(b) to (e) The same introduction steps [the steps (b) to (e)] as the above-described in the case (3-4) of "(3) a specific method for separating" is carried out.

(f) The same concentration and reaction step [the step (f)] as the above-described in the case (3-4) of "(3) a specific method for separating" is carried out.

(g) The same separation step [the step (g)] as the above-described in the case (3-4) of "(3) a specific method for separating" is carried out.

(h) The amount of a labeling substance contained in the separated complex or the amount of a labeling substance contained in a labeled reaction improvement CFS not involved in formation of said complex is measured by a method corresponding to property (kind) of a labeling substance, and the amount of an analyte in a sample is calculated by applying the measurement result (measurement value) to a calibration curve showing relation between the amount of an analyte, and amount of a labeling substance contained in the separated complex or the amount of a labeling substance contained in a labeled reaction improvement CFS not involved in formation of said complex, obtained by a similar method using a sample containing a known concentration of an analyte.

[Method B; The Case for Using an Internal Standard]:

A known concentration of a detectable substance as an internal standard is added to at least one of a solution containing an analyte and a solution containing a labeled reaction improvement CFS in the above-described [method A], and the above-described steps (a) to (g) are carried out using that solution containing the internal standard. The amount of a labeling substance contained in the separated complex or the amount of a labeling contained substance in a labeled reaction improvement CFS not involved in formation of said complex is measured by a method corresponding to property (kind) of a labeling substance, and the amount of an analyte in a sample is calculated by comparing the measurement result (measurement value) with the amount of said substance added as internal standard. In more specifically, the amount of the analyte in the sample is relatively calculated by measuring the amount of the labeling substance contained in the separated complex or the amount of the labeling substance contained the labeling reaction improvement CFS not involved in formation of said complex, by a method corresponding to property (kind) of the labeling substance, and further the amount of the internal standard added is measured by a method corresponding to property (kind) of the internal standard, and by comparing these resultant measurement values to determine the ratio, and then based on the ratio and the known addition amount of said internal standard.

(3-1-5) A Case when a CFS not Bound with a Labeling Substance and a Reaction Improvement Substance, and a Reaction Improvement CFS are Used.

In this case, for example, it may be carried out as the following [method A] or [method B].

[Method A; The Case for Using a Calibration Curve]:

(a) The same preparation step [the step (a)] as the above-described in the case (3-5) of "(3) a specific method for separating" is carried out.

(b) to (g) The same introduction steps [the steps (b) to (g)] as the above-described in the case (3-5) of "(3) a specific method for separating" is carried out.

(h) The same concentration and reaction step [the step (h)] as the above-described in the case (3-5) of "(3) a specific method for separating" is carried out.

(i) The same separation step [the step (i)] as the above-described in the case (3-5) of "(3) a specific method for separating" is carried out.

(j) The amount of a CFS contained in the separated complex or the amount of a reaction improvement CFS contained in the separated complex, or the amount of a CFS not involved in formation of said complex or the amount of a reaction improvement CFS not involved in formation of said complex is measured by a method corresponding to property (kind) of a CFS or a reaction improvement CFS, and the amount of an analyte in a sample is calculated by applying the measurement result (measurement value) to a calibration curve showing relation between the amount of an analyte, and the amount of a CFS contained in the separated complex or the amount of a reaction improvement CFS contained in the separated complex, or the amount of a CFS not involved in formation of said complex or the amount of a reaction improvement CFS not involved in formation of said complex, obtained by a similar method using a sample containing a known concentration of an analyte.

[Method B; The Case for Using an Internal Standard]:

A known concentration of a detectable substance as an internal standard is added to at least one selected from a solution containing an analyte, a solution containing a CFS and a solution containing a reaction improvement CFS in the above-described [method A], and the above-described steps (a) to (i) are carried out using that solution containing the internal standard. The amount of a CFS contained in the separated complex or the amount of a reaction improvement CFS contained in the separated complex, or the amount of a CFS not involved in formation of said complex or the amount of a reaction improvement CFS not involved in formation of said complex is measured by a method corresponding to property (kind) of a CFS or a reaction improvement CFS, and the amount of an analyte in a sample is calculated by comparing the measurement result (measurement value) with the amount of said substance added as internal standard. In more specifically, the amount of the analyte in the sample is relatively calculated by measuring the amount of the CFS or the reaction improvement CFS contained in the separated complex or the amount of the CFS or the reaction improvement CFS not involved in formation of said complex, by a method corresponding to property (kind) of the CFS or the reaction improvement CFS, and further the amount of the internal standard added is measured by a method corresponding to property (kind) of the internal standard, and by comparing these resultant measurement values to determine the ratio, and then based on the ratio and the known addition amount of said internal standard.

(3-1-6) A Case when a Labeled CFS and a Reaction Improvement CFS are Used.

In this case, for example, it may be carried out as the following [method A] or [method B].

[Method A; The Case for Using a Calibration Curve]:

(a) The same preparation step [the step (a)] as the above-described in the case (3-6) of "(3) a specific method for separating" is carried out.

(b) to (g) The same introduction steps [the steps (b) to (g)] as the above-described in the case (3-65) of "(3) a specific method for separating" is carried out.

(h) The same concentration and reaction step [the step (h)] as the above-described in the case (3-6) of "(3) a specific method for separating" is carried out.

(i) The same separation step [the step (i)] as the above-described in the case (3-6) of "(3) a specific method for separating" is carried out.

(j) The amount of a labeling substance contained in the separated complex or the amount of a labeling substance contained in a labeled CFS not involved in formation of said complex is measured by a method corresponding to property (kind) of a labeling substance, and the amount of an analyte in a sample is calculated by applying the measurement result (measurement value) to a calibration curve showing relation between the amount of an analyte, and the amount of a labeling substance contained in the separated complex or the amount of a labeling substance contained in a labeled CFS not involved in formation of said complex, obtained by a similar method using a sample containing a known concentration of an analyte.

[Method B; The Case for Using an Internal Standard]:

A known concentration of a detectable substance as an internal standard is added to at least one selected from a solution containing an analyte, a solution containing a labeled CFS and a solution containing a reaction improvement CFS in the above-described [method A], and the above-described steps (a) to (i) are carried out using that solution containing the internal standard. The amount of a labeling substance contained in the separated complex or the amount of a labeling substance contained in a labeled CFS not involved in formation of said complex is measured by a method corresponding to property (kind) of a labeling substance, and the amount of an analyte in a sample is calculated by comparing the measurement result (measurement value) with the amount of said substance added as internal standard. In more specifically, the amount of the analyte in the sample is relatively calculated by measuring the amount of the labeling substance contained in the separated complex or the amount of the labeling substance contained in the labeling CFS not involved in formation of said complex, by a method corresponding to property (kind) of the labeling substance, and further the amount of the internal standard added is measured by a method corresponding to property (kind) of the internal standard, and by comparing these resultant measurement values to determine the ratio, and then based on the ratio and the known addition amount of said internal standard.

(3-1-7) A Case when a CFS not Bound with a Labeling Substance and a Reaction Improvement Substance, and a Labeled Reaction Improvement CFS are Used.

In this case, for example, it may be carried out as the following [method A] or [method B].

[Method A; The Case for Using a Calibration Curve]:

(a) The same preparation step [the step (a)] as the above-described in the case (3-5) of "(3) a specific method for separating" is carried out.

(b) to (g) The same introduction steps [the steps (b) to (g)] as the above-described in the case (3-5) of "(3) a specific method for separating" is carried out.

(h) The same concentration and reaction step [the step (h)] as the above-described in the case (3-5) of "(3) a specific method for separating" is carried out.

(i) The same separation step [the step (i)] as the above-described in the case (3-5) of "(3) a specific method for separating" is carried out.

(j) The amount of a labeling substance contained in the separated complex or the amount of a labeling substance contained in a labeled reaction improvement CFS not involved in formation of said complex is measured by a method corresponding to property (kind) of a labeling substance, and the amount of an analyte in a sample is calculated by applying the measurement result (measurement value) to a calibration curve showing relation between the amount of an analyte, and the amount of a labeling substance contained in the separated complex or the amount of a labeling substance contained in a labeled reaction improvement CFS not involved in formation of said complex, obtained by a similar method using a sample containing a known concentration of an analyte.

[Method B; The Case for Using an Internal Standard]:

A known concentration of a detectable substance as an internal standard is added to at least one selected from a solution containing an analyte, a solution containing a CFS and a solution containing a labeled reaction improvement CFS in the above-described [method A], and the above-described steps (a) to (i) are carried out using that solution containing the internal standard. The amount of a labeling substance contained in the separated complex or the amount of a labeling substance contained in a labeled reaction improvement CFS not involved in formation of said complex is measured by a method corresponding to property (kind) of a labeling substance, and the amount of an analyte in a sample is calculated by comparing the measurement result (measurement value) with the amount of said substance added as internal standard. In more specifically, the amount of the analyte in the sample is relatively calculated by measuring the amount of the labeling substance contained in the separated complex or the amount of the labeling substance contained in the labeling reaction improvement CFS not involved in formation of said complex, by a method corresponding to property (kind) of the labeling substance, and further the amount of the internal standard added is measured by a method corresponding to property (kind) of the internal standard, and by comparing these resultant measurement values to determine the ratio, and then based on the ratio and the known addition amount of said internal standard.

(3-2) A Competitive Method

For example, a competitive method is as follows.

(3-2-1) A Case when a Labeled Analogue and a CFS are Used. (The Use of a Solution Including Both an Analyte and an Analogue.)

In this case, for example, it may be carried out as the following [method A] or [method B].

[Method A; The Case for Using a Calibration Curve]:

(a) The same preparation step [the step (a)] as the above-described in the case (3-8) of "(3) a specific method for separating" is carried out.

(b) to (e) The same introduction steps [the steps (b) to (e)] as the above-described in the case (3-8) of "(3) a specific method for separating" is carried out.

(f) The same concentration and reaction step [the step (f)] as the above-described in the case (3-8) of "(3) a specific method for separating" is carried out.

(g) The same separation step [the step (g)] as the above-described in the case (3-8) of "(3) a specific method for separating" is carried out.

(h) The amount of a labeling substance contained in the separated complex B or the amount of a labeling substance contained in a labeled analogue not involved in formation of said complex B is measured by a method corresponding to property (kind) of a labeling substance, and the amount of an analyte in a sample is calculated by applying the measurement result (measurement value) to a calibration curve showing relation between the amount of an analyte, and the amount of a labeling substance contained in the separated complex B or the amount of a labeling substance contained in a labeled analogue not involved in formation of said complex B, obtained by a similar method using a sample containing a known concentration of an analyte.

[Method B; The Case for Using an Internal Standard]:

A known concentration of a detectable substance as an internal standard is added to a solution including a sample having an analyte and a labeled analogue (or a solution including a sample having an analyte, a labeled analogue and not less than one kind of CFSs) or a solution containing a CFS in the above-described [method A], and the above-described steps (a) to (g) are carried out using that solution containing the internal standard. The amount of a labeling substance contained in the separated complex B or the amount of a labeling substance contained in a labeled analogue not involved in formation of said complex B is measured by a method corresponding to property (kind) of a labeling substance, and the amount of an analyte in a sample is calculated by comparing the measurement result (measurement value) with the amount of said substance added as internal standard. In more specifically, the amount of the analyte in the sample is relatively calculated by measuring the amount of the labeling substance contained in the separated complex B, or the amount of labeling substance contained in the labeling analogue not involved in formation of said complex B, by a method corresponding to property (kind) of the labeling substance, and further the amount of the internal standard added is measured by a method corresponding to property (kind) of the internal standard, and by comparing these resultant measurement values to determine the ratio, and then based on the ratio and the known addition amount of said internal standard.

(3-2-2) A Case when a Labeled Analogue and a Reaction Improvement CFS are Used. (The Use of a Solution Including Both an Analyte and an Analogue.)

In this case, for example, it may be carried out as the following [method A] or [method B].

[Method A; The Case for Using a Calibration Curve]:

(a) The same preparation step [the step (a)] as the above-described in the case (3-9) of "(3) a specific method for separating" is carried out.

(b) to (e) The same introduction steps [the steps (b) to (e)] as the above-described in the case (3-9) of "(3) a specific method for separating" is carried out.

(f) The same concentration and reaction step [the step (f)] as the above-described in the case (3-9) of "(3) a specific method for separating" is carried out.

(g) The same separation step [the step (g)] as the above-described in the case (3-9) of "(3) a specific method for separating" is carried out.

(h) The amount of a labeling substance contained in the separated complex B or the amount of a labeling substance contained in a labeled analogue not involved in formation of said complex B is measured by a method corresponding to property (kind) of a labeling substance, and the amount of an analyte in a sample is calculated by applying the measurement result (measurement value) to a calibration curve showing relation between the amount of an analyte, and the amount of a labeling substance contained in the separated complex B or the amount of a labeling substance contained in a labeled analogue not involved in formation of said complex B, obtained by a similar method using a sample containing a known concentration of an analyte.

[Method B; The Case for Using an Internal Standard]:

A known concentration of a detectable substance as an internal standard is added to a solution including a sample having an analyte and a labeled analogue (or a solution including a sample having an analyte, a labeled analogue and not less than one kind of CFSs) or a solution containing a reaction improvement CFS in the above-described [method A], and the above-described steps (a) to (g) are carried out using that solution containing the internal standard. The amount of a labeling substance contained in the separated complex B or the amount of a labeling substance contained in a labeled analogue not involved in formation of said complex B is measured by a method corresponding to property (kind) of a labeling substance, and the amount of an analyte in a sample is calculated by comparing the measurement result (measurement value) with the amount of said substance added as internal standard. In more specifically, the amount of the analyte in the sample is relatively calculated by measuring the amount of the labeling substance contained in the separated complex B, or the amount of labeling substance contained in a labeling analogue not involved in formation of said complex B, by a method corresponding to property (kind) of the labeling substance, and further the amount of the internal standard added is measured by a method corresponding to property (kind) of the internal standard, and by comparing these resultant measurement values to determine the ratio, and then based on the ratio and the known addition amount of said internal standard.

(3-2-3) A Case when a Labeled Analogue, a CFS and a Reaction Improvement CFS are Used. (The Use of a Solution Including Both an Analyte and an Analogue.)

In this case, for example, it may be carried out as the following [method A] or [method B].

[Method A; The Case for Using a Calibration Curve]:

(a) The same preparation step [the step (a)] as the above-described in the case (3-10) of "(3) a specific method for separating" is carried out.

(b) to (g) The same introduction steps [the steps (b) to (g)] as the above-described in the case (3-10) of "(3) a specific method for separating" is carried out.

(h) The same concentration and reaction step [the step (h)] as the above-described in the case (3-10) of "(3) a specific method for separating" is carried out.

(i) The same separation step [the step (i)] as the above-described in the case (3-10) of "(3) a specific method for separating" is carried out.

(j) The amount of a labeling substance contained in the separated complex B or the amount of a labeling substance contained in a labeled analogue not involved in formation of said complex B is measured by a method corresponding to property (kind) of a labeling substance, and the amount of an analyte in a sample is calculated by applying the measurement result (measurement value) to a calibration curve showing relation between the amount of an analyte, and the amount of a labeling substance contained in the separated complex B or the amount of a labeling substance contained in a labeled analogue not involved in formation of said complex B, obtained by a similar method using a sample containing a known concentration of an analyte.

[Method B; The Case for Using an Internal Standard]:

A known concentration of a detectable substance as an internal standard is added to at least one selected from a solution including a sample having an analyte and a labeled analogue (or a solution including a sample having an analyte, a labeled analogue and not less than one kind of CFSs), a solution containing a CFS and a solution containing a reaction improvement CFS in the above-described [method A], and the above-described steps (a) to (i) are carried out using that solution containing the internal standard. The amount of a labeling substance contained in the separated complex B or the amount of a labeling substance contained in a labeled analogue not involved in formation of said complex B is measured by a method corresponding to property (kind) of a labeling substance, and the amount of an analyte in a sample is calculated by comparing the measurement result (measurement value) with the amount of said substance added as internal standard. In more specifically, the amount of the analyte in the sample is relatively calculated by measuring the amount of the labeling substance contained in the separated complex B, or the amount of labeling substance contained in the labeling analogue not involved in formation of said complex B, by a method corresponding to property (kind) of the labeling substance, and further the amount of the internal standard added is measured by a method corresponding to property (kind) of the internal standard, and by comparing these resultant measurement values to determine the ratio, and then based on the ratio and the known addition amount of said internal standard.

(3-2-4) A Case when a Reaction Improvement Analogue and a Labeled CFS are Used. (The Use of a Solution Including Both an Analyte and an Analogue.)

In this case, for example, it may be carried out as the following [method A] or [method B].

[Method A; The Case for Using a Calibration Curve]:

(a) The same preparation step [the step (a)] as the above-described in the case (3-11) of "(3) a specific method for separating" is carried out.

(b) to (e) The same introduction steps [the steps (b) to (e)] as the above-described in the case (3-11) of "(3) a specific method for separating" is carried out.

(f) The same concentration and reaction step [the step (f)] as the above-described in the case (3-11) of "(3) a specific method for separating" is carried out.

(g) The same separation step [the step (g)] as the above-described in the case (3-11) of "(3) a specific method for separating" is carried out.

(h) The amount of a labeling substance contained in the separated complex B or the amount of a labeling substance contained in the separated complex A is measured by a method corresponding to property (kind) of a labeling substance, and the amount of an analyte in a sample is calculated by applying the measurement result (measurement value) to a calibration curve showing relation between the amount of an analyte, and the amount of a labeling substance contained in the separated complex B or the amount of a labeling substance contained in the separated complex A, obtained by a similar method using a sample containing a known concentration of an analyte.

[Method B; The Case for Using an Internal Standard]:

A known concentration of a detectable substance as an internal standard is added to a solution including a sample having an analyte and a reaction improvement analogue (or a solution including a sample having an analyte, a reaction improvement analogue and not less than one kind of CFSs) or a solution containing a labeled CFS in the above-described [method A], and the above-described steps (a) to (g) are carried out using that solution containing the internal standard. The amount of a labeling substance contained in the separated complex B or the amount of a labeling substance contained in said the separated complex A is measured by a method corresponding to property (kind) of a labeling substance, and the amount of an analyte in a sample is calculated by comparing the measurement result (measurement value) with the amount of said substance added as internal standard. In more specifically, the amount of the analyte in the sample is relatively calculated by measuring the amount of the labeling substance contained in the separated complex B, or the amount of the labeling substance contained in the separated complex A, by a method corresponding to property (kind) of the labeling substance, and further the amount of the internal standard added is measured by a method corresponding to property (kind) of the internal standard, and by comparing these resultant measurement values to determine the ratio, and then based on the ratio and the known addition amount of said internal standard.

(3-2-5) A case when a labeled analogue and a CFS are used. (The use of two separate solutions of a solution including an analyte and a solution containing an analogue.)

In this case, for example, it may be carried out as the following [method A] or [method B].

[Method A; The Case for Using a Calibration Curve]:

(a) The same preparation step [the step (a)] as the above-described in the case (3-12) of "(3) a specific method for separating" is carried out.

(b) to (e) The same introduction steps [the steps (b) to (e)] as the above-described in the case (3-12) of "(3) a specific method for separating" is carried out.

(f) The same concentration and reaction step [the step (f)] as the above-described in the case (3-12) of "(3) a specific method for separating" is carried out.

(g) The same separation step [the step (g)] as the above-described in the case (3-12) of "(3) a specific method for separating" is carried out.

(h) The amount of a labeling substance contained in the separated complex B or the amount of a labeling substance contained in a labeled analogue not involved in formation of said complex B is measured by a method corresponding to property (kind) of a labeling substance, and the amount of an analyte in a sample is calculated by applying the measurement result (measurement value) to a calibration curve showing relation between the amount of an analyte, and the amount of a labeling substance contained in the separated complex B or the amount of a labeling substance contained in a labeled analogue not involved in formation of said complex B, obtained by a similar method using a sample containing a known concentration of an analyte.

[Method B; The Case for Using an Internal Standard]:

A known concentration of a detectable substance as an internal standard is added to a solution including a sample having an analyte and not less than one kind of CFSs or a solution containing a labeled analogue in the above-described [method A], and the above-described steps (a) to (g) are carried out using that solution containing the internal standard. The amount of a labeling substance contained in the separated complex B or the amount of a labeling substance contained in a labeled analogue not involved in formation of said complex B is measured by a method corresponding to property (kind) of a labeling substance, and the amount of an analyte in a sample is calculated by comparing the measurement result (measurement value) with the amount of said substance added as internal standard. In more specifically, the amount of the analyte in the sample is relatively calculated by measuring the amount of the labeling substance contained in the separated complex B, or the amount of the labeling substance contained in the labeling analogue not involved in formation of said complex B, by a method corresponding to property (kind) of the labeling substance, and further the amount of the internal standard added is measured by a method corresponding to property (kind) of the internal standard, and by comparing these resultant measurement values to determine the ratio, and then based on the ratio and the known addition amount of said internal standard.

(3-2-6) A Case when a Labeled Analogue and a Reaction Improvement CFS are Used. (The Use of Two Separate Solutions of a Solution Including an Analyte and a Solution Containing an Analogue.)

In this case, for example, it may be carried out as the following [method A] or [method B].

[Method A; The Case for Using a Calibration Curve]:

(a) The same preparation step [the step (a)] as the above-described in the case (3-13) of "(3) a specific method for separating" is carried out.

(b) to (e) The same introduction steps [the steps (b) to (e)] as the above-described in the case (3-13) of "(3) a specific method for separating" is carried out.

(f) The same concentration and reaction step [the step (f)] as the above-described in the case (3-13) of "(3) a specific method for separating" is carried out.

(g) The same separation step [the step (g)] as the above-described in the case (3-13) of "(3) a specific method for separating" is carried out.

(h) The amount of a labeling substance contained in the separated complex B or the amount of a labeling substance contained in a labeled analogue not involved in formation of said complex B is measured by a method corresponding to property (kind) of a labeling substance, and the amount of an analyte in a sample is calculated by applying the measurement result (measurement value) to a calibration curve showing relation between the amount of an analyte, and the amount of a labeling substance contained in the separated complex B or the amount of a labeling substance contained in a labeled analogue not involved in formation of said complex B, obtained by a similar method using a sample containing a known concentration of an analyte.

[Method B; The Case for Using an Internal Standard]:

A known concentration of a detectable substance as an internal standard is added to a solution including a sample having an analyte and not less than one kind of reaction improvement CFSs or a solution containing a labeled analogue in the above-described [method A], and the above-described steps (a) to (g) are carried out using that solution containing the internal standard. The amount of a labeling substance contained in the separated complex B or the amount of a labeling substance contained in a labeled analogue not involved in formation of said complex B is measured by a method corresponding to property (kind) of a labeling substance, and the amount of an analyte in a sample is calculated by comparing the measurement result (measurement value) with the amount of said substance added as internal standard. In more specifically, the amount of the analyte in the sample is relatively calculated by measuring the amount of the labeling substance contained in the separated complex B, or the amount of the labeling substance contained in the labeling analogue not involved in formation of said complex B, by a method corresponding to property (kind) of the labeling substance, and further the amount of the internal standard added is measured by a method corresponding to property (kind) of the internal standard, and by comparing these resultant measurement values to determine the ratio, and then based on the ratio and the known addition amount of said internal standard.

(3-2-7) A Case when a Labeled Analogue, a CFS and a Reaction Improvement CFS are Used. (The Use of Two Separate Solutions of a Solution Including an Analyte and a Solution Containing an Analogue.)

In this case, for example, it may be carried out as the following [method A] or [method B].

[Method A; The Case for Using a Calibration Curve]:

(a) The same preparation step [the step (a)] as the above-described in the case (3-14) of "(3) a specific method for separating" is carried out.

(b) to (g) The same introduction steps [the steps (b) to (g)] as the above-described in the case (3-14) of "(3) a specific method for separating" is carried out.

(h) The same concentration and reaction step [the step (h)] as the above-described in the case (3-14) of "(3) a specific method for separating" is carried out.

(i) The same separation step [the step (i)] as the above-described in the case (3-14) of "(3) a specific method for separating" is carried out.

(j) The amount of a labeling substance contained in the separated complex B or the amount of a labeling substance contained in a labeled analogue not involved in formation of said complex B is measured by a method corresponding to property (kind) of a labeling substance, and the amount of an analyte in a sample is calculated by applying the measurement result (measurement value) to a calibration curve showing relation between the amount of an analyte, and the amount of a labeling substance contained in the separated complex B or the amount of a labeling substance contained in a labeled analogue not involved in formation of said complex B, obtained by a similar method using a sample containing a known concentration of an analyte.

[Method B; The Case for Using an Internal Standard]:

A known concentration of a detectable substance as an internal standard is added to at least one selected from a solution including a sample having an analyte and not less than one kind of a CFS (or not less than one kind of a reaction improvement CFS), a solution containing a labeled analogue and a solution containing not less than one kind of a reaction improvement CFS (or not less than one kind of a CFS) in the above-described [method A], and the above-described steps (a) to (i) are carried out using that solution containing the internal standard. The amount of a labeling substance contained in the separated complex B or the amount of a labeling substance contained in a labeled analogue not involved in formation of said complex B is measured by a method corresponding to property (kind) of a labeling substance, and the amount of an analyte in a sample is calculated by comparing the measurement result (measurement value) with the amount of said substance added as internal standard. In more specifically, the amount of the analyte in the sample is relatively calculated by measuring the amount of the labeling substance contained in the separated complex B, or the amount of the labeling substance contained in the labeling analogue not involved in formation of said complex B, by a method corresponding to property (kind) of the labeling substance, and further the amount of the internal standard added is measured by a method corresponding to property (kind) of the internal standard, and by comparing these resultant measurement values to determine the ratio, and then based on the ratio and the known addition amount of said internal standard.

(3-2-8) A Case when a Reaction Improvement Analogue and a Labeled CFS are Used. (The Use of Two Separate Solutions of a Solution Including an Analyte and a Solution Containing an Analogue.)

In this case, for example, it may be carried out as the following [method A] or [method B].

[Method A; The Case for Using a Calibration Curve]:

(a) The same preparation step [the step (a)] as the above-described in the case (3-15) of "(3) a specific method for separating" is carried out.

(b) to (e) The same introduction steps [the steps (b) to (e)] as the above-described in the case (3-15) of "(3) a specific method for separating" is carried out.

(f) The same concentration and reaction step [the step (f)] as the above-described in the case (3-15) of "(3) a specific method for separating" is carried out.

(g) The same separation step [the step (g)] as the above-described in the case (3-15) of "(3) a specific method for separating" is carried out.

(h) The amount of a labeling substance contained in the separated complex B or the amount of a labeling substance contained in the separated complex A is measured by a method corresponding to property (kind) of a labeling substance, and the amount of an analyte in a sample is calculated by applying the measurement result (measurement value) to a calibration curve showing relation between the amount of an analyte, and the amount of a labeling substance contained in the separated complex B or the amount of a labeling substance contained in the separated complex A, obtained by a similar method using a sample containing a known concentration of an analyte.

[Method B; The Case for Using an Internal Standard]:

A known concentration of a detectable substance as an internal standard is added to a solution including a sample having an analyte and not less than one kind of a labeled CFS or a solution containing a reaction improvement analogue in the above-described [method A], and the above-described steps (a) to (g) are carried out using that solution containing the internal standard. The amount of a labeling substance contained in the separated complex B or the amount of a labeling substance contained in said the separated complex A is measured by a method corresponding to property (kind) of a labeling substance, and the amount of an analyte in a sample is calculated by comparing the measurement result (measurement value) with the amount of said substance added as internal standard. In more specifically, the amount of the analyte in the sample is relatively calculated by measuring the amount of the labeling substance contained in the separated complex B, or the amount of the labeling substance contained in the separated complex A, by a method corresponding to property (kind) of the labeling substance, and further the amount of the internal standard added is measured by a method corresponding to property (kind) of the internal standard, and by comparing these resultant measurement values to determine the ratio, and then based on the ratio and the known addition amount of said internal standard.

(3-2-9) A Case when a Labeled Reaction Improvement Analogue, and a CFS not Bound with a Labeling Substance and a Reaction Improvement Substance are Used. (The Use of a Solution Including Both an Analyte and an Analogue.)

In this case, for example, it may be carried out as the following [method A] or [method B].

[Method A; The Case for Using a Calibration Curve]:

(a) The same preparation step [the step (a)] as the above-described in the case (3-16) of "(3) a specific method for separating" is carried out.

(b) to (e) The same introduction steps [the steps (b) to (e)] as the above-described in the case (3-16) of "(3) a specific method for separating" is carried out.

(f) The same concentration and reaction step [the step (f)] as the above-described in the case (3-16) of "(3) a specific method for separating" is carried out.

(g) The same separation step [the step (g)] as the above-described in the case (3-16) of "(3) a specific method for separating" is carried out.

(h) The amount of a labeling substance contained in the separated complex B or the amount of a labeling substance contained in a labeled reaction improvement analogue not involved in formation of said complex B is measured by a method corresponding to property (kind) of a labeling substance, and the amount of an analyte in a sample is calculated by applying the measurement result (measurement value) to a calibration curve showing relation between the amount of an analyte, and the amount of a labeling substance contained in the separated complex B or the amount of a labeling substance contained in a labeled reaction improvement analogue not involved in formation of said complex B, obtained by a similar method using a sample containing a known concentration of an analyte.

[Method B; The Case for Using an Internal Standard]:

A known concentration of a detectable substance as an internal standard is added to at least one selected from a solution including a sample having an analyte and a labeled reaction improvement analogue (or a solution including a sample having an analyte, a labeled reaction improvement analogue and not less than one kind of CFSs), and a solution containing not less than one kind of CFS not bound with a labeling substance and a reaction improvement substance in the above-described [method A], and the above-described steps (a) to (g) are carried out using that solution containing the internal standard. The amount of a labeling substance contained in the separated complex B or the amount of a labeling substance contained in a labeled reaction improvement analogue not involved in formation of said complex B is measured by a method corresponding to property (kind) of a labeling substance, and the amount of an analyte in a sample is calculated by comparing the measurement result (measurement value) with the amount of said substance added as internal standard. In more specifically, the amount of the analyte in the sample is relatively calculated by measuring the amount of the labeling substance contained in the separated complex B, or the amount of labeling substance contained in the labeled reaction improvement analogue not involved in formation of said complex B, by a method corresponding to property (kind) of the labeling substance, and further the amount of the internal standard added is measured by a method corresponding to property (kind) of the internal standard, and by comparing these resultant measurement values to determine the ratio, and then based on the ratio and the known addition amount of said internal standard.

(3-2-10) A Case when a Labeled Reaction Improvement Analogue, and a CFS not Bound with a Labeling Substance and a Reaction Improvement Substance are Used. (The Use of Two Separate Solutions of a Solution Including an Analyte and a Solution Containing an Analogue.)

In this case, for example, it may be carried out as the following [method A] or [method B].

[Method A; The Case for Using a Calibration Curve]:
(a) The same preparation step [the step (a)] as the above-described in the case (3-17) of "(3) a specific method for separating" is carried out.
(b) to (e) The same introduction steps [the steps (b) to (e)] as the above-described in the case (3-17) of "(3) a specific method for separating" is carried out.
(f) The same concentration and reaction step [the step (f)] as the above-described in the case (3-17) of "(3) a specific method for separating" is carried out.
(g) The same separation step [the step (g)] as the above-described in the case (3-17) of "(3) a specific method for separating" is carried out.
(h) The amount of a labeling substance contained in the separated complex B or the amount of a labeling substance contained in a labeled reaction improvement analogue not involved in formation of said complex B is measured by a method corresponding to property (kind) of a labeling substance, and the amount of an analyte in a sample is calculated by applying the measurement result (measurement value) to a calibration curve showing relation between the amount of an analyte, and the amount of a labeling substance contained in the separated complex B or the amount of a labeling substance contained in a labeled reaction improvement analogue not involved in formation of said complex B, obtained by a similar method using a sample containing a known concentration of an analyte.

[Method B; The Case for Using an Internal Standard]:
A known concentration of a detectable substance as an internal standard is added to at least one selected from a solution including a sample having an analyte, and not less than one kind of CFS not bound with a labeling substance and a reaction improvement substance, and a solution containing a labeled reaction improvement analogue in the above-described [method A], and the above-described steps (a) to (g) are carried out using that solution containing the internal standard. The amount of a labeling substance contained in the separated complex B or the amount of a labeling substance contained in a labeled reaction improvement analogue not involved in formation of said complex B is measured by a method corresponding to property (kind) of a labeling substance, and the amount of an analyte in a sample is calculated by comparing the measurement result (measurement value) with the amount of said substance added as internal standard. In more specifically, the amount of the analyte in the sample is relatively calculated by measuring the amount of the labeling substance contained in the separated complex B, or the amount of labeling substance contained in the labeled reaction improvement analogue not involved in formation of said complex B, by a method corresponding to property (kind) of the labeling substance, and further the amount of the internal standard added is measured by a method corresponding to property (kind) of the internal standard, and by comparing these resultant measurement values to determine the ratio, and then based on the ratio and the known addition amount of said internal standard.

A method for measurement of the present invention may be carried out in accordance with the above-described known methods themselves except by using a method for separation of the present invention, and reagents to be used may also be selected, as appropriate, in accordance with known methods themselves.

9. A Kit of the Present Invention

A kit of the present invention includes a micro fluidic device and a micro fluidic system of the present invention and is one to be used for carrying out the above-described method of introducing a solution, method for forming a complex, method for separation and method for measurement of the present invention.

As such a kit, the following items should be included:
(1) At least the above-described micro fluidic device and the micro fluidic system of the present invention;
(2) At least (i) the micro fluidic device and the micro fluidic system of the present invention described above, (ii) the reagent containing a CFS, and (iii) if necessary an analogue; or
(3) (i) said item(s) described above (1) or (2), and (ii) an instruction book to be used in the above-described method of introducing a solution, method for forming a complex, method for separation and method for measurement of the present invention.

In this connection, said "instruction book" means a handling manual (instruction manual) of said kit, attached documents (covering letter) or a pamphlet (leaflet), and the like, wherein features, principle, operation procedure, and the like, of a method of the present invention are substantially described by writing or drawings, and the like.

Preferable embodiments and specific examples of these composition elements are as described above.

Furthermore, a kit of the present invention may also contain reagents other than the above. Such reagents include, for example, a buffer solution for electrophoresis separation, a reagent diluent, internal standard, a calibrator (a standard solution), control, reagents (enzyme substrate, coupling enzymes, and the like) for measurement of labeling substances (for example, enzyme, dyes, luminescent substances, fluorescent substances, and the like), reagents for focusing a detector, and the like, but not limited thereto.

The present invention is explained in more detail below by referring to Examples, however, the present invention should not be limited thereby.

EXAMPLES

Example 1

An Analyte

An Antigen

α-Fetoprotein (AFP) (Manufactured by Wako Pure Chemical Industries, Ltd.)
A Reaction Improvement CFS (A DNA Labeled Antibody)
According to the procedure shown in FIG. 27, anti-AFP antibody Fab' fragment bound with DNA was prepared.

Namely, a 250 bp DNA fragment introduced with an NH₂ group at the 5' terminal was purified first by a common method. Subsequently, the NH₂ group introduced to the DNA fragment, and a succinimidyl group of a sulfosuccinimidyl 4-(p-maleimidophenyl)butyrate (Sulfo-SMPB) linker (a linker having a succinimidyl group and a maleimido group: manufactured by Pierce Co.) were subjected to a reaction by a common method. Then, by gel filtration treatment, unreacted linkers were removed to give a 250 bp DNA fragment bound with a linker. The resultant 250 bp DNA fragment bound with a linker, and an anti-AFP antibody WA1 Fab' fragment, prepared in advance using an anti-AFP antibody WA1 (manufactured by Wako Pure Chemical Industries, Ltd.) in accordance with a common method, were subjected to a reaction. The resultant reaction products were each purified using a DEAE column to prepare an anti-AFP antibody WA1 Fab' fragment bound with a 250 bp DNA fragment (a 250 bp DNA labeled antibody)

[A Labeled CFS (A Fluorescence Labeled Antibody)]

An anti-AFP antibody WA2 (manufactured by Wako Pure Chemical Industries, Ltd.) which recognizes an epitope of AFP different from a WA1 antibody, was treated by a common method to give an anti-AFP antibody WA2 Fab' fragment. A fluorescent substance Alexa647 (manufactured by Molecular Probes Inc.) was introduced to an amino group of said fragment by a common method to prepare an Alexa647 labeled anti-AFP antibody WA2 Fab' fragment (a fluorescence labeled antibody).

[A Capillary Chip]

A capillary chip having a layout shown in FIG. 28 was produced according to a method described in "Technology and application of microchemistry chip", T. Kitamori et al., published in 2004 (Maruzen Co., Ltd.) as follows:

Namely, a photo resist layer (film) was formed on Si layer (film) which was formed on a quartz substrate. This photo resist was exposed using a mask having a capillary design (layout) shown in FIG. 28 and developed. Si at the part, where a photo resist was removed by development, was removed by sputtering, and then wet etching was carried out using a solution of hydrogen fluoride to produce a capillary channel groove (capillary) at the quartz substrate. After removing a photo resist and a Si film remained on the quartz substrate, said quartz substrate and a cover plate having a hole for a fluid reservoir were adhered together by an HF bonding technique to produce a capillary chip.

In this connection, in FIG. 28, L1 and L2 show represent a well for introducing a leading buffer, T shows a well for introducing a trailing buffer, S/R1 and S/R2 show represent a well for introducing a sample or a reagent, and W1, W2 and W3 show represent a well for drain, respectively.

[Electrophoresis]

(1) An Electrophoresis Sample 1

Into a 0.5 mL tube, 1 μL of 1 nM AFP, 1 μL of 2 μM a fluorescence labeled antibody and 8 μL of a leading buffer containing 50 mM Cl⁻ ion were mixed to prepare 10 μL of a reaction solution. The reaction solution was stood still on ice to be subjected to an antigen-antibody reaction for about 30 minutes to form a [fluorescence labeled antibody-AFP] immune complex. In this connection, the final concentration of AFP was 100 pM, and the final concentration of the fluorescence labeled antibody was 200 nM.

The obtained reaction solution containing the [fluorescence labeled antibody-AFP] immune complex was used as an electrophoresis sample 1.

(2) An Electrophoresis Sample 2

Into a 0.5 mL tube, 1 μL of 1 nM AFP, 1 μL of 1 μM a 250 bp DNA labeled antibody and 8 μL of a leading buffer containing 50 mM Cl⁻ ion were mixed to prepare 10 μL of a reaction solution. The reaction solution was stood still on ice to be subjected to an antigen-antibody reaction for about 30 minutes to form a [250 bp DNA labeled antibody-AFP] immune complex. In this connection, the final concentration of AFP was 100 pM, and the final concentration of the 250 bp DNA labeled antibody was 100 nM.

The obtained reaction solution containing the [250 bp DNA labeled antibody-AFP] immune complex was used as an electrophoresis sample 2.

(3) A Reagent Solution 1 (a Solution Containing a 250 bp DNA Labeled Antibody)

A leading buffer (containing 50 mM Cl⁻ ion) containing 0 to 100 nM of a 250 bp DNA labeled antibody was used as a reagent solution 1.

(4) A Reagent Solution 2 (a Solution Containing a Fluorescence Labeled Antibody)

A leading buffer (containing 50 mM Cl⁻ ion) containing 0 to 200 nM of a fluorescence labeled antibody was used as a reagent solution 2.

(5) Procedure of Electrophoresis a) Introduction of an Electrophoresis Sample and a Reagent Solution Into an S/R1 well (a well for introducing a sample or a reagent solution) shown in FIG. 28, 10 μL of an electrophoresis sample 1 (a solution containing a [fluorescence labeled antibody-AFP] immune complex) was delivered by drops, 10 μL of a reagent solution 1 (a solution containing a DNA labeled antibody) was delivered by drops into an S/R2 well (a well for introducing a sample or a reagent solution), 10 μL of a leading buffer (a leading buffer containing 50 mM of Cl⁻ ion) were delivered by drops into L1 well and L2 well, and 10 μL of a trailing buffer (a trailing buffer containing 75 mM of an HEPES ion) was delivered by drops into a T well, respectively, and by application of a pressure of −5 psi for 15 seconds onto W1 (a well for drain), W2 (a well for drain) and W3 (a well for drain) an electrophoresis sample 1, a reagent solution 1, a leading buffer and a trailing buffer were introduced into a channel.

Into an S/R1 well (a well for introducing a sample or a reagent solution) shown in FIG. 28, 10 μL of a reagent solution 2 (a solution containing a fluorescence labeled antibody) was delivered by drops, 10 μL of an electrophoresis sample 2 (a solution containing a [DNA labeled antibody-AFP] immune complex) was delivered by drops into an S/R2 well (a well for introducing a sample or a reagent solution), 10 μL of a leading buffer (a leading buffer containing 50 mM of Cl⁻ ion) were delivered by drops into L1 well and L2 well, and 10 μL of a trailing buffer (a trailing buffer containing 75 mM of an HEPES ion) was delivered by drops into a T well, respectively, and by application of a pressure of −5 psi for 15 seconds onto W1 (a well for drain), W2 (a well for drain) and W3 (a well for drain) an electrophoresis sample 2, a reagent solution 2, a leading buffer and a trailing buffer were introduced into a channel. Arrangement relation of each solution in a capillary was schematically shown in FIG. 29. In this connection, in FIG. 29, a shaded area shows an arrangement area of a solution (an electrophoresis sample 1 or a reagent solution 2) introduced from the S/R1 well, and a dotted area shows an arrangement area of a solution (a reagent solution 1 or an electrophoresis sample 2) introduced from the S/R2 well, respectively.

b) Concentration and Reaction

By applying a voltage of 600 V, 1200 V or 1800 V between an T well and an L1 well in FIG. 29 at a chip temperature of 10° C., a 250 bp DNA labeled antibody in the reagent solution 1 was contacted and reacted with a [fluorescence labeled antibody-AFP] immune complex in the electrophoresis sample 1, while concentrating a 250 bp DNA labeled antibody in a reagent solution 1, to form a [fluorescence labeled antibody-AFP-250 bp DNA labeled antibody] immune complex.

By applying a voltage of 600 V, 1200 V or 1800 V between an T well and an L1 well in FIG. 29 at a chip temperature of 10° C., a [250 bp DNA labeled antibody-AFP] immune complex in the electrophoresis sample 2 was contacted and reacted with a fluorescence labeled antibody in the reagent solution 2, while concentrating a [250 bp DNA labeled antibody-AFP] immune complex in the electrophoresis sample 2, to form a [fluorescence labeled antibody-AFP-250 bp DNA labeled antibody] immune complex.

In this connection, reaction time was about 100 seconds in application of a voltage of 600 V, about 50 seconds in application of a voltage of 1200 V, and about 40 seconds in application of a voltage of 1800 V.

c) Separation and Detection

When a [fluorescence labeled antibody-AFP-250 bp DNA labeled antibody] immune complex overtook through a crossing part of an L2 channel and a main channel (a first channel), 2000 V was applied onto the L2 well and 1000 V was applied onto an L1 well, for 100 seconds to separate and detect said immune complex.

In this connection, the detection was carried out by serial measurement of fluorescent intensity by laser excitation of 635 nm at a capillary part at 2 cm from the crossing part of the L2 channel, using a fluorescent microscope (BX-50, manufactured from KS Olympus Co., Ltd.) In this connection, the above-described procedure (a) to (c) was repeated twice.

[Results]

FIG. 30 shows relation between concentration of a 250 bp DNA labeled antibody and reaction efficiency in the case of formation of an immune complex of [a fluorescent labeled antibody-AFP-a 250 bp DNA labeled antibody] by introducing an electrophoresis sample 1 (a solution containing a [fluorescence labeled antibody-AFP] immune complex) from an S/R1 well and a reagent solution 1 (a solution containing a DNA labeled antibody) from an S/R2 well, and then subjecting these to a reaction. In this connection, in FIG. 30, reaction efficiency means efficiency of a reaction between a 250 bp DNA labeled antibody and a [fluorescence labeled antibody-AFP] immune complex, and is a relative value of a signal (peak area) of a [fluorescence labeled antibody-AFP-a 250 bp DNA labeled antibody] immune complex obtained by using a 250 bp DNA labeled antibody having predetermined concentration, obtained when a signal (peak area) of a [fluorescence labeled antibody-AFP-a 250 bp DNA labeled antibody] immune complex was detected similarly as above after reacting a fluorescence labeled antibody, AFP and a 250 bp DNA labeled antibody at 10° C. for 30 minutes in advance outside a capillary to obtain 10 µL of a reaction solution containing 200 nM of a fluorescence labeled antibody, 100 pM of AFP and 100 nM of a 250 bp DNA labeled antibody, and introducing the obtained reaction solution from an S/R2 well, was taken as 100%.

In addition, FIG. 31 shows relation between concentration of a fluorescence labeled antibody and reaction efficiency in the case of formation of an immune complex of [a fluorescent labeled antibody-AFP-a 250 bp DNA labeled antibody] by introducing a reagent solution 2 (a solution containing a fluorescence labeled antibody) from an S/R1 well and an electrophoresis sample 2 (a solution containing a [DNA labeled antibody-AFP] immune complex) from an S/R2 well, and then subjecting these to a reaction. In this connection, in FIG. 31, reaction efficiency means efficiency of a reaction between a fluorescence labeled antibody and a [DNA labeled antibody-AFP] immune complex, and is a relative value of a signal (peak area) of a [fluorescence labeled antibody-AFP-a 250 bp DNA labeled antibody] immune complex obtained by using a fluorescence labeled antibody having predetermined concentration, obtained when a signal (peak area) of a [fluorescence labeled antibody-AFP-a 250 bp DNA labeled antibody] immune complex was detected similarly as above after reacting a fluorescence labeled antibody, AFP and a 250 bp DNA labeled antibody at 10° C. for 30 minutes in advance outside a capillary to obtain 10 µL of a reaction solution containing 200 nM of a fluorescence labeled antibody, 100 pM of AFP and 100 nM of a 250 bp DNA labeled antibody, and introducing the obtained reaction solution from an S/R2 well, was taken as 100%. In FIG. 30, vertical axis shows reaction efficiency and horizontal axis shows concentration of a 250 bp DNA labeled antibody, respectively. In addition, in FIG. 30, ○ and ● show the results obtained by carrying out the above-described operation b) at 600 V, x and * show the results obtained by carrying out the above-described operation b) at 1200 V, and ◇ and ◆ show the results obtained by carrying out the above-described operation b) at 1800 V, respectively. A dotted line ( - - - ) shows a reaction curve in the result by carrying out the above-described operation b) at 600 V, a solid line (-) shows a reaction curve in the result by carrying out the above-described operation b) at 1200 V, and a dotted dashed line (-•-) shows a reaction curve in the result by carrying out the above-described operation b at 1800 V. In FIG. 31, vertical axis shows reaction efficiency and horizontal axis shows concentration of a fluorescence labeled antibody, respectively. In addition, in FIG. 31, ○ and ● show the results obtained by carrying out the above-described operation b) at 600 V, x and * show the results obtained by carrying out the above-described operation b) at 1200 V, and ◇ and ◆ show the results obtained by carrying out the above-described operation b) at 1800 V, respectively. A dotted line ( - - - ) shows a reaction curve in the result by carrying out the above-described operation b) at 600 V, a solid line (-) shows a reaction curve in the result by carrying out the above-described operation b) at 1200 V, and a dotted dashed line (-•-) shows a reaction curve in the result by carrying out the above-described operation b at 1800 V.

From the above-described Example, it is found that by using a structure (a capillary chip) of introducing a solution of the present invention a plurality of 2 or more kinds of solutions can be easily introduced into a main channel (a first channel). Furthermore, it is clear that a reaction between an analyte or an analogue thereof in a solution and a substance binding to said analyte or analogue thereof (a CFS) in a solution can be carried out in a short time and in high reaction efficiency.

In this connection, from the results in FIGS. 30 and 31, a complex is found to be formed depending on voltage and concentration of a CFS (an antibody), namely a complex is easily formed in lower voltage and in higher concentration of a CFS (an antibody).

Example 2

An Analyte

An Antigen

The same one as in Example 1 was used.
[A Reaction Improvement CFS (A DNA Labeled Antibody)]
The same one as in Example 1 was used.
[A Labeled CFS (A Fluorescence Labeled Antibody)]
The same one as in Example 1 was used.

[A Capillary Chip]

A capillary chip having a layout shown in FIG. 32 was produced according to a method described in "Technology and application of microchemistry chip", T. Kitamori et al., published in 2004 (Maruzen Co., Ltd.) as follows:

Namely, a photo resist layer (film) was formed on Si layer (film) which was formed on a quartz substrate. This photo resist was exposed using a mask having a capillary design (layout) shown in FIG. 32 and developed. Si at the part, where a photo resist was removed by development, was removed by sputtering, and then wet etching was carried out using a solution of hydrogen fluoride to prepare a capillary channel groove (capillary) at the quartz substrate. After removing a photo resist and a Si film remained on the quartz substrate, said quartz substrate and a cover plate having a hole for a fluid reservoir were adhered together by an HF bonding technique to prepare a capillary chip.

In this connection, in FIG. 32, L1 and L2 show represent a well for introducing a leading buffer, T shows a well for introducing a trailing buffer, S/R1, S/R2 and S/R3 show represent a well for introducing a sample or a reagent, and W1, W2, W3 and W4 show represent a well for drain, respectively.

[Electrophoresis]

(1) An Electrophoresis Sample (a Solution Containing AFP)

A leading buffer (containing 50 mM of $Cl^-$ ion) containing 100 pM of AFP was used as the electrophoresis sample.

(2) The $1^{st}$ reagent solution (a solution containing a 250 bp DNA labeling antibody)

A leading buffer (containing 50 mM of $Cl^-$ ion) containing 25 nM of a 250 bp DNA labeled antibody was used as the $1^{st}$ reagent solution.

(3) The $2^{nd}$ Reagent Solution (a Solution Containing a Fluorescence Labeled Antibody)

A leading buffer (containing 50 mM of $Cl^-$ ion) containing 100 nM of a fluorescence labeled antibody was used as the $2^{nd}$ reagent solution (4) Procedure of Electrophoresis a) Introduction of the Electrophoresis Sample, the $1^{st}$ reagent Solution and the $2^{nd}$ Reagent Solution Into L1 well and L2 well shown in FIG. 32, 10 µL of a leading buffer (a leading buffer containing 50 mM of $Cl^-$ ion) were delivered by drops, 10 µL of a trailing buffer (a trailing buffer containing 75 mM of an HEPES ion) was delivered by drops into a T well, 10 µL of a $2^{nd}$ reagent solution (a solution containing a fluorescence labeled antibody) was delivered by drops into an S/R1 well, 10 µL of an electrophoresis sample (a solution containing AFP) was delivered by drops into an S/R2 well, and 10 µL of a $1^{st}$ reagent solution (a solution containing a 250 bp DNA labeling antibody) was delivered by drops into an S/R3 well, respectively, and by application of a pressure of −5 psi for 15 seconds onto W1, W2, W3 and W4 an electrophoresis sample, a $1^{st}$ reagent solution, a $2^{nd}$ reagent solution, a leading buffer and a trailing buffer were introduced into a channel. By this procedure, a zone of the $2^{nd}$ reagent solution, a zone of the electrophoresis sample, and a zone of the $1^{st}$ reagent solution were formed in a channel from the downstream side. Arrangement relation of the electrophoresis sample, the $1^{St}$ reagent solution and the $2^{nd}$ reagent solution in a capillary was schematically shown in FIG. 33. In this connection, in FIG. 33, a vertical line area shows an arrangement area of the $2^{nd}$ reagent solution, a shaded area shows the electrophoresis sample and a dotted area shows, the $1^{st}$ reagent solution, respectively.

b) Concentration and Reaction

By applying a voltage of 600 V between the T well (a well for introducing a trailing buffer) and the L1 well (a well for introducing a leading buffer), a DNA labeled antibody in the $1^{st}$ reagent solution, AFP in the electrophoresis sample and a fluorescence labeled antibody in the $2^{nd}$ reagent solution were contacted and reacted, while concentrating these, to form a [fluorescence labeled antibody-AFP-250 bp DNA labeled antibody] immune complex at 10° C.

In this connection, reaction time is about 200 seconds.

c) Separation and Detection

When a [fluorescence labeled antibody-AFP-250 bp DNA labeled antibody] immune complex overtook through a crossing part of an L2 channel and a main channel (a first channel), 2000 V was applied onto the L2 well and 1000 V was applied onto an L1 well, for 100 seconds to separate and detect said immune complex.

In this connection, the detection was carried out by serial measurement of fluorescent intensity by laser excitation of 635 nm at a capillary part at 2 cm from the crossing part of the L2 channel, using a fluorescent microscope (BX-50, manufactured from KS Olympus Co., Ltd.)

Results

Table 2 shows reproducibility when operations (a) to (c) in the above-described procedure (4) were repeated eight times. In this connection, AFP peak area in this Table represents a signal (peak area) of a [fluorescence labeled antibody-AFP-a 250 bp DNA labeled antibody] immune complex.

TABLE 2

|  | AFP Peak Area |
|---|---|
| 1 | 257 |
| 2 | 269 |
| 3 | 254 |
| 4 | 250 |
| 5 | 255 |
| 6 | 238 |
| 7 | 259 |
| 8 | 260 |
| Average | 255.3 |
| SD | 8.3 |
| CV | 3.3 |

From the above-described Example, it is found that by using a structure (a capillary chip) of introducing a solution of the present invention a plurality of 3 kinds of solutions can be easily introduced into a main channel (a first channel). In addition, it is clear from the result in Table 2 that CV value shows a high reproducibility of 3.3%, and a structure (a micro fluidic device) of introducing a solution of the present invention is found to enable to introduce a plurality of solutions into a channel in highly accurate volume and easily.

From the above results, it is suggested that by using a structure (a micro fluidic device) of introducing a solution of the present invention and a method of the present invention using the same, a reaction between an analyte or an analogue thereof in a solution and a substance binding to said analyte or analogue thereof (a CFS) in a solution can be carried out in a short time and in high reaction efficiency, and a complex between an analyte or an analogue thereof, and a CFS can be separated from a CFS not involved in formation of said complex or an analogue not involved in formation of said complex quickly, simply and in high accuracy, and further high sensitivity measurement of an analyte in a sample can be possible, based on the amount of a separated complex or the amount of a CFS not involved in formation of said complex or the amount of a separated analogue not involved in formation of said complex.

INDUSTRIAL APPLICABILITY

The present invention relates to a structure for introducing a plurality of solutions (a sample and/or a reagent solution) into a channel, in particular a channel of micro fluidic device, a micro fluidic device having said structure, a method for introducing a solution using said device, a method for separation of a substance and a method for measurement of a substance.

In accordance with a method of the present invention, a plurality of solutions (a sample and/or a reagent solution) for example, those having different viscosity each other, can be introduced into a channel, in particular a channel of a micro fluidic device, in highly accurate volume, in high amount and simply. In addition, by quantitatively forming a zone composed of a plurality of solutions in a channel and subjecting a electrophoretically concentration, a reaction between an analyte or an analogue thereof in a sample, and a substance binding to said analyte or analogue thereof (a CFS) can be carried out in a short time and in high reaction efficiency, and a complex between said analyte or analogue thereof, and CFS can be separated from a CFS not involved in formation of said complex or analogue not involved in formation of said complex rapidly, simply and in high accuracy, and furthermore high sensitivity measurement of an analyte or an analogue thereof in a sample becomes possible, based on the amount of a separated complex or the amount of a separated CFS not involved in formation of said complex or the amount of a separated analogue not involved in formation of said complex.

We claim:

1. A method for introducing not less than 2 kinds of samples and/or reagent solutions to a channel of a micro fluidic device, which comprises:
   (a) providing a micro fluidic device comprising at least one structure for introducing a sample or a reagent solution to a first channel (1) in a substrate, said the structure comprising;
      (i) the first channel (1);
      (ii) not less than 3 side channels (2) for drain, each said side channel (2) for drain having a opening (2-1) opened on a wall of said first channel (1), and said openings (2-1) arranged in spaced relation to one another, wherein said side channel (2) for drain is connected to a waste reservoir (4); and
      (iii) not less than 2 side channels (3) for introducing a sample or a reagent solution, each said side channel (3) for introducing a sample or a reagent solution having a opening (3-1) opened on the wall of said first channel (1) at the different position (part) from said openings (2-1) of said side channels (2) for drain, and each said opening (3-1) arranged between adjacent 2 openings (2-1) of side channels (2) for drain, wherein each said opening (3-1) of these not less than 2 side channels (3) for introducing a sample or a reagent solution are each arranged at the different portion between adjacent 2 openings (2-1) of side channels (2) for drain, and side channel (3) for introducing a sample or a reagent solution is connected to a sample or a reagent solution reservoir (5);
   (b) putting a sample into at least one sample or reagent solution reservoir (5) connecting to said side channel (3) for introducing a sample or a reagent solution;
   (c) putting a reagent solution into at least one sample or reagent solution reservoir (5) connecting to said side channel (3) for introducing a sample or a reagent solution, wherein said sample or reagent reservoir (5) being different from one used in said step (b);
   (d) introducing said sample in said side channel (3) for introducing a sample or a reagent solution connected with said sample or reagent solution reservoir (5) used in said step (b), 2 side channels (2) for drain adjacent to said side channel (3) for introducing a sample or a reagent solution in an axis direction and a first channel region between said 2 side channels (2) for drain, by moving said sample from said sample or reagent solution reservoir (5) where said sample is put in said step (b) to said 2 side channels (2) for drain adjacent to said side channel (3) for introducing a sample or a reagent solution connected with said sample or reagent solution reservoir (5) in an axis direction, via said side channel (3) for introducing a sample or a reagent solution connected with said reservoir (5); and
   (e) introducing said reagent solution in said side channel (3) for introducing a sample or a reagent solution connected with said sample or reagent solution reservoir (5) used in said step (c), 2 side channels (2) for drain adjacent to said side channel (3) for introducing a sample or a reagent solution in an axis direction and a first channel region between said 2 side channels (2) for drain, by moving said reagent solution from said sample or reagent solution reservoir (5) where said reagent solution is put in said step (c) to said 2 side channels (2) for drain adjacent to said side channel (3) for introducing a sample or a reagent solution connected with said sample or reagent solution reservoir (5) in an axis direction, via said side channel (3) for introducing a sample or a reagent solution connected with said reservoir (5).

2. A method for forming a complex between an analyte or an analogue thereof in a sample, and a substance binding to said analyte or analogue thereof, which comprises:
   (a) providing a micro fluidic device comprising at least one structure for introducing a sample or a reagent solution to a first channel (1) in a substrate, said the structure comprising:
      (i) the first channel (1);
      (ii) not less than 3 side channels (2) for drain, each said side channel (2) for drain having a opening (2-1) opened on a wall of said first channel (1), and said openings (2-1) arranged in spaced relation to one another, wherein said side channel (2) for drain is connected to a waste reservoir (4); and
      (iii) not less than 2 side channels (3) for introducing a sample or a reagent solution, each said side channel (3) for introducing a sample or a reagent solution having a opening (3-1) opened on the wall of said first channel (1) at the different position (part) from said openings (2-1) of said side channels (2) for drain, and each said opening (3-1) arranged between adjacent 2 openings (2-1) of side channels (2) for drain, wherein each said opening (3-1) of these not less than 2 side channels (3) for introducing a sample or a reagent solution are each arranged at the different portion between adjacent 2 openings (2-1) of side channels (2) for drain, and side channel (3) for introducing a sample or a reagent solution is connected to a sample or a reagent solution reservoir (5);
   (b) putting a sample into at least one sample or reagent solution reservoir (5) connecting to said side channel (3) for introducing a sample or a reagent solution;
   (c) putting a reagent solution into at least one sample or reagent solution reservoir (5) connecting to said side channel (3) for introducing a sample or a reagent solution, wherein said sample or reagent solution reservoir (5) being different from one used in said step (b);

(d) introducing said sample in said side channel (3) for introducing a sample or a reagent solution connected with said sample or reagent solution reservoir (5) used in said step (b), 2 side channels (2) for drain adjacent to said side channel (3) for introducing a sample or a reagent solution in an axis direction and a first channel region between said 2 side channels (2) for drain, by moving said sample from said sample or reagent solution reservoir (5) where said sample is put in said step (b) to said 2 side channels (2) for drain adjacent to said side channel (3) for introducing a sample or a reagent solution connected with said sample or reagent reservoir (5) in an axis direction, via said side channel (3) for introducing a sample or a reagent solution connected with said reservoir (5);

(e) introducing said reagent solution in said side channel (3) for introducing a sample or a reagent solution with said sample or reagent reservoir (5) used in said step (c), 2 side channels (2) for drain adjacent to said side channel (3) for introducing a sample or a reagent solution in an axis direction and a first channel region between said 2 side channels (2) for drain, by moving said reagent solution from said sample or reagent solution reservoir (5) where said reagent solution is put in said step (c) to said 2 side channels (2) for drain adjacent to said side channel (3) for introducing a sample or a reagent solution connected with said sample or reagent reservoir (5) in an axis direction, via said side channel (3) for introducing a sample or a reagent solution connected with said reservoir (5); and (f) reacting an analyte or an analogue thereof in a sample with at least one kind of a substances binding to said analyte or analogue thereof while concentrating said analyte or said analogue thereof in the sample and/or at least one kind of the substances binding to said analyte or analogue thereof in the reagent solution to form the complex between said analyte or said analogue thereof and the substances binding to said analyte or analogue thereof, by applying a voltage to said first channel (1).

* * * * *